(12) United States Patent
Wan et al.

(10) Patent No.: US 9,926,556 B2
(45) Date of Patent: Mar. 27, 2018

(54) LINKAGE MODIFIED OLIGOMERIC COMPOUNDS

(71) Applicant: Ionis Pharmaceuticals, Inc., Carlsbad, CA (US)

(72) Inventors: W. Brad Wan, Fallbrook, CA (US); Michael T. Migawa, Carlsbad, CA (US); Michael Oestergaard, Carlsbad, CA (US); Eric E. Swayze, Encinitas, CA (US); Punit P. Seth, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/305,742

(22) PCT Filed: Apr. 28, 2015

(86) PCT No.: PCT/US2015/028076
§ 371 (c)(1),
(2) Date: Oct. 21, 2016

(87) PCT Pub. No.: WO2015/168172
PCT Pub. Date: Nov. 5, 2015

(65) Prior Publication Data
US 2017/0044526 A1 Feb. 16, 2017

Related U.S. Application Data

(60) Provisional application No. 61/985,196, filed on Apr. 28, 2014, provisional application No. 62/114,153, filed on Feb. 10, 2015.

(51) Int. Cl.
| | | |
|---|---|---|
| C12N 15/11 | (2006.01) |
| C07H 19/067 | (2006.01) |
| C07H 19/167 | (2006.01) |
| C07H 21/02 | (2006.01) |
| C07H 19/06 | (2006.01) |
| C07H 19/16 | (2006.01) |
| C07H 21/00 | (2006.01) |
| C12N 15/113 | (2010.01) |

(52) U.S. Cl.
CPC ............ *C12N 15/111* (2013.01); *C07H 19/06* (2013.01); *C07H 19/067* (2013.01); *C07H 19/16* (2013.01); *C07H 19/167* (2013.01); *C07H 21/00* (2013.01); *C07H 21/02* (2013.01); *C12N 15/1135* (2013.01); *C12N 15/1136* (2013.01); *C12N 15/1137* (2013.01); *C12N 15/1138* (2013.01); *C12N 2310/11* (2013.01); *C12N 2310/315* (2013.01); *C12N 2310/321* (2013.01); *C12N 2310/3231* (2013.01); *C12N 2310/341* (2013.01); *C12N 2310/346* (2013.01); *C12N 2310/351* (2013.01)

(58) Field of Classification Search
CPC .............. C12N 15/111; C12N 2310/11; C12N 2310/312
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,500,707 A | 2/1985 | Caruthers et al. |
| 4,668,777 A | 5/1987 | Caruthers et al. |
| 4,725,677 A | 2/1988 | Koster et al. |
| 4,751,219 A | 6/1988 | Kempen |
| 4,845,205 A | 7/1989 | Huynh et al. |
| 4,973,679 A | 11/1990 | Caruthers et al. |
| 5,023,243 A | 6/1991 | Tullis |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,175,273 A | 12/1992 | Bischofberger et al. |
| 5,177,198 A | 1/1993 | Spielvogel et al. |
| 5,223,618 A | 6/1993 | Cook et al. |
| 5,256,775 A | 10/1993 | Froehler et al. |
| 5,264,423 A | 11/1993 | Cohen et al. |

(Continued)

FOREIGN PATENT DOCUMENTS

| | | |
|---|---|---|
| WO | WO 1992/013869 | 8/1992 |
| WO | WO 1993/025565 | 12/1993 |

(Continued)

OTHER PUBLICATIONS

Abbas et al., "Commercially Available 5'-DMT Phosphoramidites as Reagents for the Synthesis of Vinylphosphonate-Linked Oligonucleic Acids" Organic Letters (2001) 3(21):3365-3367.

Abifadel et al., "Mutations and polymorphisms in the proprotein convertase subtilisin kexin 9 (PCSK9) gene in cholesterol metabolism and disease" Hum. Mutat. (2009) 30(4):520-529.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Allart et al., "D-Altritol Nucleic Acids (ANA): Hybridisation Properties, Stability, and Initial Structural Analysis" Chem. Eur. J. (1999) 5(8):2424-2431.

(Continued)

*Primary Examiner* — Dana H Shin
(74) *Attorney, Agent, or Firm* — McNeill Baur PLLC

(57) ABSTRACT

The present invention provides oligomeric compounds comprising at least one neutral methoxypropyl phosphonate modified internucleoside linkage. Such oligomeric compounds have one or more improved properties such as selectivity, potency, improved toxicity profile and or improved proinflammatory profile. Such oligomeric compounds have enhanced stability to exposure to base during synthesis. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell.

21 Claims, 1 Drawing Sheet

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,286,717 A | 2/1994 | Cohen et al. |
| 5,302,240 A | 4/1994 | Hort et al. |
| 5,314,893 A | 5/1994 | Tino et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,432,272 A | 7/1995 | Benner |
| 5,434,257 A | 7/1995 | Matteucci |
| 5,457,187 A | 10/1995 | Gmelner et al. |
| 5,459,255 A | 10/1995 | Cook et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,508,270 A | 4/1996 | Baxter et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,607,922 A | 3/1997 | De Clercq et al. |
| 5,610,289 A | 3/1997 | Cook et al. |
| 5,614,617 A | 3/1997 | Cook et al. |
| 5,625,050 A | 4/1997 | Beaton et al. |
| 5,645,985 A | 7/1997 | Froehler et al. |
| 5,646,269 A | 7/1997 | Matteucci |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 5,994,517 A | 11/1999 | Ts'o et al. |
| 6,005,096 A | 12/1999 | Matteucci et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,426,220 B1 | 7/2002 | Bennett et al. |
| 6,455,507 B1 | 9/2002 | Townsend et al. |
| 6,525,031 B2 | 2/2003 | Manoharan |
| 6,525,191 B1 | 2/2003 | Ramasamy |
| 6,620,916 B1 | 9/2003 | Takahara et al. |
| 6,660,720 B2 | 12/2003 | Manoharan et al. |
| 6,670,461 B1 | 12/2003 | Wengel et al. |
| 6,693,187 B1 | 2/2004 | Dellinger |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 7,034,133 B2 | 4/2006 | Wengel et al. |
| 7,053,207 B2 | 5/2006 | Wengel |
| 7,262,177 B2 | 8/2007 | Ts'o et al. |
| 7,276,592 B2 | 10/2007 | Bergmann et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,582,744 B2 | 9/2009 | Manoharan et al. |
| 7,723,509 B2 | 5/2010 | Manoharan et al. |
| 7,741,457 B2 | 6/2010 | Seth et al. |
| 7,851,615 B2 | 12/2010 | Manoharan et al. |
| 8,088,904 B2 | 1/2012 | Allerson et al. |
| 8,106,022 B2 | 1/2012 | Manoharan et al. |
| 8,137,695 B2 | 3/2012 | Rozema et al. |
| 8,158,601 B2 | 4/2012 | Chen et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Rajeev et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,536,320 B2 | 9/2013 | Prakash et al. |
| 8,541,548 B2 | 9/2013 | Rozema |
| 8,546,556 B2 | 10/2013 | Seth et al. |
| 8,552,163 B2 | 10/2013 | Lee et al. |
| 8,604,192 B2 | 12/2013 | Seth et al. |
| 8,796,437 B2 | 8/2014 | Siwkowski et al. |
| 9,021,421 B1 | 4/2015 | Egoroy et al. |
| 2002/0058802 A1 | 5/2002 | Dellinger et al. |
| 2003/0077829 A1 | 4/2003 | MacLachlan |
| 2003/0082807 A1 | 5/2003 | Wengel |
| 2003/0119724 A1 | 6/2003 | Ts'o et al. |
| 2003/0158403 A1 | 8/2003 | Manohamn et al. |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0033967 A1 | 2/2004 | Van Aerschot et al. |
| 2004/0116687 A1 | 6/2004 | Dellinger |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2004/0219565 A1 | 11/2004 | Kauppinen et al. |
| 2005/0130923 A1 | 6/2005 | Bhat et al. |
| 2005/0164235 A1 | 7/2005 | Manoharan et al. |
| 2006/0148740 A1 | 7/2006 | Platenburg |
| 2006/0183886 A1 | 8/2006 | Tso et al. |
| 2007/0287831 A1 | 12/2007 | Seth et al. |
| 2008/0038745 A1 | 2/2008 | Bergmann et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0240730 A1 | 9/2010 | Beigelman et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0101148 A1 | 4/2012 | Akinc et al. |
| 2012/0128760 A1 | 5/2012 | Manoharan et al. |
| 2012/0136042 A1 | 5/2012 | Rajeev et al. |
| 2012/0157509 A1 | 6/2012 | Hadwiger et al. |
| 2012/0165393 A1 | 6/2012 | Rozema et al. |
| 2012/0230938 A1 | 9/2012 | Rozema et al. |
| 2013/0004427 A1 | 1/2013 | El-Sayed et al. |
| 2013/0033961 A1 | 2/2013 | Bumstad et al. |
| 2013/0084576 A1 | 4/2013 | Prakash et al. |
| 2013/0109817 A1 | 5/2013 | Yurkovetskiy et al. |
| 2013/0121954 A1 | 5/2013 | Wakefield et al. |
| 2013/0178512 A1 | 7/2013 | Manoharan et al. |
| 2013/0236968 A1 | 9/2013 | Rajeev et al. |

FOREIGN PATENT DOCUMENTS

| | | |
|---|---|---|
| WO | WO 1994/002499 | 2/1994 |
| WO | WO 1994/017093 | 8/1994 |
| WO | WO 1997/020563 | 6/1997 |
| WO | WO 1997/046098 | 12/1997 |
| WO | WO 1998/013381 | 4/1998 |
| WO | WO 1999/014226 | 3/1999 |
| WO | WO 2001/049687 | 7/2001 |
| WO | WO 2002/018406 | 3/2002 |
| WO | WO 2002/036743 | 5/2002 |
| WO | WO 2002/043771 | 6/2002 |
| WO | WO 2004/024757 | 3/2004 |
| WO | WO 2004/101619 | 11/2004 |
| WO | WO 2004/106356 | 12/2004 |
| WO | WO 2005/021570 | 3/2005 |
| WO | WO 2005/049582 | 6/2005 |
| WO | WO 2006/047842 | 5/2006 |
| WO | WO 2007/134181 | 11/2007 |

(56) References Cited

FOREIGN PATENT DOCUMENTS

| WO | WO 2008/098788 | 8/2008 |
|---|---|---|
| WO | WO 2008/101157 | 8/2008 |
| WO | WO 2008/154401 | 12/2008 |
| WO | WO 2009/082607 | 7/2009 |
| WO | WO 2009/126933 | 10/2009 |
| WO | WO 2009/134487 | 11/2009 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/148013 | 12/2010 |
| WO | WO 2011/038356 | 3/2011 |
| WO | WO 2011/100131 | 8/2011 |
| WO | WO 2011/120053 | 9/2011 |
| WO | WO 2011/163121 | 12/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/177947 | 12/2012 |
| WO | WO 2013/022966 | 2/2013 |
| WO | WO 2013/033230 | 3/2013 |
| WO | WO 2013/075035 | 5/2013 |
| WO | WO 2013/165816 | 11/2013 |
| WO | WO 2013/166121 | 11/2013 |

OTHER PUBLICATIONS

Allart et al., "Synthesis of Protected D-Altritol Nucleosides as Building Blocks for Oligonucleotide Synthesis" Tetrahedren (1999) 55:6527-6546.
Altmann et al., "Second Generation of Antisense Oligonucleotides: From Nuclease Resistance to Biological Efficacy in Animals" Chimia (1996) 50:168-176.
Alves et al., "Allele-specific RNA silencing of mutant ataxin-3 mediates neuroprotection in a rat model of Machado-Joseph disease" PLoS One (2008) 3(10):e3341.
Anderson et al., "The Synthesis of Modified D- and L-Anhydrohexitol Nucleosides" Tetrahedron Lett. (1996) 37(45):8147-8150.
Atkins et al., "Evaluation of the cellular uptake of hexitol nucleic acids in HeLa cells" Parmazie (2000) 55(8):615-617.
Augustyns et al., Nucleic Acids Res. (1993) 21(20):4670-4676.
Beigelman et al., "Synthesis of 5'-C-Methyl-D-Allo- & L-Talo-Ribonucleoside 3'-0-Phosphoramidites & their incorporation info Hammerhead Ribozymes" Nucleosides Nucleotides (1995) 14(35-):901-905.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Biessen et al., "Novel hepatotrophic prodrugs of the antiviral nucleoside 9-(2-phosphonylmethoxyethyl)adenine with improved pharmacokinetics and antiviral activity" FASEB. J. (2000) 14(12):1784-1792.
Biessen et al., "Synthesis of Cluster Galactosides with High Affinity for the Hepatic Asialoglycoprotein Receptor" J. Med. Chem. (1995) 38:1538-1546.
Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.
Bogorad et al., "Identification of a gain-of-function mutation of the prolactin receptor in women with benign breast tumors" Proc Natl Acad Sci (2008) 105(38):14533-14538.
Boudou et al., "Base pairing of anhydrohexitol nucleosides with 2,6-diaminopurine, 5-methylcytosine and uracil asbase moiety." Nucliec Acids Res. (1999) 27(6):1450-1456.
Braasch et al., "Locked nucleic acid (LNA): fine-tuning the recognition of DNA and RNA" Chem. Biol. (2001) 8:1-7.

Brown et al., "Activity of Novel Adenine Nucleotide Derivatives as Agonists and Antagonists at Recombinant Rat P2X Receptors" Drug Dev. Res. (2000) 49:253-259.
Bruijn et al., "Aggregation and motor neuron toxicity of an ALS-linked SOD1 mutant independent from wild-type SOD1" Science (1998) 281(53M):1851-1854.
Carrell et al., "Alphal-antitrypsin deficiency—a model for conformational diseases" N. Engl. J. Med. (2002) 346(1):45-53.
Chen et al., "Allelic origin of the abnormal prion protein isoform in familial prion diseases." Nat. Med. (1997) 3(9):1009-1015.
Chiang et al., "Antisense Oligonucleotides Inhibit Intercellular Adhesion Molecule 1 Expression by Two Distinct Mechanisms" J Biol Chem (1991) 266(27)L18162-18171.
Connolly et al., "Binding and endocytosis of cluster glycosides by rabbit hepatocytes. Evidence for a short-circuit pathway that does not lead to degradation" J Biol Chem (1982) 257(2): 939-945.
Crooke et al., "Pharmacokinetic Properties of Several Novel Oligonucleotide Analogs in mice" J. Pharmacol. Exp. Ther. (1996) 277(2):923-937.
Daiger et al., "Mutations in known genes account for 58% of autosomal dominant retinitis pigmentosa (adRP)" Adv. Exp. Med. Biol. (2008) 613:203-209.
Dawson et al., "Rare genetic mutations shed light on the pathogenesis of Parkinson disease" J. Clin. Invest. (2003) 111(2):145-151.
De Gobbi et al., "A regulatory SNP causes a human genetic disease by creating a new transcriptional promoter" Science (2006) 312(5777):1215-1217.
Dellinger et al., "Solid-phase chemical synthesis of phosphonoacetate and thiophosphonoacetate oligodeoxynucleotides." J. Am. Chem. Soc. (2003) 125(4): 940-950.
Duff et al., "Intrabody tissue-specific delivery of antisense conjugates in animals: ligand-linker-antisense oligomer conjugates" Methods Enzymol (2000) 313: 297-321.
Eckstein, "Oligonucleotides Attached to Intercalators, Photoreactive & Cleavage Agents" Oligonucleotides and Analogues, a Practical Approach, Ed., Oxford University Press, New York (1991) 283-306.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Eppacher et al., "Synthesis and Incorporation of C(5')-Ethynylated Uracil-Derived Phosphoramidites into RNA" Helvetica Chimica Acta (2004) 87(12):3004-3020.
Ewart-Toland et al., "A gain of function TGFB1 polymorphism may be associated with late stage prostate cancer" Cancer Epeidemiol. Biomarkers Prev. (2004) 13(5):759-764.
Fairhurst et al., "Synthesis and Hybridisation Properties of Phosphonamidate Ester Modified Nucleic Acid" Synlett (2001) 4:467-472.
Feng et al., "Allele-specific silencing of Alzheimer's disease genes: the amyloid precursor protein genes with Swedish or London mutations" Gene (2006) 371(1):68-74.
Flores et al., "Antimalarial antisense activity of hexitol nucleic acids" Parasitol Res. (1999) 85:864-866.
Fontana et al., "P2Y12 H2 haplotype is associated with peripheral arterial disease: a case-control study" Circulation (2003) 108(24):2971-2973.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Froeyen et al., Helv. Chim Acta. (2000) 83:2153-2182.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Geze et al., "Synthesis of sinefungin and its C-6' epimer" J. Am. Chem. Soc. (1983) 105(26):7638-7640.

(56) References Cited

OTHER PUBLICATIONS

Gow et al., "The unfolded protein response in protein aggregating diseases" NeuroMol. Med. (2003) 4(1-2):73-94.
Gu et al., "Enzymatic Resolution and Base Pairing Properties of D- and L-Cylohexenyl Nucleic Acids (CeNA)" Nucleosides, Nucleotides & Nucleic Acids (2005) 24(5-7): 993-998.
Gu et al., "Synthesis of enantiomeric-pure cyclohexenyl nucleoside building blocks for oligonucleotide synthesis" Tetrahedron (2004) 60(9): 2111-2123.
Hagemann et al., "Alexander disease-associated glial fibrillary acidic protein mutations in mice induce Rosenthal fiber formation and a white matter stress response" J. Neurosci. (2006) 26(43):11162-11173.
Hampton et al. "Design of Substrate-Site-Directed Inhibitors of Adenylate Kinase and Hexokinase. Effect of Substrate Substituents on Affinity for the Adenine Nucleotide Sites" J. Med. Chem. (1976) 19:1371-1377.
Hampton et al., "Synthesis of 6' -Cyano-6'-deoxyhomoadenosine-6'-phosphonic Acid and Its Phosphoryl and P.yrophosphoryl Anhydrides and Studies of Their Interactions with Adenine Nucleotide Utilizing Enzymes" J. Am. Chem. Soc. (1973) 95(13):4404-4414.
Harlan et al., "Variants in Apaf-1 segregating with major depression promote apoptosome function" Mol. Psychiatry (2006) 11(1):76-85.
Hendrix et al., "1',5'-Anhydrohexitol Oligonucleotides: Synthesis, Base Pairing and Recognition by Regular Oligodeoxyribonucleotides and Oligoribonucleotides" Chem. Eur. J. (1997) 3(1):110-120.
Hendrix et al., "1',5'-Anhydrohexitol Oligonucleotides: Hybridisation and Strand Displacement with Oligoribonucleotides, Interaction with Rnase H and HIV Reverse Transcriptase" Chem. Eur. J. (1997) 3(9):1513-1520.
Herdewijn et al., "Targeting RNA with Conformationally Restricted Oligonucleotides" Liebigs Ann.(1996): 1337-1348.
Hizawa et al., "Functional single nucleotide polymorphisms of the CCL5 gene and nonemphysematous phenotype in COPD patients" Eur. Respir. J. (2008) 32(2):372-378.
Horvath et al., "Stereoselective synthesis of (−)-ara-cyclohexenyl-adenine" Tetrahedron Letters (2007) 48: 3621-3623.
Hossain et al., "Oligonucleotides Compoased of 2'-Deoxy-1',5'-anhydro-D-mannitol Nucleosides with a Purine Base Moiety" J. Org. Chem. (1998) 63:1574-1582.
Jayaprakash et al., "Non-nucleoside building blocks for copper-assisted and copper-free click chemistry for the efficient synthesis of RNA conjugates" Org Lett (2010) 12(23): 5410-5413.
Jung et al., "Synthesis of Phosphonate Derivatives of Uridine, Cytidine, and Cytosine Arabinoside" Bioorg. Med. Chem. (2000) 8:2501-2509.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kabashi et al., "Gain and loss of function of ALS-related mutations of TARDBP (TDP-43) cause motor deficits in vivo" Hum. Mol. Genet. (2010) 19(4):671-683.
Kang et al., "Inhibition of MDR1 gene expression by chimeric HNA antisense oligonucleotides." Nucleic Acids Research (2004) 32(14):4411-4419.
Kappler et al., "Isozyme-Specific Enzyme Inhibitors. 11. L-Homocysteine-ATP S-C5' Covalent Adducts as Inhibitors of Rat Methionine Adenosyltrassferases" J. Med. Chem. (1986) 29:1030-1038.
Kappler et al., "Species- or isozyme-selective enzyme inhibitors. 8. Synthesis of disubstituted two-substrate condensation products as inhibitors of rat adenylate kinases" J. Med. Chem. (1982) 25(10):1179-1184.
Kato et al., "N-acetylgalactosamine incorporation into a peptide containing consecutive threonine residues by UDP-N-acetyl-D-galactosaminide:polypeptide N-acetylgalactosaminyltransferases" Glycobiol (2001) 11(10): 821-829.

Khorev et al., "Trivalent, Gal/GaINAc-containing ligands designed for the asialoglycoprotein receptor" Bioorg Med Chem (2008) 16(9): 5216-5231.
Kim et al., "Oligomeric Glycopeptidomimetics Bearing the Cancer Related Tn-Antigen" Tetrahedron Lett. (1997) 38(20): 3487-3490.
Kornilova et al., "Development of a fluorescence polarization binding assay for asialoglycoportein receptor" Analyt Biochem (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kozlov et al., "Nonenzymatic template-directed reactions on altritol oligomers, preorganized analogues of oligonucleotides." Chem. Eur. J. (2000) 6(1):151-155.
Kozlov et al., "A highly enantio-selective hexitol nucleic acid template for nonenzymatic oligoguanylate synthesis." J. Am. Chem. Soc. (1999) 121:1108-1109.
Kozlov et al., "Nonenzymatic synthesis of RNA and DNA oligomers on hexitol nucleic acid templates: the importance of the a structure." J. Am. Chem. Soc. (1999) 121:2653-2656.
Kozlov et al., "Efficient transfer of information from hexitol nucleic acids to RNA during nonenzymatic oligomerization." J. Am. Chem. Soc. (1999) 121:5856-5859.
Krishna et al., "Alkynyl phosphonate DNA: a versatile "click"able backbone for DNA-based biological applications." J. Am. Chem. Soc. (2012) 134(28): 11618-11631.
Kroschwitz, "Polynucleotides" Concise Encyclopedia of Polymer Science and Engineering (1990) John Wiley & Sons, NY pp. 858-859.
Kumar et al., "The first analogues of Lna (locked nucleic acids): phosphorothioate-LNA and 2'-thio-LNA" Bioorg Med Chem Lett. (1998) 8:2219-2222.
Lai et al., "Molecular genetic studies in atrial fibrillation" Cardiology (2003) 100(3):109-113.
Landgraf, "The involvement of the vasopressin system in stress-related disorders" CNS Neurol. Disord. Drug Targets (2006) 5(2):167-179.
Lauritsen et al., "Methylphosphonate LNA: a locked nucleic acid with a methylphosphonate linkage" Bioorg. Med. Chem. Lett. (2003) 13: 253-256.
Hu et al, "Serotonin Transporter Promoter Gain-of-Function Genotypes Are Linked to Obsessive-Compulsive Disorder" Am. J. Hum. Genet. (2006) 78(5):815-826.
Lee et al., "New and more efficient multivalent glyco-ligands for asialoglycoprotein receptor of mammalian hepatocytes" Bioorganic & Medicinal Chemistry (2011) 19:2494-2500.
Lee et al., "New Synthetic Clister Ligands for Galacose/N-Acetylgalactosamine-Specific Lectin of Mamalian Liver" Biochem (1984) 23: 4255-4261.
Lee et al., "Preparation of Cluster Glycosides of N-Acetylgalactosamine That Have Subnanomolar Binding Constants Towards the Mammalian Hepatic Gal/GalNAc-specific Receptor" Glycoconjugate J (1987) 4: 317-328.
Lee et al., "Protein microarrays to study charbohydrate-recognition events" Bioorg Med Chem Lett (2006) 16(19): 5132-5135.
Lee et al., "Synthesis of Multivalent Neoglyconjugates of MUC1 by the Conjugation of Carbohydrate-Centered, Triazole-Linked Glycoclusters to MUC1 Peptides Using Click Chemistry" J Org Chem (2012) 77: 7564-7571.
Lee et al., "Synthesis of Peptide-Based Trivalent Scaffold for Preparation of Cluster Glycosides" Methods Enzymol (2003) 362: 38-43.
Lee Y.C., "Synthesis of some cluster glycosides suitable for attachment to proteins or solid matrices" Carbohydr Res (1978) 67: 509-514.
Lera et al., "A new one-Pot synthesis of alkynylphosphonates" Org. Lett. (2000) 2(24):3873-3875.
Lescrinier et al., "Solution Structure of a Hexitol Nucleic Acid Duplex with Four Consecutive T T Base Pairs" Hely. Chem. Acta. (2000) 83:1291-1310.

(56) References Cited

OTHER PUBLICATIONS

Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Li et al., "Gain-of-function polymorphism in mouse and human Ltk: implications for the pathogenesis of systemic lupus erythematosus" Hum. Mol. Genet. (2004) 13(2):171-179.
Maier et al., "Synthesis of Antisense Oligonucleotides Conjugated to a Multivalent Carbohydrate Cluster for Cellular Targeting," *Bioconjugate Chemistry*, 2003, (14): 18-29.
Vandermeeren et al., "Biological Activity of Hexitol Nucleic Acids Targeted at Ha-ras and Intercellular Adhesion Molecule-1 mRNA" (2000) 59:656-663.
Maierhofer et al., "Probing multivalent carbohydrate—lectin interactions by an enzyme-linked lectin assay employing covalently immobilized carbohydrates" Bioorg Med Chem (2007) 15: 7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "Oligonucleotide Conjugates: Alteration of the Pharmacokinetic Properties of Antisense Agents" Nucleosides & Nucleotides (1995) 14(3-5):969-973.
Manoharan, M., "Oligonucleotide Conjugates as Potential Antisense Drugs with Improved Uptake, Biodistribution, Targeted Delivery, and Mechanism of Action" Antisense Nucleic Acid Drug Dev (2002) 12: 103-128.
Mantaring et al., "Genotypic variation in ATP-binding cassette transporter-1 (ABCA1) as contributors to the high and low high-density lipoprotein-cholesterol (HDL-C) phenotype" Transl. Res. (2007) 149(4):205-210.
Margolis et al., "Expansion explosion: new clues to the pathogenesis of repeat expansion neurodegenerative diseases" Trends Mol. Med. (2001) 7(11):479-482.
Marzolini et al., "A common polymorphism in the bile acid receptor famesoid X receptor is associated with decreased hepatic target gene expression" Mol. Endocrinol. (2007) 21(8):1769-1780.
McWhinney et al., "Intronic single nucleotide polymorphisms in the RET protooncogene are associated with a subset of apparently sporadic pheochromocytoma and may modulate age of onset" J. Clin. Endocrinol. Metab. (2003) 88(10):4911-4916.
Merwin et al. "Targeting Delivery of DNA Using YEE(GalNAcAH)3, a Synthetic Glycopeptide Ligand for the Asialoglycoprotein Receptor" Bioconjug Chem (1994) 5: 612-620.
Meurillon et al., "Exploring synthetic routes to nucleoside alkynylphosphonates." Nucleic Acids Symp. Ser. (2008) 52(1):565-566.
Meurillon et al., "Developing an efficient route to the synthesis of nucleoside 1-alkynylphosphonates" Tetrahedron (2009) 65:6039-6049.
Mikhailov et al., "Substrate Properties of C'-Methylnucleoside and C'-Methyl-2'-Deoxynucleoside 5'-Triphosphates in RNA and DNA Synthesis Reactions Catalysed by RNA and DNA Polymerases" Nucleosides &Nucleotides (1991) 10(1-3):339-343.
Mishra et al., "Improved leishmanicidal effect of phosphorotioate antisense oligonucleotides by LDL-mediated delivery" Biochim. Biophys. Acta (1995) 1264:229-237.

Nauwelaerts et al., "Cyclohexenyl nucleic acids: conformationally flexible oligonucleotides" Nucleic Acids Research (2005) 33(8): 2452-2463.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
Nawrot et al., "A novel class of DNA analogs bearing 5'-C-phosphonothymidine units: synthesis and physicochemical and biochemical properties." Oligonucleotides (2006) 16(1):68-82.
Nishina et al., "Chimeric Antisense Oligonucleotide Conjugated to a α-Tocopherol." Mol Ther Nucliec Acids (2015) 4:e220.
Nishina et al., "Efficient in Vivo Delivery of siRNA to the Liver by Conjugation of α-Tocopherol " (2008) 16(4):734-740.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Ostrowski et al., "5-Substituted pyrimidines with a 1,5-anhydro-2, 3-dideoxy-D-arabino-hexitol moiety at N-1: synthesis, antiviral activity, conformational analysis, and interaction with viral thymidine kinase." J. Med. Chem. (1998) 441:4343-4353.
Palazzolo et al., "The role of the polyglutamine tract in androgen receptor" J. Steroid Biochem. Mol. Biol. (2008) 108(3-5):245-253.
Pavia et al., "Syntheitc $T_N$ glycopeptide related to human glycophorin $A^{M}$" Int J Pep Protein Res (1983) 22: 539-548.
Persichetti et al., "Differential expression of normal and mutant Huntington's disease gene alleles" Neurobiol. Dis. (1996) 3(3):183-190.
Pochet et al., "Replicative Capability of Anhydrohexitol Analogues of Nucleotides" Nucleosides & Nucleotides (1999) 18(4&5):1015-1017.
Pujol et al., "A Sulfur Tripod Glycoconjugate tha Releases a High-Affinity Copper Chelator in Hepatocytes" *Angew Chemie Int Ed Engl* (2012) 51: 7445-7448.
Rajasekaran et al., "Human alpha B-crystallin mutation causes oxido-reductive stress and protein aggregation cardiomyopathy in mice" Cell (2007) 130(3):427-439.
Rajur et al., "Covalent Protien - Oligonucleotide Conjugates for Efficient Delivery of Antisense Molecules" *Bioconjug Chem* (1997) 8: 935-940.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes In Vitro and In Vivo" J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vasc Biol (2006) 26: 169-175.
Robertson et al., "Localized mutations in the gene encoding the cytoskeletal protein filamin a cause diverse malformations in humans" Nat. Genet. (2003) 33(4):487-491.
Robeyns et al., "Oligonucleotides with cyclohexene-nucleoside building blocks: crystallization and preliminary X-ray studies of a left-handed sequence GTGTACAC." Acta Crystallogr Sect F Struct Biol Cryst Commun. (2005) F61(6): 585-586.
Robeyns et al., "Structure of the Fully Modified Left-Handed Cyclohexene Nucleic Acid Sequence GTGTACAC" J. Am. Chem. Soc. (2008) 130(6): 1979-1984.
Saha et al., "5'-Me-DNA—A New Oligonucleotide Analog: Synthesis and Biochemical Properties" J. Org. Chem. (1995) 60:788-789.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

(56) References Cited

OTHER PUBLICATIONS

Sanghvi et al., Carbohydrate Modifications in Antisense Research; Eds., ACS Symposium Series (1994) 580: Chapters 3 and 4, 40-65.
De Mesmaeker et al., "Amide-Modified Oligonucleotides with Preorganized Backbone and Furanose Rings: Highly Increased Thermodynamic Stability of the Duplexes Formed with their RNA and DNA Complements" Synlett (1997) 11:1287-1290.
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Scaringe, "RNA Oligonucleotide Synthesis via 5'-Silyl-2'Orthoester Chemistry" Methods (2001) 23: 206-217.
Scholefield et al., "Design of RNAi hairpins for mutation-specific silencing of ataxin-7 and correction of a SCA7 phenotype" PLoS One (2009) 4(9):e7232.
Sen et al., "Role of histidine interruption in mitigating the pathological effects of long polyglutamine stretches in SCA1: A molecular approach" Protein Sci. (2003) 12(5):953-962.
Shashidharan et al., "TorsinA accumulation in Lewy bodies in sporadic Parkinson's disease" Brain Res. (2000) 877(2):379-381.
Shea et al., "Synthesis, hybridization properties and antiviral activity of lipid-oligodeoxynucleotide conjugates" Nucl. Acids Res. (1990) 18(13):3777-3783.
Sheehan et al., "Biochemical properties of phosphonoacetate and thiophosphonoacetate oligodeoxyribonucleotides" Nucleic Acids Research (2003) 31(14): 4109-4118.
Shiels et al., "CHMP4B, a novel gene for autosomal dominant cataracts linked to chromosome 20q" Am. J. Hum. Genet. (2007) 81(3):596-606.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Swayze et al., "The Medicinal Chemistry of Oligonucleotides" Antisense Drug Technology: Principles, Strategies, and Applications, Chapter 6, pp. 143-182, Jul. 25, 2007, CRC Press.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Valentijn et al., "Solid-phase Synthesis of Lysine-based Cluster Galactosides with High Affinity for the Asialoglycoprotein Receptor" Tetrahedron (1997) 53(2): 759-770.
Van Aerschot et al., "1,5-Anydrohexitol Nucleic Acids, a New Promising Antisense Construct" Angew. Chem. Int. Ed. Engl. (1995) 34(12):1338-1339.
Van Rossenberg et al., "Stable polyplexes based on arginine-containing oligopeptides for in vivo gene delivery" Gene Ther (2004) 11: 457-464.
Verbeure et al., "RNase H mediated cleavage of RNA by cyclohexene nucleic acid (CeNA)" Nucleic Acids Research (2001) 29(24): 4941-4947.
Verheggen et al., "Synthesis, Biological Evaluation, and Structure Analysis of a Series of New 1,5-Anhydrohexitol Nucleosides" J.Med. Chem. (1995) 38:826-835.

Verheggen et al., "Synthesis of 1,5-Anhydrohexitol Nucleosides as Mimics of AZT, D4T and DDC" Nucleosides Nucleotides (1996) 15(1-3) 325-335.
Verheggen et al., J. Med. Chem. (1993) 36:2033-2040.
Vezzoli et al., "R990G polymorphism of calcium-sensing receptor does produce a gain-of-function and predispose to primary hypercalciuria" Kidney Int. (2007) 71(11):1155-1162.
Vrudhula et al., "Isozyme-Specific Enzyme Inhibitors. 13. S-[5'(R)-[(N-Triphosphoamino)methyl]adenosyl]-L-homocysteine, a Potent Inhibitor of Rat Methionine Adenosyltransferases" J. Med. Chem. (1987) 30:888-894.
Wahlested et al., "Potent and nontoxic antisense oligonucleotide containing locked nucleic acids" Proc. Natl. Acad. Sci. USA (2000) 97: 5633-5638.
Wang et al., "A Straightforward Stereoselective Synthesis of D- and L-5-Hydroxy-4-hydroxymethyl-2-cyclohexenylguanine" J. Org. Chem. (2001) 66: 8478-8482.
Wang et al., "Biophysical and Biochemical Properties of Oligodeoxynucleotides Containing 4'-C- and 5'-C-Substituted Thymidines" Bioorg. Med. Chem. Lett. (1999) 9:885-890.
Wang et al., "Cyclohexene Nucleic Acids (CeNA) Form Stable Duplexes With RNA and Induce RNASE H Activity"Nucleosides, Nucleotides & Nucleic Acids (2001) 20(4-7) 785-788.
Wang et al., "Stereocontrolled Synthesis of Ara-Type Cyclohexenyl Nucleosides" J. Org. Chem. (2003) 68: 4499-4505.
Wang et al., "Synthesis of Azole Nucleoside 5'-Monophosphate Mimics (P1Ms) and Their Inhibitory Properties of IMP Dehydrogenases" Nucleosides Nucleotides & Nucleic Acids (2004) 23(1&2):317-337.
Wang et al., "Antisense Anti-MDM2 Oligonucleotides as a Novel Therapeutic Approach to Human Breast Cancer: In Vitro and In Vivo Activities and Mechanisms" J. Am. Chem. (2000) 7:719-731.
Webster et al., "Mutation in the AChR ion channel gate underlies a fast channel congenital myasthenic syndrome" Neurology (2004) 62(7):1090-1096.
Weinstein et al., "Genetic diseases associated with heterotrtmeric G proteins" Trends Pharmacol. Sci. (2006) 27(5):260-266.
Wesierlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.
Whittaker et al., "Stereoselective synthesis of highly functionalised P-stereogenic nucleosides via palladium-catalysed P-C cross-coupling reactions" Tetrahedron Letters (2008) 49:6984-6987.
Wouters et al., "5-Substituted pyrimidine 1,5-anhydrohexitols: Conformational analysis and interaction with viral thymidine kinase" Bioorg. Med. Chem. Lett. (1999) 1563-1566.
Wu et al., "Functionalization of the Sugar Moiety of Oligoribonucleotides on Solid Support" Bioconjugate Chem. (1999) 10:921-924.
Wu et al., "Synthesis of 5'-C- and 2'-0-(Bromoalkyl)-Substituted Ribonucleoside Phosphoramidites for the Post-synthetic Functionalization of Oligonucleotides on Solid Support" Helvetica Chimica Acta (2000) 83:1127-1143.
Yu et al., "Structure, inhibitor, and regulatory mechanism of Lyp, a lymphoid-specific tyrosine phosphatase implicated in autoimmune diseases" Proc. Natl. Acad. Sci. U.S.A. (2007) 104(50):19767-19772.
Zamecnik et al., "Inhibition of Rous sarcoma virus replication and cell transformation by a specific oligodeoxynucleotide" PNAS (1978) 75:280-284.
Zhao, "Synthesis and preliminary biochemical studies with 5'-deoxy-5'-methylidyne phosphonate linked thymidine oligonucleotides" Tetrahedron Letters (1996) 37(35):6239-6242.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Bertram et al."Vinylphosphonate internucleotide linkages inhibit the activity of PcrA DNA helicase." Biochemistry (2002) 41:7725-7731.

(56) References Cited

OTHER PUBLICATIONS

Perez-Perez et al., "Synthesis and antiviral activity of 2-deoxy-1,5-anhydro-D-mannitol nucleosides containing a pyrimidine base moiety" Bioorg. Med. Chem. Lett. (1996) 6(13):1457-1460.
International Search Report for PCT/US15/28076 dated Aug. 20, 2015.

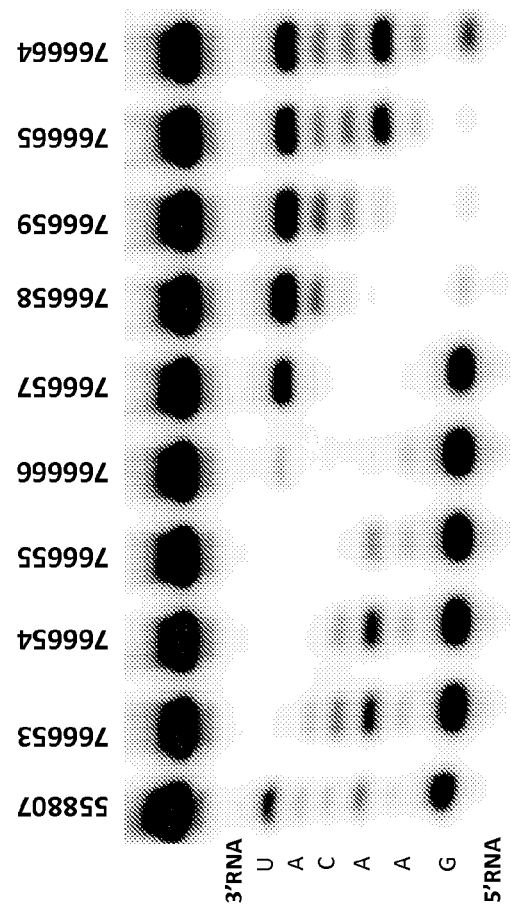

LINKAGE MODIFIED OLIGOMERIC COMPOUNDS

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CHEM0091USASEQ_ST25.txt, created Sep. 28, 2016, which is 284 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

The synthesis and biochemical properties of oligonucleotides containing phosphorus-modified phosphonoacetate and thio-phosphonoacetate deoxyribonucleotides have been described in scientific journals and patent literature (see Dellinger et al., *J. Am. Chem. Soc.* 2003, 125(4), 940-950; Sheehan et al., *Nucl. Acids Res.* 2003, 31(14), 4109-4118; also see published U.S. patent applications (U.S. 2004/0116687 and U.S. 2002/0058802) and U.S. Pat. No. 6,693,187.

DNA or RNA containing oligonucleotides comprising alkylphosphonate internucleoside linkage backbone have been disclosed (see U.S. Pat. Nos. 5,264,423 and 5,286,717).

The synthesis of oligodeoxyribonucleotides containing a methyl phosphonate locked nucleic acid (LNA) thymine monomer has been described. The Tm values of the duplexes with their DNA or RNA complements have also been reported (see Lauritsen et al., *Bioorg. Med. Chem. Lett.* 2003, 13(2), 253-256).

Oligomeric compounds have been prepared using Click chemistry wherein alkynyl phosphonate internucleoside linkages on an oligomeric compound attached to a solid support are converted into the 1,2,3-triazolylphosphonate internucleoside linkages and then cleaved from the solid support (Krishna et al., *J. Am. Chem. Soc.* 2012, 134(28), 11618-11631).

Targeting disease-causing gene sequences was first suggested more than thirty years ago (Belikova et al., *Tet. Lett.* 1967, 8(37), 3557-3562), and antisense activity was demonstrated in cell culture more than a decade later (Zamecnik et al., *Proc. Natl. Acad. Sci. U.S.A.* 1978, 75(1), 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The synthesis of 5'-substituted DNA and RNA derivatives and their incorporation into oligomeric compounds has been reported in the literature (Saha et al., *J. Org. Chem.* 1995, 60, 788-789; Wang et al., *Bioorg. Med. Chem. Lett.* 1999, 9(6), 885-890; and Mikhailov et al., *Nucleosides Nucleotides* 1991, 10(1-3), 339-343; Beigelman et al., *Nucleosides Nucleotides* 1995, 14(3-5), 901-905; and Eppacher et al., *Helv. Chim. Acta.* 2004, 87, 3004-3020). The 5'-substituted monomers have also been made as the monophosphate with modified bases (Wang et al., *Nucleosides Nucleotides Nucleic Acids* 2004, 23 (1 & 2), 317-337).

A genus of modified nucleosides including optional modification at a plurality of positions including the 5'-position and the 2'-position of the sugar ring and oligomeric compounds incorporating these modified nucleosides therein has been reported (see International Application Number: PCT/U.S.94/02993, Published on Oct. 13, 1994 as WO 94/22890).

The synthesis of 5'-$CH_2$—R substituted 2'-O-protected nucleosides and their incorporation into oligomers has been previously reported (see Wu et al., *Helv. Chim. Acta.* 2000, 83, 1127-1143 and Wu et al., *Bioconjug. Chem.* 1999, 10, 921-924).

Amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (De Mesmaeker et al., *Synlett* 1997, 11, 1287-1290).

A genus of 2'-substituted 5'-$CH_2$—R (or O) modified nucleosides and a discussion of incorporating them into oligonucleotides has been previously reported (see International Application Number: PCT/U.S.92/01020, published on Feb. 7, 1992 as WO 92/13869).

The synthesis of modified 5'-methylene phosphonate monomers having 2'-substitution and their use to make modified antiviral dimers has been previously reported (see U.S. patent application Ser. No. 10/418,662, published on Apr. 6, 2006 as U.S. 2006/0074035).

Various analogs of 5'-alkynylphosphonate ribonucleosides have been prepared and reported in the literature (see Meurillon et al., *Tetrahedron* 2009, 65, 6039-6046; Meurillon et al., *Nucleic Acids Symp. Ser.* 2008, 52(1), 565-566; Lera et al., *Org. Lett.* 2000, 2(24), 3873-3875).

The preparation of 5'-vinylphosphonate DNA and RNA monomers and their use to make dimeric compounds for oligonucleotide synthesis have been described. Their biochemical studies have also been discussed (see Whittaker et al., *Tet. Lett.* 2008, 49, 6984-6987; Abbas et al., *Org. Lett.* 2001, 3(21), 3365-3367; Bertram et al., *Biochemistry* 2002, 41, 7725-7731; Zhao et al., *Tet. Lett.* 1996, 37(35), 6239-6242 and Jung et al., *Bioorg. Med. Chem.* 2000, 8, 2501-2509).

Various BNA's have been prepared and reported in the patent literature as well as in scientific literature, see for example: Singh et al., *Chem. Commun.* 1998, 4, 455-456; Koshkin et al., *Tetrahedron* 1998, 54, 3607-3630; Wahlestedt et al., *Proc. Natl. Acad. Sci. U.S.A.* 2000, 97, 5633-5638; Kumar et al., *Bioorg. Med. Chem. Lett.* 1998, 8, 2219-2222; Wengel et al., PCT International Application WO 98-DK393 19980914; Singh et al., *J. Org. Chem.* 1998, 63, 10035-10039, the text of each is incorporated by reference herein, in their entirety. Examples of issued U.S. patents and published applications include for example: U.S. Pat. Nos. 7,053,207, 6,770,748, 6,268,490 and 6,794,499 and published U.S. applications 2004/0219565, 2004/0014959, 2003/0207841, 2004/0192918, 2003/0224377, 2004/0143114 and 2003/0082807; the text of each is incorporated by reference herein, in their entirety.

The synthesis of various cyclohexitol nucleoside analogs (tetrahydropyran nucleoside analogs) has been reported in the literature, see for example: Verheggen et al., *J. Med. Chem.* 1995, 38, 826-835; Altmann et al., *Chimia* 1996, 50, 168-176; Herdewijn et al., *Bioorg. Med. Chem. Lett.* 1996, 6(13), 1457-1460; Verheggen et al., *Nucleosides Nucleotides* 1996, 15(1-3), 325-335; Ostrowski et al., *J. Med. Chem.* 1998, 41, 4343-4353; Allart et al., *Tetrahedron.* 1999, 55, 6527-6546; Wouters et al., *Bioorg. Med. Chem. Lett.* 1999, 9, 1563-1566; Brown et al., *Drug Dev. Res.* 2000, 49, 253-259; published PCT application: WO 93/25565; WO 02/18406; and WO 05/049582; U.S. Pat. Nos. 5,314,893; 5,607,922; and 6,455,507. Various cyclohexitol nucleoside analogs (tetrahydropyran nucleoside analogs) have been described as monomers and have also been incorporated into oligomeric compounds (see for example: Published PCT application, WO 93/25565, published Dec. 23, 1993; Augustyns et al., *Nucleic Acids Res.* 1993, 21(20), 4670-4676; Verheggen et al., *J. Med. Chem.,* 1993, 36, 2033-2040; Van Aerschol et al., *Angew. Chem. Int. Ed. Engl.,* 1995, 34(12), 1338-1339; Anderson et al., *Tetrahedron Lett.* 1996, 37(45), 8147-8150; Herdewijn et al., *Liebigs Ann.* 1996, 1337-1348; De Bouvere et al., *Liebigs Ann./Recueil* 1997, 1453-1461; 1513-1520; Hendrix et al., *Chem. Eur. J.* 1997, 3(1), 110-120; Hendrix et al., *Chem. Eur. J.* 1997, 3(9), 1513-1520; Hossain et al, *J. Org. Chem.* 1998, 63, 1574-1582; Allart et al., *Chem. Eur. J.* 1999, 5(8), 2424-2431; Boudou et al., *Nucleic Acids Res.* 1999, 27(6), 1450-1456; Kozlov et al., *J. Am. Chem. Soc.* 1999, 121, 1108-1109; Kozlov et al., *J. Am. Chem. Soc.,* 1999, 121, 2653-2656; Kozlov et al., *J. Am. Chem. Soc.,* 1999, 121, 5856-5859; Pochet et al., *Nucleosides & Nucleotides,* 1999, 18 (4&5), 1015-1017; Vastmans et al., *Collection Symposium Series,* 1999, 2, 156-160; Froeyen et al., *Helv. Chim. Acta.* 2000, 83, 2153-2182; Kozlov et al., *Chem. Eur. J.,* 2000, 6(1), 151-155; Atkins et al., *Parmazie,* 2000, 55(8), 615-617; Lescrinier et al., *Chemistry & Biology,* 2000, 7, 719-731; Lescrinier et al., *Helv. Chim. Acta.* 2000, 83, 1291-1310; Wang et al., *J. Am. Chem.* 2000, 122, 8595-8602; U.S. Patent Application U.S. 2004/0033967; Published U.S. Patent Application U.S. 2008/0038745; Published and Issued U.S. Pat. No. 7,276,592). DNA analogs have also been reviewed in an article (see: Leumann, *Bioorg. Med. Chem.* 2002, 10, 841-854) which included a general discussion of cyclohexitol nucleoside analogs (under the name: hexitol nucleic acid family).

Oligomeric compounds having phosphodiester linked hexitol nucleic acids (HNA, or 1,5-anhydrohexitol nucleic acids, 3'-H tetrahydropyran nucleoside analogs) have also been prepared for evaluation in cell assays. The different motifs that have been evaluated are fully modified wherein each monomer is a phosphodiester linked hexitol nucleic acid analog and gapped wherein each monomer in the 3' and 5' external regions of the oligomeric compound are each phosphodiester linked hexitol nucleic acid analogs and each monomer in the internal region is a phosphorothioate linked deoxyribonucleoside (see: Kang et al., *Nucleic Acids Research,* 2004, 32(14), 4411-4419; Vandermeeren et al., 2000, 55, 655-663; Flores et al., *Parasitol Res.,* 1999, 85, 864-866; and Hendrix et al., *Chem. Eur. J,* 1997, 3(9), 1513-1520).

Oligomeric compounds having phosphodiester linked analogs having the 3'-OH group which are referred to in the art as ANA or D-altritol nucleic acids (3'-OH tetrahydropyran nucleoside analogs) have been prepared and evaluated both structurally and in vitro (Allart et al., *Chem. Eur. J.* 1999, 5(8), 2424-2431).

Chemically modified siRNA's having incorporated hexitol nucleotides (also referred to in the art as HNA, hexitol nucleic acids and tetrahydropyran nucleoside analogs) have been prepared and tested for silencing capacity (see: Published PCT application, WO 06/047842, published May 11, 2006.

Cyclohexenyl nucleic acids (ceNA) and analogs thereof have been reported in the scientific and patent literature as monomers as well as in oligomeric compounds, see for example: Robeyns et al., *J. Am. Chem. Soc.* 2008, 130(6), 1979-1984; Horváth et al., *Tetrahedron Lett.* 2007, 48, 3621-3623; Nauwelaerts et al., *J. Am. Chem. Soc.* 2007, 129(30), 9340-9348; Gu et al., *Nucleosides Nucleotides Nucleic Acids* 2005, 24(5-7), 993-998; Nauwelaerts et al., *Nucleic Acids Res.* 2005, 33(8), 2452-2463; Robeyns et al., *Acta Crystallogr. F Struct. Biol. Commun.* 2005, F61(6), 585-586; Gu et al., *Tetrahedron* 2004, 60(9), 2111-2123; Gu et al., *Oligonucleotides* 2003, 13(6), 479-489; Wang et al., *J. Org. Chem.* 2003, 68, 4499-4505; Verbeure et al., *Nucleic Acids Res.* 2001, 29(24), 4941-4947; Wang et al., *J. Org. Chem.* 2001, 66, 8478-82; Wang et al., *Nucleosides Nucleotides Nucleic Acids* 2001, 20(4-7), 785-788; Wang et al., *J. Am. Chem.* 2000, 122, 8595-8602; Published PCT application, WO 06/047842; and Published PCT Application WO 01/049687; the text of each is incorporated by reference herein, in their entirety.

The synthesis of 5'-phosphonate deoxyribonucleoside monomers and dimers having a 5'-phosphate group and their incorporation into oligomeric compounds have been described. Their physico-chemical properties including thermal stability as well as substrate activity toward certain nucleases have also been discussed (see Nawrot et al., *Oligonucleotides* 2006, 16(1), 68-82).

Nucleosides having a 6'-phosphonate group have been reported wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (see Fairhurst et al., *Synlett* 2001, 4, 467-472; Kappler et al., *J. Med. Chem.* 1986, 29, 1030-1038; Kappler et al., *J. Med. Chem.* 1982, 25, 1179-1184; Vrudhula et al., *J. Med. Chem.* 1987, 30, 888-894; Hampton et al., *J. Med. Chem.* 1976, 19, 1371-1377; Geze et al., *J. Am. Chem. Soc.* 1983, 105(26), 7638-7640 and Hampton et al., *J. Am. Chem. Soc.* 1973, 95(13), 4404-4414).

The synthesis and biochemical properties of oligonucleotides containing phosphorus-modified phosphonoacetate and thio-phosphonoacetate deoxyribonucleotides have been described in scientific journals and patent literature (see Dellinger et al., *Am. Chem. Soc.* 2003, 125, 940-950; Sheehan et al., *Nucleic Acids Res.* 2003, 31(14), 4109-4118); also see published U.S. patent applications (U.S. 2004/0116687 and U.S. 2002/0058802) and U.S. Pat. No. 6,693,187.

DNA or RNA containing oligonucleotides comprising alkylphosphonate internucleoside linkage backbone have been disclosed (see U.S. Pat. Nos. 5,264,423 and 5,286,717).

The synthesis of oligodeoxyribonucleotides containing a methyl phosphonate locked nucleic acid (LNA) thymine monomer has been described. The Tm values of the duplexes with their DNA or RNA complements have also been reported (see Lauritsen et al., *Bioorg. Med. Chem. Lett.* 2003, 13(2), 253-256).

Oligomeric compounds have been prepared using Click chemistry wherein alkynyl phosphonate internucleoside linkages on an oligomeric compound attached to a solid support are converted into the 1,2,3-triazolylphosphonate internucleoside linkages and then cleaved from the solid support (Krishna et al., *J. Am. Chem. Soc.* 2012, 134(28), 11618-11631).

SUMMARY OF THE INVENTION

Provided herein are oligomeric compounds comprising at least one modified internucleoside linkage having Formula I.

In certain embodiments, the oligomeric compounds provided herein comprise gapped oligomeric compounds comprising at least one modified internucleoside linkage having Formula I. In certain embodiments, the oligomeric compounds provided herein hybridize to a portion of a target RNA resulting in loss of normal function of the target RNA. In certain embodiments, the oligomeric compounds disclosed herein provide improved selectivity for a target RNA. In certain embodiments, the oligomeric compounds disclosed herein provide improved selectivity for a target RNA relative to an off target RNA. In certain embodiments, the oligomeric compounds provide improved potency for a target RNA. In certain embodiments, the oligomeric compounds provided herein provide enhanced stability to base exposure. In certain embodiments, the oligomeric compounds provided herein provide enhanced stability to base exposure during synthesis of the oligomeric compound. In certain embodiments, the oligomeric compounds provided herein provide an enhanced off target profile.

The variables are defined individually in further detail herein. It is to be understood that the oligomeric compounds provided herein include all combinations of the embodiments disclosed and variables defined herein.

Provided herein are oligomeric compounds comprising a contiguous sequence of monomer subunits linked by internucleoside linking groups wherein at least one of the internucleoside linking groups has Formula I:

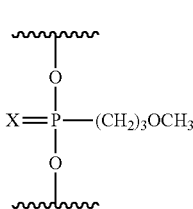

wherein each X is independently O or S;

and each ∿∿ represents an attachment to a monomer subunit within said oligomeric compound.

In certain embodiments, each internucleoside linking group of Formula I forms a 3'-5' linkage between two monomer subunits comprising furanosyl sugar moieties within the oligomeric compound. In certain embodiments, one or more internucleoside linking groups of Formula I forms a 2'-3' and or a 2'-5' linkage between two monomer subunits comprising furanosyl sugar moieties within the oligomeric compound.

In certain embodiments, one or more internucleoside linking groups of Formula I forms a linkage between a 3' or a 5'-position on a monomer subunit comprising a furanosyl sugar moiety and a ring atom on a sugar surrogate group as disclosed herein. In certain embodiments, one or more internucleoside linking groups of Formula I form a linkage between two monomer subunits comprising sugar surrogate groups as disclosed herein.

In certain embodiments, oligomeric compounds are provided comprising a contiguous sequence of monomer subunits linked by internucleoside linking groups wherein at least one of the internucleoside linking groups has Formula I, wherein the oligomeric compound comprises a gapped oligomeric compound having a gap region of from 6 to 14 contiguous monomer subunits selected from β-D-2'-deoxyribonucleosides and modified nucleosides that are DNA-like that each adopt a 2'-endo conformational geometry located between a 5'-region and a 3'-region wherein the 5' and 3'-regions each, independently, have from 2 to 8 contiguous monomer subunits selected from RNA-like modified nucleosides that each adopt a 3'-endo conformational geometry.

In certain embodiments, oligomeric compounds are provided comprising from 12 to 24 monomer subunits. In certain embodiments, oligomeric compounds are provided comprising from 14 to 20 monomer subunits.

In certain embodiments, gapped oligomeric compounds are provided wherein the gap region has 10 contiguous monomer subunits and the 5' and 3'-regions each, independently, have 2, 3 or 5 contiguous monomer subunits. In certain embodiments, the gap region has 10 contiguous monomer subunits and the 5' and 3'-regions each have 5 contiguous monomer subunits. In certain embodiments, the gap region has 10 contiguous monomer subunits and the 5' and 3'-regions each have 3 contiguous monomer subunits. In certain embodiments, the gap region has 10 contiguous monomer subunits and the 5' and 3'-regions each have 2 contiguous monomer subunits. In certain embodiments, gapped oligomeric compounds are provided wherein the gap region has 8 contiguous monomer subunits and the 5' and 3'-regions each, independently, have 4 contiguous monomer subunits.

In certain embodiments, oligomeric compounds are provided comprising from 1 to 10 internucleoside linking groups of Formula I. In certain embodiments, oligomeric compounds are provided comprising from 1 to 5 internucleoside linking groups of Formula I. In certain embodiments, oligomeric compounds are provided comprising from 1 to 3 internucleoside linking groups of Formula I. In certain embodiments, oligomeric compounds are provided comprising 1 internucleoside linking group of Formula I. In certain embodiments, oligomeric compounds are provided comprising 4 internucleoside linking groups of Formula I. In certain embodiments, oligomeric compounds are provided comprising 3 internucleoside linking groups of Formula I. In certain embodiments, oligomeric compounds are provided comprising 2 internucleoside linking groups of Formula I.

In certain embodiments, oligomeric compounds are provided wherein internucleoside linking groups of Formula I are contiguous. Contiguous internucleoside linkages means that each successive linkage is an internucleoside linking groups of Formula I such as 2, 3, 4, 5 in a row or wherein each internucleoside linkage in an oligomeric compound is an internucleoside linking group of Formula I.

In certain embodiments, gapped oligomeric compounds are provided wherein each internucleoside linking group of Formula I is, independently, located in the gap region or between the gap region and the 5' or 3'-region. In certain embodiments, gapped oligomeric compounds are provided wherein each internucleoside linking group of Formula I is, independently, located in the gap region or between the gap region and the 5'-region or the 3'-region. In certain embodiments, gapped oligomeric compounds are provided wherein each internucleoside linking group of Formula I is, independently, located in the 5'-region, the 3'-region or between the gap region and the 5'-region or the 3'-region.

In certain embodiments, oligomeric compounds are provided wherein each internucleoside linking group of Formula I is, independently, located in the 5'-region. In certain embodiments, each internucleoside linking group of Formula I is, independently, located in the 3'-region. In certain embodiments, each internucleoside linking group of Formula I is, independently, located in the 5'-region or the gap region. In certain embodiments, each internucleoside linking group of Formula I is, independently, located in the 3'-region or the gap region. In certain embodiments, at least one internucleoside linking group of Formula I is located between the gap region and the 5'-region. In certain embodiments, at least one internucleoside linking group of Formula I is located in the gap region between monomer subunits 1 and 2 counting from the first monomer subunit at the 5' end of the gap region.

In certain embodiments, oligomeric compounds are provided having two internucleoside linking groups of Formula I wherein one internucleoside linking group of Formula I is located between the gap region and the 5'-region and the other internucleoside linking group of Formula I is located in the gap region between monomer subunits 1 and 2 counting from the first monomer subunit at the 5' end of the gap region.

In certain embodiments, oligomeric compounds are provided wherein at least one internucleoside linking group of Formula I is located in the gap region between monomer subunits 2 and 3 counting from the first monomer subunit at the 5' end of the gap region. In certain embodiments, oligomeric compounds are provided having two internucleoside linking groups of Formula I wherein one internucleoside linking group of Formula I is located in the gap region between monomer subunits 1 and 2 counting from the first monomer subunit at the 5' end of the gap region and the other internucleoside linking group of Formula I is located in the gap region between monomer subunits 2 and 3 counting from the first monomer subunit at the 5' end of the gap region.

In certain embodiments, oligomeric compounds are provided wherein at least one internucleoside linking group of Formula I is located in the gap region between monomer subunits 3 and 4 counting from the first monomer subunit at the 5' end of the gap region. In certain embodiments, oligomeric compounds are provided having two internucleoside linking groups of Formula I wherein one internucleoside linking group of Formula I is located in the gap region between monomer subunits 2 and 3 counting from the first monomer subunit at the 5' end of the gap region and the other internucleoside linking group of Formula I is located in the gap region between monomer subunits 3 and 4 counting from the first monomer subunit at the 5' end of the gap region.

In certain embodiments, oligomeric compounds are provided wherein at least one internucleoside linking group of Formula I is located in the gap region between monomer subunits 4 and 5 counting from the first monomer subunit at the 5' end of the gap region. In certain embodiments, oligomeric compounds are provided having two internucleoside linking groups of Formula I wherein one internucleoside linking group of Formula I is located in the gap region between monomer subunits 3 and 4 counting from the first monomer subunit at the 5' end of the gap region and the other internucleoside linking group of Formula I is located in the gap region between monomer subunits 4 and 5 counting from the first monomer subunit at the 5' end of the gap region.

In certain embodiments, oligomeric compounds are provided wherein at least one internucleoside linking group of Formula I is located between the gap region and the 3'-region. In certain embodiments, at least one internucleoside linking group of Formula I is located in the gap region between monomer subunits 1 and 2 counting from the first monomer subunit at the 3' end of the gap region. In certain embodiments, oligomeric compounds are provided having two internucleoside linking groups of Formula I wherein one internucleoside linking group of Formula I is located between the gap region and the 3'-region and the other internucleoside linking group of Formula I is located in the gap region between monomer subunits 1 and 2 counting from the first monomer subunit at the 3' end of the gap region.

In certain embodiments, oligomeric compounds are provided wherein at least one internucleoside linking group of Formula I is located in the gap region between monomer subunits 2 and 3 counting from the first monomer subunit at the 3' end of the gap region. In certain embodiments, oligomeric compounds are provided having two internucleoside linking groups of Formula I wherein one internucleoside linking group of Formula I is located in the gap region between monomer subunits 1 and 2 counting from the first monomer subunit at the 3' end of the gap region and the other internucleoside linking group of Formula I is located in the gap region between monomer subunits 2 and 3 counting from the first monomer subunit at the 3' end of the gap region.

In certain embodiments, oligomeric compounds are provided wherein at least one internucleoside linking group of Formula I is located in the gap region between monomer subunits 3 and 4 counting from the first monomer subunit at the 3' end of the gap region. In certain embodiments, oligomeric compounds are provided having two internucleoside linking groups of Formula I wherein one internucleoside linking group of Formula I is located in the gap region between monomer subunits 2 and 3 counting from the first monomer subunit at the 3' end of the gap region and the other internucleoside linking group of Formula I is located in the gap region between monomer subunits 3 and 4 counting from the first monomer subunit at the 3' end of the gap region.

In certain embodiments, oligomeric compounds are provided wherein at least one internucleoside linking group of Formula I is located in the gap region between monomer subunits 4 and 5 counting from the first monomer subunit at the 3' end of the gap region. In certain embodiments, oligomeric compounds are provided having two internucleoside linking groups of Formula I wherein one internucleoside linking group of Formula I is located in the gap region between monomer subunits 3 and 4 counting from the first monomer subunit at the 3' end of the gap region and the other internucleoside linking group of Formula I is located in the gap region between monomer subunits 4 and 5 counting from the first monomer subunit at the 3' end of the gap region.

In certain embodiments, oligomeric compounds are provided wherein each internucleoside linking group is, independently, a phosphodiester, a phosphorothioate or an internucleoside linking group of Formula I. In certain embodiments, oligomeric compounds are provided wherein each internucleoside linking group is, independently, a phosphorothioate or an internucleoside linking group of Formula I.

In certain embodiments, oligomeric compounds are provided wherein each monomer subunit comprises an optionally protected heterocyclic base moiety independently selected from thymine, cytosine, 5-methylcytosine, adenine and guanine.

In certain embodiments, oligomeric compounds are provided wherein each X is O. In certain embodiments, oligomeric compounds are provided wherein each X is S.

In certain embodiments, the chirality of each internucleoside linking group having Formula I is $R_P$. In certain embodiments, the chirality of each internucleoside linking group having Formula I is $S_P$.

In certain embodiments, gapped oligomeric compounds are provided wherein each modified nucleoside in the 5' and 3'-regions comprises a modified sugar moiety independently selected from a bicyclic nucleoside comprising a bicyclic furanosyl sugar moiety, a modified nucleoside comprising a furanosyl sugar moiety having at least one substituent group and a modified nucleoside comprising a sugar surrogate group. In certain embodiments, each modified nucleoside in the 5' and 3'-regions is, independently, selected from a bicyclic nucleoside comprising a bicyclic furanosyl sugar moiety having a bridging group between the 4' and 2' carbon atoms of the furanosyl ring independently selected from 4'-(CH$_2$)—O-2', 4'-(CH$_2$)$_2$—O-2', 4'-CH(CH$_3$)—O-2', 4'-CH$_2$—NCH$_3$—O-2', 4'-CH$_2$—C—(H)(CH$_3$)-2' and 4'-CH$_2$—C(=CH$_2$)-2' and a modified nucleoside comprising a ribofuranosyl sugar moiety having at least a 2'-substituent group independently selected from F, OCH$_3$, O(CH$_2$)$_2$—OCH$_3$ and OCH$_2$C(=O)—N(H)CH$_3$. In certain embodiments, each modified nucleoside in the 5' and 3'-regions is, independently, selected from a bicyclic nucleoside comprising a bicyclic furanosyl sugar moiety having a 4'-CH[(S)—(CH$_3$)]—O-2' bridging group and a modified nucleoside comprising a ribofuranosyl sugar moiety having a 2'-O(CH$_2$)$_2$—OCH$_3$ substituent group. In certain embodiments, each modified nucleoside in the 5' and 3'-regions is, independently, selected from a bicyclic nucleoside comprising a bicyclic furanosyl sugar moiety having a 4'-CH$_2$—O-2' or 4'-CH[(S)—(CH$_3$)]—O-2' bridging group and a modified nucleoside comprising a ribofuranosyl sugar moiety having a 2'-O(CH$_2$)$_2$—OCH$_3$ substituent group.

In certain embodiments, gapped oligomeric compounds are provided wherein the modified nucleosides in the 5' and 3'-regions comprise at least 2 different types of sugar moieties. In certain embodiments, one or more of the modified nucleosides in the 5' and 3'-regions comprises a sugar surrogate.

In certain embodiments, gapped oligomeric compounds are provided wherein essentially each monomer subunit in the gap region is a β-D-2'-deoxyribonucleoside. In certain embodiments, at least one monomer subunit in the gap region is a modified nucleoside.

In certain embodiments, gapped oligomeric compounds are provided comprising at least one 5' or 3'-terminal group. In certain embodiments, gapped oligomeric compounds are provided comprising one 5' or 3'-conjugate group. In certain embodiments, the conjugate group comprises a cell targeting moiety. In certain embodiments, the cell targeting moiety has the formula:

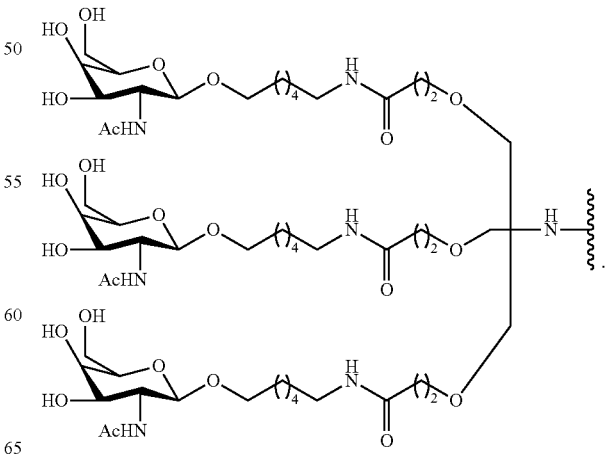

In certain embodiments, the cell targeting moiety has the formula:

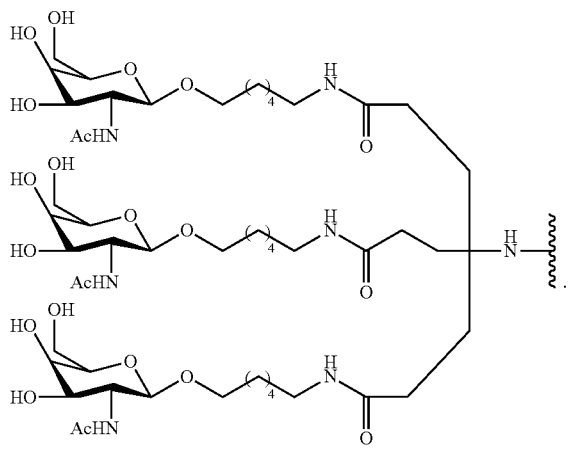

In certain embodiments, the attachment of the cell targeting moiety to the oligomeric compound includes a conjugate linker having the formula: —C(=O)—(CH$_2$)$_3$—C(=O)N(H)—(CH$_2$)$_6$—O—.

In certain embodiments, the attachment of the cell targeting moiety to the oligomeric compound includes a conjugate linker and a cleavable moiety. In certain embodiments, the cleavable moiety has the formula:

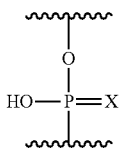

wherein X is O or S.

In certain embodiments, X is O. In certain embodiments, X is S.

In certain embodiments, attachment of the cell targeting moiety to the oligomeric compound includes a conjugate linker and a cleavable moiety.

In certain embodiments, the gap region has from 8 to 12 contiguous monomer subunits and the 5'- and 3'-regions each, independently, have from 2 to 5 contiguous monomer subunits. In certain embodiments, the gap region has from 9 to 10 contiguous monomer subunits. In certain embodiments, the gap region has 10 contiguous monomer subunits.

In certain embodiments, the 5'- and 3'-regions each have 5 contiguous monomer subunits. In certain embodiments, the 5'- and 3'-regions each have 2 to 3 contiguous monomer subunits. In certain embodiments, the 5'- and 3'-regions each have 3 contiguous monomer subunits.

In certain embodiments, oligomeric compounds are provided comprising from 2 to 3 internucleoside linking groups of Formula I. In certain embodiments, the internucleoside linking groups having Formula I are contiguous.

In certain embodiments, each internucleoside linking group of Formula I is, independently, located in the gap region or between the gap region and the 5'-region or the 3'-region. In certain embodiments, each internucleoside linking group of Formula I is, independently, located in the 5'-region, the 3'-region or between the gap region and the 5'-region or the 3'-region.

In certain embodiments, oligomeric compounds are provided comprising only 1 internucleoside linking group of Formula I. In certain embodiments, oligomeric compounds are provided comprising a gapped oligomeric compound comprising only 1 internucleoside linking group of Formula I. In certain embodiments, the internucleoside linking group of Formula I is located in between two monomer subunits in the gap region.

In certain embodiments, oligomeric compounds are provided wherein each internucleoside linking group is, independently, a phosphodiester, a phosphorothioate or an internucleoside linking group of Formula I. In certain embodiments, each internucleoside linking group is a phosphorothioate or an internucleoside linking group of Formula I.

In certain embodiments, oligomeric compounds are provided wherein each monomer subunit comprises an optionally protected heterocyclic base moiety independently selected from a purine, substituted purine, pyrimidine or substituted pyrimidine. In certain embodiments, each heterocyclic base moiety is independently selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, oligomeric compounds are provided comprising a contiguous sequence of monomer subunits linked by internucleoside linking groups wherein at least one of the internucleoside linking groups has Formula I, wherein each X is O. In certain embodiments, each X is S.

In certain embodiments, the chirality of each internucleoside linking group having Formula I is R$_P$. In certain embodiments, the chirality of each internucleoside linking group having Formula I is S$_P$.

In certain embodiments, gapped oligomeric compounds are provided wherein each modified nucleoside in the 5'-region and the 3'-region provides enhanced hybridization affinity for an RNA target as compared to an unmodified nucleoside. In certain embodiments, each modified nucleoside in the 5' and 3'-regions comprises a modified sugar moiety. In certain embodiments, each modified nucleoside in the 5' and 3'-regions is, independently, a bicyclic nucleoside comprising a bicyclic furanosyl sugar moiety, a modified nucleoside comprising a furanosyl sugar moiety having at least one substituent group or a modified nucleoside comprising a sugar surrogate group. In certain embodiments, each modified nucleoside in the 5' and 3'-regions is, independently, a bicyclic nucleoside comprising a bicyclic furanosyl sugar moiety or a modified nucleoside comprising a ribofuranosyl sugar moiety having at least a 2'-substituent group.

In certain embodiments, one or more of the modified nucleosides in the 5' and 3'-regions comprises a modified sugar moiety having 2'-substituent group independently selected from halogen, OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$, O(CH$_2$)$_2$—SCH$_3$, O(CH$_2$)$_2$—OCF$_3$, O(CH$_2$)$_3$—N(R$_3$)(R$_4$), O(CH$_2$)$_2$—ON(R$_3$)(R$_4$), O(CH$_2$)$_2$—O(CH$_2$)$_2$—N(R$_3$)(R$_4$), OCH$_2$C(=O)—N(R$_4$)(R$_4$), OCH$_2$C(=O)—N(R$_5$)—(CH$_2$)$_2$—N(R$_3$)(R$_4$) and O(CH$_2$)$_2$—N(R$_5$)—C(=NR$_6$)[N(R$_3$)(R$_4$)] wherein R$_3$, R$_4$, R$_5$ and R$_6$ are each, independently, H and C$_1$-C$_6$ alkyl. In certain embodiments, each 2'-substituent group is independently selected from F, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$ and OCH$_2$—N(H)—C (=NH)NH$_2$. In certain embodiments, each 2'-substituent group is independently selected from F, OCH$_3$, O(CH$_2$)$_2$—OCH$_3$ and OCH$_2$C(=O)—N(H)CH$_3$. In certain embodiments, each 2'-substituent group is O(CH$_2$)$_2$—OCH$_3$.

In certain embodiments, one or more of the modified nucleosides in the 5' and 3'-regions is a bicyclic nucleoside comprising a bicyclic furanosyl sugar moiety having a bridging group between the 4' and 2' carbon atoms of the furanosyl ring independently selected from 4'-(CH$_2$)—O-2', 4'-(CH$_2$)—S-2', 4'-(CH$_2$)$_2$—O-2', 4'-CH(CH$_3$)—O-2', 4'-CH(CH$_2$OCH$_3$)—O-2', 4'-C(CH$_3$)$_2$—O-2', 4'-CH$_2$—N(OCH$_3$)-2', 4'-CH$_2$—O—N(CH$_3$)-2', 4'-CH$_2$—NCH$_3$—O-2', 4'-CH$_2$—C(H)(CH$_3$)-2' and 4'-CH$_2$—C(=CH$_2$)-2'. In certain embodiments, each of the bridging groups is selected from 4'-(CH$_2$)—O-2', 4'-(CH$_2$)$_2$—O-2', 4'-CH(CH$_3$)—O-2', 4'-CH$_2$—NCH$_3$—O-2', 4'-CH$_2$—C(H)(CH$_3$)-2' and 4'-CH$_2$—C(=CH$_2$)-2'. In certain embodiments, each bridging group is 4'-CH[(S)—(CH$_3$)]—O-2'.

In certain embodiments, gapped oligomeric compounds are provided wherein each modified nucleoside in the 5' and 3'-regions have identical sugar moieties. In certain embodiments, the modified nucleosides in the 5' and 3'-regions have at least two different types of sugar moieties. In certain embodiments, the different types of sugar moieties are selected from bicyclic furanosyl sugar moieties and furanosyl sugar moieties having at least one substituent group. In certain embodiments, the different types of sugar moieties are selected from bicyclic ribofuranosyl sugar moieties having a 4'-CH[(S)—(CH$_3$)]—O-2' bridging group and 2'-O(CH$_2$)$_2$—OCH$_3$ substituted ribonucleosides.

In certain embodiments, gapped oligomeric compounds are provided wherein at least one modified nucleosides in the 5' and 3'-regions comprises a sugar surrogate.

In certain embodiments, gapped oligomeric compounds are provided wherein each monomer subunit in the gap region is a β-D-2'-deoxyribonucleoside. In certain embodiments, at least one monomer subunit in the gap region is a modified nucleoside.

In certain embodiments, oligomeric compounds are provided comprising at least one 5' or 3'-terminal group.

In certain embodiments, methods of inhibiting gene expression are provided comprising contacting one or more cells, a tissue or an animal with an oligomeric compound as provided herein wherein the oligomeric compound is complementary to a target RNA. In certain embodiments, the cells are in a human. In certain embodiments, the target RNA is human mRNA. In certain embodiments, the target RNA is cleaved thereby inhibiting its function.

In certain embodiments, methods of inhibiting gene expression are provided comprising contacting one or more cells or a tissue with an oligomeric compound as provided herein.

In certain embodiments, in vivo methods of inhibiting gene expression are provided comprising contacting one or more cells, a tissue or an animal with an oligomeric compound as provided herein.

In certain embodiments, oligomeric compound as provided herein are used in medical therapy.

BRIEF DESCRIPTION OF THE FIGURE

FIG. 1 is a picture of a polyacrylamide gel showing cleavage patterns resulting from RNaseH 1 treatment of RNA/ASO duplexes. The ASO strands are 3/10/3 cEt gap-mers having 2 contiguous MOP linkages walked from the 5'-gap junction to the 3'-gap junction one nucleoside at a time (see Example 38).

DETAILED DESCRIPTION OF THE INVENTION

Provided herein are oligomeric compounds comprising at least one modified internucleoside linkage having Formula I. In certain embodiments, the oligomeric compounds provided herein comprise gapped oligomeric compounds comprising at least one modified internucleoside linkage having Formula I. In certain embodiments, the oligomeric compounds provided herein hybridize to a portion of a target RNA resulting in loss of normal function of the target RNA. In certain embodiments, the oligomeric compounds disclosed herein provide improved selectivity for a target RNA. In certain embodiments, the oligomeric compounds disclosed herein provide improved selectivity for a target RNA relative to an off target RNA. In certain embodiments, the oligomeric compounds provide improved potency for a target RNA. In certain embodiments, the oligomeric compounds provided herein provide enhanced stability to base exposure. In certain embodiments, the oligomeric compounds provided herein provide enhanced stability to base exposure during synthesis. In certain embodiments, the oligomeric compounds provided herein provide an enhanced off target profile.

The oligomeric compounds provided herein comprise a contiguous sequence of monomer subunits linked by internucleoside linking groups wherein at least one of the internucleoside linking groups has Formula I:

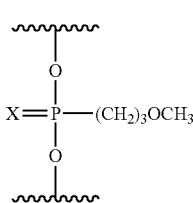

wherein each X is independently O or S.

In certain embodiments, the oligomeric compounds provided herein comprise gapped oligomeric compounds that each have a gap region of from 6 to 14 contiguous monomer subunits selected from β-D-2'-deoxyribonucleosides and modified nucleosides that are DNA-like that each adopt a 2'-endo conformational geometry located between a 5'-region and a 3'-region wherein the 5' and 3'-regions each, independently, have from 2 to 8 contiguous monomer subunits selected from RNA-like modified nucleosides that each adopt a 3'-endo conformational geometry.

The gapped oligomeric compounds provided herein have been shown to have improved properties. In certain embodiments, the activity of an otherwise unmodified gapped oligomeric compound against a target nucleic acid is enhanced by incorporation of one internucleoside linking group having Formula I in the gap region. In certain embodiments, at least one internucleoside linking group having Formula I is located in the gap but not at a gap junction. In certain embodiments, at least one internucleoside linking group having Formula I is located at the gap junction on the 5' side wherein the internucleoside linkage separates the gap region from the wing 5'-region. In certain embodiments, at least one internucleoside linking group having Formula I is located at the gap junction on the 3' side. In certain embodiments, at least one internucleoside linking group having Formula I is located in at least one of the 5' and 3'-regions. As indicated in the data provided in the example section herein, such properties include selectivity and potency.

In certain embodiments, a gapped oligomeric compound of interest is identified and then a series of identical oligomeric compounds are prepared with a single internucleoside linking group having Formula I walked across the gap region. If there are 8 monomer subunits in the gap then there will be 8 oligomeric compounds prepared having the internucleoside linking group having Formula I located at a different position in each of the oligomeric compounds which are subsequently assayed in one or more assays as illustrated herein to determine the lead from the series.

In certain embodiments, a gapped oligomeric compound of interest is identified and then a series of identical oligomeric compounds are prepared with two contiguous internucleoside linking group having Formula I walked across the gap region. If there are 10 monomer subunits in the gap then there will be 10 oligomeric compounds prepared having the internucleoside linking groups of Formula I located at a different positions in each of the oligomeric compounds which are subsequently assayed in one or more assays as illustrated herein to determine the lead from the series (such as a 3/10/3 gapmer, see for example, Example 38).

In certain embodiments, additional internucleoside linking groups having Formula I are incorporated into the gap region of the lead oligomeric compound and assayed in one or more assays as illustrated herein. In certain embodiments, the lead compound is further functionalized with one or more terminal groups such as for example a conjugate group. In certain embodiments, a gapped oligomeric compound of interest is identified and then a series of identical oligomeric compounds are prepared with blocks of at least two internucleoside linking group having Formula I walked across the gap region.

In certain embodiments, gapped oligomeric compounds having a single internucleoside linking group having Formula I are provided having enhanced or comparable ($IC_{50}$) and enhanced selectivity when compared to unmodified gapped oligomeric compounds and otherwise identical oligomeric compounds having a methyl phosphonate linkage. Oligomeric compounds comprising a single internucleoside linking group having Formula I have also been shown to have enhanced stability to aqueous ammonia during the deblocking and cleavage steps of oligomeric compound synthesis as compared to an otherwise identical oligomeric compounds having a methyl phosphonate linkage substituted for the internucleoside linking group having Formula I.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a 2'-deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl ring and that is capable of replacing the naturally occurring sugar moiety of a nucleoside, such that the resulting nucleoside sub-units or monomer subunits are capable of linking together and/or linking to other nucleosides or other monomer subunits to form an oligomeric compound which is capable of hybridizing to a complementary oligomeric compound such as a nucleic acid target. Such structures include rings comprising a different number of atoms than furanosyl (e.g., 4, 6, or 7-membered rings); replacement of the oxygen atom of a furanosyl with a non-oxygen atom (e.g., carbon, sulfur, or nitrogen, wherein replacement of the oxygen atom with sulfur in furanose is generally considered a modified nucleoside as opposed to a sugar surrogate but can be considered both); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols. The synthesis and incorporation of modified nucleosides that include a sugar surrogate is well known in the art (see for example: U.S. Pat. Nos. 8,530,640; 8,088,904; 8,604,192; and 8,536,320, each of which are commonly owned and is incorporated herein by reference in its entirety).

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein the term "nucleobase" generally refers to the nucleobase of a nucleoside or modified nucleoside. The term "heterocyclic base moiety" is broader than the term nucleobase in that it includes any heterocyclic base that can be attached to a sugar to prepare a nucleoside or modified nucleoside. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines).

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose or modified furanose sugar group such as a 4'-S analog (4'-S-modified nucleoside and 4'-S-ribonucleoside refer to replacement of the furanose oxygen atom with S). Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2' bridge. In certain embodiments, the cEt comprises a comprising a 4'-CH((S)—CH$_3$)—O-2' bridge. In certain embodiments, the cEt comprises a comprising a 4'-CH((R)—CH$_3$)—O-2' bridge.

As used herein, "locked nucleic acid nucleoside" or "LNA" means a nucleoside comprising a bicyclic sugar moiety comprising a 4'-CH$_2$—O-2'-bridge.

As used herein, "2'-substituted nucleoside" means a ribofuranosyl nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H(H) furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside other than a β-D-ribose nucleoside that provides an A-form (northern) duplex when incorporated into an oligomeric compound and duplexed with a complementary RNA. RNA-like nucleosides are used as replacements for RNA nucleosides in oligomeric compounds to enhance one or more properties such as, for example, nuclease resistance and or hybridization affinity. RNA-like nucleosides include, but are not limited to modified furanosyl nucleosides that adopt a 3'-endo conformational geometry when put into an oligomeric compound. RNA-like nucleosides also include RNA surrogates such as F-HNA. RNA-like nucleosides include but are not limited to modified nucleosides comprising a 2'-substituent group selected from F, $O(CH_2)_2OCH_3$ (MOE) and $OCH_3$. RNA-like nucleosides also include but are not limited to modified nucleosides comprising bicyclic furanosyl sugar moiety comprising a 4'-$CH_2$—O-2', 4'-$(CH_2)_2$—O-2', 4'-C(H)[(R)—$CH_3$]—O-2' or 4'-C(H)[(S)—$CH_3$]—O-2' bridging group.

As used herein, "DNA-like nucleoside" means a modified nucleoside other than a β-D-2'-doxyribose nucleoside that provides a B-form (southern) duplex when incorporated into an oligomeric compound and duplexed with a complementary DNA. DNA-like nucleosides provide an intermediate duplex when incorporated into an oligomeric compound and duplexed with a complementary RNA that is between A-form and B-form. DNA-like nucleosides are used as replacements for DNA nucleosides in oligomeric compounds to enhance one or more properties. DNA-like nucleosides include, but are not limited to modified nucleosides that adopt a 2'-endo conformational geometry when put into an oligomeric compound.

As used herein, the term "single-stranded" refers to an oligomeric compound that is not hybridized to its complement and that does not have sufficient self-complementarity to form a hair-pin structure under physiologically relevant conditions. A single-stranded compound may be capable of binding to its complement to become a double-stranded or partially double-stranded compound.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein the term "monomer subunit" is meant to include all manner of monomers that are amenable to oligomer synthesis. In general a monomer subunit includes at least a sugar moiety or modified sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribnucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—$CHR_a$-4' bridging group, wherein $R_a$ is H, alkyl or substituted alkyl), other modified nucleosides and nucleosides having sugar surrogates.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/ or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide or oligomeric compound wherein at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "RNAi compound" refers to an oligomeric compound that acts, at least in part, through an RNAi mechanism to modulate a target nucleic acid and/or protein encoded by a target nucleic acid. RNAi compounds include, but are not limited to double-stranded short interfering RNA (siRNA), single-stranded RNA (ssRNA), and microRNA, including microRNA mimics.

As used herein, "mRNA" means an RNA molecule that encodes a protein.

As used herein, "pre-mRNA" means an RNA transcript that has not been fully processed into mRNA. Pre-RNA includes one or more intron.

As used herein, "pdRNA" refers to a pre-selected RNA molecule that interacts with one or more promoter to modulate transcription.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.\

As used herein, "target microRNA" refers to a pre-selected non-coding RNA molecule about 18-30 nucleobases in length that modulates expression of one or more proteins or to a precursor of such a non-coding molecule.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "seed region" refers to a region at or near the 5'-end of an antisense compound having a nucleobase sequence that is import for target nucleic acid recognition by the antisense compound. In certain embodiments, a seed region comprises nucleobases 2-8 of an antisense compound. In certain embodiments, a seed region comprises nucleobases 2-7 of an antisense compound. In certain embodiments, a seed region comprises nucleobases 1-7 of an antisense compound. In certain embodiments, a seed region comprises nucleobases 1-6 of an antisense compound. In certain embodiments, a seed region comprises nucleobases 1-8 of an antisense compound.

As used herein, "microRNA seed region" refers to a seed region of a microRNA or microRNA mimic. In certain embodiments, a microRNA seed region comprises nucleobases 2-8 of a microRNA or microRNA mimic. In certain embodiments, a microRNA seed region comprises nucleobases 2-7 of a microRNA or microRNA mimic. In certain embodiments, a microRNA seed region comprises nucleobases 1-7 of a microRNA or microRNA mimic. In certain embodiments, a microRNA seed region comprises nucleobases 1-6 of a microRNA or microRNA mimic. In certain embodiments, a microRNA seed region comprises nucleobases 1-8 of a microRNA or microRNA mimic.

As used herein, "seed match segment" refers to a portion of a target nucleic acid having nucleobase complementarity to a seed region. In certain embodiments, a seed match segment has nucleobase complementarity to nucleobases 2-8 of an siRNA, ssRNA, natural microRNA or microRNA mimic. In certain embodiments, a seed match segment has nucleobase complementarity to nucleobases 2-7 of an siRNA, ssRNA, microRNA or microRNA mimic. In certain embodiments, a seed match segment has nucleobase complementarity to nucleobases 1-6 of an siRNA, ssRNA, microRNA or microRNA mimic. In certain embodiments, a seed match segment has nucleobase complementarity to nucleobases 1-7 of an siRNA, ssRNA, microRNA or microRNA mimic. In certain embodiments, a seed match segment has nucleobase complementarity to nucleobases 1-8 of an siRNA, ssRNA, microRNA or microRNA mimic.

As used herein, "seed match target nucleic acid" refers to a target nucleic acid comprising a seed match segment.

As used herein, "microRNA family" refers to a group of microRNAs that share a microRNA seed sequence. In certain embodiments, microRNA family members regulate a common set of target nucleic acids. In certain embodiments, the shared microRNA seed sequence is found at the same nucleobase positions in each member of a microRNA family. In certain embodiments, the shared microRNA seed sequence is not found at the same nucleobase positions in each member of a microRNA family. For example, a microRNA seed sequence found at nucleobases 1-7 of one member of a microRNA family may be found at nucleobases 2-8 of another member of a microRNA family.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein "positionally modified" means an oligomeric compound or portion thereof comprising any modification at any position. In certain embodiments, positionally modified is used to describe sugar or linkage modified nucleosides. In certain embodiments, the term positionally modified includes a sequence of β-D-ribonucleosides wherein the sequence is interrupted by two or more regions comprising from 1 to about 4 sugar modified nucleosides. The positionally modified motif includes internal regions of sugar modified nucleoside and can also include one or both termini. Each particular sugar modification within a region of sugar modified nucleosides is variable with uniform modification desired. The sugar modified regions can have the same sugar modification or can vary such that one region may have a different sugar modification than another region. Positionally modified oligomeric compounds are distinguished from gapped motifs, hemimer motifs, blockmer motifs and alternating motifs because the pattern of regional substitution defined by any positional motif is not defined by these other motifs.

As used herein, "uniform modified" or "uniformly modified" means an oligomeric compound or a portion thereof that comprise the same modifications. In certain embodiments, the nucleosides of the oligomeric compound or a region thereof will all have identical sugar moieties. In certain embodiments, the internucleoside linkages of the oligomeric compound or a region thereof will be identical. As such the term uniform modification applies to the sugar moieties and or the internucleoside linkages and is independent of the heterocyclic bases present in the oligomeric compound.

As used herein, "fully modified" or "fully modified motif" means an oligomeric compound or portion thereon wherein each nucleoside comprises a modified sugar moiety other than β-D-ribose or β-D-2'-deoxyribose. The modified sugar moieties of the nucleosides of a fully modified oligomeric compound may all be the same (uniformly modified) or one or more may be different from one another. As such the term fully modified applies to the sugar moieties and is independent of the heterocyclic bases present in the oligomeric compound.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cx}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. Alkyl groups as used herein may optionally include one or more further substituent groups.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

The term "phosphate moiety" means a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

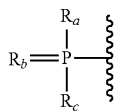

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

B. Oligomeric Compounds

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups. In certain embodiments, oligomeric compounds comprise a contiguous sequence of monomer subunits wherein each monomer subunit comprises a heterocyclic base moiety and a sugar moiety. In certain embodiments, oligomeric compounds include one or more abasic sites. In certain embodiments, oligomeric compounds include one or more acyclic nucleosides.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

i. Certain Modified Nucleosides

Provided herein are oligomeric compounds comprising modified nucleosides. Such modified nucleosides comprise a modified sugar moeity, a modified nucleobase, or both a modified sugar moiety and a modified nucleobase.

a. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituents, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position are selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S);

5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., U.S. 2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Zhou et al., *J. Org. Chem.* 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups (generally forming a 4 to 6 membered ring with the parent sugar moiety) independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Ethylene(methoxy) (4'-(CH(CH$_2$OMe)-O-2') BNA (also referred to as constrained MOE or cMOE) as depicted below.

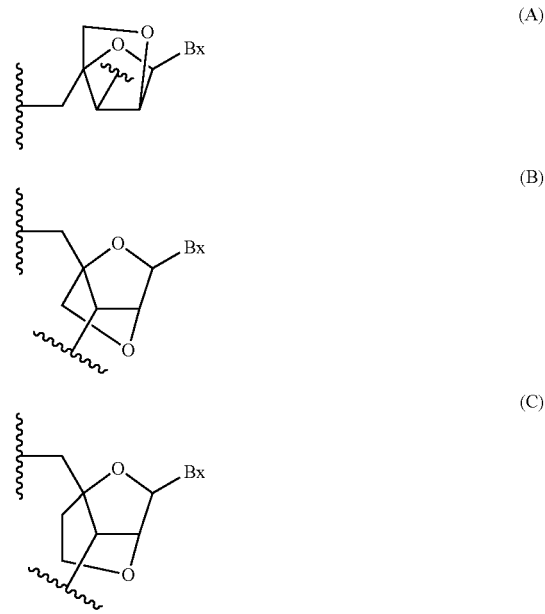

(A)

(B)

(C)

-continued (D) 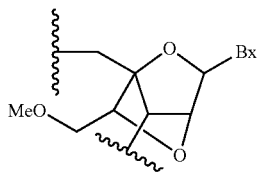

(E)

(F)

(G)

(H)

(I)

(J)

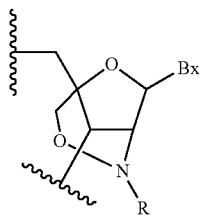

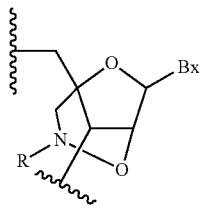

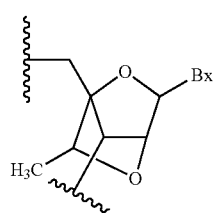

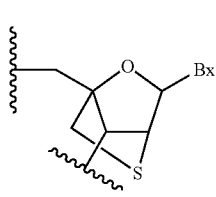

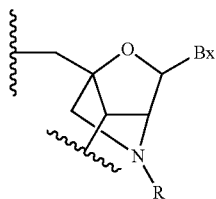

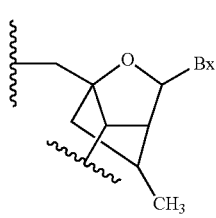

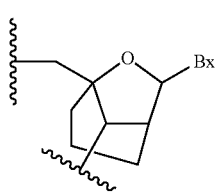

-continued (K)

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.* 1998, 4, 455-456; Koshkin et al., *Tetrahedron,* 1998, 54, 3607-3630; Wahlestedt et al., *Proc. Natl. Acad. Sci. U.S.A.* 2000, 97, 5633-5638; Kumar et al., *Bioorg. Med. Chem. Lett.* 1998, 8, 2219-2222; Singh et al., *J. Org. Chem.* 1998, 63, 10035-10039; Srivastava et al. *J. Am. Chem. Soc.* 2007, 129(26) 8362-8379; Elayadi et al., *Curr. Opin. Investig. Drugs* 2001, 2, 558-561; Braasch et al., *Chem. Biol.* 2001, 8, 1-7; Orum et al., *Curr. Opin. Mol. Ther.* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. U.S. 2004/0171570, U.S. 2007/0287831, and U.S. 2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/U.S. 2008/064591, PCT/U.S. 2008/066154, and PCT/U.S. 2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Res.* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application U.S. 2005/0130923, published on Jun. 16, 2005) and/or the 5' position. By way of additional example, carbocyclic bicyclic nucleosides having a 4'-2' bridge have been described (see, e.g., Freier et al., *Nucleic Acids Res.* 1997, 25(22), 4429-4443 and Albaek et al., *J. Org. Chem.* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, *Bioorg. Med. Chem.* 2002, 10, 841-854), fluoro HNA (F-HNA, see e.g., U.S. Pat. Nos. 8,088,904; 8,440,803; and 8,796,437, F-HNA can also be referred to as a F-THP or 3'-fluoro tetrahydropyran), and including further compounds also having Formula VII:

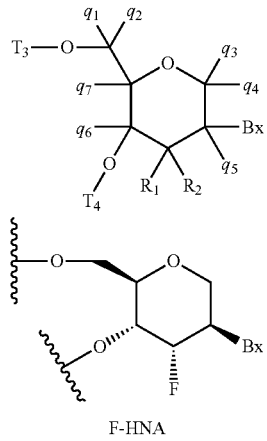

F-HNA wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H. In certain embodiments, the modified THP nucleoside is F-THP.

Many other bicyclo and tricyclo sugar surrogate ring systems are also known in the art that can be used to modify nucleosides for incorporation into antisense compounds (see, e.g., review article: Leumann, *Bioorg. Med. Chem.* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application U.S. 2005/0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleosides.

In certain embodiments, the oligomeric compounds provided herein include RNA-like nucleosides that have been modified to influence the sugar conformation to have predominantly 3'-endo conformational geometry. In certain embodiments, such modified nucleosides include synthetic modifications of the heterocyclic base moiety, the sugar moiety or both to induce a 3'-endo sugar conformation. In certain embodiments, RNA-like nucleosides are selected from RNA surrogates such as including, but not limited to, F-HNA or cyclohexenyl nucleic acid. RNA-like nucleosides are used to replace and mimic RNA nucleosides in an oligomeric compound so that particular properties of the oligomeric compound can be enhanced. Typically RNA-like nucleosides are used in the 5' and 3'-regions (wings) of gapped oligomeric compounds to improve stability in the presence of nucleases and also to increase the affinity for nucleic a nucleic acid target. Other properties that can also be enhanced by using RNA-like nucleosides include but aren't limited to modulation of pharmacokinetic properties through modification of protein binding, protein off-rate, absorption and clearance as well as chemical stability and specificity of the oligomeric compound (affinity and specificity for enzymes as well as for complementary sequences); and increasing efficacy of RNA cleavage.

In certain embodiments, RNA-like nucleosides include modified nucleosides comprising one or more 2', 3', 4' and 5' substituent groups, bicyclic nucleosides and RNA-surrogates. In certain embodiments, RNA-like nucleosides include, but are not limited to modified nucleosides comprising 2'-ribo-substituent groups selected from: F, $OCH_3$, O—$C_2$-$C_4$ alkyl, O—$CH_2CH=CH_2$, O—$(CH_2)_2$—O—$CH_3$ (MOE), O—$(CH_2)_3$—$NH_2$, O—$(CH_2)_2$—O—$N(R_1)_2$, O—$CH_2C(O)$—$N(R_1)_2$, O—$(CH_2)_2$—O—$(CH_2)_2$—$N(R_1)_2$, O—$(CH_2)_3$—$NHR_1$ and O—$CH_2$—N(H)—C(=$NR_1$)[$N(R_1)_2$] wherein each $R_1$ is, typically H, $C_1$-$C_{12}$ alkyl or a protecting group. RNA-like nucleosides also include but are not limited to modified nucleosides having a bicyclic furanosyl sugar moiety (bicyclic nucleosides) comprising a bridging group between the 4' and 2'-carbon atoms. Such bicyclic nucleosides include, but are not limited to bridging groups consisting of from 1 to 3 linked biradical groups selected from O, S, $NR_a$, $C(R_b)(R_c)$, C=O, $C(R_b)$=$C(R_c)$ and C[=$C(R_b)(R_c)$] wherein $C(R_b)$=$C(R_c)$ counts as 2 of said biradical groups wherein each $R_a$, $R_b$ and $R_c$ is, independently, H, $C_1$-$C_6$ alkyl, $C_1$-$C_6$ alkoxy, $C_2$-$C_6$ alkenyl or $C_2$-$C_6$ alkynyl. In certain embodiments, the bridging groups include, but are not limited to 4'-($CH_2$)—O-2', 4'-($CH_2$)—S-2', 4'-($CH_2$)$_2$—O-2', 4'-CH($CH_3$)—O-2', 4'-CH (CH₂OCH₃)—O-2', 4'-C(CH₃)₂—O-2', 4'-CH₂—N(OCH₃)-2', 4'-CH₂—O—N(CH₃)-2', 4'-CH₂—NCH₃—O-2', 4'-CH₂—C(H)(CH₃)-2' and 4'-CH₂—C(=CH₂)-2'. In certain embodiments, the bridging groups include, but are not limited to 4'-CH₂—O-2', 4'-(CH₂)₂—O-2', 4'-C(H)[(R)—CH₃]—O-2' and 4'-C(H)[(S)—CH₃]—O-2'.

In certain embodiments, the oligomeric compounds provided herein include DNA-like nucleosides that have been modified to influence the sugar conformation to have predominantly 2'-endo conformational geometry. Such modified nucleosides can include synthetic modifications of the heterocyclic base moiety, the sugar moiety or both to induce the desired 2'-endo sugar conformation. These modified nucleosides are used to mimic RNA nucleosides so that particular properties of an oligomeric compound can be enhanced while maintaining the desirable 2'-endo conformational geometry.

In certain embodiments, DNA-like nucleosides include, but are not limited to 2'-substituted furanosyl nucleosides comprising: 2'=CH₂, 2'-ara-CN, 2'-ara-F, 2'-ara-Br or 2'-ara-Cl, 2'-ara-N₃, 2'-ara-OH, 2'-ara-O—CH₃ or 2'-dehydro-2'-ara-CH₃.

The C3'-endo and C2'-endo conformational geometries are shown below:

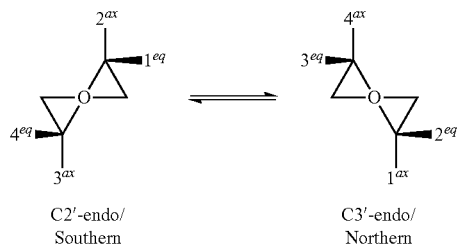

C2'-endo/
Southern

C3'-endo/
Northern ii. Certain Modified Nucleobases

In certain embodiments, nucleosides of the present invention comprise one or more unmodified nucleobases. In certain embodiments, nucleosides of the present invention comprise one or more modified nucleobases (heterocyclic base moieties).

In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. In certain embodiments, nucleobase refers to unmodified or naturally occurring nucleobases which include, but are not limited to, the purine bases adenine (A) and guanine (G), and the pyrimidine bases thymine (T), cytosine (C) and uracil (U) and analogs thereof such as 5-methyl cytosine. The terms nucleobase and heterocyclic base moiety also include optional protection for any reactive functional groups such as 4-N-benzoylcytosine, 4-N-benzoyl-5-methyl-cytosine, 6-N-benzoyladenine or 2-N-isobutyrylguanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302).

Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

ii. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH₂—N(CH₃)—O—CH₂—), thiodiester (—O—C(O)—S—), thionocarbamate (—O—C(O)(NH)—S—); siloxane (—O—Si(H)₂—O—); and N,N'-dimethylhydrazine (—CH₂—N(CH₃)—N(CH₃)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

iii. Certain Motifs

In certain embodiments, oligomeric compounds comprise or consist of oligonucleotides. In certain embodiments, such oligonucleotides comprise one or more chemical modifications. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

a. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligomeric compounds provided herein comprise a gapmer sugar motif, which comprises two external regions or "wings" and a central or internal region or "gap" (also referred to as 5'-region and 3'-region). The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar moieties of the two wings are the same as one another (symmetric sugar gapmer). In certain embodiments, the sugar moieties of the 5'-wing differs from the sugar moieties of the 3'-wing (asymmetric sugar gapmer). In certain embodiments, the sugar moieties in the two wings are selected from at least two different types that are different from the sugar moieties in the gap and at least one of each are in each wing.

In certain embodiments, the term "gapped oligomeric compound" refers to an oligomeric compound having two external regions or wings and an internal region or gap (also referred to as 5'-region and 3'-region). The three regions form a contiguous sequence of monomer subunits with the sugar moieties of the external regions (wings) being different than the sugar moieties of the internal region (gap). In certain embodiments, the sugar moieties of each monomer subunit within a particular region is essentially the same. In certain embodiments, the sugar moieties of each monomer subunit within each wing region is selected independently from 2 different types of modified nucleosides. In certain embodiments, the sugar moieties of each monomer subunit within each wing region is selected independently from 3 different types of modified nucleosides. In certain embodiments, the sugar moieties of each monomer subunit within each wing region is selected independently from 4 different types of modified nucleosides. In certain embodiments, the sugar moiety of essentially each monomer subunit within the internal region is essentially the same. In certain embodiments, the sugar moiety of each monomer subunit within the internal region is a β-D-2'-deoxyribonucleoside, a nucleoside that is DNA-like and/or a nucleoside that supports RNaseH when in the gap region.

In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 2, 3, 4, 5 or about 6 monomer subunits) and the monomer subunits comprise non-naturally occurring sugar moieties with the internal region comprising β-D-2'-deoxyribonucleosides. In certain embodiments, the external regions each, independently, comprise from 2 to about 8 monomer subunits having non-naturally occurring sugar moieties and the internal region comprises from 6 to 14 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. A gapped oligomeric compound can further include one or more additional groups including but not limited to capping groups, conjugate groups and other 5' or 3'-terminal groups.

In certain embodiments, gapped oligomeric compounds comprise an internal region of β-D-2'-deoxyribonucleosides with a single internucleoside linkage having Formula I. In certain embodiments, gapped oligomeric compounds comprise an internal region of β-D-2'-deoxyribonucleosides having two internucleoside linkages having Formula I. In certain embodiments, gapped oligomeric compounds comprise an internal region of β-D-2'-deoxyribonucleosides having three internucleoside linkages having Formula I.

In certain embodiments, the 5' and 3'-wing regions of gapped oligomeric compounds comprise modified nucleosides wherein all the sugar moieties have the same type of modification such as cEt or MOE. In certain embodiments, the 5' and 3'-wing regions of gapped oligomeric compounds comprise two types of modified nucleosides having sugar moieties independently selected from 2'-substituted sugar moieties and furanosyl bicyclic sugar moieties. In certain embodiments, the 5' and 3'-wing regions of gapped oligomeric compounds comprise two types of modified nucleosides having sugar moieties independently selected from 2'-MOE substituted sugar moieties and furanosyl bicyclic sugar moieties each having a 4'-CH((S)—CH$_3$)—O-2' bridge.

In certain embodiments, gapped oligomeric compounds are provided that are from about 10 to about 30 monomer subunits in length. In certain embodiments, gapped oligomeric compounds are provided that are from about 12 to about 20 monomer subunits in length. In certain embodiments, gapped oligomeric compounds are provided that are from about 14 to about 20 monomer subunits in length. In certain embodiments, gapped oligomeric compounds are provided that are from about 14 to about 18 monomer subunits in length.

b. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the gap of an oligonucleotide having a gapmer sugar motif. In certain embodiments, the sugar is an unmodified 2'-deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

c. Certain Nucleoside Motifs

In certain embodiments, oligomeric compounds comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, oligomeric compounds are provided herein wherein most if not all of the nucleosides are selected from those having particular nucleobases. In certain embodiments, nucleosides are provided wherein each nucleobase is, independently, selected from adenine, guanine, thymine, cytosine, 5-methyl cytosine and uracil. In certain embodiments, nucleosides are provided wherein each nucleobase is, independently, selected from 6-N-benzoyladenine, 2-N-isobutyrylguanine, thymine, 4-N-benzoylcytosine, 5-methyl 4-N-benzoylcytosine and uracil.

In certain embodiments, oligomeric compounds are provided herein wherein most if not all of the nucleosides are selected from those having particular sugar moieties. In certain embodiments, nucleosides are provided wherein each sugar moiety is, independently, selected from β-D-2'-deoxyribose, a ribofuranosyl sugar moiety having a 2' substituent group selected from F, OCH$_3$, MOE and NMA, a bicyclic sugar selected from LNA, cEt, R-cEt or S-cEt, and a sugar moiety comprising a F-substituted hexitol as in a F-HNA. In certain embodiments, nucleosides are provided wherein each sugar moiety is, independently, selected from β-D-2'-deoxyribose, a ribofuranosyl sugar moiety having a 2' substituent group selected from MOE and NMA, a bicyclic sugar selected from LNA or S-cEt, and a sugar moiety comprising a F-substituted hexitol as in a F-HNA. In certain embodiments, nucleosides are provided wherein each sugar moiety is, independently, selected from β-D-2'-deoxyribose, a 2'-MOE substituted ribofuranosyl sugar moiety, and a bicyclic sugar selected from S-cEt.

In certain embodiments, oligomeric compounds are provided herein wherein most if not all of the nucleosides are selected from those having particular sugar moieties. In certain embodiments, nucleosides are provided wherein each sugar moiety is, independently, selected from β-D-ribose, a ribofuranosyl sugar moiety having a 2' substituent group selected from F, OCH$_3$ and MOE, a 4'-thio ribofuranosyl sugar moiety and a 4'-thio-2'-modified nucleoside wherein the 2'-substituent is selected from F, OCH$_3$ and MOE. In certain embodiments, nucleosides are provided wherein each sugar moiety is, independently, selected from β-D-ribose and a ribofuranosyl sugar moiety having a 2' substituent group selected from F, OCH$_3$ and MOE.

In certain embodiments, oligomeric compounds provided herein include a 5'-stabilized nucleoside. In certain embodiments, the oligomeric compound is a single stranded RNAi compound. In certain embodiments, the 5'-stabilized nucleoside has the formula:

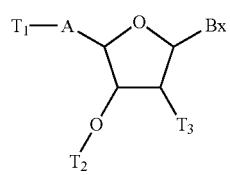

wherein:

T₁ is an optionally protected phosphorus moiety;

A has one of the formulas:

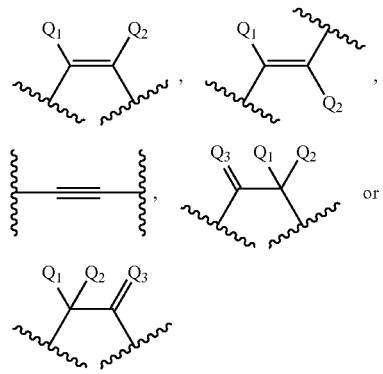

Q₁ and Q₂ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

Q₃ is O, S, $N(R_5)$ or $C(R_6)(R_7)$;

each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;

Bx is a heterocyclic base moiety;

T₃ is a 2'-substituent group; and

T₂ is an internucleoside linkage connecting the 5'-stabilized nucleoside to the remainder of an oligomeric compound.

In certain embodiments, the 5'-stabilized nucleoside has the configuration of the formula:

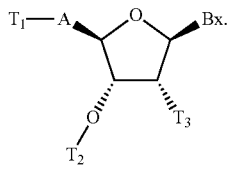

In certain embodiments, the 5'-stabilized nucleoside has the formula:

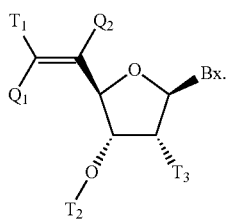

In certain embodiments, the 5'-stabilized nucleoside has the formula:

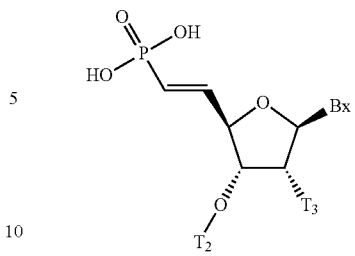

or a protected analog thereof.

In certain embodiments, the oligomeric compounds comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

d. Certain 5'wings

In certain embodiments, the 5'-wing of a gapmer consists of 2 to 8 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides. In certain embodiments, the 5'-wing of a gapmer consists of 7 linked nucleosides. In certain embodiments, the 5'-wing of a gapmer consists of 8 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside.

In certain embodiments, the 5'-wing of a gapmer has a nucleoside motif selected from among the following: ABBA; ABB; ABAA; AABAA; AAABAA; AAAABAA; AAAAABAA; AAABAA; AABAA; ABAB; AAABB; AAAAA; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type and each C is a modified nucleoside of a third type. In certain embodiments, such an oligomeric compound is a gapmer. In certain such embodiments, the 3'-wing of the gapmer may comprise any nucleoside motif.

1. Certain 3'-wings

In certain embodiments, the 3'-wing of a gapmer consists of 2 to 8 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides. In certain embodiments, the 3'-wing of a gapmer consists of 7 linked nucleosides. In certain embodiments, the 3'-wing of a gapmer consists of 8 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside.

In certain embodiments, the 3'-wing of a gapmer has a nucleoside motif selected from among the following: ABB; ABAA; AAABAA, AAAAABAA; AABAA; AAAABAA; AAABAA; ABAB; AAAAA; AAABB; AAAAAAAA; AAAAAAA; AAAAAA; AAAAB; AAAA; AAA; AA; AB; ABBB; ABAB; AABBB; wherein each A is a modified nucleoside of a first type, each B is a modified nucleoside of a second type. In certain embodiments, an oligonucleotide comprises any 3'-wing motif provided herein. In certain such embodiments, the 5'-wing of the gapmer may comprise any nucleoside motif.

e. Certain Central Regions (gap regions)

In certain embodiments, the gap of a gapmer consists of 6 to 20 linked nucleosides. In certain embodiments, the gap of a gapmer consists of 6 to 14 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides. In certain embodiments, the gap of a gapmer consists of 13 linked nucleosides. In certain embodiments, the gap of a gapmer consists of 14 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like". In certain embodiments, "DNA-like" means that the nucleoside has similar characteristics to DNA, such that a duplex comprising the gapmer and an RNA molecule is capable of activating RNase H. In certain embodiments, modified nucleosides that are DNA-like are 2'-endo. For example, under certain conditions, 2'-(ara)-F have been shown to support RNase H activation, and thus is DNA-like and further has 2'-endo conformation geometry. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, the gap comprise a stretch of unmodified 2'-deoxynucleosides interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

f. Certain Gapmer Motifs

In certain embodiments, a gapmer comprises a 5'-wing, a gap comprising at least one internucleoside linkage of Formula I, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting table:

TABLE 1

Certain Gapmer Nucleoside Motifs

| 5'-wing region | Gap region | 3'-wing region |
|---|---|---|
| AAAAAAA | DDDDDDDDDD | AAA |
| AAAAABB | DDDDDDDD | BBAAAAA |
| ABB | DDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDDD | BBA |
| ABAB | DDDDDDDD | BBA |
| AA | DDDDDDDD | BBBBBBBB |
| ABB | DDDDDD | ABADB |
| AAAAB | DDDDDDD | BAAAA |
| ABBB | DDDDDDDD | AB |
| AB | DDDDDDDD | BBBA |
| ABBB | DDDDDDDD | BBBA |
| AB | DDDDDDDD | ABA | wherein each A is a modified nucleoside of a first type, each B is a modified nucleoside of a second type and each D is a β-D-2'-deoxyribonucleoside or a nucleoside that is DNA-like. Each gap region includes at least one internucleoside linkage of Formula I.

In certain embodiments, each A comprises a modified sugar moiety. In certain embodiments, each A comprises a 2'-substituted sugar moiety. In certain embodiments, each A comprises a 2'-substituted sugar moiety selected from among F, $OCH_3$, $OCH_2$—C(=O)—N(H)(CH_3) and $O(CH_2)_2$ —$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A is a modified nucleoside comprising a sugar surrogate selected from morpholino, cyclohexenyl and cyclohexitol. In certain embodiments, each A is a modified nucleoside comprising a sugar surrogate selected from morpholino and F-tetrahydropyran (F-HNA). In certain embodiments, each A comprises a F-HNA surrogate modified nucleoside. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, OCH$_3$, OCH$_2$—C(=O)—N(H)(CH$_3$) and O(CH$_2$)$_2$ —OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B is a modified nucleoside comprising a sugar surrogate selected from morpholino, cyclohexenyl and cyclohexitol. In certain embodiments, each B is a modified nucleoside comprising a sugar surrogate selected from morpholino and F-tetrahydropyran (F-HNA). In certain embodiments, each B comprises a F-HNA surrogate modified nucleoside. In certain embodiments, each B comprises a modified nucleobase. In certain embodiments, each B comprises a modified nucleobase selected from among 2-thio-thymidine nucleoside and 5-propyne uridine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B comprises a sugar surrogate selected from morpholino, cyclohexenyl and cyclohexitol and the other of A or B comprises a 2'-substituted sugar moiety. In certain embodiments, one of A or B comprises a sugar surrogate selected from morpholino, cyclohexenyl and cyclohexitol and the other of A or B comprises a 2'-MOE sugar moiety. In certain embodiments, one of A or B comprises a F-THP sugar surrogate and the other of A or B comprises a 2'-substituted sugar moiety. In certain embodiments, one of A or B comprises a F-THP sugar surrogate and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, each A and B is, independently, a modified nucleoside comprising a bicyclic sugar moiety comprising a 4'-CH(CH$_3$)—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(S)—(CH$_3$)]—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(R)—(CH$_3$)]—O-2' bridge or a modified nucleoside comprising a 2'-OCH$_2$CH$_2$OCH$_3$ (MOE) substituent group. In certain embodiments, at least one modified nucleoside comprising a 2'-OCH$_2$CH$_2$OCH$_3$ (MOE) substituent group and at least one modified nucleoside comprising a 4'-CH(CH$_3$)—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(S)—(CH$_3$)]—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(R)—(CH$_3$)]—O-2' bridge is located in each of the 3' and 5' wings.

g. Certain Internucleoside Linkage Motifs

In certain embodiments, oligomeric compounds comprise modified internucleoside linkages arranged along the oligomeric compound or region thereof in a defined pattern or modified internucleoside linkage motif provided that at least one internucleoside linkage has Formula I. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligomeric compounds having a gapped internucleoside linkage motif may or may not have a gapped nucleoside motif and if it does have a gapped nucleoside motif, the wing and gap lengths may or may not be the same.

In certain embodiments, oligomeric compounds comprise a region having an alternating internucleoside linkage motif. In certain embodiments, oligomeric compounds of the present invention comprise a region of uniformly modified internucleoside linkages. In certain such embodiments, the oligomeric compound comprises a region that is uniformly linked by phosphorothioate internucleoside linkages. In certain embodiments, the oligonucleotide is uniformly linked by phosphorothioate. In certain embodiments, each internucleoside linkage of the oligomeric compound is selected from phosphodiester and phosphorothioate. In certain embodiments, each internucleoside linkage of the oligomeric compound is selected from phosphodiester and phosphorothioate and at least one internucleoside linkage is phosphorothioate. In certain embodiments, at least one internucleoside linkage of the oligomeric compound is selected from other than phosphodiester and phosphorothioate.

In certain embodiments, oligomeric compounds comprise a positionally modified internucleoside linkage motif. In certain embodiments, oligomeric compounds as provided herein comprise a region of uniformly modified internucleoside linkages. In certain such embodiments, the oligomeric compound comprises one or more modified internucleoside linkages of one or more different types.

In certain embodiments, the oligomeric compound comprises at least 6 phosphorothioate internucleoside linkages. In certain embodiments, the oligomeric compound comprises at least 8 phosphorothioate internucleoside linkages. In certain embodiments, the oligomeric compound comprises at least 10 phosphorothioate internucleoside linkages. In certain embodiments, the oligomeric compound comprises at least one block of at least 6 consecutive phosphorothioate internucleoside linkages. In certain embodiments, the oligomeric compound comprises at least one block of at least 8 consecutive phosphorothioate internucleoside linkages. In certain embodiments, the oligomeric compound comprises at least one block of at least 10 consecutive phosphorothioate internucleoside linkages. In certain embodiments, the oligomeric compound comprises at least one block of at least one 12 consecutive phosphorothioate internucleoside linkages. In certain such embodiments, at least one such block is located at the 3' end of the oligomeric compound. In certain such embodiments, at least one such block is located within 3 nucleosides of the 3' end of the oligomeric compound. In certain embodiments, each internucleoside linkage a phosphorothioate internucleoside linkage.

h. Certain Modification Motifs

Modification motifs define oligonucleotides by nucleoside motif (sugar motif and nucleobase motif) and linkage motif. For example, certain oligonucleotides have the following modification motif:

AAADDDDDDDDBBB;

wherein each A is a modified nucleoside comprising a 2'-substituted sugar moiety; each D is a β-D-2'-deoxyribonucleoside or a modified nucleoside having B form conformation geometry and each B is a modified nucleoside comprising a bicyclic sugar moiety wherein at least one internucleoside linkage had Formula I. The following non-limiting Table further illustrates certain modification motifs:

TABLE 2

| Certain Modification Motif | | |
|---|---|---|
| 5'-wing region | Gap region | 3'-wing region |
| BB | DDDDDDDD | AAAAAAAA |
| ABB | DDDDDDDD | BBA |
| ABB | DDDDDDDD | BBA |

TABLE 2-continued

| Certain Modification Motif | | |
|---|---|---|
| 5'-wing region | Gap region | 3'-wing region |
| ABBB | DDDDDDDD | BBABB |
| ABB | DDDDDDDD | BBABB |
| BBABB | DDDDDDDD | BBA |
| ABB | DDDDDDDD | BBABBBB |
| AABAA | DDDDDDDD | BBA |
| AAABAA | DDDDDDDD | BBA |
| AABAA | DDDDDDDD | AABAA |
| AAABAA | DDDDDDDD | AABAAA |
| AAAABAA | DDDDDDDD | BBA |
| ABAB | DDDDDDDD | BABA |
| ABAB | DDDDDDDD | AABAA |
| ABB | DDDDDDDD | BABA |
| BBABBBB | DDDDDDDD | BABA |
| AAAAA | DDDDDDDD | AAAAA |
| AAAAA | DDDDDDD | AAAAA |
| AAAAA | DDDDDDDD | BBABBBB |
| AAABB | DDDDDDD | BBA |
| ABAB | DDDDDDDD | BBA |
| ABAB | DDDDDDD | AAABB |
| AAAAB | DDDDDDD | BAAAA |
| BB | DDDDDDDD | AA |
| AA | DDDDDDD | AAAAAAAA |
| AAA | DDDDDDD | AAAAAAA |
| AAA | DDDDDDD | AAAAAA |
| AB | DDDDDDD | BBBA |
| ABBB | DDDDDDDD | BA |
| AB | DDDDDDDD | BBBA |
| AAABB | DDDDDDD | BBAAA |
| AAAAB | DDDDDDD | BAAAA |
| AABBB | DDDDDDD | BBBAA |
| AAAAB | DDDDDDD | AAAAA |
| AAABB | DDDDDDD | AAAAA |
| AABBB | DDDDDDD | AAAAA |
| AAAAA | DDDDDDD | BAAAA |
| AAAAA | DDDDDDD | BBAAA |
| AAAAA | DDDDDDD | BBBAA | wherein each A is a modified nucleoside of a first type, each B is a modified nucleoside of a second type and each D is a β-D-2'-deoxyribonucleoside or a nucleoside that is DNA-like. Each gap region includes at least one internucleoside linkage of Formula I.

In certain embodiments, each A comprises a modified sugar moiety. In certain embodiments, each A comprises a 2'-substituted sugar moiety. In certain embodiments, each A comprises a 2'-substituted sugar moiety selected from among F, $OCH_3$, $OCH_2$—C(=O)—N(H)($CH_3$) and O($CH_2$)$_2$—$OCH_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A is a modified nucleoside comprising a sugar surrogate selected from morpholino, cyclohexenyl and cyclohexitol. In certain embodiments, each A is a modified nucleoside comprising a sugar surrogate selected from morpholino and F-tetrahydropyran (F-HNA). In certain embodiments, each A comprises a F-HNA sugar surrogate modified nucleoside. In certain embodiments, each A comprises a modified nucleobase. In certain embodiments, each A comprises a modified nucleobase selected from among 2-thio-thymidine nucleoside and 5-propyne uridine nucleoside.

In certain embodiments, each B comprises a modified sugar moiety. In certain embodiments, each B comprises a 2'-substituted sugar moiety. In certain embodiments, each B comprises a 2'-substituted sugar moiety selected from among F, $OCH_3$, $OCH_2$—C(=O)—N(H)($CH_3$) and O($CH_2$)$_2$ $OCH_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B is a modified nucleoside comprising a sugar surrogate selected from morpholino, cyclohexenyl and cyclohexitol. In certain embodiments, each B is a modified nucleoside comprising a sugar surrogate selected from morpholino and F-tetrahydropyran (F-HNA). In certain embodiments, each B comprises a F-HNA sugar surrogate modified nucleoside. In certain embodiments, each B comprises a modified nucleobase. In certain embodiments, each B comprises a modified nucleobase selected from among 2-thiothymidine nucleoside and 5-propyne urindine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B comprises a sugar surrogate selected from morpholino, cyclohexenyl and cyclohexitol and the other of A or B comprises a 2'-substituted sugar moiety. In certain embodiments, one of A or B comprises a sugar surrogate selected from morpholino, cyclohexenyl and cyclohexitol and the other of A or B comprises a 2'-MOE sugar moiety. In certain embodiments, one of A or B comprises a F-THP sugar surrogate and the other of A or B comprises a 2'-substituted sugar moiety. In certain embodiments, one of A or B comprises a F-THP sugar surrogate and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety. In certain embodiments, each A and B is, independently, a modified nucleoside comprising a bicyclic sugar moiety comprising a 4'-CH(CH$_3$)—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(S)—(CH$_3$)]—O-2' bridge or a modified nucleoside comprising a 2'-OCH$_2$CH$_2$OCH$_3$ (MOE) substituent group. In certain embodiments, each A and B is, independently, a modified nucleoside comprising a bicyclic sugar moiety comprising a 4'-CH[(R)—(CH$_3$)]—O-2' bridge or a modified nucleoside comprising a 2'-OCH$_2$CH$_2$OCH$_3$ (MOE) substituent group. In certain embodiments, at least one modified nucleoside comprising a 2'-OCH$_2$CH$_2$OCH$_3$ (MOE) substituent group and at least one modified nucleoside comprising a 4'-CH(CH$_3$)—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(S)—(CH$_3$)]—O-2' bridge is located in each of the 3' and 5' wings. In certain embodiments, at least one modified nucleoside comprising a 2'-OCH$_2$CH$_2$OCH$_3$ (MOE) substituent group and at least one modified nucleoside comprising a 4'-CH[(R)—(CH$_3$)]—O-2' bridge is located in each of the 3' and 5' wings.

b. Certain Antisense Activities and Mechanisms

Antisense mechanisms include any mechanism involving the hybridization of an oligomeric compound with a target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain antisense activities, hybridization of an antisense compound results in recruitment of a protein that cleaves a target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuranose sugar moieties in the nucleosides of the gap and modified sugar moieties in the nucleosides of the wings.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression. In certain embodiments, the invention provides antisense compounds that are sufficiently "DNA-like" to elicit RNase H activity. Such DNA-like antisense compounds include, but are not limited to gapmers. In certain embodiments, such gapmers comprise 2'-β-D-ribofuranose nucleosides in the gap and modified nucleosides comprising at least modified sugar moieties in the wings.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an antimicroRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

iv. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 10, 11, 12, 13, 14, 15, 16, 17, 18, 19, 20, 21, 22, 23, 24, 25, 26, 27, 28, 29 and 30; provided that X≤Y. For example, in certain embodiments, the invention provides oligomeric compounds which comprise oligonucleotides consisting of 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

In certain embodiments, oligonucleotides of the present invention are characterized by their modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

Provided herein are oligomeric compounds comprising modified nucleosides. Such modified nucleosides comprise a modified sugar moiety, a modified nucleobase, or both a modified sugar moiety and a modified nucleobase. In certain embodiments, oligomeric compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, the present invention provides oligonucleotides comprising modified nucleosides. Modified nucleosides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleosides.

Oligomeric compounds are routinely prepared using solid support methods as a preferred method over solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods* 2001, 23, 206-217; *Oligonucleotides and Analogues, a Practical Approach*, F. Eckstein, Ed., Oxford University Press, New York, 1991; Gait et al., *Applications of Chemically synthesized RNA in RNA: Protein Interactions*, Smith, Ed., 1998, 1-36; Gallo et al., *Tetrahedron* 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl](FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

v. Certain Oligonucleotides

In certain embodiments, oligonucleotides of the present invention are characterized by their modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

vi. Certain Terminal Groups/Conjugate Groups

In certain embodiments, the oligomeric compounds as provided herein are modified by covalent attachment of one or more terminal groups to the 5' and or 3'-end. Although terminal groups are generally attached at the terminal 3' or 5'-position, attachment at any available terminal or internal position is also possible. As used herein the terms "5'-terminal group", "3'-terminal group", "terminal group" and combinations thereof are meant to include useful groups known to the art skilled that can be placed on one or both of the terminal ends of an oligomeric compound or at another reactive position at a terminal end of an oligomeric compound. Such terminal groups are useful for various purposes such as enabling the tracking of an oligomeric compound (a fluorescent label or other reporter group), improving the pharmacokinetics or pharmacodynamics of an oligomeric compound (such as for example: uptake and/or delivery) or enhancing one or more other desirable properties of an oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

In certain embodiments, the oligomeric compounds as provided herein are modified by covalent attachment of one or more conjugate groups. As used herein, "conjugate group" means a radical group comprising a group of atoms that are attached to an oligomeric compound. In general, conjugate groups modify one or more properties of the compound to which they are attached, including, but not limited to pharmacodynamic, pharmacokinetic, stability, binding, absorption, cellular distribution, cellular uptake, charge and/or clearance properties. Conjugate groups are routinely used in the chemical arts and can include a conjugate linker that covalently links the conjugate group to an oligomeric compound.

In certain embodiments, conjugate groups include without limitation, intercalators, reporter molecules, polyamines, polyamides, polyethylene glycols, thioethers, peptides, carbohydrates, a vitamin moiety, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., *Proc. Natl. Acad. Sci. U.S.A.* 1989, 86, 6553-6556); cholic acid (Manoharan et al., *Bioorg. Med. Chem. Let.* 1994, 4, 1053-1060); a thioether, e.g., hexyl-S-tritylthiol (Manoharan et al., *Ann. N.Y. Acad. Sci.* 1992, 660, 306-309; and Manoharan et al., *Bioorg. Med. Chem. Let.* 1993, 3, 2765-2770); a thiocholesterol (Oberhauser et al., *Nucleic Acids Res.* 1992, 20, 533-538); an aliphatic chain, e.g., do-decan-diol or undecyl residues (Saison-Behmoaras et al., *EMBO J.* 1991, 10, 1111-1118; Kabanov et al., *FEBS Lett.* 1990, 259, 327-330; Svinarchuk et al., *Biochimie* 1993, 75, 49-54); a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.* 1995, 36, 3651-3654; Shea et al., *Nucl. Acids Res.* 1990, 18, 3777-3783); a polyamine or a polyethylene glycol chain (Manoharan et al., *Nucleosides Nucleotides,* 1995, 14, 969-973); an adamantane acetic acid (Manoharan et al., *Tetrahedron Lett.* 1995, 36, 3651-3654); a palmityl moiety (Mishra et al., *Biochim. Biophys. Acta* 1995, 1264, 229-237); an octadecylamine or hexylamino-carbonyl-oxycholesterol moiety (Crooke et al., *J. Pharmacol. Exp. Ther.* 1996, 277, 923-937); or a tocopherol group (Nishina et al., *Molecular Therapy Nucleic Acids,* 2015, 4, e220; doi:10.1038/mtna.2014.72, Published online 13 Jan. 2015; and Nishina et al., *Molecular Therapy,* 2008, 16(4), 734-740).

In certain embodiments, a conjugate group comprises an active drug substance including but not limited to aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

In certain embodiments, conjugate groups are directly attached to oligomeric compounds. In certain embodiments, conjugate groups are attached to oligomeric compounds by a conjugate linking group. In certain such embodiments, conjugate linking groups include bifunctional linking moieties which are known in the art and are useful for attaching conjugate groups to oligomeric compounds. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl group having at least two functional groups. One of the functional groups is selected to bind to a parent molecule or compound of interest and the other is selected to bind essentially any selected group such as chemical functional group or a conjugate group. In certain embodiments, the conjugate linking group comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In certain embodiments, bifunctional linking moieties include one or more groups selected from, but not limited to, alkyl, alkenyl, alkynyl, amino, amido, hydroxyl, thiol, acyl and carboxyl.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, one or more conjugate groups are attached to the 5'-end of an oligomeric compound. In certain embodiments, conjugate groups are near the 5'-end. In certain embodiments, conjugates are attached at the 5'-end of an oligomeric compound, but before one or more terminal group nucleosides.

In certain embodiments, one or more conjugate groups are attached to the 3'-end of an oligomeric compound. In certain embodiments, conjugate groups are near the 3'-end. In certain embodiments, conjugates are attached at the 3'-end of an oligomeric compound, but before one or more terminal group nucleosides. In certain embodiments, conjugate groups are placed within a terminal group.

In certain embodiments, conjugate groups include a cleavable moiety that covalently links the conjugate group to an oligomeric compound. In certain embodiments, conjugate groups include a conjugate linker and a cleavable moiety to covalently link the conjugate group to an oligomeric compound. In certain embodiments, a conjugate group has the general formula:

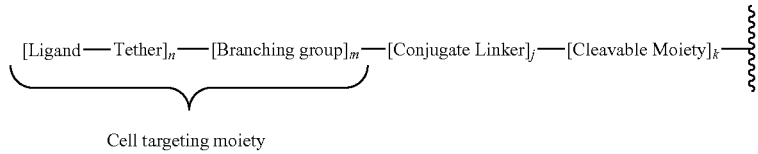

Cell targeting moiety wherein n is from 1 to about 3, m is 0 when n is 1 or m is 1 when n is 2 or 3, j is 1 or 0, k is 1 or 0 and the sum of j and k is at least one.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

Conjugate groups are shown herein as radicals, providing a bond for forming covalent attachment to an oligomeric compound such as an antisense oligonucleotide. In certain embodiments, the point of attachment on the oligomeric compound is at the 3'-terminal nucleoside or modified nucleoside. In certain embodiments, the point of attachment on the oligomeric compound is the 3'-oxygen atom of the 3'-hydroxyl group of the 3' terminal nucleoside or modified nucleoside. In certain embodiments, the point of attachment on the oligomeric compound is at the 5'-terminal nucleoside or modified nucleoside. In certain embodiments the point of attachment on the oligomeric compound is the 5'-oxygen atom of the 5'-hydroxyl group of the 5'-terminal nucleoside or modified nucleoside. In certain embodiments, the point of attachment on the oligomeric compound is at any reactive site on a nucleoside, a modified nucleoside or an internucleoside linkage.

As used herein, "cleavable moiety" and "cleavable bond" mean a cleavable bond or group of atoms that is capable of being split or cleaved under certain physiological conditions. In certain embodiments, a cleavable moiety is a cleavable bond. In certain embodiments, a cleavable moiety comprises a cleavable bond. In certain embodiments, a cleavable moiety is a group of atoms. In certain embodiments, a cleavable moiety is selectively cleaved inside a cell or sub-cellular compartment, such as a lysosome. In certain embodiments, a cleavable moiety is selectively cleaved by endogenous enzymes, such as nucleases. In certain embodiments, a cleavable moiety comprises a group of atoms having one, two, three, four, or more than four cleavable bonds.

In certain embodiments, conjugate groups comprise a cleavable moiety. In certain such embodiments, the cleavable moiety covalently attaches the oligomeric compound to the conjugate linker. In certain such embodiments, the cleavable moiety covalently attaches the oligomeric compound to the cell-targeting moiety.

In certain embodiments, a cleavable bond is selected from among: an amide, a polyamide, an ester, an ether, one or both esters of a phosphodiester, a phosphate ester, a carbamate, a di-sulfide, or a peptide. In certain embodiments, a cleavable bond is one of the esters of a phosphodiester. In certain embodiments, a cleavable bond is one or both esters of a phosphodiester. In certain embodiments, the cleavable moiety is a phosphodiester linkage between an oligomeric compound and the remainder of the conjugate group. In certain embodiments, the cleavable moiety comprises a phosphodiester linkage that is located between an oligomeric compound and the remainder of the conjugate group. In certain embodiments, the cleavable moiety comprises a phosphate or phosphodiester. In certain embodiments, the cleavable moiety is attached to the conjugate linker by either a phosphodiester or a phosphorothioate linkage. In certain embodiments, the cleavable moiety is attached to the conjugate linker by a phosphodiester linkage. In certain embodiments, the conjugate group does not include a cleavable moiety.

In certain embodiments, the cleavable moiety is a cleavable nucleoside or a modified nucleoside. In certain embodiments, the nucleoside or modified nucleoside comprises an optionally protected heterocyclic base selected from a purine, substituted purine, pyrimidine or substituted pyrimidine. In certain embodiments, the cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine.

In certain embodiments, the cleavable moiety is 2'-deoxy nucleoside that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to either the 3' or 5'-terminal nucleoside of an oligomeric compound by a phosphodiester linkage and covalently attached to the remainder of the conjugate group by a phosphodiester or phosphorothioate linkage. In certain embodiments, the cleavable moiety is 2'-deoxy adenosine that is attached to the 3'-oxygen atom of the 3'-hydroxyl group of the 3'-terminal nucleoside or modified nucleoside by a phosphodiester linkage. In certain embodiments, the cleavable moiety is 2'-deoxy adenosine that is attached to the 5'-oxygen atom of the 5'-hydroxyl group of the 5'-terminal nucleoside or modified nucleoside by a phosphodiester linkage. In certain embodiments, the cleavable moiety is attached to a 2'-position of a nucleoside or modified nucleoside of an oligomeric compound.

As used herein, "conjugate linker" in the context of a conjugate group means a portion of a conjugate group comprising any atom or group of atoms that covalently link the cell-targeting moiety to the oligomeric compound either directly or through the cleavable moiety. In certain embodiments, the conjugate linker comprises groups selected from alkyl, amino, oxo, amide, disulfide, polyethylene glycol, ether, thioether (—S—) and hydroxylamino (—O—N(H)—). In certain embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus linking group. In certain embodiments, the conjugate linker comprises at least one phosphodiester group. In certain embodiments, the conjugate linker includes at least one neutral linking group.

In certain embodiments, the conjugate linker is covalently attached to the oligomeric compound. In certain embodiments, the conjugate linker is covalently attached to the oligomeric compound and the branching group. In certain embodiments, the conjugate linker is covalently attached to the oligomeric compound and a tethered ligand. In certain embodiments, the conjugate linker is covalently attached to the cleavable moiety. In certain embodiments, the conjugate linker is covalently attached to the cleavable moiety and the branching group. In certain embodiments, the conjugate linker is covalently attached to the cleavable moiety and a tethered ligand. In certain embodiments, the conjugate linker includes one or more cleavable bonds. In certain embodiments, the conjugate group does not include a conjugate linker.

As used herein, "branching group" means a group of atoms having at least 3 positions that are capable of forming covalent linkages to two or more tether-ligands and the remainder of the conjugate group. In general a branching group provides a plurality of reactive sites for connecting tethered ligands to the oligomeric compound through the conjugate linker and/or the cleavable moiety. In certain embodiments, the branching group comprises groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, the branching group is covalently attached to the conjugate linker. In certain embodiments, the branching group is covalently attached to the cleavable moiety. In certain embodiments, the branching group is covalently attached to the conjugate linker and each of the tethered ligands. In certain embodiments, the branching group comprises one or more cleavable bond. In certain embodiments, the conjugate group does not include a branching group.

In certain embodiments, conjugate groups as provided herein include a cell-targeting moiety that has at least one tethered ligand. In certain embodiments, the cell-targeting moiety comprises two tethered ligands covalently attached to a branching group. In certain embodiments, the cell-targeting moiety comprises three tethered ligands covalently attached to a branching group.

As used herein, "tether" means a group of atoms that connect a ligand to the remainder of the conjugate group. In certain embodiments, each tether is a linear aliphatic group comprising one or more groups selected from alkyl, substituted alkyl, ether, thioether, disulfide, amino, oxo, amide, phosphodiester and polyethylene glycol groups in any combination. In certain embodiments, each tether is a linear aliphatic group comprising one or more groups selected from alkyl, ether, thioether, disulfide, amino, oxo, amide and polyethylene glycol groups in any combination. In certain embodiments, each tether is a linear aliphatic group comprising one or more groups selected from alkyl, substituted alkyl, phosphodiester, ether and amino, oxo, amide groups in any combination. In certain embodiments, each tether is a linear aliphatic group comprising one or more groups selected from alkyl, ether and amino, oxo, amide groups in any combination. In certain embodiments, each tether is a linear aliphatic group comprising one or more groups selected from alkyl, amino and oxo groups in any combination. In certain embodiments, each tether is a linear aliphatic group comprising one or more groups selected from alkyl and oxo groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, tethers include one or more cleavable bond. In certain embodiments, each tethered ligand is attached to a branching group. In certain embodiments, each tethered ligand is attached to a branching group through an amide group. In certain embodiments, each tethered ligand is attached to a branching group through an ether group. In certain embodiments, each tethered ligand is attached to a branching group through a phosphorus linking group or neutral linking group. In certain embodiments, each tethered ligand is attached to a branching group through a phosphodiester group. In certain embodiments, each tether is attached to a ligand through either an amide or an ether group. In certain embodiments, each tether is attached to a ligand through an ether group.

In certain embodiments, each tether comprises from about 8 to about 20 atoms in chain length between the ligand and the branching group. In certain embodiments, each tether comprises from about 10 to about 18 atoms in chain length between the ligand and the branching group. In certain embodiments, each tether comprises about 13 atoms in chain length.

In certain embodiments, the present disclosure provides ligands wherein each ligand is covalently attached to the remainder of the conjugate group through a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (Gal-NAc). In certain embodiments, the targeting moiety comprises 1 to 3 ligands. In certain embodiments, the targeting moiety comprises 3 ligands. In certain embodiments, the targeting moiety comprises 2 ligands. In certain embodiments, the targeting moiety comprises 1 ligand. In certain embodiments, the targeting moiety comprises 3 N-acetyl galactoseamine ligands. In certain embodiments, the targeting moiety comprises 2 N-acetyl galactoseamine ligands. In certain embodiments, the targeting moiety comprises 1 N-acetyl galactoseamine ligand.

In certain embodiments, each ligand is a carbohydrate, carbohydrate derivative, modified carbohydrate, multivalent carbohydrate cluster, polysaccharide, modified polysaccharide, or polysaccharide derivative. In certain embodiments, each ligand is an amino sugar or a thio sugar. For example, amino sugars may be selected from any number of compounds known in the art, for example glucosamine, sialic acid, α-D-galactosamine, N-acetylgalactosamine, 2-acetamido-2-deoxy-D-galactopyranose (GalNAc), 2-amino-3-O—[(R)-1-carboxyethyl]-2-deoxy-β-D-glucopyranose (β-muramic acid), 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from the group consisting of 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups as provided herein comprise a carbohydrate cluster. As used herein, "carbohydrate cluster" means a portion of a conjugate group wherein two or more carbohydrate residues are attached to a branching group through tether groups. (see, e.g., Maier et al., *Bioconjug. Chem.* 2003, 14, 18-29, which is incorporated herein by reference in its entirety, or Rensen et al., *J. Med. Chem.* 2004, 47, 5798-5808, for examples of carbohydrate conjugate clusters).

As used herein, "modified carbohydrate" means any carbohydrate having one or more chemical modifications relative to naturally occurring carbohydrates.

As used herein, "carbohydrate derivative" means any compound which may be synthesized using a carbohydrate as a starting material or intermediate.

As used herein, "carbohydrate" means a naturally occurring carbohydrate, a modified carbohydrate, or a carbohydrate derivative.

In certain embodiments, conjugate groups are provided wherein the cell-targeting moiety has the formula:

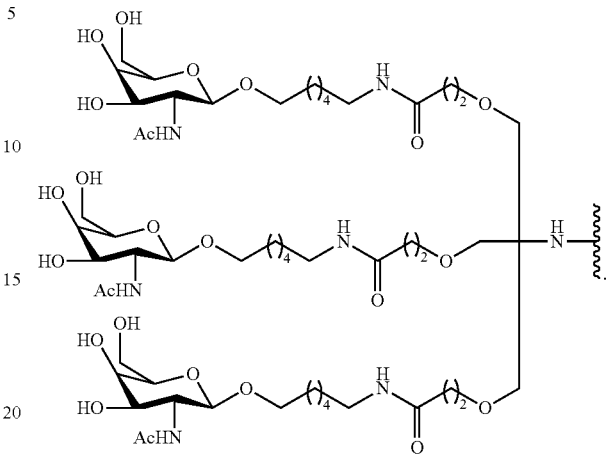

In certain embodiments, conjugate groups are provided wherein the cell-targeting moiety has the formula:

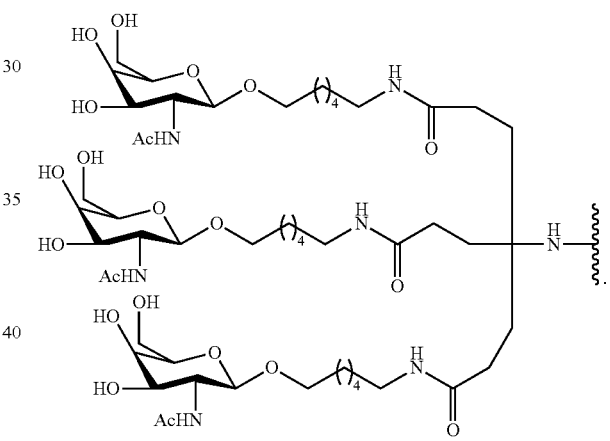

In certain embodiments, conjugate groups are provided wherein the cell-targeting moiety has the formula:

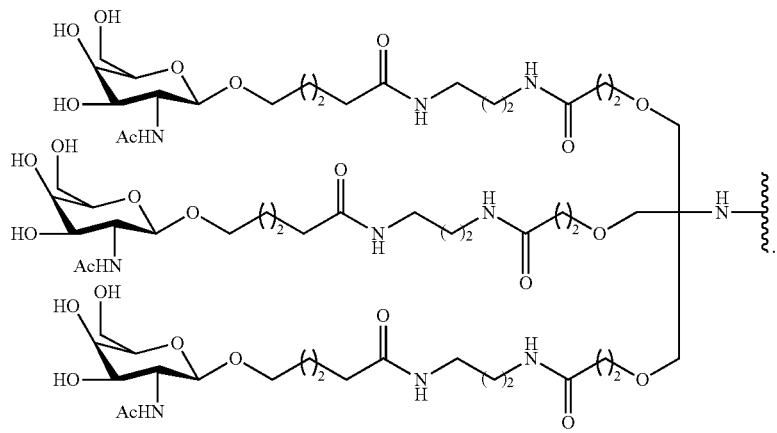

In certain embodiments, conjugate groups have the formula:

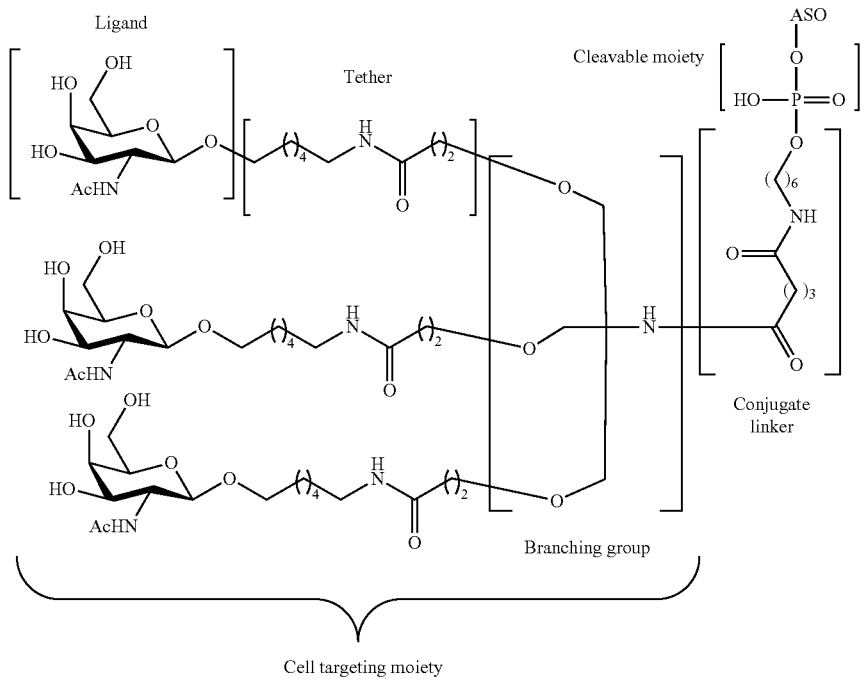

Representative United States patents, United States patent application publications, and international patent application publications that teach the preparation of certain of the above noted conjugates, conjugated oligomeric compounds such as antisense compounds, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, U.S. 2006/0148740, U.S. 2011/0123520, WO 2013/033230 and WO 2012/037254, each of which is incorporated by reference herein in its entirety.

Representative publications that teach the preparation of certain of the above noted conjugates, conjugated oligomeric compounds such as antisense compounds, tethers, conjugate linkers, branching groups, ligands, cleavable moieties as well as other modifications include without limitation, Biessen et al., *J. Med. Chem.* 1995, 38, 1846-1852; Biessen et al., *J. Med. Chem.*, 1995, 38, 1538-1546, Lee et al., *Bioorg. Med. Chem.* 2011, 19, 2494-2500; Rensen et al., *J. Biol. Chem.* 2001, 276(40), 37577-37584; Rensen et al., *J. Med. Chem.* 2004, 47, 5798-5808, Sliedregt et al., *J. Med. Chem.* 1999, 42, 609-618, and Valentijn et al., *Tetrahedron* 1997, 53(2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, *Carbohydr Res.* 1978, 67, 509-514; Connolly et al., *J. Biol. Chem.* 1982, 257, 939-945; Pavia et al., *Int. J. Pep. Protein Res.* 1983, 22, 539-548; Lee et al., *Biochem* 1984, 23, 4255-4261; Lee et al., *Glycoconjugate J.* 1987, 4, 317-328; Toyokuni et al., *Tetrahedron Lett.* 1990, 31, 2673-2676; Biessen et al., *J. Med. Chem.* 1995, 38, 1538-1546; Valentijn et al., *Tetrahedron* 1997, 53, 759-770; Kim et al., *Tetrahedron Lett.* 1997, 38, 3487-3490; Lee et al., *Bioconjug. Chem.* 1997, 8, 762-765; Kato et al., *Glycobiol.* 2001, 11, 821-829; Rensen et al., *J. Biol. Chem.* 2001, 276, 37577-37584; Lee et al., *Methods Enzymol.* 2003, 362, 38-43; Westerlind et al., *Glycoconj. J.* 2004, 21, 227-241; Lee et al., *Bioorg. Med. Chem. Lett.* 2006, 16(19), 5132-5135; Maierhofer et al., *Bioorg. Med. Chem.* 2007, 15, 7661-7676; Khorev et al., *Bioorg. Med. Chem.* 2008, 16, 5216-5231; Lee et al., *Bioorg. Med. Chem.* 2011, 19, 2494-2500; Kornilova et al., *Analyt. Biochem.* 2012, 425, 43-46; Pujol et al., *Angew. Chemie. Int. Ed. Engl.* 2012, 51, 7445-7448; Biessen et al., *J. Med. Chem.* 1995, 38, 1846-1852; Sliedregt et al., *J. Med. Chem.* 1999, 42, 609-618; Rensen et al., *J. Med. Chem.* 2004, 47, 5798-5808; Rensen et al., *Arterioscler. Thromb. Vasc. Biol.* 2006, 26, 169-175; van Rossenberg et al., *Gene Ther.* 2004, 11, 457-464; Sato et al., *J. Am. Chem. Soc.* 2004, 126, 14013-14022; Lee et al., *J. Org. Chem.* 2012, 77, 7564-7571; Biessen et al., *FASEB J.* 2000, 14, 1784-1792; Rajur et al., *Bioconjug. Chem.* 1997, 8, 935-940; Duff et al., *Methods Enzymol.* 2000, 313, 297-321; Maier et al., *Bioconjug. Chem.* 2003, 14, 18-29; Jayaprakash et al., *Org. Lett.* 2010, 12, 5410-5413; Manoharan, *Antisense Nucleic Acid Drug. Dev.* 2002, 12, 103-128; Merwin et al., *Bioconjug. Chem.* 1994, 5, 612-620; Tomiya et al., *Bioorg. Med. Chem.* 2013, 21, 5275-5281; International applications WO 1998/013381; WO 2011/038356; WO 1997/046098; WO 2008/098788; WO 2004/101619; WO 2012/037254; WO 2011/120053; WO 2011/100131; WO 2011/163121; WO 2012/177947; WO 2013/033230; WO 2013/075035; WO 2012/083185; WO 2012/083046; WO 2009/082607; WO 2009/134487; WO 2010/144740; WO 2010/148013; WO 1997/020563; WO 2010/088537; WO 2002/043771; WO 2010/129709; WO 2012/

068187; WO 2009/126933; WO 2004/024757; WO 2010/054406; WO 2012/089352; WO 2012/089602; WO 2013/166121; WO 2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications U.S. 2011/0097264; U.S. 2011/0097265; U.S. 2013/0004427; U.S. 2005/0164235; U.S. 2006/0148740; U.S. 2008/0281044; U.S. 2010/0240730; U.S. 2003/0119724; U.S. 2006/0183886; U.S. 2008/0206869; U.S. 2011/0269814; U.S. 2009/0286973; U.S. 2011/0207799; U.S. 2012/0136042; U.S. 2012/0165393; U.S. 2008/0281041; U.S. 2009/0203135; U.S. 2012/0035115; U.S. 2012/0095075; U.S. 2012/0101148; U.S. 2012/0128760; U.S. 2012/0157509; U.S. 2012/0230938; U.S. 2013/0109817; U.S. 2013/0121954; U.S. 2013/0178512; U.S. 2013/0236968; U.S. 2011/0123520; U.S. 2003/0077829; U.S. 2008/0108801; and U.S. 2009/0203132; each of which is incorporated by reference in its entirety.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

B. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

i. Certain Antisense Activities and Mechanisms

Antisense mechanisms include any mechanism involving the hybridization of an oligomeric compound with a target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

One type of antisense mechanism involving degradation of target RNA is RNase H mediated antisense. RNase H is a cellular endonuclease which cleaves the RNA strand of an RNA:DNA duplex wherein the DNA strand may comprise modified nucleosides at one or more positions. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression. In certain embodiments, the invention provides antisense compounds that are sufficiently "DNA-like" to elicit RNase H activity. Such DNA-like antisense compounds include, but are not limited to gapmers. In certain embodiments, such gapmers comprise 2'-β-D-ribofuranose nucleosides in the gap and modified nucleosides comprising at least modified sugar moieties in the wings.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of potency divided by measure of toxicity).

ii. Selective Antisense Compounds

In certain embodiments, antisense compounds provided herein are selective for a target relative to a non-target nucleic acid. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNase H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

a. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

1. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{rd}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

2. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleic acid is at positions 1, 2, 3, or 4 of the antisense compounds from the 5'-end of the wing region. In certain embodiments, a mismatch relative to the target nucleic acid is at positions 4, 3, 2, or 1 of the antisense compounds from the 3'-end of the wing region.

3. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

ABCXXXXXXXXXC'B'A';
ABCXXXXXXX(X/C')(X/B')(X/A');
(X/A)(X/B)(X/C)XXXXXXXXC'B'A' where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

4. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

C. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

i. Single-Nucleotide Polymorphism

Embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Feng et al., *Gene* 2006, 371(1), 68-74); the PrP gene encoding prion protein involved in Creutzfeldt-Jakob disease and in fatal familial insomnia (Chen et al., *Nat. Med.* 1997, 3, 1009-1015); GFAP gene encoding glial fibrillary acidic protein involved in Alexander disease (Hagemann et al., *J. Neurosci.* 2006, 26(43), 11162-11173); alpha-synuclein gene encoding alpha-synuclein protein involved in Parkinson's disease (Dawson et al., *J. Clin. Invest.* 2003, 111(2), 145-151); SOD-1 gene encoding the SOD-1 protein involved in amyotrophic lateral sclerosis (Bruijn et al., *Science* 1998, 281 (5384), 1851-1854); atrophin-1 gene encoding atrophin-1 protein involved in dentato-rubral and pallido-luysian atrophy (DRPA) (Margolis et al., Trends Mol. Med. 2001, 7, 479-482); SCA1 gene encoding ataxin-1 protein involved in spino-cerebellar ataxia-1 (SCA1) (Sen et al., Protein Sci. 2003, 12(5), 953-962); PLP gene encoding proteolipid protein involved in Pelizaeus-Merzbacher disease (Gow et al., Neuromolecular Med. 2003, 4, 73-94); DYT1 gene encoding torsinA protein involved in Torsion dystonia (Shashidharan et al., Brain Res. 2000, 877(2), 379-381); and alpha-B crystalline gene encoding alpha-B crystalline protein involved in protein aggregation diseases, including cardiomyopathy (Rajasekaran et al., Cell 2007, 130, 427-439); alpha1-antitrypsin gene encoding alpha1-antitrypsin protein involved in chronic obstructive pulmonary disease (COPD), liver disease and hepatocellular carcinoma (Carrell et al., N. Engl. J. Med. 2002, 346, 45-53); Ltk gene encoding leukocyte tyrosine kinase protein involved in systemic lupus erythematosus (Li et al., Hum. Mol. Gen. 2004, 13(2), 171-179); PCSK9 gene encoding PCSK9 protein involved in hypercholesterolemia (Abifadel et al., Hum. Mutat. 2009, 30(4), 520-529); prolactin receptor gene encoding prolactin receptor protein involved in breast tumors (Bogorad et al., Proc. Natl. Acad. Sci. U.S.A. 2008, 105(38), 14533-14538); CCL5 gene encoding the chemokine CCL5 involved in COPD and asthma (Hizawa et al., Eur. Respir. J. 2008, 32, 372-378); PTPN22 gene encoding PTPN22 protein involved in Type 1 diabetes, Rheumatoid arthritis, Graves disease, and SLE (Yu et al., Proc. Natl. Acad. Sci. U.S.A. 2007, 104, 19767-19772); androgen receptor gene encoding the androgen receptor protein involved in spinal and bulbar muscular atrophy or Kennedy's disease (Palazzolo et al., J. Steroid Biochem. Mol. Biol. 2008, 108(3-5), 245-253); CHMP4B gene encoding chromatin modifying protein-4B involved in progressive childhood posterior subcapsular cataracts (Shiels et al., Am. J. Hum. Genet. 2007, 81(3), 596-606); FXR/NR1H4 gene encoding Farnesoid X receptor protein involved in cholesterol gallstone disease, arthrosclerosis and diabetes (Marzolini et al., Mol. Endocrinol. 2007, 21(8), 1769-1780); ABCA1 gene encoding ABCA1 protein involved in cardiovascular disease (Mantaring et al., Transl. Res. 2007, 149(4), 205-210); CaSR gene encoding the calcium sensing receptor protein involved in primary hypercalciuria (Vezzoli et al., Kidney Int. 2007, 71, 1155-1162); alpha-globin gene encoding alpha-globin protein involved in alpha-thallasemia (De Gobbi et al., Science 2006, 312 (5777), 1215-1217); httlpr gene encoding HTTLPR protein involved in obsessive compulsive disorder (Xian-Zhang et al., Am. J. Hum. Genet. 2006, 78(5), 815-826); AVP gene encoding arginine vasopressin protein in stress-related disorders such as anxiety disorders and comorbid depression (Landgraf, CNS Neurol. Disord. Drug Targets 2006, 5(2), 167-179); GNAS gene encoding G proteins involved in congenital visual defects, hypertension, metabolic syndrome (Weinstein et al., Trends Pharmacol. Sci. 2006, 27(5), 260-266); APAF1 gene encoding APAF1 protein involved in a predisposition to major depression (Harlan et al., Mol. Psychiatry 2006, 11(1), 76-85); TGF-beta1 gene encoding TGF-beta1 protein involved in breast cancer and prostate cancer (Ewart-Toland et al., Cancer Epidemiol. Biomarkers Prev. 2004, 13(5), 759-764); AChR gene encoding acetylcholine protein involved in congenital myasthenic syndrome (Webster et al., Neurology 2004, 62(7), 1090-1096); P2Y12 gene encoding adenosine diphosphate (ADP) receptor protein involved in risk of peripheral arterial disease (Fontana et al., Circulation 2003, 108, 2971-2973); LQT1 gene encoding LQT1 protein involved in atrial fibrillation (Lai et al., Cardiology 2003, 100, 109-113); RET protooncogene encoding RET protein involved in sporadic pheochromocytoma (McWhinney et al., J. Clin. Endocrinol. Metab. 2003, 88(10), 4911-4916); filamin A gene encoding filamin A protein involved in various congenital malformations (Robertson et al., Nat. Genet. 2003, 33(4), 487-491); TARDBP gene encoding TDP-43 protein involved in amyotrophic lateral sclerosis (Kabashi et al., Hum. Mol. Genet. 2010, 19(4), 671-683); SCA3 gene encoding ataxin-3 protein involved in Machado-Joseph disease (Alves et al., PLoS One 2008, 3(10), e3341); SCA7 gene encoding ataxin-7 protein involved in spino-cerebellar ataxia-7 (Scholefield et al., PLoS One 2009, 4(9), e7232); and HTT gene encoding huntingtin protein involved in Huntington's disease (Persichetti et al., Neurobiol. Dis. 1996, 3(3), 183-190); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Daiger et al., Adv. Exp. Med. Biol. 2008, 613, 203-209)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congential myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

a. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 2.

Table 3 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a T at SNP position rs6446723.

TABLE 3

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | C |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C | ii. Single-Stranded RNAi Compounds

In certain embodiments, oligomeric compounds as provided herein are particularly suited for use as single-stranded antisense compounds. In certain such embodiments, such oligomeric compounds are single-stranded RNAi (ssRNA) compounds. In certain embodiments, such oligomeric compounds are ssRNA compounds or microRNA mimics. In certain embodiments, ssRNA compounds comprise a 5'-stabilized nucleoside such as a 5'-terminal nucleosides described herein that provide enhanced nuclease resistance to such ssRNA compounds. Certain such 5'-terminal nucleosides are disclosed having a 5'-phosphate group wherein the 5'-nucleoside is modified to provide the enhanced stability. Certain such 5'-terminal nucleosides are disclosed wherein a 5'-phosphorus moiety provides the enhanced stability. Certain such 5'-terminal nucleosides are disclosed wherein a 5'-phosphorus moiety in combination with the modified 5'-nucleoside provides the enhanced stability. In certain embodiments, the 5'-terminal nucleoside provides enhanced RISC loading. In certain embodiments, the 3'-terminal nucleoside(s) is also selected to provide enhanced stability.

In certain instances, a single-stranded oligomeric compound comprising a 5'-phosphorous moiety is desired. For example, in certain embodiments, such 5'-phosphorous moiety is necessary or useful for RNAi compounds, particularly, ssRNA compounds. In such instances, it is further desirable to stabilize the phosphorous moiety against degradation or de-phosphorylation, which may inactivate the compound. Further, it is desirable to stabilize the entire 5'-nucleoside from degradation, which could also inactivate the compound. Thus, in certain embodiments, oligonucleotides in which both the 5'-phosphorous moiety and the 5'-nucleoside have been stabilized are desired. In certain embodiments, modified nucleosides are disclosed that may be placed at the 5'-end of an oligomeric compound, resulting in stabilized phosphorous and or stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligomeric compound. Certain 5'-stabilized nucleosides comprising a 5'-phosphate, 5'-phosphorus moiety, modified 5'-nucleoside or combinations thereof have been previously disclosed (see U.S. published applications U.S. 2013/033961 and U.S. 2013/0084576).

In certain embodiments, ssRNA oligomeric compounds comprise at least one modification at or between positions 6, 7 and 8 of the oligomeric compound (from the 5'-end) in addition to a 5'-terminal stabilizing nucleoside as described herein. Modification at or between positions 6, 7 and 8 is expected to alleviate distortion at position 6 which was observed from crystal structure data of an ssRNA Ago-2 complex. Chemical modifications in and or near this observed distortion is expected to improve one or more properties of the ssRNA oligomeric compound. Such properties, include, but are not limited to pharmakodynamic, pharmacokinetic, binding, absorption, cellular distribution, cellular uptake, charge and clearance. In certain embodiments, it is expected that chemical modification at or between positions 6, 7 and 8 will improve the loading of the ssRNA oligomeric compounds provided herein to Ago-2 protein and therefore improve slicer activity of the ssRNA oligomeric compound. Although certain oligomeric compounds as provided herein have particular use as single-stranded compounds, such compounds may also be paired with a second strand to create a double-stranded oligomeric compound.

In certain embodiments, oligomeric compounds as provided herein bind and/or activate one or more nucleases. In certain embodiments, such binding and/or activation ultimately results in antisense activity. In certain embodiments, an oligomeric compound of the invention interacts with a target nucleic acid and with a nuclease, resulting in activation of the nuclease and cleavage of the target nucleic acid. In certain embodiments, an oligomeric compound of the invention interacts with a target nucleic acid and with a nuclease, resulting in activation of the nuclease and inactivation of the target nucleic acid. In certain embodiments, an oligomeric compound of the invention forms a duplex with a target nucleic acid and that duplex activates a nuclease, resulting in cleavage and/or inactivation of one or both of the oligomeric compound and the target nucleic acid. In certain embodiments, an oligomeric compound of the invention binds and/or activates a nuclease and the bound and/or activated nuclease cleaves or inactivates a target nucleic acid. Nucleases include, but are not limited to, ribonucleases (nucleases that specifically cleave ribonucleotides), double-strand nucleases (nucleases that specifically cleave one or both strands of a double-stranded duplex), and double-strand ribonucleases. For example, nucleases include, but are not limited to RNase H, an argonaute protein (including, but not limited to Ago2), and dicer.

In certain embodiments, oligomeric compounds as provided herein interact with an argonaute protein (Ago). In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain embodiments, such oligomeric compounds comprise a modified 5'-phosphate group. In certain embodiments, the invention provides methods of modulating the expression or amount of a target nucleic acid in a cell comprising contacting the cell with an oligomeric compound capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiment the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, oligomeric compounds as provided herein interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. Incertain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one strand of a dicer duplex is an antisense oligomeric compound and the other strand is its sense complement.

In certain embodiments, the dicer duplex comprises a 3'-overhang at one or both ends. In certain embodiments, such overhangs are additional nucleosides. In certain embodiments, the dicer duplex comprises a 3' overhang on the sense oligonucleotide and not on the antisense oligonucleotide. In certain embodiments, the dicer duplex comprises a 3' overhang on the antisense oligonucleotide and not on the sense oligonucleotide. In certain embodiments, 3' overhangs of a dicer duplex comprise 1-4 nucleosides. In certain embodiments, such overhangs comprise two nucleosides. In certain embodiments, the nucleosides in the 3'-overhangs comprise purine nucleobases. In certain embodiments, the nucleosides in the 3' overhangs comprise adenine nucleobases. In certain embodiments, the nucleosides in the 3' overhangs comprise pyrimidines. In certain embodiments, dicer duplexes comprising 3'-purine overhangs are more active as antisense compounds than dicer duplexes comprising 3' pyrimidine overhangs. In certain embodiments, oligomeric compounds of a dicer duplex comprise one or more 3' deoxy nucleosides. In certain such embodiments, the 3' deoxy nucleosides are dT nucleosides.

In certain embodiments, the 5' end of each strand of a dicer duplex comprises a phosphorus moiety. In certain embodiments the antisense strand of a dicer duplex comprises a phosphorus moiety and the sense strand of the dicer duplex does not comprise a phosphorus moiety. In certain embodiments the sense strand of a dicer duplex comprises a phosphorus moiety and the antisense strand of the dicer duplex does not comprise a phosphorus moiety. In certain embodiments, a dicer duplex does not comprise a phosphorus moiety at the 3' end. In certain embodiments, a dicer duplex is cleaved by dicer. In such embodiments, dicer duplexes do not comprise 2'-OMe modifications on the nucleosides at the cleavage site. In certain embodiments, such cleavage site nucleosides are RNA.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

a. Dicer

In certain embodiments, oligomeric compounds as provided herein interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds. In certain embodiments, oligomeric compounds that interact with dicer are single-stranded RNAi compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one strand of a dicer duplex is an antisense oligomeric compound and the other strand is its sense complement.

In certain embodiments, the invention provides single-stranded oligomeric compounds that interact with dicer. In certain embodiments, such single-stranded dicer compounds comprise a 5'-stabilized nucleoside. In certain embodiments, single-stranded dicer compounds do not comprise a phosphorous moiety at the 3'-end. In certain embodiments, such single-stranded dicer compounds may comprise a 3'-overhangs. In certain embodiments, such 3'-overhangs are additional nucleosides. In certain embodiments, such 3'-overhangs comprise 1-4 additional nucleosides that are not complementary to a target nucleic acid and/or are differently modified from the adjacent 3' nucleoside of the oligomeric compound. In certain embodiments, a single-stranded oligomeric compound comprises an antisense oligonucleotide having two 3'-end overhang nucleosides wherein the overhang nucleosides are adenine or modified adenine nucleosides. In certain embodiments, single stranded oligomeric compounds that interact with dicer comprise a 5'-stabilized nucleoside.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

b. Ago

In certain embodiments, oligomeric compounds as provided herein interact with Ago. In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain such embodiments, the Ago is in a cell. In certain such embodiments, the cell is in an animal.

E. CERTAIN methods/uses

In certain embodiments, the present invention provides compounds and methods for reducing the amount or activity of a target nucleic acid. In certain embodiments, the invention provides antisense compounds and methods. In certain embodiments, the invention provides antisense compounds and methods based on activation of RNase H. In certain embodiments, the invention provides RNAi compounds and methods.

In certain instances it is desirable to use an antisense compound that functions at least in part through RISC. In certain such instances unmodified RNA, whether single-stranded or double stranded is not suitable. Single-stranded RNA is relatively unstable and double-stranded RNA does not easily enter cells. The challenge has been to identify modifications and motifs that provide desirable properties, such as improved stability, without interfering with (and possibly even improving upon) the antisense activity of RNA through RNAi.

In certain embodiments, the present invention provides oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at to 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif of the present invention, may comprise another motif of modifications or may be unmodified.

It has been shown that in certain circumstances for single-stranded RNA comprising a 5'-phosphate group has RNAi activity if but has much less RNAi activity if it lacks such 5'-phosphate group. The present inventors have recognized that in certain circumstances unmodified 5'-phosphate groups may be unstable (either chemically or enzymatically). Accordingly, in certain circumstances, it is desirable to modify the oligonucleotide to stabilize the 5'-phosphate. In certain embodiments, this is achieved by modifying the phosphate group (phosphorus moiety). In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, oligonucleotides are provided comprising a phosphate-stabilizing modification and a motif described herein. In certain embodiments, such oligonucleotides are useful as single-stranded RNAi compounds (ssRNA) having desirable properties. In certain embodiments, such oligonucleotides may be paired with a second strand to form a double-stranded RNAi compound. In such embodiments, the second strand may comprise a motif of the present invention, may comprise another motif of modifications or may be unmodified RNA.

The target for such antisense compounds comprising a motif and/or 5'-phosphate stabilizing modification of the present invention can be any naturally occurring nucleic acid. In certain embodiments, the target is selected from: pre-mRNA, mRNA, non-coding RNA, small non-coding RNA, pd-RNA, and microRNA. In embodiments, in which a target nucleic acid is a pre-RNA or a mRNA, the target may be the same as that of a naturally occurring micro-RNA (i.e., the oligonucleotide may be a microRNA mimic). In such embodiments, there may be more than one target mRNA.

In certain embodiments, the invention provides compounds and methods for antisense activity in a cell. In certain embodiments, the cell is in an animal. In certain embodiments, the animal is a human. In certain embodiments, the invention provides methods of administering a compound of the present invention to an animal to modulate the amount or activity or function of one or more target nucleic acid.

F. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M $NH_4OAc$ with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., *J. Biol. Chem.* 1991, 266(27), 18162-18171. Results obtained with HPLC-purified material are generally similar to those obtained with non-HPLC purified material.

Example 4

Synthesis of Oligomeric Compounds using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments Involving Treatment of Cells with Oligomeric Compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-time Quantitative PCR Analysis of target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9

Design of Phenotypic Assays and in Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 3).

```
Forward primer:
                                     (SEQ ID NO: 4)
AATGGCTAAGTGAAGATGACAATCAT Reverse primer:
                                     (SEQ ID NO: 5)
TGCACATATCATTACACCAGTTCGT
```

And the PCR Probe:
FAM-TTGCAGCAATTCACTGTAAAGCTG-GAAAGG-TAMRA (SEQ ID NO: 6), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 2

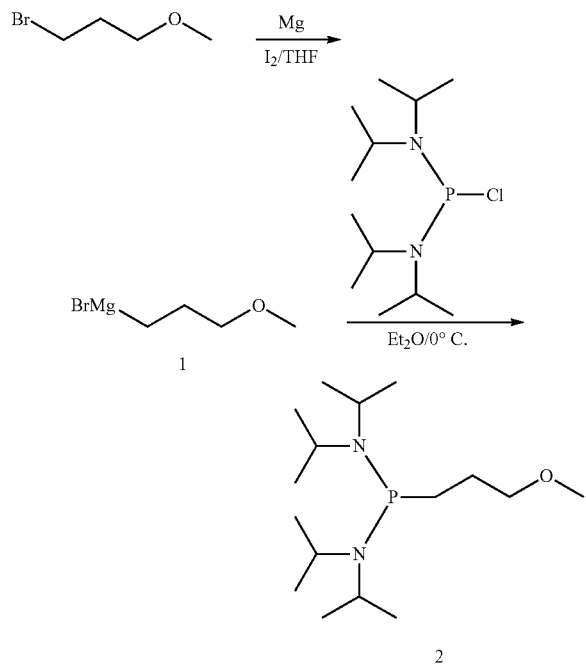

To a suspension of Mg/I$_2$ (297 mg, 8.25 mmol) in THF (16 mL) was added 1-bromo-3-methoxypropane (1.26 g, 8.25 mmol, commercially available) with stirring at room temperature for about 50 minutes to provide Compound 1. In a separate flask, bis(diisopropylaminochlorophos-phine (2.0 g, 7.50 mmol, commercially available) was dissolved in diethyl ether (125 mL) with cooling to 0° C. The solution of Compound 1 was cooled to about 0° C. and cannulated into the stirred solution of bis(diisopropylamino)chlorophosphine with the temperature of the reaction mixture maintained at about 0° C. The reaction was monitored by $^{31}$P NMR. After about 1 hour the reaction mixture was allowed to warm to room temperature and filtered. The filtrate was concentrated under reduced pressure and the residue washed with hexane. The remaining residue was dissolved in acetonitrile and extracted with hexane. The hexane layers were combined, dried over Na$_2$SO$_4$, filtered and concentrated under reduced pressure to provide Compound 2 (1.7 g).

Reaction repeated starting with 22.0 g 1-bromo-3-methoxypropane to provide 22.5 g Compound 2 (76% yield). The structure of Compound 2 was confirmed by $^1$H NMR.

Example 14

Preparation of Methoxypropyl (MOP)-diisopropylaminophosphonamidite DMT-T, Compound 3

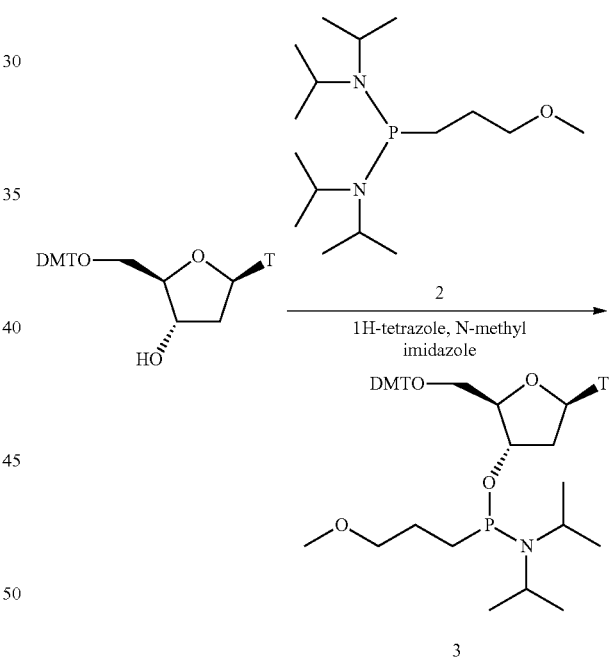

Dimethoxytrityl thymidine (3.0 g, 5.59 mmol, commercially available) and 1H-tetrazole (587 mg, 8.39 mmol) were dissolved in DMF (20 mL). N-methyl imidazole (116 mg, 1.40 mmol) and Compound 2 were added with stirring at room temperature for 1 hour at which time the reaction was complete by TLC. The reaction was diluted with ethyl acetate and quenched by addition of saturated NaHCO$_3$. The ethyl acetate layer was collected and dried over MgSO$_4$, filtered and concentrated under reduced pressure. The residue was purified by column chromatography (eluted with ethyl acetate/hexane 50/50 v/v) to provide Compound 3 (1.67 g, 78%). The structure of Compound 3 was confirmed by $^1$H NMR.

Example 15

Preparation of Protected MOP-phosphonate linked TT Dimer, Compound 4

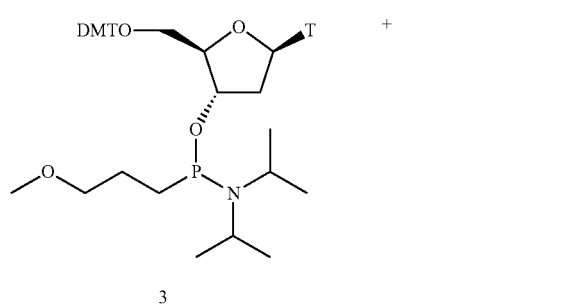

3

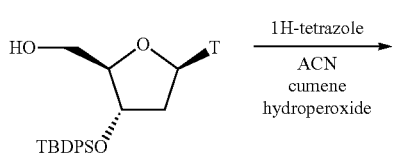

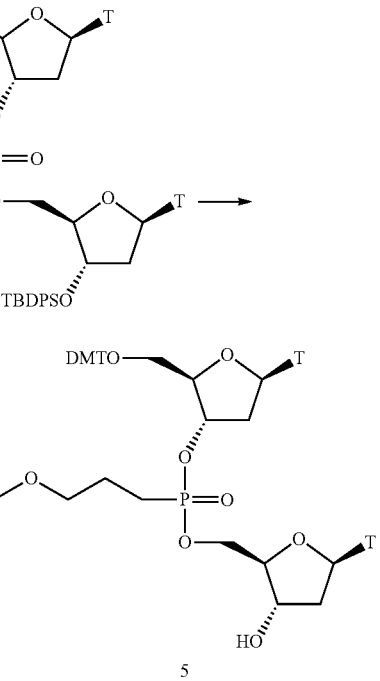

4

Dry 3'-O-t-butyldiphenylsilyl thymidine (400 mg, 0.832 mmol, commercially available) dissolved in ACN was cannulated into dry 1H-tetrazole (408 mg, 5.83 mmol) followed by Compound 3 (746 mg, 0.998 mmol) in ACN with stirring for 8 minutes. Cumene hydroperoxide (171 mg, 0.72 mL, 1.123 mmol) was added and the reaction was stirred for about 10 minutes. The reaction was quenched by addition of sodium bisulfite solution (1 g/mL) followed by extraction with ethyl acetate. Ethyl acetate layers were combined, dried over MgSO$_4$, filtered and concentrated under reduced pressure. The residue was purified by column chromatography to provide three fractions. The first fraction that eluted from the column (the fast fraction) was identified as the Rp isomer of Compound 4 (241 mg). The slower fractions were isolated and identified as the Sp isomer and the racemic mixture of Compound 4. The structure of Compound 4 was confirmed by $^1$H NMR.

Example 16

Preparation of 5'-ODMT MOP-phosphonate linked TT Dimer, Compound 5

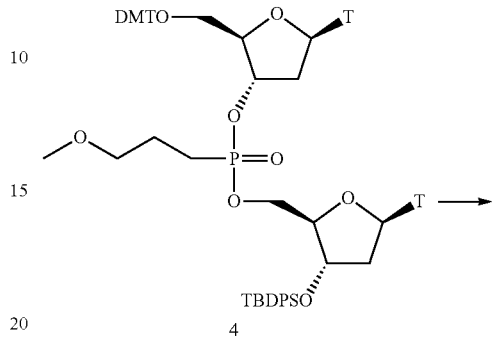

4

5

A solution of tetrabutylammonium fluoride (0.42 mL, 0.42 mmol, 1 N/THF) was added to a solution of Compound 4 (241 mg, 0.21 mmol) in THF (2 mL) with stirring for 2 hours. The reaction was diluted with water and extracted with ethyl acetate. The combined ethyl acetate layers were combined, dried over MgSO$_4$, filtered and concentrated under reduced pressure. The residue was purified by column chromatography (10% EtOH/ethyl acetate) to provide Compound 5 (146 mg, 76.8%).

Example 17

Preparation of 5'-ODMT-3'-phosphoramidite MOP-phosphonate linked TT dimer, Compound

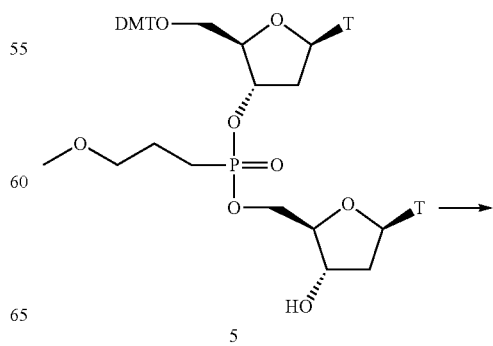

5

99

-continued

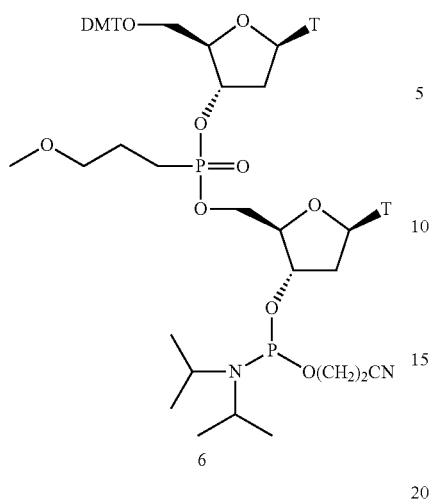

6

To a solution of Compound 5 in DMF (10 mL) was added 1H-tetrazole (127 mg, 1.82 mmol) followed by N-methyl imidazole (46 mg, 0.567 mmol) with stirring. 2-Cyanoethyl-N,N,N',N'-tetra-isopropylphosphorodiamidite (73 mg, 0.08 mL, 0.243 mmol) was added and the reaction mixture was stirred at room temperature for about 3 hours. The reaction was quenched by addition of saturated NaCl and extracted with ethyl acetate. The ethyl acetate layers were combined, dried over $Na_2SO_4$, filtered and concentrated under reduced pressure. The residue was purified by column chromatography (Biotage, 80% EtOAc/hexanes) to provide Compound 6 (90 mg).

Example 18

General Preparation of 5'-ODMT methoxypropyl-diisopropylaminophosphonamidite nucleoside, Compound 8

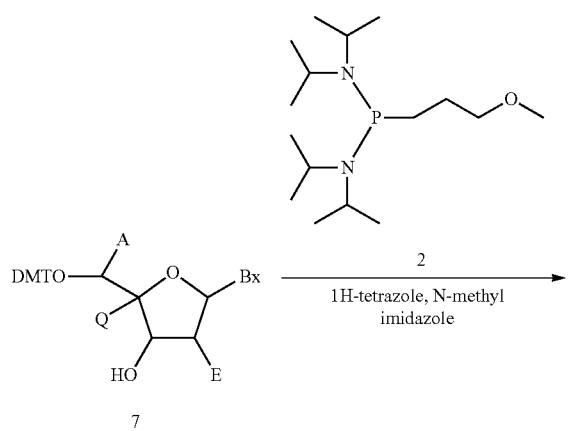

100

-continued

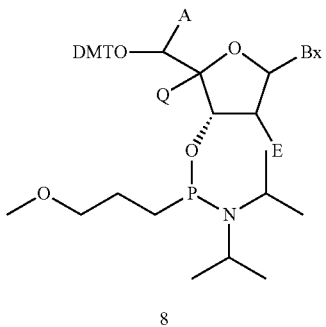

8

Following the procedures illustrated in Example 14 or optionally the procedures illustrated in Example 21, an optionally modified nucleoside having the formula of Compound 7 is converted to the methoxypropyl phosphonamidite having the formula of Compound 8. Many such optionally modified nucleosides represented by Compound 7 are disclosed herein and well known to the art skilled, many of which are commercially available. Included in Compound 7 are ribonucleosides and 2'-deoxyribonucleosides as well as optionally substituted analogs such as 2'-substituted nucleosides (A and Q are each H and E is a 2'-substituent group); 5'-substituted modified nucleosides (Q and E are H and A is a 5'-substituent group); 2',5'-substituted modified nucleosides (Q is H and E is a 2'-substituent group and A is a 5'-substituent group); and bicyclic nucleosides (A is H or an optional 5'-substituent group and Q and E together form a bridging group).

Modified nucleosides and or modified nucleosides that have been functionalized as methoxypropyl phosphonamidites can be incorporated into an oligomeric compound directly as the DMT phosphonamidite or as a DMT phosphonamidate dimer, prepared as per the procedures illustrated examples 15 to 17, following standard oligonucleotide synthesis protocols. Any nucleoside or modified nucleoside can be coupled to the DMT phosphonamidite to prepare the DMT phosphoramidite dimer such as the TT dimer illustrated in Example 17. The modified nucleoside can also have any heterocyclic base with uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine being preferred.

Example 19

General Preparation of Methoxypropyl Phosphonamidite Monomers Comprising a Sugar Surrogate Group, Preparation of F-HNA methoxypropyl phosphoramidite, Compound 10

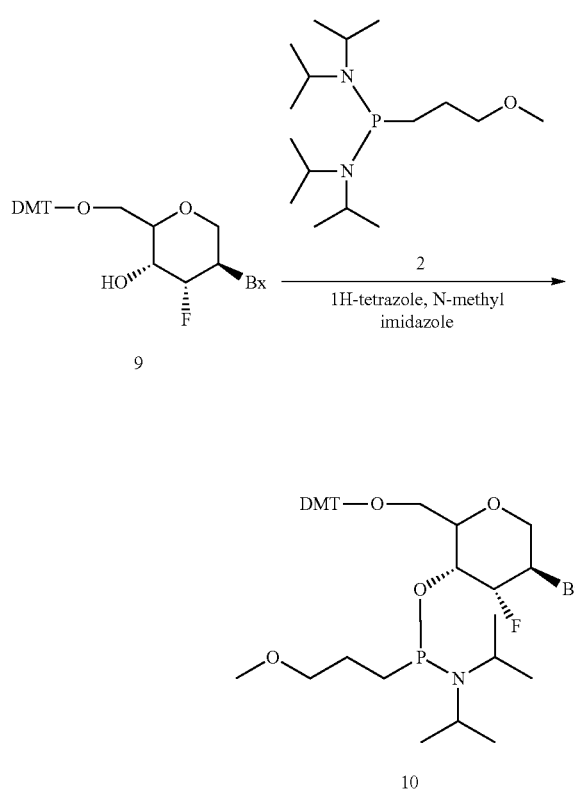

Following the procedures illustrated in Example 14 or optionally the procedures illustrated in Example 21, a DMT protected modified nucleoside comprising a sugar surrogate group having a free hydroxyl group (DMT-F-HNA, Formula 9 prepared as per U.S. Pat. No. 8,088,904) is converted to the methoxypropyl phosphoramidite of Formula 10. Such DMT protected modified nucleosides comprising a sugar surrogate group having a free hydroxyl group are disclosed herein and well known to the art skilled, many of which are commercially available.

Modified nucleosides comprising sugar surrogate groups that have been functionalized as methoxypropyl phosphoramidites can be incorporated into an oligomeric compound directly as the DMT phosphoramidite as per Formula 10 or as a DMT phosphoramidite dimer, prepared as per the procedures illustrated examples 15 to 17, following standard oligonucleotide synthesis protocols. Any nucleoside or modified nucleoside can be coupled to a DMT phosphoramidite comprising a sugar surrogate (such as Formula 10) to prepare a DMT phosphoramidite dimer such as illustrated in Example 17. The modified nucleoside can also have any heterocyclic base with uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine being preferred.

Example 20

Preparation of cEt Methoxypropyl Phosphonamidite, Compound 12

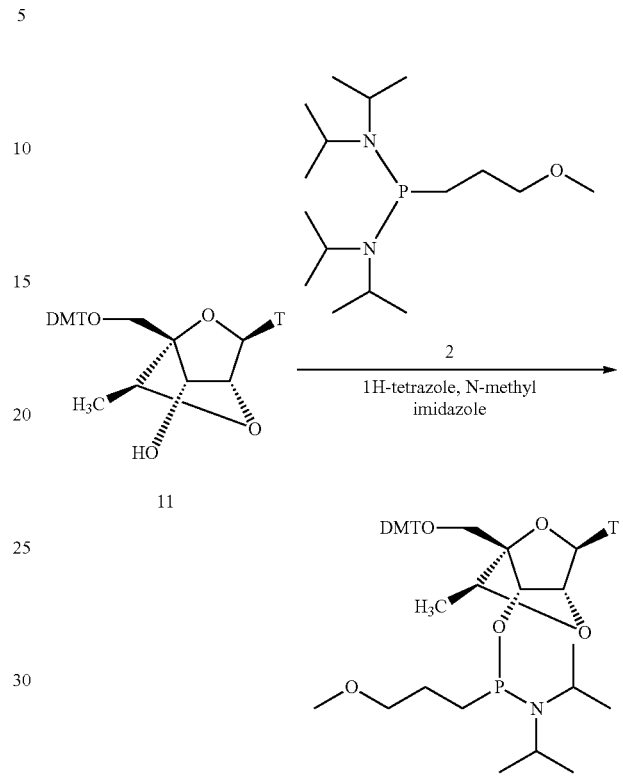

DMT cEt thymidine (Compound 11, prepared as per published literature procedures, 5.0 g, 8.43 mmol) and 1H-tetrazole (1.0 g, 14.3 mmol) were dried over phosphorus pentoxide for 4 hours and dissolved in DMF (20 mL) with stirring under nitrogen. N-methyl imidazole (350 mg, 4.26 mmol) and Compound 2 (7.0 g, 23.0 mmol) were added with stirring at room temperature for about 5 hours at which time the reaction was complete by TLC. The reaction was diluted with EtOAc (100 mL) and the organic layer was washed with half-saturated brine (200 mL), half saturated NaHCO₃ (2×200 mL), half saturated brine (1×200 mL), brine (1×100 mL), dried over MgSO4, filtered through a sintered glass funnel and concentrated under reduced pressure. Purify by biotage, 50 gram column pre-washed with 0.5% TEA in hexanes, then equilibrated in 2% EtOAc in hexanes. The crude material was loaded using ACN (~10 mL) and the column was washed with flash 3 CV of 2% EtOAc in hexanes followed by 20% EtOAc in hexanes over 5 CV and 80% EtOAc in hexanes. The fractions containing the desired compound were pooled and concentrated to give the final product was a white solid. The structure of Compound 12 was confirmed by ¹H NMR.

Example 21

General Procedure for Preparation of diisopropylamino-methoxypropyl phosphonate monomer subunits To a solution of 1H-tetrazole (1.5 eq), 1-methyl imidazole (0.4 eq) and a commercially available or synthesized monomer subunit such as a nucleoside, modified nucleoside or a nucleoside comprising a surrogate sugar group having a free hydroxyl group (5'-ODMT/or equivalent position, with optional base protection, 1.0 eq) dissolved in DMF (160 mL) is added dropwise a solution of Compound 2 (2.0 eq) dissolved in THF. The reaction is stirred at room temperature overnight and then the reaction was stopped by addition of Et₃N (0.5 mL) and then water (20 mL). The resulting milky solution is washed with hexane (3×100 mL) and the hexane layers were decanted. To the remaining aqueous layer containing an oil is added toluene/hexane (200 mL, 3/1, v/v) to obtained two layers.

DMF/water (20 mL, 3/2, v/v) is added with mixing and then the bottom DMF/water layer is removed in a separatory funnel. The organic layer is washed twice with additional DMF/water (50 mL, 3/2, v/v) followed by saturated NaHCO₃ (30 mL, Sat) and brine (30 mL). The organic layer is separated, dried over Na₂SO₄, filtered and evaporated to dryness.

The resulting colorless oil is purified using silica gel flash column chromatography eluted with ETOAc/hexane to provide the monomer subunit with the free hydroxyl group functionalized with the methoxypropyl phosphonate group, Compound 13:

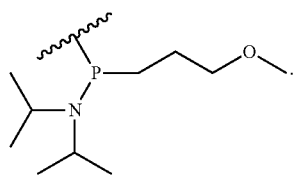

13

Example 22

Preparation of Compound 15

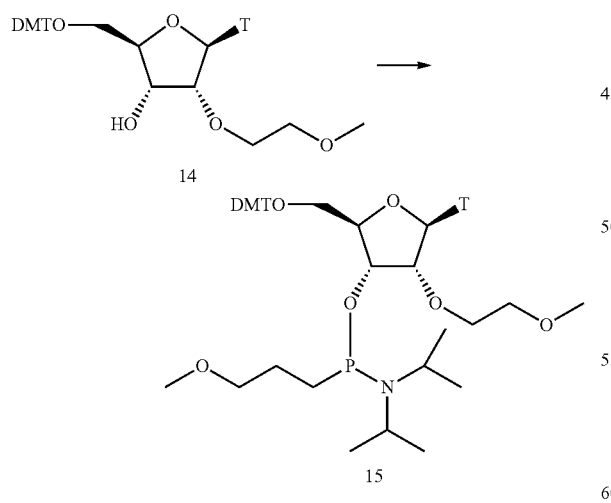

Compound 15 was prepared as per the procedure of Example 21 based on 1 eq., of Compound 14 (prepared as per published literature procedures, 10.0 g, 0.016 mol, 1.0 eq), Compound 2 (7.38 g, 0.024 mol, 2.0 eq), 1H-tetrazole (1.68 g, 0.024 mol, 1.5 eq), and 1-methyl imidazole (0.58 g, 0.007 mol, 0.4 eq). The resulting material was purified by passing through plug of silica gel eluted with ETOAc/Hexane (7/3, v/v) to afford 8.40 g of Compound 15 (63% yield). NMRs (¹H and ³¹P) were consistent Compound 15.

Example 23

Preparation of Compound 17

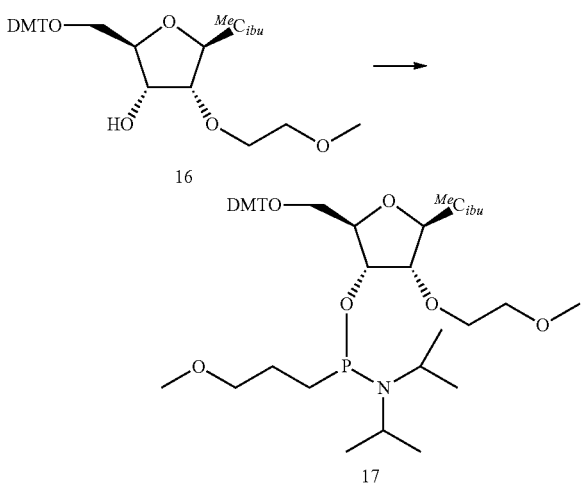

Compound 17 was prepared as per the procedure of Example 21 based on 1 eq., of Compound 16 (prepared as per published procedures, 10.0 g, 0.014 mol, 1.0 eq), Compound 2 (8.85 g, 0.029 mol, 2.0 eq), 1H-tetrazole (1.50 g, 0.021 mol, 1.5 eq), and 1-methyl imidazole (0.52 g, 0.006 mol, 0.4 eq). The resulting material was purified by passing through plug of silica gel eluted with ETOAc/hexane (7/3, v/v) to afford 7.70 g of Compound 17 (60% yield). NMRs (¹H and ³¹P) were consistent Compound 17.

Example 24

Preparation of Compound 19

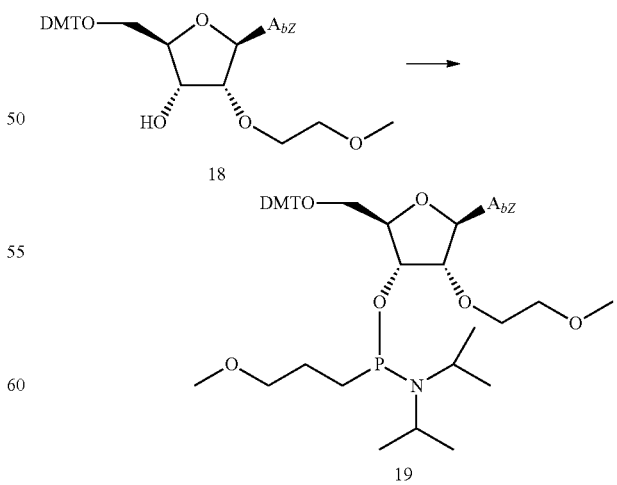

Compound 19 was prepared as per the procedure of Example 21 based on 1 eq., of Compound 18 (prepared as per published procedures, 10.0 g, 0.013 mol, 1.0 eq), Compound 2 (8.32 g, 0.027 mol, 2.0 eq), 1H-tetrazole (1.43 g, 0.020 mol, 1.5 eq), and 1-methyl imidazole (0.50 g, 0.006 mol, 0.4 eq). The resulting material was purified by passing through plug of silica gel eluted with ETOAc/hexane (7/3, v/v) to afford 3.51 g of Compound 19 (27% yield). NMRs ($^1$H and $^{31}$P) were consistent Compound 19.

Example 25

Preparation of Compound 21

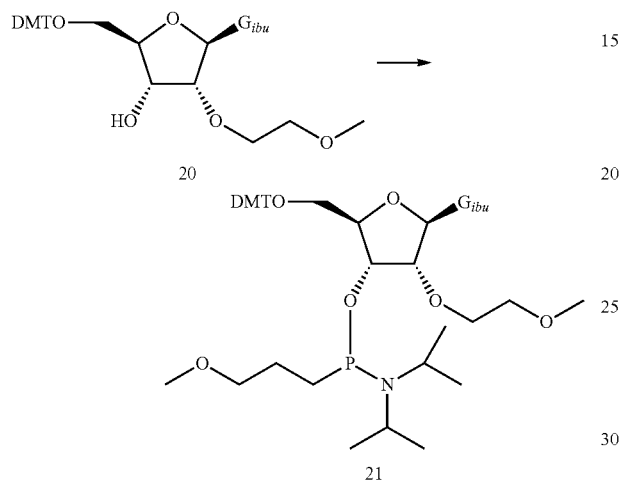

Compound 21 was prepared as per the procedure of Example 21 based on 1 eq., of Compound 20 (prepared as per published procedures, 10.0 g, 0.014 mol, 1.0 eq), Compound 2 (8.53 g, 0.028 mol, 2.0 eq), 1H-tetrazole (1.47 g, 0.021 mol, 1.5 eq), and 1-methyl imidazole (0.50 g, 0.006 mol, 0.4 eq). The resulting material was purified by passing through plug of silica gel eluted with ETOAc/hexane (7/3, v/v) to afford 9.65 g of Compound 21 (75% yield). NMRs ($^1$H and $^{31}$P) were consistent Compound 21.

Example 26

Preparation of Compound 23

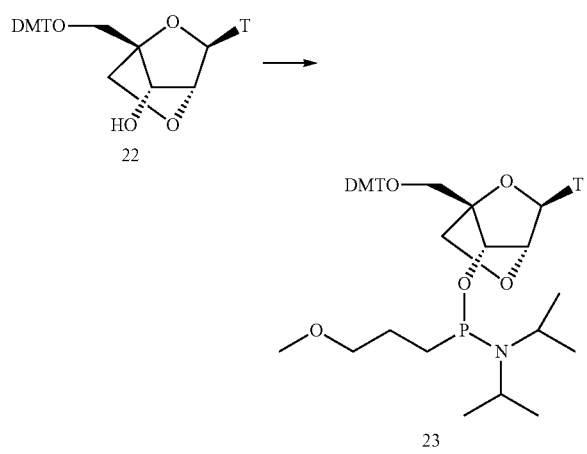

Compound 23 was prepared as per the procedure of Example 21 based on 1 eq., of Compound 22 (prepared as per published procedures, 3 g, 0.005 mol, 1.0 eq), Compound 2 (4.78 g, 0.015 mol, 3.0 eq), 1H-tetrazole (0.55 g, 0.007 mol, 1.5 eq), and 1-methyl imidazole (0.190 g, 0.002 mol, 0.4 eq). The resulting material was purified by passing through plug of silica gel eluted with ETOAc/hexane (7/3, v/v) to afford 2.7 g of Compound 23 (67% yield). NMRs ($^1$H and $^{31}$P) were consistent Compound 23.

Example 27

Preparation of Compound 25

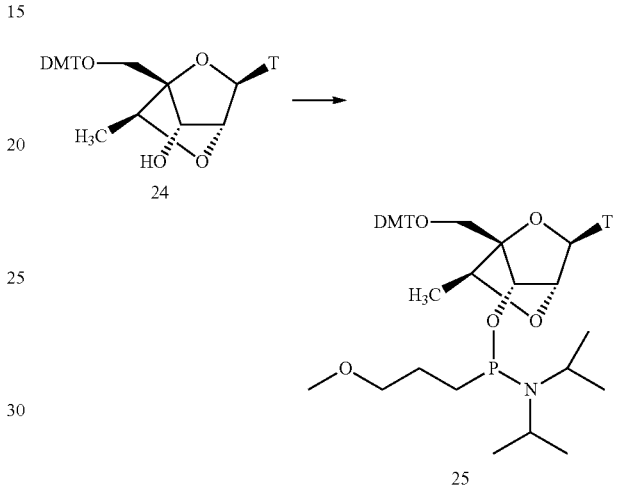

Compound 25 was prepared as per the procedure of Example 21 based on 1 eq., of Compound 24 (prepared as per published procedures, 10.0 g, 0.014 mol, 1.0 eq), Compound 2 (8.70 g, 0.029 mol, 2.0 eq), 1H-tetrazole (1.50 g, 0.021 mol, 1.5 eq), and 1-methyl imidazole (0.46 g, 0.006 mol, 0.4 eq). The resulting material was purified by passing through plug of silica gel eluted with ETOAc/hexane (7/3, v/v) to afford 11.13 g of Compound 25 (88% yield). NMRs ($^1$H and $^{31}$P) were consistent Compound 25.

Example 28

General Procedure for Synthesis of Oligomeric Compounds Comprising at Least One Methoxypropyl Phosphonate Internucleoside Linkage, Synthesis of Oligomeric Compounds ISIS-619442 to ISIS-619444

Oligomeric compounds were synthesized on a 2 µmol scale on an ABI 394 DNA/RNA synthesizer using MOE $^m$C$^{Bz}$ loaded primer support (loading: 215 µmol/g). Oligomeric compounds ISIS-619441 and ISIS-619442 were prepared using the thymidine methoxypropyl phosphoramidite monomer prepared as per the procedures illustrated in Example 14 and oligomeric compounds ISIS-619443 and ISIS-619444 were prepared using the thymidine methoxypropyl phosphoramidite dimer prepared as per the procedures illustrated in example 15 to 17. The other phosphoramidites (optionally protected: dA$^{bz}$, dG$^{DMF}$, d$^m$C$^{Bz}$, cEt A$^{Bz}$ and cEt $^m$C$^{Bz}$) were incorporated using standard solid-phase synthesis, i.e. 3% dichloroacetic acid in DCM for deblocking, 1 M 4,5-dicyanoimidazole 0.1 M N-methylimidazole in acetonitrile as activator, acetic acid in THF and 10%

1-methyl-imidazole in THF/pyridine for capping, 0.2 M phenylacetyl disulfide in pyridine:acetonitrile 1:1 (v:v) for thiolation and 10% tert-butyl hydroperoxide in acetonitrile for MOP oxidation. DNA and MOE amidites were dissolved to 0.1 M in acetonitrile while S-cEt amidites were dissolved to 0.2 M in acetonitrile:toluene 1:1 (v:v). DNA amidites were coupled for 2 times 4 min. while DNA MOP, MOE and S-cEt amidites were coupled for 2 times 6 min.

After synthesis was complete cyanoethyl groups were removed by treatment with trietylamine:acetonitrile 1:1 (v:v) for 25 min. The remaining protecting groups were cleaved in aq. conc. ammonia at room temperature for 6 h. The resulting oligomeric compounds were purified by strong anionic ion-exchange high performance liquid chromatography using a linear gradient of buffer A to B. Buffer A: 50 mM NaHCO$_3$; Buffer B: 50 mM NaHCO$_3$ 1.5 M NaBr, both buffers in acetonitrile:water 3:7 (v:v). Purified oligomeric compounds were desalted using a C18 reverse-phase cartridge. The identity of the oligomeric compounds was determined by electrospray ionization mass spectrometry.

| SEQ ID NO./ ISIS NO. | Composition (5' to 3') | Linkage/ isomer |
|---|---|---|
| 09/619441 | T$_e$A$_k$A$_k$ATT$_q$GT$^m$CAT$^m$CA$_k$$^m$C$_k$$^m$C$_e$ | MOP |
| 09/619442 | T$_e$A$_k$A$_k$AT$_q$TGT$^m$CAT$^m$CA$_k$$^m$C$_k$$^m$C$_e$ | MOP |
| 09/619443 | T$_e$A$_k$A$_k$AT$_{q(S)}$TGT$^m$CAT$^m$CA$_k$$^m$C$_k$$^m$C$_e$ | MOP/Sp |
| 09/619444 | T$_e$A$_k$A$_k$AT$_{q(R)}$TGT$^m$CAT$^m$CA$_k$$^m$C$_k$$^m$C$_e$ | MOP/Rp |

Between adjacent nucleosides subscript "q" indicates a methoxypropyl phosphonate modified internucleoside linkage (—P(CH$_3$O—(CH$_2$)$_3$—)(═O)—, MOP) between adjacent nucleosides and all other internucleoside linkages are phosphorothioate internucleoside linkages. Subscript "(R)" or "(S)" indicates the isomer of the internucleoside linkage as Rp or Sp respectively. Each nucleoside followed by a subscript "e" indicates a 2'-O-methoxyethyl (MOE) modified nucleoside and each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^m$C" is a 5-methyl cytosine modified nucleoside. Nucleosides followed by subscripts "e" or "k" are further illustrated below.

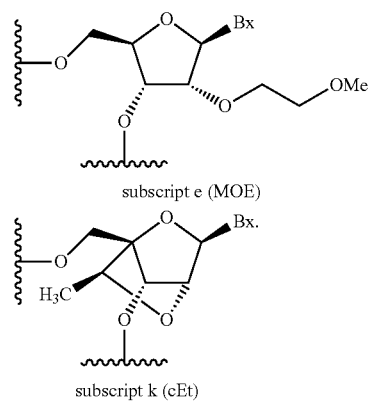

subscript e (MOE)

subscript k (cEt)

Example 29

Modified Methods for Deprotection and Cleavage of Oligonucleotides with Modified Internucleoside Linkages (synthesis of ISIS 736646)

The SRB-1 targeted oligonucleotide ISIS 736646 (see examples 34 and 35) was synthesized using standard methods on a 40 μM scale. The first base ($^m$C$_k$, 3'-end) was pre-loaded on VIMAD solid support via succinate at 326 mol/gram. For the modified methods non-standard protecting groups were used for particular amidites. The exocyclic amino groups of 2'-deoxy $^m$C and $^m$C$_k$ were protected with isobutyryl groups and the exocyclic amino group of 2'-deoxy G was protected with DMF.

| SEQ ID NO./ ISIS NO. | Composition (5' to 3') | Linkage |
|---|---|---|
| 12/736646 | T$_k$T$_k$$^m$C$_k$AGT$^m$CATGA$^m$CTT$_{kx}$$^m$C$_{kx}$$^m$C$_k$ | MP |
| MW 5638.325 (DMT on), MW 5335.325 (DMT off) | | |

Between adjacent nucleosides subscript "x" indicates a methyl phosphonate modified internucleoside linkage (—P(CH$_3$)(═O)—, MP) and all other internucleoside linkages are phosphorothioate internucleoside linkages. Each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^m$C" is a 5-methyl cytosine nucleoside.

400 mg fully protected oligo on VIMAD resin was placed in a glass pressure vial with a magnetic stir bar. Dry THF (5 mL) was added, and the mixture was allowed to stir and swell for 15 minutes. Ethylenediamine (EDA, 5 mL) was added via syringe with stirring at room temperature. The reaction was heated 55° C. with stirring in an oil bath for 15 minutes. The reaction was cooled in an ice bath and diluted with THF (5 mL). The reaction was centrifuged (3000 rpm, 5 minutes), and the solvent was removed via pipette. The residue was re-suspended in dry THF (7 mL) and was stirred vigorously for 5 minutes, followed by centrifugation and removal of solvent. The THF rinse process was repeated a third time. The pellet was suspended in 50% EtOH in H$_2$O (7 mL) with vigorous stirring (5 minutes). The spent resin was removed by filtration, and was rinsed with 50% EtOH (15 mL). The crude cleavage solution was diluted to a final volume of 25 mL. Quantification of the crude cleavage solution (UV, 260 nm) indicated 19.54 μmol recovery (crude, 50%).

The modified cleavage and deprotection methods are amenable to any of the modified internucleoside linkages, including those disclosed herein such as the methoxypropyl phosphonate modified internucleoside linkages (—P(CH$_3$O—(CH$_2$)$_3$—)(═O,S)—, MOP) and are merely exemplified for ISIS 736646.

Example 30

Thermal Stability Assay

A series of modified oligomeric compounds were evaluated in a thermal stability (T$_m$) assay.

A Cary 100 Bio spectrophotometer with the Cary Win UV Thermal program was used to measure absorbance vs. temperature. For the T$_m$ experiments, oligomeric compounds were prepared at a concentration of 8 μM in a buffer of 100 mM Na+, 10 mM phosphate and 0.1 mM EDTA (pH 7). The concentration of the oligonucleotides was determined at 85° C. The concentration of each oligomeric compound was 4 μM after mixing of equal volumes of test oligomeric compound and complimentary RNA strand. Oligomeric compounds were hybridized with the complimentary RNA strand by heating the duplex to 90° C. for 5 minutes followed by cooling to room temperature. Using the spectrophotometer, $T_m$ measurements were taken by heating the duplex solution at a rate of 0.5° C./min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The oligomeric compounds were hybridized to complementary RNA (ISIS 606581). The results are presented below.

| SEQ ID NO./ ISIS NO. | Composition (5' to 3') | Tm | ΔTm | Linkage/chemistry |
|---|---|---|---|---|
| 07/606581 | UCGAGAACAUCC | n/a | | PO/RNA complement |
| 08/606339 | GGATGTTCTCGA | 49.4 | std. | PO/DNA unmodified |
| 08/614338 | GGATGT$_x$TCTCGA | 47.5 | −1.9 | MP |
| 08/614362 | GGATGT$_{x(S)}$TCTCGA | 45.2 | −4.2 | MP(Sp) |
| 08/614361 | GGATGT$_{x(R)}$TCTCGA | 48.9 | −0.9 | MP(Rp) |
| 08/618681 | GGATGT$_q$TCTCGA | 48.7 | −0.7 | MOP |
| 08/619024 | GGATGT$_{q(S)}$TCTCGA | 44.8 | −4.6 | MOP(Sp) |
| 08/619025 | GGATGT$_{q(R)}$TCTCGA | 48.9 | −0.9 | MOP(Rp) |
| 08/606346 | GGATGT$_k$TCTCGA | 54.7 | 5.3 | PO/cEt |
| 08/614341 | GGATGT$_{kx}$TCTCGA | 53.5 | 4.1 | MP/cEt |
| 08/614365 | GGATGT$_{kx(S)}$TCTCGA | 50.2 | 0.8 | MP(Sp)/cEt |
| 08/614366 | GGATGT$_{kx(R)}$TCTCGA | 54.2 | 4.8 | MP(Rp)/cEt |
| 08/618684 | GGATGT$_{kq}$TCTCGA | 53.9 | 4.5 | MOP/cEt |
| 08/606349 | GGATGT$_k$T$_k$CTCGA | 62.3 | 6.5 | cEt (x2) |
| 08/614342 | GGATGT$_{kx}$T$_k$CTCGA | 59.6 | 5.1 | MP/cEt (x2) |
| 08/618685 | GGATGT$_{kq}$T$_k$CTCGA | 59.4 | 5.0 | MOP/cEt (x2) |

Between adjacent nucleosides subscript "x" indicates a methyl phosphonate modified internucleoside linkage (—P(CH$_3$)(=O)—, MP), subscript "q" indicates a methoxypropyl phosphonate modified internucleoside linkage (—P(CH$_3$O—(CH$_2$)$_3$—)(=O)—, MOP) and all other internucleoside linkages are phosphodiester (PO) internucleoside linkages. Subscript "(R)" or "(S)" indicates the isomer of the internucleoside linkage as Rp or Sp respectively. ΔTm's are calculated relative to 606339. Each nucleoside followed by a subscript "k" is a bicyclic ribofuranosyl nucleoside having a 4'-CH((S)—CH$_3$))—O-2' bridging group.

Example 31

Thermal Stability Assay

A series of modified oligomeric compounds were evaluated in a thermal stability ($T_m$) assay following the procedures illustrated in Example 30. The results are presented below.

| SEQ ID NO./ ISIS NO. | Composition (5' to 3') | Tm | ΔTm | Linkage |
|---|---|---|---|---|
| 07/606581 | UCGAGAACAUCC | n/a | | PO (RNA) |
| 08/606339 | GGATGTTCTCGA | 49.4 | std. | PO (DNA) |
| 08/748260 | GGAT$_{kq}$GTTCTCGA | 54.2 | 4.8 | MOP |

-continued

| SEQ ID NO./ ISIS NO. | Composition (5' to 3') | Tm | ΔTm | Linkage |
|---|---|---|---|---|
| 08/748261 | GGATGT$_{kq}$TCTCGA | 52.9 | 3.5 | MOP |
| 08/748262 | GGATGTT$_{kq}$CTCGA | 54.9 | 5.5 | MOP |
| 08/748263 | GGATGTCT$_{kq}$CGA | 52.5 | 3.1 | MOP |
| 08/748256 | GGAT$_{kx}$GTTCTCGA | 55.0 | 5.6 | MP |
| 08/748257 | GGATGT$_{kx}$TCTCGA | 52.3 | 2.9 | MP |
| 08/748258 | GGATGTT$_{kx}$CTCGA | 55.0 | 5.6 | MP |
| 08/748259 | GGATGTCT$_{kx}$CGA | 52.6 | 3.2 | MP. | between adjacent nucleosides subscript "x" indicates a methyl phosphonate modified internucleoside linkage (—P(CH$_3$)(=O)—, MP), subscript "q" indicates a methoxypropyl modified internucleoside linkage (—P(CH$_3$O—(CH$_2$)$_3$—)(=O)—, MOP) and all other internucleoside linkages are phosphodiester internucleoside linkages. Each nucleoside followed by a subscript "1" is a bicyclic ribofuranosyl nucleoside having a 4'-CH$_2$—O-2' bridging group (LNA). ΔTm's are calculated relative to 606339.

Example 32

Stability of Modified Linkages to Aqueous Ammonia

To evaluate internucleoside linkage stability under conditions similar to those encountered during deblocking and cleavage steps of oligomeric compound synthesis a comparative assay was performed with 2 sets of 2 identical oligomeric compounds wherein the only difference in each set is that one of the oligomeric compounds had a single methoxypropyl phosphonate modified internucleoside linkage (—P(CH$_3$O—(CH$_2$)$_3$—)(=O)— MP) and the other oligomeric compound had a single methylene phosphonate modified internucleoside linkage (—P(CH$_3$)(=O)—, MP). The stability was measured up to 16 days.

Each oligonucleotide was subjected to standard deprotection conditions used for automated oligonucleotide synthesis (ammonium hydroxide aqueous). Each oligonucleotide listed (10 nmol) is dissolved in concentrated aqueous ammonia (0.5 mL) and mixed at room temperature. Aliquots are taken out at the time points indicated and analyzed using LCMS.

| SEQ ID NO./ ISIS NO. | Composition (5' to 3') | Linkage/ isomer |
|---|---|---|
| 09/619442 | T$_e$A$_k$A$_k$AT$_q$TGT$^m$CAT$^m$CA$_k$$^m$C$_k$$^m$C$_e$ | MOP full PS |
| 09/558256 | T$_e$A$_k$A$_k$AT$_x$TGT$^m$CAT$^m$CA$_k$$^m$C$_k$$^m$C$_e$ | MP full PS |
| 08/748262 | G$_o$G$_o$A$_o$T$_o$G$_o$T$_o$T$_{lq}$C$_o$T$_o$C$_o$G$_o$A | MOP full PO |
| 08/748258 | G$_o$G$_o$A$_o$T$_o$G$_o$T$_o$T$_{lx}$C$_o$T$_o$C$_o$G$_o$A | MP full PO |

Between adjacent nucleosides subscript "x" indicates a methyl phosphonate modified internucleoside linkage (—P(CH$_3$)(=O)—, MP), subscript "q" indicates a methoxypropyl phosphonate modified internucleoside linkage (—P(CH$_3$O—(CH$_2$)$_3$—)(=O)—, MOP), subscript "o" indicates a phosphodiester (PO) internucleoside linkage and all other internucleoside linkages are phosphorothioate (PS) internucleoside linkages. Each nucleoside followed by a subscript "k" is a bicyclic nucleoside having a 4'-CH((S)—CH$_3$))—O-2' bridging group, each nucleoside followed by a subscript "1" is a bicyclic nucleoside having a 4'-CH$_2$—O-2' bridging group and all other nucleosides are 2'-deoxyribonucleosides. Each "$^m$C" is a 5-methyl cytosine nucleoside.

| SEQ ID NO./ ISIS NO. | % Cleavage | | | | | | Linkages | |
|---|---|---|---|---|---|---|---|---|
| | Day-1 | Day-2 | Day-3 | Day-4 | Day-8 | Day-16 | | |
| 09/619442 | <1 | | | 2 | 7 | 12 | MOP | (PS) |
| 09/558256 | <1 | | | 4 | 35 | 43 | MP | (PS) |
| 08/748262 | 40 | 57 | 75 | | | | MOP | (PO) |
| 08/748258 | 86 | 95 | 100 | | | | MP | (PO). |

To determine the effect of ammonium hydroxide treatment on the overall yield of various oligomeric compounds, a series of oligomeric compounds were prepared for comparison. The oligomeric compounds were prepared in pairs that differ only in having either MOP or MP internucleoside linkages at the same locations. The demonstrated degradation caused by treatment with ammonium hydroxide also results in a reduction in yield during the standard deblocking and cleavage steps. The lability of each oligomeric compound will depend on the chemistry and position of each modified internucleoside linkage. The oligomeric compounds listed below were prepared having either MOP or MP internucleoside linkages located at selected positions. The syntheses were performed on 40 μmol scale. It is shown that overall the MOP internucleoside linkage leads to a higher yield.

| SEQ ID NO./ ISIS NO. | Composition (5' to 3') | Linkage | |
|---|---|---|---|
| 12/736674 | T$_k$T$_{kq}$$^m$C$_{kq}$AGT$^m$CATGA$^m$CTT$_k$$^m$C$_k$$^m$C$_k$ | MOP | 24% |
| 12/736645 | T$_k$T$_{kx}$$^m$C$_{kx}$AGT$^m$CATGA$^m$CTT$_k$$^m$C$_k$$^m$C$_k$ | MP | 10% |
| 12/736648 | T$_k$T$_k$$^m$C$_k$A$_q$G$_q$T$^m$CATGA$^m$CTT$_k$$^m$C$_k$$^m$C$_k$ | MOP | 21% |
| 12/582074 | T$_k$T$_k$$^m$C$_k$A$_x$G$_x$T$^m$CATGA$^m$CTT$_k$$^m$C$_x$$^m$C$_k$ | MP | 11% |
| 12/736649 | T$_k$T$_k$$^m$C$_k$AGT$^m$CATGA$^m$C$_q$T$_q$T$_k$$^m$C$_k$$^m$C$_k$ | MOP | 21% |
| 12/736673 | T$_k$T$_k$$^m$C$_k$AGT$^m$CATGA$^m$C$_x$T$_x$T$_k$$^m$C$_k$$^m$C$_k$ | MP | 5% |
| 12/736675 | T$_k$T$_k$$^m$C$_k$AGT$^m$CATGA$^m$CTT$_{kq}$$^m$C$_{kq}$$^m$C$_k$ | MOP | 16% |
| 12/736646 | T$_k$T$_k$$^m$C$_k$AGT$^m$CATGA$^m$CTT$_{kx}$$^m$C$_{kx}$$^m$C$_k$ | MP | 31% |
| 12/736676 | T$_k$T$_{kq}$$^m$C$_{kq}$AGT$^m$CATGA$^m$CTT$_{kq}$$^m$C$_{kq}$$^m$C$_k$ | MOP | 19% |
| 12/736647 | T$_k$T$_{kx}$$^m$C$_{kx}$AGT$^m$CATGA$^m$CTT$_{kx}$$^m$C$_{kx}$$^m$C$_k$ | MP | 11%. |

Example 33

Modified Oligonucleotides Comprising a Methoxypropyl Phosphonate Internucleoside Linkage Targeting HTT SNP in Vitro Study Modified oligonucleotides were designed based on ISIS 460209, having a 3/9/3 gapmer motif wherein each internucleoside linkage is a phosphorothioate, the gap region contains nine β-D-2'-deoxyribonucleosides and each wing contains 3 modified nucleosides. For each of the modified oligonucleotides a modified internucleoside linkage was placed between nucleosides 5 and 6, from the 5'-end. The modified oligonucleotides were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to the control ISIS 460209 which was identical to the other oligonucleotides but did not include a modified linkage. The position on the oligonucleotides opposite to the SNP position, as counted from the 5'-terminus is position 8.

The modified oligonucleotides were tested in vitro using heterozygous fibroblast GM04022 cell line was used (from Coriell Institute). Cultured GM04022 cells at a density of 25,000 cells per well were transfected using electroporation with 0.1, 0.4, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 µM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The half maximal inhibitory concentration ($IC_{50}$) of each oligonucleotide is presented below and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity as expressed in "fold" was calculated by dividing the $IC_{50}$ for inhibition of the wild-type HTT versus the $IC_{50}$ for inhibiting expression of the mutant HTT mRNA and the results are presented below.

The modified oligomeric compounds were also evaluated in a thermal stability ($T_m$) assay using the procedure illustrated in Example 30. The oligomeric compounds were hybridized to a complementary region of an RNA 30mer (ISIS 539568). The results are presented below.

Between adjacent nucleosides subscript "x" indicates a methyl phosphonate modified internucleoside linkage (—P($CH_3$)(=O)—, MP), subscript "q" indicates a methoxypropyl phosphonate modified internucleoside linkage (—P($CH_3O$—$(CH_2)_3$—)(=O)— MOP) and all other internucleoside linkages are phosphorothioate internucleoside linkages except that each internucleoside linkage for the RNA complement (539568) is a phosphodiester internucleoside linkage. Subscript "(R)" or "(S)" indicates the isomer of the internucleoside linkage as Rp or Sp respectively. Each nucleoside followed by a subscript "e" indicates a 2'-O-methoxyethyl (MOE) modified nucleoside and each nucleoside followed by a subscript "k" is a bicyclic nucleoside having a 4'-CH((S)—$CH_3$))—O-2' bridging group (cEt) and all other nucleosides are 2'-deoxyribonucleosides. Each "$^mC$" is a 5-methyl cytosine modified nucleoside. $\Delta Tm$'s are calculated relative to 460209.

| SEQ ID NO./ ISIS NO. | Mut $IC_{50}$ (µM) | Wt $IC_{50}$ (µM) | Fold Selectivity (mut vs. wt) | Modified linkage |
| --- | --- | --- | --- | --- |
| 09/460209 | 0.50 | 2.5 | 5.0 | Positive control (3/9/3) |
| 09/558256 | 0.34 | 4.76 | 14 | MP |
| 09/622261 | 0.62 | 8.86 | 14 | MP(Sp) |
| 09/622262 | 0.45 | >10 | >22 | MP(Rp) |
| 09/619442 | 0.44 | >10 | >34 | MOP |
| 09/619443 | 1.14 | 9.46 | 8.3 | MOP(Sp) |
| 09/619444 | 0.33 | 8.25 | 25 | MOP(Rp). |

Example 34

Modified Oligonucleotides Targeting SRB-1 in vitro study

Modified oligonucleotides were designed based on the control oligonucleotide ISIS 449093, having a 3/10/3 gapmer motif wherein each internucleoside linkage is a phosphorothioate, the gap region contains ten β-D-2'-deoxyribonucleosides and each wing contains 3 cEt bicyclic nucleosides. Either 2 or 4 methoxypropyl modified internucleoside linkages were positioned in each of the modified oligonucleotides which were tested for their ability to inhibit SRB-1 mRNA expression levels. The potency of the modified oligonucleotides was evaluated and compared to the control oligonucleotide.

| SEQ ID NO./ ISIS NO. | Composition (5' to 3') | Tm/ΔTm | Linkage (isomer) |
| --- | --- | --- | --- |
| 09/460209 | $T_e A_k A_k$ATTGT$^m$CAT$^m$CA$_k^m$C$_k^m$C$_e$ | 54.7/— | unmodified (full PS) |
| 09/558256 | $T_e A_k A_k$AT$_x$TGT$^m$CAT$^m$CA$_k^m$C$_k^m$C$_e$ | 53.8/−0.9 | MP |
| 09/622261 | $T_e A_k A_k$AT$_{x(S)}$TGT$^m$CAT$^m$CA$_k^m$C$_k^m$C$_e$ | 51.3/−3.4 | MP(Sp) |
| 09/622262 | $T_e A_k A_k$AT$_{x(R)}$TGT$^m$CAT$^m$CA$_k^m$C$_k^m$C$_e$ | 53.1/−1.6 | MP(Rp) |
| 09/619442 | $T_e A_k A_k$AT$_q$TGT$^m$CAT$^m$CA$_k^m$C$_k^m$C$_e$ | 53.6/−1.1 | MOP |
| 09/619443 | $T_e A_k A_k$AT$_{q(s)}$TGT$^m$CAT$^m$CA$_k^m$C$_k^m$C$_e$ | 51.7/−3.0 | MOP(Sp) |
| 09/619444 | $T_e A_k A_k$AT$_{q(R)}$TGT$^m$CAT$^m$CA$_k^m$C$_k^m$C$_e$ | 53.8/−0.9 | MOP(Rp) |

| SEQ ID NO. | Sequence (5' to 3', RNA complement) | |
| --- | --- | --- |
| 10/539568 | AGACUUUUCUGGUGAUGACAAUUUAUUAA | RNA (full PO) |

The modified oligonucleotides were tested in vitro in primary mouse hepatocyte cells. Cells at a density of 35,000 cells per well were transfected using electroporation with 0.000976, 0.0039, 0.0156, 0.0625, 0.250 and 1.000 nM concentrations of each of the oligonucleotides listed below. After a treatment period of approximately 24 hours, RNA is isolated from the cells and mRNA levels are measured by quantitative real-time PCR wherein the SRB-1 mRNA levels are adjusted according to total RNA content, as measured by RIBOGREEN®.

| SEQ ID NO./ ISIS NO. | Composition (5' to 3') | Linkage |
|---|---|---|
| 17/463290 | AA<u>GGAAGUCAUGACUGA</u>AGC | RNA (full PO) |
| 12/449093 | $T_kT_k{}^mC_kAGT^mCATGA_mCTT_k{}^mC_k{}^mC_k$ | unmodified (full PS) |
| 12/736674 | $T_kT_{kq}{}^mC_{kq}AGT^mCATGA^mCTT_k{}^mC_k{}^mC_k$ | MOP |
| 12/736648 | $T_kT_k{}^mC_kA_qG_qT^mCATGA^mCTT_k{}^mC_k{}^mC_k$ | MOP |
| 12/736649 | $T_kT_k{}^mC_kAGT^mCATGA^mC_qT_qT_k{}^mC_k{}^mC_k$ | MOP |
| 12/736675 | $T_kT_k{}^mC_kAGT^mCATGA^mCTT_{kq}{}^mC_{kq}{}^mC_k$ | MOP |
| 12/736676 | $T_kT_{kq}{}^mC_{kq}AGT^mCATGA^mCTT_{kq}{}^mC_{kq}{}^mC_k$ | MOP |

Between adjacent nucleosides subscript "q" indicates a methoxypropyl phosphonate (MOP) modified internucleoside linkage (—P(CH$_3$O—(CH$_2$)$_3$—)(=O)—) and all other internucleoside linkages are phosphorothioate internucleoside linkages. Each nucleoside followed by a subscript "k" is a bicyclic nucleoside having a 4'-CH((S)—CH$_3$)—O-2' bridging group (cEt) and all other nucleosides are 2'-deoxyribonucleosides. Each "$^m$C" indicates that this nucleoside comprises a 5-methyl cytosine heterocyclic base. The hybridizing region of the RNA complementary strand is underlined.

| SEQ ID NO./ ISIS NO. | Tm, °C. | ΔTm, °C. | IC$_{50}$ free uptake | IC 50 electroporation |
|---|---|---|---|---|
| 12/449093 | 70.4 | n/a | 1.0 | 9.9 |
| 12/736674 | 64.9 | −2.8 | 12.1 | 22.9 |
| 12/736648 | 68.1 | −1.2 | 2.0 | 14.2 |
| 12/736649 | 68.8 | −0.8 | 2.9 | 13.7 |
| 12/736675 | 68.4 | −1.0 | 2.9 | 10 |
| 12/736676 | 66.0 | −1.1 | 12.5 | 23.3 |

The half maximal inhibitory concentration (IC$_{50}$) of each oligonucleotide listed above is calculated by plotting the concentrations of oligonucleotides used versus the percent inhibition of SRB-1 mRNA expression achieved at each concentration, and noting the concentration of oligonucleotide at which 50% inhibition of SRB-1 mRNA expression is achieved compared to the control. ΔTm's are calculated relative to 449093.

Example 35

Modified Oligonucleotides Targeting SRB-1 in vivo study

Modified oligonucleotides were designed based on the control oligonucleotide ISIS 449093, having a 3/10/3 gapmer motif wherein each internucleoside linkage is a phosphorothioate, the gap region contains ten β-D-2'-deoxyribonucleosides and each wing contains 3 cEt bicyclic nucleosides. Either 2 or 4 methoxypropyl (MOP) modified internucleoside linkages were positioned in each of the modified oligonucleotides which were tested for their ability to inhibit SRB-1 mRNA expression levels. The study included unmodified oligonucleotide 449093 for comparison. The potency of the modified oligonucleotides was evaluated and compared to the control oligonucleotide.

Six week old BALB/C mice (Jackson Laboratory, Bar Harbor, Me.) were injected subcutaneously once at dosage of 3, 10, 30 or 100 mg/kg with the modified oligonucleotides targeted to SRB-1 mRNA. The mice were sacrificed 72 hrs following administration. Liver tissues were homogenized and mRNA levels were quantitated using real-time PCR as described herein for comparison to untreated control levels (% UTC). Organs (liver, kidney and spleen) were collected for PK.

| SEQ ID NO./ ISIS NO. | Composition (5' to 3') | Linkage |
|---|---|---|
| 12/449093 | $T_kT_k{}^mC_kAGT^mCATGA_mCTT_k{}^mC_k{}^mC_k$ | full PS |
| 12/736674 | $T_kT_{kq}{}^mC_{kq}AGT^mCATGA^mCTT_k{}^mC_k{}^mC_k$ | MOP |
| 12/736648 | $T_kT_k{}^mC_kA_qG_qT^mCATGA^mCTT_k{}^mC_k{}^mC_k$ | MOP |
| 12/736649 | $T_kT_k{}^mC_kAGT^mCATGA^mC_qT_qT_k{}^mC_k{}^mC_k$ | MOP |
| 12/736675 | $T_kT_k{}^mC_kAGT^mCATGA^mCTT_{kq}{}^mC_{kq}{}^mC_k$ | MOP |
| 12/736676 | $T_kT_{kq}{}^mC_{kq}AGT^mCATGA^mCTT_{kq}{}^mC_{kq}{}^mC_k$ | MOP |

Between adjacent nucleosides subscript "q" indicates a methoxypropyl phosphonate (MOP) modified internucleoside linkage (—P(CH$_3$O—(CH$_2$)$_3$—)(=O)—) and all other internucleoside linkages are phosphorothioate internucleoside linkages. Each nucleoside followed by a subscript "k" is a bicyclic nucleoside having a 4'-CH((S)—CH$_3$)—O-2' bridging group (cEt) and all other nucleosides are 2'-deoxyribonucleosides. Each "$^m$C" indicates that this nucleoside comprises a 5-methyl cytosine heterocyclic base.

| SEQ ID NO./ ISIS NO. | ED$_{50}$ | MTD | TI | Linkage |
|---|---|---|---|---|
| 12/449093 | 3.2 | 10 | 3.1 | full PS |
| 12/736674 | 13 | >100 | >7.7 | MOP |
| 12/736648 | 7.6 | >100 | >13 | MOP |
| 12/736649 | 11.3 | >100 | >8.8 | MOP |
| 12/736675 | 5.7 | 30 | 5.3 | MOP |
| 12/736676 | 28 | >100 | >3.6 | MOP |

The ED$_{50}$, is the effective dose, for 50% of the animals receiving the drug. The ED$_{50}$ is commonly used as a measure of the reasonable expectancy of a drug effect. The ED$_{50}$s listed in the table below were calculated by plotting the concentrations of oligonucleotides used versus the percent inhibition of SRB-1 mRNA expression achieved at each concentration, and noting the concentration of oligonucleotide at which 50% inhibition of SRB-1 mRNA expression was achieved compared to the control.

The mean tolerable dose (MTD) is the lowest dose wherein the ALT is normal (generally less than 3 times the value of the saline treated animal).

The therapeutic index (TI) is calculated as the MTD divided by the $ED_{50}$.

| SEQ ID NO./ ISIS NO. | ALT 3 mg/kg | ALT 10 mg/kg | ALT 30 mg/kg | ALT 100 mg/kg |
|---|---|---|---|---|
| saline | 38 | | | |
| 12/449093 | 92 | 47 | 473 | 2246 |
| 12/736674 | 53 | 66 | 51 | 41 |
| 12/736648 | 68 | 35 | 35 | 74 |
| 12/736649 | 55 | 73 | 63 | 55 |
| 12/736675 | 43 | 42 | 55 | 297 |
| 12/736676 | 108 | 58 | 56 | 35. |

Example 36

Modified Oligonucleotides Targeting FXI in Vitro Study

Modified oligonucleotides were designed based on the control oligonucleotide ISIS 464917, having a 3/10/3 gapmer motif wherein each internucleoside linkage is a phosphorothioate, the gap region contains ten β-D-2'-deoxyribonucleosides and each wing contains 3 cEt bicyclic nucleosides. Two methoxypropyl phosphonate modified internucleoside linkages were positioned in each of the modified oligonucleotides which are tested for their ability to inhibit FXI mRNA expression levels. The potency of the modified oligonucleotides are evaluated and compared to the control oligonucleotide.

The modified oligonucleotides are tested in vitro in primary mouse hepatocyte cells. Cells at a density of 35,000 cells per well are transfected using electroporation with 0.015, 0.056, 0.234, 0.937, 3.750 and 15.000 µM concentrations of each of the oligonucleotides listed below. After a treatment period of approximately 24 hours, RNA is isolated from the cells and mRNA levels are measured by quantitative real-time PCR and the SRB-1 mRNA levels are adjusted according to total RNA content, as measured by RIBOGREEN®.

| SEQ ID NO./ ISIS NO. | Composition (5' to 3') | Linkage |
|---|---|---|
| 11/464917 | $G_kT_k{}^mC_kTGTG^mCAT^mCT^mCT_k{}^mC_k{}^mC_k$ | full PS |
| 11/718411 | $G_kT_{kq}{}^mC_{kq}TGTG^mCAT^mCT^mCT_k{}^mC_k{}^mC_k$ | MOP |
| 11/718413 | $G_kT_k{}^mC_kT_qG^qTG^mCAT^mCT^mCT_k{}^mC_k{}^mC_k$ | MOP |
| 11/718416 | $G_kT_k{}^mC_kTGTG^mCAT^mCT_q{}^mC_qT_k{}^mC_k{}^mC_k$ | MOP |
| 11/718417 | $G_kT_k{}^mC_kTGTG^mCAT^mCT^mCT_{kq}{}^mC_{kq}{}^mC_k$ | MOP |
| 11/718418 | $G_kT_{kq}{}^mC_kT_qGTG^mCAT^mCT^mCT_k{}^mC_k{}^mC_k$ | MOP |

Between adjacent nucleosides subscript "q" indicates a methoxypropyl phosphonate (MOP) modified internucleoside linkage (—P($CH_3O$—($CH_2$)$_3$—)(=O)—) and all other internucleoside linkages are phosphorothioate internucleoside linkages. Each nucleoside followed by a subscript "k" is a bicyclic nucleoside having a 4'-CH((S)—$CH_3$)—O-2' bridging group (cEt) and all other nucleosides are 2'-deoxyribonucleosides. Each "$^m$C" indicates that this nucleoside comprises a 5-methyl cytosine heterocyclic base.

The half maximal inhibitory concentration ($IC_{50}$) of each oligonucleotide listed above is calculated by plotting the concentrations of oligonucleotides used versus the percent inhibition of FXI mRNA expression achieved at each concentration, and noting the concentration of oligonucleotide at which 50% inhibition of FXI mRNA expression is achieved compared to the control.

Example 37

Modified Oligonucleotides Targeting CXCL12 in Vitro Study

Modified oligonucleotides were designed based on the control oligonucleotide ISIS 558807, having a 3/10/3 gapmer motif wherein each internucleoside linkage is a phosphorothioate, the gap region contains ten β-D-2'-deoxyribonucleosides and each wing contains 3 cEt bicyclic nucleosides. Methoxypropyl phosphonate internucleoside linkages were positioned at various positions within gap of the oligonucleotides as illustrated below. The resulting modified oligonucleotides were tested for their ability to inhibit CXCL12 (Chemokine ligand 12) and Raptor mRNA expression levels. The potency of the modified oligonucleotides was evaluated and compared to the control oligonucleotide. The table is divided into 6 sections to reflect that 6 separate assays were performed (3 assays targeting CXCL12 and 3 assays targeting Raptor).

The modified oligonucleotides were tested in vitro in mouse b.END cells by electroporation. Cells at a density of 20,000 cells per well are transfected using electroporation with 0.027, 0.082, 0.25, 0.74, 2.22, 6.67 and 20 uM concentrations of each of the oligonucleotides listed below. After a treatment period of approximately 24 hours, RNA is isolated from the cells and mRNA levels are measured by quantitative real-time PCR and the CXCL12 mRNA and Raptor mRNA levels are adjusted according to total RNA content, as measured by RIBOGREEN®.

| SEQ ID NO./ ISIS NO. | Composition (5' to 3') | Tm/ΔTm ° C. | Linkage |
|---|---|---|---|
| 15/558807 | $G_k{}^mC_kA_kTGTT^mCT^mCA^mCAT_kT_kA_k$ | 63.7/std | full PS |
| 15/766653 | $G_k{}^mC_kA_kT_qG_qCT^mCT^mCA^mCAT_kT_kA_k$ | 60.3/-1.7 | MOP/PS |
| 15/766654 | $G_k{}^mC_kA_kTG_qT_qCT^mCA^mCAT_kT_kA_k$ | 60.0/-1.9 | MOP/PS |
| 15/766655 | $G_k{}^mC_kA_kTGT_q{}^mCT^mCA^mCAT_kT_kA_k$ | 61.9/-0.9 | MOP/PS |
| 15/766666 | $G_k{}^mC_kA_kTGTT_q{}^mC_q{}^mCA^mCAT_kT_kA_k$ | 61.2/-1.3 | MOP/PS |
| 15/766657 | $G_k{}^mC_kA_kTGTT^mC_qT_q{}^mCA^mCAT_kT_kA_k$ | 60.1/-1.8 | MOP/PS |

-continued

| SEQ ID NO./ ISIS NO. | Composition (5' to 3') | Tm/ΔTm °C. | Linkage |
|---|---|---|---|
| 15/766658 | $G_k{}^mC_kA_k$TGTT${}^m$CT$_q{}^m$C$_q$A${}^m$CAT$_k$T$_k$A$_k$ | 54.5/−4.6 | MOP/PS |
| 15/766659 | $G_k{}^mC_kA_k$TGTT${}^m$CT${}^m$C$_q$A$_q{}^m$CAT$_k$T$_k$A$_k$ | 61.0/−1.4 | MOP/PS |
| 15/766665 | $G_k{}^mC_kA_k$TGTT${}^m$CT${}^m$CA$_q{}^m$C$_q$AT$_k$T$_k$A$_k$ | 61.6/−1.1 | MOP/PS |
| 15/766664 | $G_k{}^mC_kA_k$TGTT${}^m$CT${}^m$CA${}^m$C$_q$A$_q$T$_k$T$_k$A$_k$ | 61.3/−1.2 | MOP/PS |

Between adjacent nucleosides subscript "q" indicates a methoxypropyl phosphonate modified internucleoside linkage (—P(CH$_3$O—(CH$_2$)$_3$—)(=O)—, MOP) and all other internucleoside linkages are phosphorothioate internucleoside linkages. Each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^m$C" indicates that this nucleoside comprises a 5-methyl cytosine heterocyclic base. Tm's were performed following essentially the procedures illustrated in Example 30.

The half maximal inhibitory concentration (IC$_{50}$) of each oligonucleotide listed above was calculated by plotting the concentration of oligonucleotide versus the percent inhibition of CXCL12 mRNA or Raptor mRNA expression achieved at each concentration, and noting the concentration of oligonucleotide at which 50% inhibition of CXCL12 mRNA expression is achieved compared to the control.

| SEQ ID NO./ ISIS NO. | IC$_{50}$/CXCL12 | Linkage |
|---|---|---|
| 15/558507 | 150 | full PS |
| 15/766653 | 200 | MOP/PS |
| 15/766654 | 250 | MOP/PS |
| 15/766655 | 250 | MOP/PS |
| 15/558807 | 200 | full PS |
| 15/766666 | 200 | MOP/PS |
| 15/766657 | 200 | MOP/PS |
| 15/766658 | 350 | MOP/PS |
| 15/558807 | 100 | full PS |
| 15/766659 | 100 | MOP/PS |
| 15/766665 | 100 | MOP/PS |
| 15/766664 | 100 | MOP/PS |

| SEQ ID NO./ ISIS NO. | IC$_{50}$/Raptor | Linkage |
|---|---|---|
| 15/558807 | 3000 | full PS |
| 15/766653 | >20000 | MOP/PS |
| 15/766654 | >20000 | MOP/PS |
| 15/766655 | >20000 | MOP/PS |
| 15/558807 | 4000 | full PS |
| 15/766666 | >20000 | MOP/PS |
| 15/766657 | 6000 | MOP/PS |
| 15/766658 | 6000 | MOP/PS |
| 15/558807 | 2500 | full PS |
| 15/766659 | 2000 | MOP/PS |
| 15/766665 | 1500 | MOP/PS |
| 15/766664 | 2000 | MOP/PS |

Addition modified oligonucleotides were designed based on the control oligonucleotide ISIS 558807, having a 3/10/3 gapmer motif wherein each internucleoside linkage is a phosphorothioate, the gap region contains ten β-D-2'-deoxyribonucleosides and each wing contains 3 cEt bicyclic nucleosides for evaluation in the above illustrated assays.

| SEQ ID NO./ ISIS NO. | Composition (5' to 3') | Linkage |
|---|---|---|
| 15/558807 | $G_k{}^mC_kA_k$TGTT${}^m$CT${}^m$CA${}^m$CAT$_k$T$_k$A$_k$ | full PS |
| 15/766676 | $G_k{}^mC_kA_kT_q$GTT${}^m$CT${}^m$CA${}^m$CAT$_k$T$_k$A$_k$ | MOP/PS |
| 15/766677 | $G_k{}^mC_kA_k$TG$_q$TT${}^m$CT${}^m$CA${}^m$CAT$_k$T$_k$A$_k$ | MOP/PS |
| 15/766678 | $G_k{}^mC_kA_k$TGT$_q$T${}^m$CT${}^m$CA${}^m$CAT$_k$T$_k$A$_k$ | MOP/PS |
| 15/766679 | $G_k{}^mC_kA_k$TGTT$_q{}^m$CT${}^m$CA${}^m$CAT$_k$T$_k$A$_k$ | MOP/PS |
| 15/766680 | $G_k{}^mC_kA_k$TGTT${}^m$C$_q{}^m$CA${}^m$CAT$_k$T$_k$A$_k$ | MOP/PS |
| 15/766681 | $G_k{}^mC_kA_k$TGTT${}^m$CT$_q{}^m$CA${}^m$CAT$_k$T$_k$A$_k$ | MOP/PS |
| 15/766682 | $G_k{}^mC_kA_k$TGTT${}^m$CT${}^m$C$_q$A${}^m$CAT$_k$T$_k$A$_k$ | MOP/PS |
| 15/766683 | $G_k{}^mC_kA_k$TGTT${}^m$CT${}^m$CA$_q{}^m$CAT$_k$T$_k$A$_k$ | MOP/PS |
| 15/766684 | $G_k{}^mC_kA_k$TGTT${}^m$CT$^M$CA${}^m$C$_q$AT$_k$T$_k$A$_k$ | MOP/PS |
| 15/766685 | $G_k{}^mC_kA_k$TGTT${}^m$CT${}^m$CA${}^m$CA$_q$T$_k$T$_k$A$_k$ | MOP/PS |
| 16/558765 | $A_k{}^mC_kA_kT{}^m$CTT${}^m$CAGAT${}^m$CA$_k$T$_k$T$_k$ | full PS |
| 16/766686 | $A_k{}^mC_kA_kT_q{}^mC_q$TT${}^m$CAGAT${}^m$CA$_k$T$_k$T$_k$ | MOP/PS |
| 16/766687 | $A_k{}^mC_kA_kT{}^mC_qT_q$T${}^m$CAGAT${}^m$CA$_k$T$_k$T$_k$ | MOP/PS |
| 16/766688 | $A_k{}^mC_kA_kT{}^m$CT$_q$T$_q{}^m$CAGAT${}^m$CA$_k$T$_k$Tk | MOP/PS |
| 16/766689 | $A_k{}^mC_kA_kT{}^m$CTT$_q{}^m$C$_q$AGAT${}^m$CA$_k$T$_k$T$_k$ | MOP/PS |
| 16/766690 | $A_k{}^mC_kA_kT{}^m$CTT${}^m$C$_q$A$_q$GAT${}^m$CA$_k$T$_k$T$_k$ | MOP/PS |
| 16/766691 | $A_k{}^mC_kA_kT{}^m$CTT${}^m$CA$_q$G$_q$AT${}^m$CA$_k$T$_k$T$_k$ | MOP/PS |
| 16/766692 | $A_k{}^mC_kA_kT{}^m$CTT${}^m$CAG$_q$A$_q$T${}^m$CA$_k$T$_k$T$_k$ | MOP/PS |
| 16/766693 | $A_k{}^mC_kA_kT{}^m$CTT${}^m$CAGA$_q$T$_q{}^m$CA$_k$T$_k$T$_k$ | MOP/PS |
| 16/766694 | $A_k{}^mC_kA_kT{}^m$CTT${}^m$CAGAT$_q{}^m$C$_q$A$_k$T$_k$T$_k$ | MOP/PS |
| 16/766695 | $A_k{}^mC_kA_kT_q{}^m$CTT${}^m$CAGAT${}^m$CA$_k$T$_k$T$_k$ | MOP/PS |
| 16/766696 | $A_k{}^mC_kA_kT{}^mC_q$TT${}^m$CAGAT${}^m$CA$_k$T$_k$T$_k$ | MOP/PS |
| 16/766697 | $A_k{}^mC_kA_kT{}^m$CT$_q$T${}^m$CAGAT${}^m$CA$_k$T$_k$T$_k$ | MOP/PS |
| 16/766698 | $A_k{}^mC_kA_kT{}^m$CTT$_q{}^m$CAGAT${}^m$CA$_k$T$_k$T$_k$ | MOP/PS |
| 16/766699 | $A_k{}^mC_kA_kT{}^m$CTT${}^m$C$_q$AGAT${}^m$CA$_k$T$_k$T$_k$ | MOP/PS |
| 16/766700 | $A_k{}^mC_kA_kT{}^m$CTT${}^m$CA$_q$GAT$^M$CA$_k$T$_k$T$_k$ | MOP/PS |
| 16/766701 | $A_k{}^mC_kA_kT{}^m$CTT${}^m$CAG$_q$AT${}^m$CA$_k$T$_k$T$_k$ | MOP/PS |
| 16/766702 | $A_k{}^mC_kA_kT{}^m$CTT${}^m$CAGA$_q$T${}^m$CA$_k$T$_k$T$_k$ | MOP/PS |

-continued

| SEQ ID NO./ ISIS NO. | Composition (5' to 3') | Linkage |
|---|---|---|
| 16/766703 | $A_k{}^mC_kA_kT^mCTT^mCAGAT_q{}^mCA_kT_kT_k$ | MOP/PS |
| 16/766704 | $A_k{}^mC_kA_kT^mCTT^mCAGAT^mC_qA_kT_kT_k$ | MOP/PS. |

Example 38

Stability and Cleavage Patterns of Modified Oligonucleotides (RNA/ASO duplexes) Subjected to RNaseH 1 Treatment Modified oligonucleotides were designed based on the control oligonucleotide ISIS 558807, having a 3/10/3 gapmer motif wherein each internucleoside linkage is a phosphorothioate, the gap region contains ten β-D-2'-deoxyribonucleosides and each wing contains 3 cEt bicyclic nucleosides. Methoxypropyl phosphonate internucleoside linkages were positioned at various positions within gap of the oligonucleotides as illustrated below. The resulting modified oligonucleotides (ASOs) were hybridized to complementary RNA strands to provide RNA/ASO duplexes that were then treated with Human RNase H1.

Human RNase H1 (1:100 dilution) was prepared by adding Human RNase H1 (1.0 μL) to RNase H1 dilution buffer (72 μL) (RNase H1 dilution buffer: glycerol 30%; 20 mM Tris pH7.5; 50 mM NaCl) and RNAseOUT (8 μL). The dilution was allowed to incubate for 1 hour prior to use.

RNA/ASO duplexes were prepared by heating a buffered solution of each of the modified oligonucleotides (400 nM) listed in the table below with the complementary RNA (IDT, 200 nm unlabeled and 1 nm 5'-$^{32}$P labeled) to 90° C. for 2 minutes. The buffered solution is prepared having 20 mM Tris pH 7.5; 50 mM NaCl; 2 mM MgCl; 0.2 mM TCEP; and 2 μL RNAseOUT.

To each of the RNA/ASO duplexes (20 μL) is added the Human RNase H1 solution (1 μL) in a heat block at 37° C. for 30 minutes. The samples are then quenched with urea (20 μL, 8M) and heated to 90° C. for 2 minutes.

The percent cleavage at the 30 minute is shown below.

Between adjacent nucleosides subscript "q" indicates a methoxypropyl phosphonate modified internucleoside linkage (—P(CH$_3$O—(CH$_2$)$_3$—)(=O)—, MOP) and all other internucleoside linkages are phosphorothioate internucleoside linkages. Each nucleoside followed by a subscript "k" is a bicyclic nucleoside having a 4'-CH((S)—CH$_3$))—O-2' bridging group (cEt) and all other nucleosides are 2'-deoxyribonucleosides except for the complementary RNA sequence Seq Id No.: 17. Each "$^m$C" indicates that this nucleoside comprises a 5-methyl cytosine heterocyclic base. The complementary RNA was purchased from IDT.

The cleavage products were resolved on polyacrylamide gel and quantitated further quantitated using GE Image quant software. The polyacrylamide gel is shown in FIG. 1.

Example 39

Modified Oligonucleotides Targeting Malat1 in Vitro Study

Modified oligonucleotides were designed based on the control oligonucleotide ISIS 602056, having a 5/10/5 gapmer motif wherein each internucleoside linkage is a phosphorothioate except that 3 of the oligonucleotides have some of the phosphorothioate internucleoside linkages replaced with phosphodiester internucleoside linkages (mixed backbone), the gap region contains ten β-D-2'-deoxyribonucleosides and each wing contains 5 2'-MOE modified nucleosides. Methoxypropyl phosphonate internucleoside linkages are positioned at various positions within the oligonucleotides as illustrated below. The resulting modified oligonucleotides are tested for their ability to inhibit Malat1 mRNA expression levels. The potency of the modified oligonucleotides is evaluated and compared to the control oligonucleotide.

The modified oligonucleotides are tested in vitro in primary mouse hepatocyte cells. Cells at a density of 35,000 cells per well are transfected using electroporation with 0.000976, 0.0039, 0.0156, 0.0625, 0.250 and 1.000 nM concentrations of each of the oligonucleotides listed below. After a treatment period of approximately 24 hours, RNA is isolated from the cells and mRNA levels are measured by quantitative real-time PCR wherein the Malat1 mRNA levels are adjusted according to total RNA content, as measured by RIBOGREEN®.

| SEQ ID NO./ ISIS NO. | Composition (5' to 3') | Cleavage % | Linkage |
|---|---|---|---|
| 17/IDT | UAAUGUGAGAACAUGC | n/a | RNA |
| 15/558807 | $G_k{}^mC_kA_kTGTT^mCT^mCA^mCAT_kT_kA_k$ | 36.80 | full PS |
| 15/766653 | $G_k{}^mC_kA_kT_qG_qTT^mCT^mCA^mCAT_kT_kA_k$ | 50.10 | MOP/PS |
| 15/766654 | $G_k{}^mC_kA_kTG_qT_qT^mCT^mCA^mCAT_kT_kA_k$ | 48.60 | MOP/PS |
| 15/766655 | $G_k{}^mC_kA_kTGT_qT_q{}^mCT^mCA^mCAT_kT_kA_k$ | 44.30 | MOP/PS |
| 15/766666 | $G_k{}^mC_kA_kTGTT_q{}^mC_qT^mCA^mCAT_kT_kA_k$ | 45.00 | MOP/PS |
| 15/766657 | $G_k{}^mC_kA_kTGTT^mC_qT_q{}^mCA^mCAT_kT_kA_k$ | 48.70 | MOP/PS |
| 15/766658 | $G_k{}^mC_kA_kTGTT^mCT_q{}^mC_qA^mCAT_kT_kA_k$ | 44.40 | MOP/PS |
| 15/766659 | $G_k{}^mC_kA_kTGTT^mCT^mC_qA_q{}^mCAT_kT_kA_k$ | 40.30 | MOP/PS |
| 15/766665 | $G_k{}^mC_kA_kTGTT^mCT^mCA_q{}^mC_qAT_kT_kA_k$ | 44.40 | MOP/PS |
| 15/766664 | $G_k{}^mC_kA_kTGTT^mCT^mCA^mC_qA_qT_kT_kA_k$ | 50.30 | MOP/PS |

| SEQ ID NO./ ISIS NO. | Composition (5' to 3') | Linkage |
|---|---|---|
| 13/602056 | $G_e{}^mC_e{}^mC_eA_eG_eG^m$CTGGTTATGA$_e{}^mC_eT_e{}^mC_eA_e$ | full PS |
| 13/766753 | $G_{eq}{}^mC_e{}^mC_{eq}A_eG_{eq}G^m$CTGGTTATGA$_e{}^mC_eT_e{}^mC_eA_e$ | MOP/PS |
| 13/766754 | $G_{eq}{}^mC_{eq}{}^mC_{eq}A_eG_eG^m$CTGGTTATGA$_e{}^mC_eT_e{}^mC_eA_e$ | MOP/PS |
| 13/766755 | $G_e{}^mC_e{}^mC_{eq}A_{eq}G_{eq}G^m$CTGGTTATGA$_e{}^mC_eT_e{}^mC_eA_e$ | MOP/PS |
| 13/766756 | $G_e{}^mC_e{}^mC_{eq}A_eG_{eq}G^m$CTGGTTATGA$_e{}^mC_eT_e{}^mC_eA_e$ | MOP/PS |
| 13/761957 | $G_e{}^mC_e{}^mC_eA_eG_eG^m$CTGGTTATGA$_{eq}{}^mC_eT_{eq}{}^mC_eA_e$ | MOP/PS |
| 13/766757 | $G_e{}^mC_e{}^mC_eA_eG_eG^m$CTGGTTATGA$_e{}^mC_{eq}T_{eq}{}^mC_{eq}A_e$ | MOP/PS |
| 13/766758 | $G_e{}^mC_e{}^mC_eA_eG_eG^m$CTGGTTATGA$_{eq}{}^mC_{eq}T_{eq}{}^mC_eA_e$ | MOP/PS |
| 13/766759 | $G_e{}^mC_{eq}{}^MC_{eq}A_{eq}G_{eq}G^m$CTGGTTATGA$_{eq}{}^mC_{eq}T_e{}^mC_eA_e$ | MOP/PS |
| 13/766766 | $G_{eq}{}^mC_{eo}{}^mC_{eo}A_{eo}G_{eo}G^m$CTGGTTATGA$_{eo}C_{eo}T_{eq}{}^mC_{eq}A_e$ | MOP/PO/PS |
| 13/766761 | $G_{eq}{}^mC_{eq}{}^mC_{eo}A_{eo}G_eG^m$CTGGTTATGA$_{eo}{}^mC_{eo}T_{eq}{}^mC_{eq}A_e$ | MOP/PO/PS |
| 13/766762 | $G_{eq}{}^mC_{eo}{}^mC_{eq}A_eG_eG^m$CTGGTTATGA$_e{}^mC_{eq}T_{eo}{}^mC_{eq}A_e$ | MOP/PO/PS |
| 13/766763 | $G_{eq}{}^mC_{eq}{}^mC_{eq}A_{eq}G_{eq}G^m$CTGGTTATGA$_e{}^mC_eT_e{}^mC_eA_e$ | MOP/PS |
| 13/766764 | $G_e{}^mC_e{}^mC_eA_eG_eG^m$CTGGTTATGA$_{eq}{}^mC_{eq}T_{eq}{}^mC_{eq}A_e$ | MOP/PS |
| 13/766765 | $G_{eq}{}^mC_{eq}{}^mC_{eq}A_{eq}G_{eq}G^m$CTGGTTATGA$_{eq}{}^mC_{eq}T_{eq}{}^mC_{eq}A_e$ | MOP/PS |
| 13/766767 | $G_e{}^mC_e{}^mC_eA_eG_eG_q{}^mC_q$TGGTTATGA$_e{}^mC_eT_e{}^mC_eA_e$ | MOP/PS |
| 13/766768 | $G_e{}^mC_e{}^mC_eA_eG_eG^m{}^mC_qT_q$GGTTATGA$_e{}^mC_eT_e{}^mC_eA_e$ | MOP/PS |
| 13/766769 | $G_e{}^mC_e{}^mC_eA_eG_eG^m$CT$_qG_q$GTTATGA$_e{}^mC_eT_e{}^mC_eA_e$ | MOP/PS |
| 13/766770 | $G_e{}^mC_e{}^mC_eA_eG_eG^m$CTG$_qG_q$TTATGA$_e{}^mC_eT_e{}^mC_eA_e$ | MOP/PS |
| 13/766771 | $G_e{}^mC_e{}^mC_eA_eG_eG^m$CTGG$_qT_q$TATGA$_e{}^mC_eT_e{}^mC_eA_e$ | MOP/PS |
| 13/766772 | $G_e{}^mC_e{}^mC_eA_eG_eG^m$CT GGT$_qT_q$ATGA$_e{}^mC_eT_e{}^mC_eA_e$ | MOP/PS |
| 13/766773 | $G_e{}^mC_e{}^mC_eA_eG_eG^m$CTGGTT$_qA_q$TGA$_e{}^mC_eT_e{}^mC_eA_e$ | MOP/PS |
| 13/766774 | $G_e{}^mC_e{}^mC_eA_eG_eG^m$CTGGTTA$_qT_q$GA$_e{}^mC_eT_e{}^mC_eA_e$ | MOP/PS |
| 13/766775 | $G_e{}^mC_e{}^mC_eA_eG_eG^m$CTGGTTAT$_qG_qA_e{}^mC_eT_e{}^mC_eA_e$ | MOP/PS |
| 13/766784 | $G_e{}^mC_e{}^mC_eA_eG_eG_q{}^m$CTGGTTATG$_qA_e{}^mC_eT_e{}^mC_eA_e$ | MOP/PS |
| 13/766785 | $G_e{}^mC_e{}^mC_eA_eG_eG_q{}^mC_q$TGGTTAT$_qG_qA_e{}^mC_eT_e{}^mC_eA_e$ | MOP/PS |
| 13/766787 | $G_e{}^mC_e{}^mC_eA_eG_eG_q{}^mC_qT_qG_q$GTT$_qA_qT_qG_{Ae}{}^mC_eT_e{}^mC_eA_e$ | MOP/PS |
| 13/766776 | $G_e{}^mC_e{}^mC_eA_eG_eG_q{}^mC_qT_q$GGTTATGA$_e{}^mC_eT_e{}^mC_eA_e$ | MOP/PS |
| 13/766777 | $G_e{}^mC_e{}^mC_eA_eG_eG^m{}^mC_qT_qG_q$GTTATGA$_e{}^mC_eT_e{}^mC_eA_e$ | MOP/PS |
| 13/766778 | $G_e{}^mC_e{}^mC_eA_eG_eG^m$CT$_qG_qG_q$TTATGA$_e{}^mC_eT_e{}^mC_eA_e$ | MOP/PS |
| 13/766779 | $G_e{}^mC_e{}^mC_eA_eG_eG^m$CTG$_qG_qT_q$TATGA$_e{}^mC_eT_e{}^mC_eA_e$ | MOP/PS |
| 13/766780 | $G_e{}^mC_e{}^mC_eA_eG_eG^m$CTGG$_qT_qT_q$ATGA$_e{}^mC_eT_e{}^mC_eA_e$ | MOP/PS |
| 13/766781 | $G_e{}^mC_e{}^mC_eA_eG_eG^m$CTGGT$_qT_qA_q$TGA$_e{}^mC_eT_e{}^mC_eA_e$ | MOP/PS |
| 13/766782 | $G_e{}^mC_e{}^mC_eA_eG_eG^m$CTGGTT$_qA_qT_q$GA$_e{}^mC_eT_e{}^mC_eA_e$ | MOP/PS |
| 13/766783 | $G_e{}^mC_e{}^mC_eA_eG_eG^m$CTGGTTA$_qT_qG_qA_e{}^mC_eT_e{}^mC_eA_e$ | MOP/PS |

Between adjacent nucleosides subscript "q" indicates a methoxypropyl phosphonate (MOP) modified internucleoside linkage ($—P(CH_3O—(CH_2)_3—)(=O)—$) and all other internucleoside linkages are phosphorothioate internucleoside linkages. Each nucleoside followed by a subscript "e" is a 2'-O-methoxyethyl (MOE) modified nucleoside and all other nucleosides are 2'-deoxyribonucleosides. Each "$^mC$" indicates that this nucleoside comprises a 5-methyl cytosine heterocyclic base.

The half maximal inhibitory concentration ($IC_{50}$) of each oligonucleotide listed above is calculated by plotting the concentrations of oligonucleotides used versus the percent inhibition of Malat1 mRNA expression achieved at each concentration, and noting the concentration of oligonucleotide at which 50% inhibition of Malat1 mRNA expression is achieved compared to the control.

Example 40

Modified Oligonucleotides Targeting Androgen Receptor In Vitro Study

Modified oligonucleotides were designed based on the control oligonucleotide ISIS 585268, having a 4/8/4 gapmer motif wherein each internucleoside linkage is a phosphorothioate, the gap region contains 8 β-D-2'-deoxyribonucleosides and each wing contains 4 modified nucleosides independently selected from 2'-MOE modified nucleosides and bicyclic nucleosides having a 4'-CH((S)—CH$_3$))—O-2' bridging group. Additional similar motifs are also provided. Methoxypropyl phosphonate internucleoside linkages are positioned at various positions within the oligonucleotides as illustrated below. The resulting modified oligonucleotides are tested for their ability to inhibit Androgen receptor mRNA expression levels. The potency of the modified oligonucleotides is evaluated and compared to the control oligonucleotide.

The modified oligonucleotides are tested in vitro in primary mouse hepatocyte cells. Cells at a density of 35,000 cells per well are transfected using electroporation with 0.000976, 0.0039, 0.0156, 0.0625, 0.250 and 1.000 nM concentrations of each of the oligonucleotides listed below. After a treatment period of approximately 24 hours, RNA is isolated from the cells and mRNA levels are measured by quantitative real-time PCR and the Androgen receptor mRNA levels are adjusted according to total RNA content, as measured by RIBOGREEN®.

| SEQ ID NO./ ISIS NO. | Composition (5' to 3') | Linkage |
|---|---|---|
| 14/585268 | $A_kA_eG_kT_e$TGTAGTAGT$_e{}^mC_kG_e{}^mC_k$ | full PS |
| 14/766788 | $A_kA_{eq}G_{kq}T_e$TGTAGTAGT$_{eq}{}^mC_kG_e{}^mC_k$ | MOP/PS |
| 14/766789 | $A_kA_{eq}G_{kq}T_e$TGTAGTAGT$_{eq}{}^mC_{kq}G_e{}^mC_k$ | MOP/PS |
| 14/766790 | $A_kA_{eq}G_{kq}T_{eq}$TGTAGTAGT$_e{}^mC_kG_e{}^mC_k$ | MOP/PS |
| 14/766791 | $A_kA_{eq}G_{kq}T_e$TGTAGTAGT$_{eq}{}^mC_{kq}G_e{}^mC_k$ | MOP/PS |
| 14/766793 | $A_{kq}A_{eq}G_{kq}$TeqTGTAGTAGT$_e{}^mC_kG_e{}^mC_k$ | MOP/PS |
| 14/766794 | $A_kA_eG_kT_e$TGTAGTAGT$_{eq}{}^mC_{kq}G_e{}^mC_k$ | MOP/PS |
| 14/766795 | $A_{kq}A_{eq}G_{kq}T_{eq}$TGTAGTAGT$_{eq}{}^mC_{kq}G_{eq}{}^mC_k$ | MOP/PS |
| 14/766796 | $A_{kq}A_eG_{kq}T_e$TGTAGTAGT$_e{}^mC_kG_e{}^mC_k$ | MOP/PS |
| 14/766797 | $A_kA_{eq}G_kT_{eq}$TGTAGTAGT$_{eq}{}^mC_kG_{eq}{}^mC_k$ | MOP/PS |
| 14/549372 | $A_kA_kG_k$TTGTAGTAGT${}^mC_kG_k{}^mC_k$ | MOP/PS |
| 14/766798 | $A_{kq}A_{kq}G_{kq}$TTGTAGTAGT${}^mC_kG_k{}^mC_k$ | MOP/PS |
| 14/766799 | $A_kA_kG_k$TTGTAGTAGT${}^mC_{kq}G_{kq}{}^mC_k$ | MOP/PS |
| 14/766800 | $A_{kq}A_{kq}G_{kq}$TTGTAGTAGT${}^mC_{kq}G_{kq}{}^mC_k$ | MOP/PS |
| 14/766801 | $A_kA_kG_kT_qT_q$GTAGTAGT${}^mC_kG_k{}^mC_k$ | MOP/PS |
| 14/766802 | $A_kA_kG_k$TT$_qG_q$TAGTAGT${}^mC_kG_k{}^mC_k$ | MOP/PS |
| 14/766803 | $A_kA_kG_k$TTG$_qT_q$AGTAGT${}^mC_kG_k{}^mC_k$ | MOP/PS |
| 14/766804 | $A_kA_kG_k$TTGT$_qA_q$GTAGT${}^mC_kG_k{}^mC_k$ | MOP/PS |
| 14/766805 | $A_kA_kG_k$TTGTA$_qG_q$TAGT${}^mC_kG_k{}^mC_k$ | MOP/PS |
| 14/766806 | $A_kA_kG_k$TTGTAG$_qT_q$AGT${}^mC_kG_k{}^mC_k$ | MOP/PS |
| 14/766807 | $A_kA_kG_k$TTGTAGT$_qA_q$GT${}^mC_kG_k{}^mC_k$ | MOP/PS |
| 14/766808 | $A_kA_kG_k$TTGTAGTA$_qG_q$T${}^mC_kG_k{}^mC_k$ | MOP/PS |
| 14/766809 | $A_kA_kG_k$TTGTAGTAG$_qT_q{}^mC_kG_k{}^mC_k$ | MOP/PS |
| 14/766800 | $A_{kq}A_{kq}G_{kq}$TTGTAGTAGT${}^mC_{kq}G_{kq}{}^mC_k$ | MOP/PS |
| 14/766810 | $A_{kq}A_{kq}G_{kq}$TTGTAGTA$_qG_qT_q{}^mC_eG_e{}^mC_e$ | MOP/PS |
| 14/766811 | $A_{kq}A_{kq}G_{kq}$TTGTAGTAG$_qT_q{}^mC_{kq}G_e{}^mC_e$ | MOP/PS |
| 14/766812 | $A_eA_{kq}G_eT_q$TGTAGTAGT$_e{}^mC_{kq}G_e{}^mC_k$ | MOP/PS |
| 14/642460 | $A_qA_qG_q$TTGTAGTAGT${}^mC_qG_q{}^mC_q$ | MOP/PS |
| 14/642461 | $A_{kq}A_{kq}G_{kq}$TTGTAGTA$_qG_qT_q{}^mC_eG_e{}^mC_e$ | MOP/PS |
| 14/642462 | $A_{kq}A_{kq}G_{kq}$TTGTAGTAG$_qT_q{}^mC_{kq}G_e{}^mC_e$ | MOP/PS |
| 14/642463 | $A_eA_qG_eT_q$TGTAGTAGT$_e{}^mC_qG_e{}^mC_q$ | MOP/PS |
| 14/642464 | $A_qA_eG_qT_e$TGTAGTAGT$_e{}^mC_qG_e{}^mC_k$ | MOP/PS. |

Between adjacent nucleosides subscript "q" indicates a methoxypropyl phosphonate modified internucleoside linkage (—P(CH$_3$O—(CH$_2$)$_3$—)(=O)—, MOP), subscript "o" indicates a phosphodiester internucleoside linkage (PO) and all other internucleoside linkages are phosphorothioate internucleoside linkages (PS). Each nucleoside followed by a subscript "e" is a 2'-O-methoxyethyl (MOE) modified nucleoside, each nucleoside followed by a subscript "k" is a bicyclic nucleoside having a 4'-CH((S)—CH$_3$))—O-2' bridging group (cEt) and all other nucleosides are 2'-deoxyribonucleosides. Each "$^m$C" indicates that this nucleoside comprises a 5-methyl cytosine heterocyclic base.

The half maximal inhibitory concentration (IC$_{50}$) of each oligonucleotide listed above is calculated by plotting the concentrations of oligonucleotides used versus the percent inhibition of Androgen receptor mRNA expression achieved at each concentration, and noting the concentration of oligonucleotide at which 50% inhibition of Androgen receptor mRNA expression is achieved compared to the control.

The invention claimed is:

1. A gapped oligomeric compound comprising a contiguous sequence of from 12 to 24 monomer subunits linked by internucleoside linking groups having a gap region of from 6 to 14 contiguous β-D-2'-deoxyribonucleosides located between a 5'-region and a 3'-region wherein the 5' and 3'-regions each, independently, have from 2 to 8 contiguous monomer subunits selected from RNA-like modified furanosyl nucleosides that each adopt a 3'-endo conformational geometry independently selected from bicyclic nucleosides comprising a bicyclic furanosyl sugar moiety, modified nucleosides comprising a furanosyl sugar moiety having at least one substituent group and modified nucleosides comprising a sugar surrogate group; and wherein at least one of the internucleoside linking groups has Formula I:

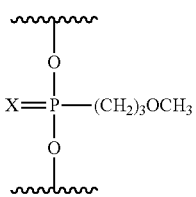

I wherein each X is independently O or S.

2. The gapped oligomeric compound of claim 1 wherein the gap region has 10 contiguous monomer subunits and the 5' and 3'-regions each, independently, have 2, 3 or 5 contiguous monomer subunits.

3. The gapped oligomeric compound of claim 1 comprising 2 internucleoside linking groups of Formula I.

4. The gapped oligomeric compound of claim 3 wherein internucleoside linking groups of Formula I are contiguous.

5. The gapped oligomeric compound of claim 1 comprising 1 internucleoside linking group of Formula I.

6. The gapped oligomeric compound of claim 1 wherein at least one internucleoside linking group of Formula I is located in the gap region between monomer subunits 1 and 2, 2 and 3, 3 and 4 or 4 and 5 counting from the first monomer subunit at the 5' end of the gap region.

7. The gapped oligomeric compound of claim 1 having two internucleoside linking groups of Formula I located in the gap region between monomer subunits 1 and 3, 2 and 4 or 3 and 5 counting from the first monomer subunit at the 5' end of the gap region.

8. The gapped oligomeric compound of claim 1 wherein each internucleoside linking group, other than the at least one internucleoside linking group of Formula I is, independently, a phosphodiester or a phosphorothioate internucleoside linking group.

9. The gapped oligomeric compound of claim 1 wherein each internucleoside linking group, other than the at least one internucleoside linking group of Formula I is, a phosphorothioate internucleoside linking group.

10. The gapped oligomeric compound of claim 1 wherein each monomer subunit comprises an optionally protected heterocyclic base moiety independently selected from thymine, cytosine, 5-methylcytosine, adenine and guanine.

11. The gapped oligomeric compound of claim 1 wherein each X is O.

12. The gapped oligomeric compound of claim 1 wherein each X is S.

13. The gapped oligomeric compound of claim 1 wherein the chirality of each internucleoside linking group having Formula I is either $R_P$ or $S_P$.

14. The gapped oligomeric compound of claim 1 wherein each modified nucleoside in the 5' and 3'-regions is, independently, selected from a bicyclic nucleoside comprising a bicyclic furanosyl sugar moiety having a 4'-CH$_2$—O-2' or 4'-CH[(S)—(CH$_3$)]—O-2' bridging group and a modified nucleoside comprising a ribofuranosyl sugar moiety having a 2'—O(CH$_2$)$_2$—OCH$_3$ substituent group.

15. The gapped oligomeric compound of claim 1 wherein the modified nucleosides in the 5' and 3'-regions comprise at least 2 different types of sugar moieties.

16. The gapped oligomeric compound of claim 1 further comprising one 5' or 3'-conjugate group comprising a cell targeting moiety and a conjugate linker wherein the conjugate linker has the formula:

—C(=O)—(CH$_2$)$_3$—C(=O)N(H)—(CH$_2$)$_6$—O—.

17. The gapped oligomeric compound of claim 16 wherein the cell targeting moiety and the conjugate linker have the formula:

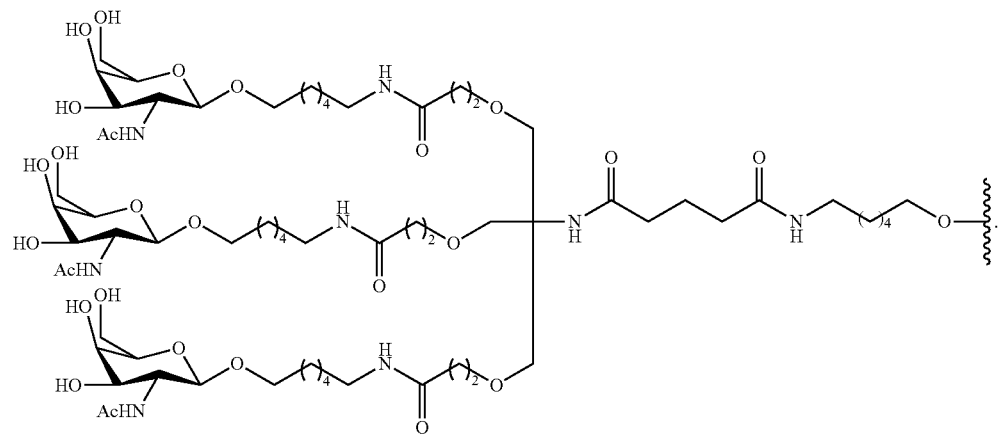

18. The gapped oligomeric compound of claim 16 wherein the conjugate group further includes a cleavable moiety between the conjugate linker and the oligomeric compound having the formula:

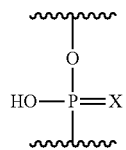
wherein X is O or S.
19. The gapped oligomeric compound of claim 18 wherein X is O.
20. The gapped oligomeric compound of claim 18 wherein X is S.
21. A method of inhibiting gene expression comprising contacting one or more cells, a tissue or an animal with the gapped oligomeric compound of claim 1 wherein said oligomeric compound is complementary to a target RNA.
* * * * *

SEQUENCE LISTING

<160> NUMBER OF SEQ ID NOS: 18

<210> SEQ ID NO 1
<211> LENGTH: 202001
<212> TYPE: DNA

<213> ORGANISM: Homo sapiens

<400> SEQUENCE: 1

| | | | | | |
|---|---|---|---|---|---:|
| gcccagcagg | tgtcagcctc | attttacccc | gcccctattc | aagatgaagt | tgttctggtt | 60 |
| ccaacgcctc | tgacatatta | gctgcatcat | tttacatttc | tttttttttt | ttccttttaa | 120 |
| atggggtctt | gctctgtcac | ccaggctgga | gtgctgtggt | atgatctcgg | ctcactgcaa | 180 |
| tctccacctc | cgaggttcca | gcgattctct | tgcctcagcc | tcccgagtag | ctgggactac | 240 |
| aggcacccac | catcatactg | gctaattttt | tgtgttttta | gtagagatgg | ggtttcccca | 300 |
| tgttgcccag | gctgatctca | aactcctggg | cttaagcaat | acagccgcgt | tggcctccca | 360 |
| aagtgttggg | attacaagca | tgagctaccc | cacccagctc | attttacatt | tccacttgtt | 420 |
| aaactgaaaa | ctggcccgag | aaagcttctg | tactgccatc | cttgcgtcct | tgcagatgaa | 480 |
| tcgtaaccta | gcatagtagg | taggcagact | gaaaacctaa | cttagcagta | ggcttctgta | 540 |
| acaacagctg | tgtctcagcc | agttcctgca | gccagacttc | aaccactcac | aggccgcaaa | 600 |
| ctgttcaaac | tgtgttcgga | gaaggcgaat | tcatctggct | gttaacgtgc | ctcacttctg | 660 |
| ctttctgtgg | ccactttccc | ttttctgtcc | ataaatttgc | tttgaccaca | cagcatccct | 720 |
| agagtctccc | tgaatctgct | gtgattctgg | gacctgcacc | atttgtgaat | tgtttttttt | 780 |
| ttccttgatc | agctaaactc | tgttcaattc | aatttgttgg | aagttttaa | cataccaatg | 840 |
| gtgcaccaag | gttccaattt | ctccacttcc | tcataaataa | gtcattttaa | atggcttttc | 900 |
| agtattccaa | tatttggaag | tattaatgtt | tctaccaatt | ttctattttt | ggacattgag | 960 |
| gttgtttcat | ttttttttc | tttttttgag | acagagtctc | gctccgtcac | ccaggctgga | 1020 |
| gtgcagtggc | ctgatcccgg | cccactgcaa | cctccacctc | cctcctcagc | ctcctgagta | 1080 |
| gctgggatta | caggtgcatg | caccaccaca | cccagctaat | ttttgtattt | ttagtagaga | 1140 |
| tggggtttca | ccatgttggt | caggctggtc | tcaaactcct | gacctcaggt | ggtccacctg | 1200 |
| ccttggcctc | ccaaaatgct | gggattacag | gcctgagcca | ctgcgcctgg | cctcatcttc | 1260 |
| ttgatattaa | tgttgctttta | acatctttgt | ccctgtgttt | tttgttttt | ttttttgagac | 1320 |
| ggagtctcat | tcattctgtc | acccaggctg | gagttcagtg | gcgtgatctc | agctcactgc | 1380 |
| aacctctgtc | tcctgggttc | cagtgattct | cctgcgtcgg | tctcctgagt | agctgtgttc | 1440 |
| ctgggtctttt | cgatggttat | ttaatacttc | cctacagtaa | tgccctgtgc | gtacatgcta | 1500 |
| agtgtgatga | atggttggc | acagttaaat | cttttgaaag | acattgccaa | gtcactcttc | 1560 |
| agaaaagtga | taggaggtca | tagcaatttt | aagaagtcct | catttctaca | tttccttact | 1620 |
| aatctcggtt | ggtgtctctt | caatctttcc | tcacacttttt | cttgggtttt | tcctgaatca | 1680 |
| tgagtctact | acatttacac | attttaaagc | atctttagaa | acaggatctc | attttgttgc | 1740 |
| ccaggctaga | gtttggtggc | atgattatag | ctcctcatac | tcctgggctc | aagtgatcct | 1800 |
| tccacctctg | aaaccccaaa | atttgagaaa | ggtctcattt | aatttagaaa | gtttattttg | 1860 |
| ccaaggttga | gggtgcacac | ctgtgatgat | atacgagtta | aaagaaatt | atttaggcag | 1920 |
| atactgaggg | taagaaagtc | ctcggtaagg | ttttcttttc | aatgaaaagc | agccccccaag | 1980 |
| cattttcttt | tctaacaaag | agcagcctgt | aaaatcgagc | tgcagacata | cacaagcaag | 2040 |
| ctggaagctt | gcacaggtga | atgctggcag | ctgtgccaat | aagaaaaggc | tacctggggc | 2100 |
| caggcagatc | caacatggcg | gctccatctt | ccctttcctt | gtcaaccatg | tgcacagtaa | 2160 |
| ggagcaggca | acatagtgtc | ccccgagtag | agaccaattt | gcataataaa | aggtgagggt | 2220 |
| agggtgggca | gcttctttgc | atgctatgta | aacattatgc | ctggtccaac | caatctttgg | 2280 |

```
gccctgtgta aattagacac cacctcctca agcctgtcta taaaaccctg tccattctgc   2340
cgcaggctgg aagacccact ggggcacccc tctctctcta taggagacag ctattcattt   2400
ttctcttcct ttcacctatt aaagctccac tcttaacccc actccgtgtg tatctatgtt   2460
cttgatttcc ttggcatgag gcaatgaacc ttgggtatta ccccagaacc ttgggtatta   2520
tgccacttca gtgacacagc ctcaggaaat cctgatgaca tgttcccaag atggtcgggg   2580
cacagcttgg tttatacat tttagggaga catgagacgt caattcatat atgtaagaag    2640
tacattggtt ccgtccagaa aggcgggac aacttgaggc agggagagag cttctaggtc    2700
acaggtagac aaatggttgc attcttttga atctccgata agcctttcca aaggaggcaa   2760
tcagaatatg cgtctattga ctgggcgcag tggctcatgc ctgtaatgcc agcactttgg   2820
gaggcggagg tgggtggatc acctgaggtc aggagtttga gagcagcccg gccaacatgg   2880
tgaaaccctg tctctactaa aaatacaaaa aattagctgg gcgtggtggc gggcgcctgt   2940
aatcccagct actcgggagg ctgaggcagg agaatagctt gaacccagaa ggaagaggtt   3000
gcagtgagct gagatggtgc cattgcactc cagcctgggc aacaagagtg aaactccatc   3060
tcagaaaaaa aaaaaaaagg cctgggcaaa gtggctcacg cctgtaatcc cagcactttg   3120
ggaagccgag gcgggcaggt cacaaagtca ggagattgag accatcctgg ctaacatgat   3180
gaaaccccat ctctactaaa aatacaaaa aactagctgg gtgtggtggc gagcacctgt    3240
agtcccagct actcggcagg ctgaggcagg agaatggcgt gaaccgggga ggcggagctt   3300
gcagtgagcc gagatcacac cactgcactc cagcccggac gacagggcaa gactctatct   3360
caaattaaaa aaaaaaaaa aaaaaaaaa aagagagag agaatatgca tctatctcag      3420
tgagcagaag gatgactttg aatggaatgg gagcagttcc tagcttgaac ttcccctta    3480
gcttcagtga tttgggggct caaggtatgt tcctttcaca tacctcagcc tcccaagtag   3540
ctgggaccac aagtgcatgc caccacacgt ggctaatgtt ttattttttt tgtaggaata   3600
gggtctcact atgtgtccag gctggtctaa aaccctgag ctcaaatggt cctcccgcct    3660
cagcctcccg aaatgctggg attacaggca tgagccagca tgcccggcct agtctacatt   3720
tttataaatt gctaattcaa agttccctct ccaaaacctc atggttttcc ctgttctcat   3780
cccctgcacc ctcccttccc ctggagtact cacctggcct tggaggtctg tgtgagccc    3840
ggacttcgat tctaggcaca gcatgtgatg agcgccccca ggtcaaacac ctcccctctg   3900
cggcctgtgc ttcaccgcct tgacagtgag aaaggtctcc cttcggctca ttctcgaagt   3960
ctcaaacttc acttctcctg tgcgctgatt ctgaattcag cccccgtcca aggtcctggc   4020
cccttctct tctgcttggc gtgttgttca tcaccactgt gcactgctga gggtaagtgc    4080
ggttctctgg acctctgctt tatcattaga acagactctt gcggtttccc acgacattcc   4140
tttcacttct cacttggaag atgagccgtg aggaaatcct gtgttgtgtg gtatgtgggc   4200
tgtgcttctg cttgacttga gggccaagca gcattgcaag ccatggtttt aaataagaaa   4260
gaacatttct aaccttcatc ttctagtaag gaaacaagtg ggctttagag ttcttgctca   4320
ggaaagacct atgtcccagt ccaaccggac ctttttactaa agagatcttc ctgatcctcc   4380
tccccaggcc aggggagggg tcctccctgg ggttggagcc tttagtaggg ggtcggagac   4440
acgacgtagc cttcatgaca ttcatagtct agttacacga tccctgtaag ggtcagttga   4500
agtaagtgct acaaaggaag ggaggtgctc agtggagagg gctctctttt atgtattata   4560
tttcttttcat ggggagggat atggatcagg gatcagcaga ggtgtttcag tcccgaggga  4620
```

| | |
|---|---|
| aagaaagtca gcgtggcttg ggagttggga gcagcaagac agtggctcaa gatatcttaa | 4680 |
| gactagtgga gtacaccttg catgttaaaa gccttgctca gggctgcctg gttcttgtag | 4740 |
| gacgacagag atggcctagc tctgcatact gcaccccag gggctcagaa cagtgcaaat | 4800 |
| gtcagtctat ctgtcagtgg cagagccagc cttggagcag gggtgcaagg aggtctctgc | 4860 |
| actggccagg catgcagaac attctgttca gtagcactgg acagaaggcc ccatctagat | 4920 |
| gagacagagc tggtggggca ggacaaagac tcctggcagc tcaaacggcc tggcagatgc | 4980 |
| ttggagagag ggggcttctt gagacagcac catttctggg aagagagtca cctgggaggg | 5040 |
| atgaggccac gctccggctt ggaggtgaag agaggggctg ctgcaagaaa gaattagaga | 5100 |
| catgccagcc tttgctgtgt tgcccaggct ggtcatgaac tcttggcctc aagcaatctt | 5160 |
| cccacctcag cctccccaag cgctgggatt atagacatga gccccatgc tggccaataa | 5220 |
| aagatgattt tatggagggg atggtggtga aggttgtggg tggtatgaaa tagtaagaaa | 5280 |
| tatatattgg tctgcaccca gttcctgcca cagagctcct aaaatcctga gaacttcctg | 5340 |
| ggtgagcatc ttttgttcta atgaggtgac tcttggtggc tcctggatag gagtgaatca | 5400 |
| ccagaaagat caagccagag ttagaagcag aaagtgctgg ctataacaca ggaaagctgt | 5460 |
| aacacaaata ataaagtttt tttttttttt tttgagatgg agcctcactc tgttgcccag | 5520 |
| gctggagtgc aatggtgcaa tctcagctca ctacaagctc tgcctcccag gttcaagtga | 5580 |
| ttctcctgcc tcagcctcct gagcagttgg gactacaggt gtgtgccacc acatctggct | 5640 |
| aattttgta tttttagcag agacgggtt tcaccatatt aaccaggctg gcctcaaact | 5700 |
| ccttaccttg tgatccgcct gcctcagcct cccaaagtgc tgggattaca ggcatgagcc | 5760 |
| accgtgcctg gccaaaagac attgttctta aagaatcaa ctaactaacc aaataaataa | 5820 |
| aaatctaacc taattaagaa actaaaaata cacaaaaatt aatttcaagg ggagaaaaat | 5880 |
| catgtaaaga gagaaagata atgaatactt tgcagaaatt tatgaacata aacataaaac | 5940 |
| ttggatgaaa tgcatttcta ggaaaacata atttatcaaa actaaccaca agtaaaatag | 6000 |
| aagcctaaat aggatatttt caagagaaga agtaaagttg tcaaagtgct acccttcaaa | 6060 |
| aaaacaccag gctcaaacaa tctgacatgg gaatgttagc acaccttaga gagcaaataa | 6120 |
| aactttgaat gggcttgaaa tattccagac tctagaaaaa caaaacttcc caattctttt | 6180 |
| tataaagcaa gtaaaattg ataccaaaat cttataaaga ccttatacaa aacttcatac | 6240 |
| caatctcttt tatgaataca aaacccttaa taaagtatta ccagacagaa cccaacaata | 6300 |
| cataaaaatg tcacatcata acatagtggg gtttatttca ataatgcatg gatggttcaa | 6360 |
| tacaaggaaa ttcagtaaca caatataata gatcatgtga atatacccaa agaaaaaata | 6420 |
| gattattttc atagatgctg taaaggcatt tgaccaaatt caacacctac ttttaggtg | 6480 |
| gtcaataaaa taaattagtt actccttctt tagcatgata aaatatattt atcagcccag | 6540 |
| aaggcatcat tttacccgat aagggcacac gctggaggga ataatgttaa aattaggaat | 6600 |
| aagaggatag ctagtttctt tcttctttt ttttttgag acggagtctt gctctgttgc | 6660 |
| caggctggag tgcagtggtg caatgttggc tcactgcacg ccccccgcct cccaggttca | 6720 |
| agcgattctc ctgcctcagc ctcccgagta gctgggacta caggcgcgca ccaccatgcc | 6780 |
| cggctaatt tttttttgtat tttagtagag atggggtttc accatgttgg tcaggctggt | 6840 |
| cttgaactcc caacctcacg tactgggatt accggtgtga gccaccacgc cagcccaact | 6900 |
| actttcaaca ttatccttaa tactgatgct tattgactta ctatgggtt acctctagat | 6960 |
| aaatccataa taagttgaaa atataagtaa aaaatgccct taatacacct aacctaccaa | 7020 |

```
acatcatagc tgagcccagc ctgccttagc tatgctcaga cactgacgtc agcctacaat    7080
tggcaaaatc acacagcagc acagtctact gcagagcatc tgctgtttgc ccttgtgact    7140
gcgtggctgc ctgggagctt cccagcttca caagacagta ttacgtagca catcactagc    7200
ctggggaaag atcaaagttg aaaatttgaa gtgtggtttc cattgaatgt gtactgcttt    7260
tgcaccatca tcaagtcaaa aaattttagt tgaaccagcc taagtttggg accatcttta    7320 tttttcaggag gaacttccat gtacattgat gacggacgat agaatccgtt tctatcatcc    7380
taatgaacat aatgaataaa tccagacaaa cataaacatt aacagagtaa gcagctttcg    7440
gggctggaag ccagaagagg gtgggagcgc agagagagag gccaaacacc agggctgctt    7500
ctgctttgcg ggtatttgct gatctggaca aggtatctgg aaggctgagc taagcctcct    7560
ttttttttga ggtggcgtct cactctgttg ccaggctgga gtgcaatggt gcgatctcag    7620
ctcactgcaa cctccacctc cctggttcaa gcgattctcc tgcctcagcc tcccgagtag    7680
ctgggattac aggctcccgc cactacaccc agctgatttt tgtaatttta gtagagacgg    7740
ggtttcacca tgttggccag gatggtctcg atctcttgac gtcatgatct gtccacctcg    7800
gcctcccaaa gtgctgggat tataggcgtg acccaccgtg ccccgtctga gctaagcctc    7860
ttgagcatag gggactaaaa atgaaatcta gcgcatgcca agtttagggt cccaggcaat    7920 tccttttccac tttggggtcc actttggggt ccaccccacc caagaagaag gatgacttgg    7980
aagtaaacca gctctgaaat atggatggtc ctctgggacc ataccaatcc cttcatatca    8040
accacatcca gttcctcaaa actggaactt ggattaagat ggcctaggac ttctagtgtc    8100
ccaggagcct ggcattgcaa acaaaaatcc tctccggaag aagataatac cttaagcttc    8160
aaatgactct ctaataaatt tcaaatacaa tgtccagcac acaaacaaa attaccagga    8220 acgtgatatg aggcctgatg gatgggaatt agcagaaact tcaggcatga gaaacatacc    8280
ctcagaggcc tagaatctat ctagtgtcta gataatggag atatgaaata cagacactta    8340
aacaactatg tttcccatgt tcaaagagga aatttgcaaa acttgaaagt gttggcagga    8400
aatcagaaac tataaaatgt gacaacagca tactttagag tcagtataaa ttacggtccc    8460
gaaaactgca gaattccaga acttaatggt aaagcaaggg tttaacagca gaatagaaat    8520
agccagagag aactaggaag taagtcagat gacactaccc agaataaggc actgagaggc    8580
caaggaatgg aaaatgcaga agaaaggata tggtgagagg atctaatata catttatttg    8640
gagtaccagg gagagagaga aggagaagaa cagaagccgt gtttcaagga cggtgactga    8700
gaggcttcga aactgatgaa agccatcagt tcacaaattc aaagcccagt gaattccaag    8760
gagaaaaaaa gaaatccata ctgtgaaagc aagtccagac aatgacaaac accatcaaca    8820
atacacagga caggcataag atgcatttaa tggggacact cagaggcaga gggttatcag    8880
aaggaggcac ttctctccca agttctcatc atcccagggc cagggacagc tggtcacacc    8940
ttagggagtt cactaggaga gggatctggc ttccttgtcat tctgggtatt tgtagggaaa    9000
ttggaaggga accgagagca cctagccaat cgcatagcaa tgggagattt caggctgtgg    9060
ggaatgtctt tgctggtgaa aagaacatcc tgaccttaga aatctttcac cgaggggggat    9120 ctgcgttcca gaacttctgg agctggtata ggtaaggctt tgagctttcc tactgagcca    9180
gcctgttgct aggttaccaa aggggacctc gagggccatc tggccaacaa gcagacttgt    9240
ctctccttac accccagac gtatcactgc aaaactacag aaaaccaaag acagagaaaa    9300
tcttaaaagc agccagattt aaaaaatggc atattagttt caaagcagca gccatgaaat    9360
```

```
tgacagctga tgtctcaaca gcaagaatga aaagtggaag acaggccagg tgtggtggct    9420
caggcctgta atcccagcac tttgggaggc cgaggcgggt ggatcacgag gtcaggagac    9480
caagaccatc ctggctaaca tggtgaaacc ccgtctctac taaaaataca aaaaattag    9540
tcgggcatgg tggtgggtgc ctgtagtccc agctactcgg gaggctgagg caggagaatg    9600
gcgtgaaccc gggaggcgga gcttgcagtg agccgagatt gtgccactgc actccagcct    9660
gggtgacaga gcaagactct gtctcaaaaa aaaaaaaaa aaaaaaaaa aaagggtgac    9720
gaagcttcaa tctcctgaaa ggaagcaact gccgcctttg attcgatacc caccaaaatc    9780
cgtgaagaag aaggcaaaa taaaacact tcctgattga actggaaaga tttccgcaat    9840
agaagaccca ctgtccaagg aattctaaag gatgctttcc aggcagaaga aaatgacccc    9900
agaggaagat cagagattca ggaaagaaat ggagagtgat aaaaatggaa aattcggggg    9960
ccaatttaaa caaaagctga ctgctctaca actgttgtgt ctctatcttt tgtaacatat   10020
atgtgtgtgt agcttttttt tttttttttg tcaagatgga ttctcactct gtcgcccagg   10080
ctacagtgaa atggcacggt ctcggctcac tgcaacctct gcccctttggg ctcaaatgat   10140
tctcttgcct cagcctcctg agtagctgag attacaggtg cctggcacaa tgcctggcta   10200
attttgtat ttttactaga gatgggattt ctccatgttg gccaggctgg tcttgaacac   10260
ctgacctcag gtgatccacc tgcctgggcc tcccaaagtg ctaggattac aggcgcgagc   10320
cactgcatct ggcctatgtg tgtgttata tggaattaaa acacatgca ataatacect   10380
ccaaattggg agaaaccaaa aatagcattt aaatgttgta agctccctgc ataatcaaga   10440
agagaataga tttacgttag attttgatac ctggaggatg aatgttgtaa tttctagggt   10500
gaccatgaaa agaggagaca acggtgtatg tttttttttt tttgagatgg agtctcactt   10560
tgtcacccag gctggagtgt tgtggtgtga tcttggctca ctgcaacctc ctcctcttgg   10620
gttcaggcca tcctcccacc taggcctcca gagtaggtgg gatcacaggc acctgccacc   10680
acacctggct aatttttttt ttttttaaa tatttagtag agatgggggtt tcaccatgtt   10740
ggccaggctg gtcttgaact cctgacctca ggcgatctgc ctacctctgc ctctcaaagt   10800
gctgggatta caggtgtgag ccatcgcgcc cggccaacag tgatcacttt caaactaaca   10860
gaggttcaaa aataaaatca gacttaacca aaaaccaggt aacagagctg gtaggatata   10920
cagaaagact gacctcacgt atatcaacga ttacagttaa tattaatgaa ggaaatgctc   10980
tagtttaaaa acgagggttg tcaaagaccc cacataagaa gctccttacc agcggtgcac   11040
ctagaaccta aggaaacagg acagatgaag gaggacgcgc cccgccgct gtcctgcgcc   11100
tcagccatcc tatgagacgg gaaaggtttc tgtctgcagc tgggcccgtg ctctttacca   11160
gctcctggct ttcttctctg gaaggttcct gcctgttttg ccctcacacc tgctcctctc   11220
tcagccctct caggggtggg gctggaggcc accaaagagc ctcctctgct ctccagttgc   11280
tcgactgctc ctcatttccc cctggggtct gcgtcagggt ttccttcttt tccagcccca   11340
ccccgcgtgc atcccacctg gtctcgggtc ggggctgctc ccgcttactg cccctgccc    11400
aggctggtgt gcacccctc tggctgcttt caaggcctct tctctcttct cggcaggaca   11460
ggcacaggca ggtggccagg tgtcatgctt agctccccgc ccagtgagat tctttcattt   11520
aacaatcttc ccctgaatag ttcatgttca ttgctgaaaa tttgaaaaat atggaaaagc   11580
acaaagatta agatataaac cgccctcaat tcccctgccc agagagagtc actgctatga   11640
cttggtgact aggaacctta tttctctctc gctcttttt ttttttttga cagagtct   11700
tgctctgtca cccaggctgg agtgcagtgg ctcgatctca gctcactgca acctccgcct   11760
```

```
cctgggttca agcgattctc ctgcctcagc ctcttgagta gctgggatta caggcacctg    11820
ccaccatgcc cggctaattt ttgtattttt agttgagaga gggtttcatc ttgttggtca    11880
ggcggacttg aactcctgac ctcaggtgat cagcccacct cggcctccca aagtgctggg    11940
attacaggtg tgagccactg cgccttcatc tctcttctgt gtatgtgtac gctgtttttt    12000
ctttagaatg ggggacgtta tcaggctcta catggtgtgt agtcggctag catgttgtaa    12060
gcctttccct gtgtcacaag tgctcatctg gaacaggatt ctaatgactg cctgtggcta    12120
tgttgggatt cctttaactc agctccttct gcccagcatc tatctttttt ccatcttttg    12180
tcctaagtgt tgctataata aatcattgat cacacatgcc tgactgtttg cataggataa    12240
attacgggaa atgttttgc tgttcaggga ctgtgcccat ttttaggcct cagagacacc     12300
atgccagact gcccagtatt gatcttact cttttagat gatgccaaac ttttctgtga      12360
actttaaaaa cctgtgtctt gacagtccat ttctgtaagt ctttcacatt agatttcctg    12420
tcaggatgat agtcaattct aggcagatga tgttttctca gccatggctg aagcagttgt    12480
gatttgttgt ggccatgtaa agtcccgatg atccattgcc tccctggatg ggttggaata    12540
atttggtttg ggagcatata acagaatgac ctggagtcac agcagctcag acggaagtgt    12600
atttctccct tacagatgaa agaattccag gccaggctgg aatgacaact gcacacagtc    12660
atctgggccc cctccttcca gctcccatca ccccaggatg tggcttttat gcagatgatc    12720
caaaatggct gctcaagtcc cagccaacac atcccattcc agggagcagg aaaaaggtgt    12780
gtctttccct tcattttatg tgattccttt ctagaagtac tactcattac ttctgcttgc    12840
atctccctgg ctagcactta cttagttata tggccatagc tagctgaagg aaggacaggg    12900
actgtcatac actagctaag aggcaaactg cttagataaa aaggtctcta aagaaggtca    12960
gagcggctgc tagggtgcaa ctctattact tattgttatg ggacgaactg tgtccctcat    13020
tcaggttgat gtcctaagcc ccagaacctc agaatgggat tgtatttgga dacaggttct    13080
ttaaggaggt aaggaggcta aaatgagatc attagggtgg gccataatcc gactgatgtc    13140
ttacaagaag agattaggac acggacatgc tcagagggac ggccacgtga ggacaccaag    13200
aaaggcagct gtctgcaagt caaggacagg gctcaggga aaccaaccttg ccaacacct    13260
tcatctcgga cttctagcct ctaggaccat gagaagatac atttctgttg tttaagctgc    13320
ccggtctgtg gtactttgtt atggcagccc aagtaaacaa atacagtcat ctgctgctgg    13380
aacaaatcac cccagcactg tggcttggca gcacacatgt ctagtcatag agttatatgt    13440
agttacgtgt agagccatat gtatcgtcac acgttctgtg ggtcaggaat ttggacccag    13500
cttaaccagc tccacttctc gccagggttc agtcaaatac cagctgcctc ccacctgaga    13560
gctcagccgg ggaagggtcc ctttccaatc tcacgtggtg ttggcaggat ccagttcctc    13620
atggcctgct ggactgagaa cctcagttct cactgcctgt tggccagagg ccgcctttat    13680
gtcctcgcca tgtgggcctc tccaacatgg cagctgactt catcagagca tccatgccaa    13740
gaaggcaaca gagagggcca gggagactga agtcataccc ttttgcgacc tagtcatggg    13800
gtgacattcc atcacctttg cccattggtt agaagcaggc caccaggtac agcccaagct    13860
cacggggagg ggtcatacaa gggtgtcaat accaggaggt gaggggtgct ggggccatct    13920
tatgagtctg cccactgagg taactaacaa ccttgaggcc tgacacagtg gacaaaggcc    13980
cttattaaca gcagagaact gggaacttta tttatttatt tatttttgag acagagtctc    14040
actcttgtca cccaggctgg agtgcaatgg catgatcttg gctcactgca acctccacct    14100
```

```
cccaggttca agcaattctg cctcagcctc cggaatagct gggactacag gcatgcacca    14160
ctacacccgg ctaattttg tatttttagt agagacaggg tttcgccatg ttggccaggc     14220
tggtctcgaa ctcctgacct ctggtgatct gcctgccttg gcctcccaaa gtgctgggat    14280
tacaggcgtg agccaccgca cctcgctgga acttaatttt tttagagaca gtgtcgctct    14340
atcacccaag ctggagtgca gtggtgcaat cctagctcac ttgcagcctc aaattcctgg    14400
gttcaggtga tcctcccaca tcagcctccc aagaactggg aactaacagc tgtttctctg    14460
ctgtccttct caagaaaagg gaggctactg ctaccccact ggggacaatg ctgggtttcc    14520
ctttaggaca ggctctgaga caaggcggag gtgctgtttg tggccacaga gcaggggact    14580
ctgggttgca ggtgtggcct ggctaaagta ggctttactg ggctcctctc tgcctgcatc    14640
accccccggc tgggcggttg tctctgaggc caaccttact ccctgctggg caggctggac    14700
agctgccctc tccgtttgcc cctctaccac ccaaaaggca ggaggctctg gagaccagga    14760
ccctgcccgc cacggcctgt gtcccaggcg tgagggggtg ccccacagac ctctgctgag    14820
ctgctgctga atgacgcccc ttgggggtcc tgccggaagg tcagagcagg ggtgcactcc    14880
cataaagaaa cgccccccagg tcgggactca ttcctgtggg cggcatcttg tggccatagc    14940
tgcttctcgc tgcactaatc acagtgcctc tgtgggcagc aggcgctgac cacccaggcc    15000
tgccccagac cctctcctcc cttccggggc gctgcgctgg gaccgatggg gggcgccagg    15060
cctgtggaca ccgccctgca ggggcctctc cagctcactg ggggtggggt gggggtcaca    15120
cttggggtcc tcaggtcgtg ccgaccacgc gcattctctg cgctctgcgc aggagctcgc    15180
ccaccctctc cccgtgcaga gagccccgca gctggctccc cgcagggctg tccgggtgag    15240
tatggctctg gccacgggcc agtgtggcgg gagggcaaac cccaaggcca cctcggctca    15300
gagtccacgg ccggctgtcg cccgctcca ggcgtcggcg ggggatcctt tccgcatggg     15360
cctgcgcccg cgctcggcgc cccctccacg gccccgcccc gtccatggcc ccgtccttca    15420
tgggcgagcc cctccatggc cctgcccctc cgcgccccac ccctccctcg ccccacctct    15480
caccttcctg cccgcccccc agcctcccca cccctcaccg gccagtcccc tccctatcc     15540 cgctccgccc ctcagccgcc ccgccccctca gccggcctgc ctaatgtccc cgtccccagc    15600
atcgccccgc cccgccccg tctcgccccg ccctcaggc ggcctccctg ctgtgccccg       15660
ccccggcctc gccacgcccc tacctcacca cgccccccgc atcgccacgc ccccccgcatc    15720 gccacgcctc ccttaccatg cagtcccgcc ccgtcccttc ctcgtcccgc ctcgccgcga    15780
cacttcacac acagcttcgc ctcaccccat tacagtctca ccacgccccg tcccctctcc    15840
gttgagcccc gcgccttcgc ccgggtgggg cgctgcgctg tcagcggcct tgctgtgtga    15900
ggcagaacct gcgggggcag gggcgggctg gttccctggc cagccattgg cagagtccgc    15960
aggctagggc tgtcaatcat gctggccggc gtggccccgc ctccgccggc gcggccccgc    16020
ctccgccggc gcagcgtctg ggacgcaagg cgccgtgggg gctgccggga cgggtccaag    16080
atggacggcc gctcaggttc tgcttttacc tgcggcccag agcccattc attgccccgg     16140 tgctgagcgg cgccgcgagt cggcccgagg cctccgggga ctgccgtgcc gggcgggaga    16200
ccgccatggc gaccctggaa aagctgatga aggccttcga gtccctcaag tccttccagc    16260
agcagcagca gcagcagcag cagcagcagc agcagcagca gcagcagcag cagcaacagc    16320
cgccaccgcc gccgccgccg ccgccgcctc ctcagcttcc tcagccgccg cgcaggcac     16380 agccgctgct gcctcagccg cagccgcccc cgccgccgcc ccgccgcca ccggccc       16440 ctgtggctga ggagccgctg caccgaccgt gagtttgggc ccgctgcagc tccctgtccc    16500
```

```
ggcgggtccc aggctacggc ggggatggcg gtaaccctgc agcctgcggg ccggcgacac   16560 gaaccccgg  ccccgcagag acagagtgac ccagcaaccc agagcccatg agggacaccc   16620 gcccctcct  ggggcgaggc cttccccac  ttcagccccg ctccctcact tgggtcttcc    16680
cttgtcctct cgcgagggga ggcagagcct tgttggggcc tgtcctgaat tcaccgaggg   16740
gagtcacggc ctcagccctc tcgcccttcg caggatgcga agagttgggg cgagaacttg   16800 tttctttta  tttgcgagaa accagggcgg gggttctttt aactgcgttg tgaagagaac   16860
ttggaggagc cgagatttgc tcagtgccac ttccctcttc tagtctgaga gggaagaggg   16920
ctgggggcgc gggacacttc gagaggaggc ggggtttgga gctggagaga tgtgggggca   16980
gtggatgaca taatgctttt aggacgcctc ggcgggagtg gcggggcagg ggggggggcgg  17040 ggagtgaggg cgcgtccaat gggagatttc ttttcctagt ggcacttaaa acagcctgag   17100
atttgaggct cttcctacat tgtcaggaca tttcatttag ttcatgatca cggtggtagt   17160
aacacgattt taagcaccac ctaagagatc tgctcatcta agcctaagtt ggtctgcagg   17220
cgtttgaatg agttgtggtt gccaagtaaa gtggtgaact tacgtggtga ttaatgaaat   17280
tatcttaaat attaggaaga gttgattgaa gttttttgcc tatgtgtgtt gggaataaaa   17340
ccaacacgtt gctgatgggg aggttaattg ccgagggatg aatgaggtgt acattttacc   17400
agtattccag tcaggcttgc cagaatacgg ggggtccgca gactccgtgg gcatctcaga   17460
tgtgccagtg aaagggtttc tgtttgcttc attgctgaca gcttgttact ttttggaagc   17520
taggggtttc tgttgcttgt tcttggggag aattttttgaa acaggaaaag agagaccatt  17580
aaaacatcta gcggaacccc aggactttcc ctggaagtct gtgtgtcgag tgtacagtag   17640
gagttaggaa gtactctggt gcagttcagg cctttctctt acctctcagt attctatttc   17700
cgatctggat gtgtcccaga tggcatttgg taagaatatc tctgttaaga ctgattaatt   17760
tttagtaata tttcttgttc tttgtttctg ttatgatcct tgtctcgtct tcaaagttta   17820
attagaaaat gattcggaga gcagtgttag cttatttgtt ggaataaaat ttaggaataa   17880
attattctaa aggatggaaa aacttttttgg atatttggag aaattttaaa acaatttggc   17940
ttatctcttc agtaagtaat ttctcatcca gaaatttact gtagtgcttt tctaggaggt   18000
aggtgtcata aaagttcaca cattgcatgt atcttgtgta aacactaaac agggctcctg   18060
atgggaagga agacctttct gctgggctgc ttcagacact tgatcattct aaaaatatgc   18120
cttctctttc ttatgctgat ttgacagaac ctgcatttgc ttatcttcaa aatatgggta   18180
tcaagaaatt tcctttgctg ccttgacaaa ggagatagat tttgtttcat tactttaagg   18240
taatatatga ttaccttatt taaaaaattt aatcaggact ggcaaggtgg cttacacctt   18300
taatccgagc actttgggag gcctaggtgg acgaatcacc tgaggtcagg agtttgagac   18360
cagcctggct aacatggtga aaccctgtct ctactaaaaa tacaaaaatt agctggtcat   18420
ggtggcacgt gcctgtaatc caagctacct gggaggctga ggcaggaaaa tcgcttgaac   18480
ccgggaggca gagtctgcag tgagttgaga tcacgccact gcactccagc ctgggtgaca   18540
gagcgagact ctatctcaaa aaaatttttt tttaatgtat tattttttgca taagtaaatac  18600 attgacatga tacaaattct gtaattacaa aagggcaata attaaaatat cttccttcca   18660 ccccttcct  ctgagtacct aactttgtcc ccaagaacaa gcactatttc agttcctcat    18720
gtatcctgcc agatataacc tgttcatatt gtaagataga tttaaaatgc tctaaaaaca   18780
aaagtagttt agaataatat atatctatat attttttgag atgtagtctc acattgtcac   18840
```

```
ccaggctgga gtgcagtgat acaatctcgg ctcactgcag tctctgcctc ccaggttcaa   18900
atgcttctcc tgcctcagcc ttctgagtag ctgggattac aggcgcccac caccatgtcc   18960
agctaatttt tgtattttta gtagagatgg ggtttcacca tgttggccag gctggtcttg   19020
aactcctgac cttgtgatct gtccacctcg gcctcccaaa gtgctgggat tacaggtgtg   19080
agccaccatg cctggctaga ataataactt ttaaaggttc ttagcatgct ctgaaatcaa   19140
ctgcattagg tttatttata gttttatagt tattttaaat aaaatgcata tttgtcatat   19200
ttctctgtat tttgctgttg agaaaggagg tattcactaa ttttgagtaa caaacactgc   19260
tcacaaagtt tggattttgg cagttctgtt cacgtgcttc agccaaaaaa tcctcttctc   19320
aaagtaagat tgatgaaagc aatttagaaa gtatctgttc tgtttttatg gctcttgctc   19380
tttggtgtgg aactgtggtg tcacgccatg catgggcctc agtttatgag tgtttgtgct   19440
ctgctcagca tacaggatgc aggagttcct tatgggctg gctgcaggct cagcaaatct   19500
agcatgcttg ggagggtcct cacagtaatt aggaggcaat taatacttgc ttctggcagt   19560
ttcttattct ccttcagatt cctatctggt gtttccctga ctttattcat tcatcagtaa   19620
atatttacta aacatgtact atgtgcctgg cactgttata ggtgcagggc tcagcagtga   19680
gcagacaaag ctctgccctc gtgaagcttt cattctaatg aaggacatag acagtaagca   19740
agatagataa gtaaaatata cagtacgtta atacgtggag gaacttcaaa gcagggaagg   19800
ggatagggaa atgtcagggt taatcgagtg ttaacttatt tttattttta aaaaattgt   19860
taagggcttt ccagcaaaac ccagaaagcc tgctagacaa attccaaaag agctgtagca   19920
ctaagtgttg acatttttat tttattttgt tttgttttgt ttttttgag acagttcttg   19980
ctctatcagc caggctggag tgcactagtg tgatcttggc tcactgcaac ctctgcctct   20040
tgggttcaag tgattctcat gcctcagcct cctgtttagc tgggattata gacatgcact   20100
gccatgcctg ggtaatttt tttttttccc ccgagacgga gtcttgctct gtcgcccagg   20160
ctggagtgca gtggcgcgat ctcagctcac tgcaagctcc gcttcccgag ttcacgccat   20220
tctcctgcct cagtctccca gtagctggga actacaggcg cctgccacca cgtccagcta   20280
attttttgt atttttaata gagacggggt ttcaccgtgt tagccaggat gatcttgatc   20340
tcctgacctc gtcatccgcc gaccttgtga tccgcccacc tcggcctccc aaagtgctgg   20400
gattacaggc atgagccact gtgcccggcc acgcctggga aattttgta tttttagtag   20460
agatggggtt ttgccatgat gagcaggctg gtctcgaact cccggcctca tgtgatctgc   20520
ctgccttggc ctcccaaagt gctaggatta caggcatgag ccaccatacc tggccagtgt   20580
tgatatttta aatacggtgt tcagggaagg tccactgaga agacagcttt ttttttttt   20640
tttttggg ttgggggca aggtcttgct ctttaaccca ggctggaatg cagtatcact   20700
atcgtagctc acttcagcct tgaactcctg ggctcaagtg atcctcccac ctcaacctca   20760
caatgtgttg ggactatagg tgtgagccat cacacctggc cagatgatgg cttttgagta   20820
aagacctcaa gcgagttaag agtctagtgt aagggtgtat gaagtagtgg tattccagat   20880
ggggggaaca ggtccaaaat cttcctgttt caggaatagc aaggatgtca ttttagttgg   20940
gtgaattgag tgaggggac atttgtagta agaagtaagg tccaagaggt caagggagtg   21000
ccatatcaga ccaatactac ttgccttgta gatggaataa agatattggc atttatgtga   21060
gtgagatggg atgtcactgg aggattagag cagaggagta gcatgatctg aatttcaatc   21120
ttaagtgaac tctggctgac aacagagtga aggggaacac cggcaaaagc agaaaccagt   21180
taggaagcca ctgcagtgct cagataagca tggtgggttc tgtcagggta ccggctgtcg   21240
```

```
gctgtgggca gtgtgaggaa tgactgactg gattttgaat gcggaaccaa ctgcacttgt   21300
tgaactctgc taagtataac aatttagcag tagcttgcgt tatcaggttt gtattcagct   21360
gcaagtaaca gaaaatcctg ctgcaatagc ttaaactggt aacaagcaag agcttatcag   21420
aagacaaaaa taagtctggg gaaattcaac aataagttaa ggaacccagg ctctttcttt   21480
tttttttttt tgaaacggag tttcgctctt gtcacccggg ctggagtgca atgatgtgat   21540
ctcagctcac taaaacctct acctcctggg ttcaagtgat tcttctgcct cagcctccca   21600
agtaactggg attacaggcg tataccacca tgcccagcta atttttgtgt ttttagtaga   21660 gatgggggttt caccatgttg gccaggctgg tctcgaactt ctgacctcag gtgatccact   21720
cgcctcagcc tgccaaagtg ctgggattac aggtttgggc cactgcaccc ggtcagaacc   21780
caggctcttt cttatactta ccttgcaaac ccttgttctc attttttccc tttgtatttt   21840
tattgttgaa ttgtaatagt tctttatata ttctggatac tggattctta tcagatagat   21900
gatttgtaaa aactctccct tcctttggat tgtcttttta ctttcttgat agtgtctttt   21960
gaagtgtaaa agttttaat tttgatgaag tcgagtttat ctattttgtc tttggttgct   22020
gtgcttcaag tgtcatatct aagaaatcat tgtctaatcc aaagtcaaaa aggtttactc   22080
ctatgttttc ttctaagaat tttagagttt tacatttaag tctgatccat tttgagttaa   22140
tttttatata tggttcaggt agaagtccaa ctttattctt ttccatgtgg ttattcagtt   22200
gtcccagcac tgtttgttga agagactatt cttttcccat ggaattatct tagtacccttt   22260 gttgaaaatt aatcgtcctt aattgtataa atttatttct agactgtcag ttctacctgt   22320
tggtctttat gtcgatcctg tgccagtacc atacagtctt gattactgaa gtttgtgtca   22380
cagtttaaat tcatgaaatg tgagttctcc aactttgttc cttttcaaga ttgatttggc   22440
catgctgggt cccttgcatt tccgtacgaa ttgtaggatc agcttgtcag tttcaacaaa   22500
gaagccaagt aggattctga gagggattgt gttgaatctg tagatcaact tggggagtat   22560
tcgcatctta acaatattgt cttccaccta tgaacatggg caaactttgt gtaaatggtc   22620
agattgtaag tatttcgggc tgtgtgggca cagtgtctct gtcacagcta cgcggctctg   22680
ccattgtagc atgaaagtag ccataagcaa tatgtatgag tgtctgtgtt ccaatagaat   22740
tttattaatg acaaggaagt ttgaatttca tataattttc acctgtcatg agatagtatt   22800
tgattatttt ggtcaaccat ttaaaaatgt aaaaacattt cttagcttgt gaactagcca   22860
aaaatatgca ggttatagtt ttcccactcc taggttaaaa tatgatagga ccacatttgg   22920
aaagcatttc ttttttttt tttttttttt ttttttgagac ggagtttcac tcttgttgcc   22980
caggctggag tgcagtggcg cgatctcggc tcactgcaac ctctgcctcc caggttcaag   23040
acattctcct gcacggcctc cctagtagct gggattacag gcatgcgcca ccacacccag   23100
ctaattttgt attttagta gagacggggt ttctccatgt tggtcaggct ggtcttgaac   23160
tcctgacctc aggtgatcca cccgcctcag cctcccaaag tgctgggatt acagggtgtg   23220
agccaccaca ccctgctgga aagcatttct ttttggctg ttttgtttt ttttttaaac   23280 tagttttgaa aattataaaa gttacacata tacattataa aaatatcttc aagcagcaca   23340
gatgaaaaac aaagcccttc ttgcaagtct gtcatctttg tctaacttcc taagaacaaa   23400
agtgtttctt gtgtcttctt cccagatttt aatatgcata tacaagcatt taaatgtgtc   23460 atttttttgtt tgcttgactg agatcacatt acatatgtat tttttttactt aacaatgtgt   23520 catagatatt gttccatagc agtacctgta attcttatta attgctatgt aatattttag   23580
```

```
aatttctttt taaaagagga cttttggaga tgtaaaggca aaggtctcac atttttgtgg   23640
ctgtagaatg tgctggtgac atattctctc taccttgaga agtccccatc cccatcacct   23700
ccatttcctg taaataagtc aaccacttga taaactacct ttgaatggat ccacactcaa   23760
aacatttagt cttattcaga caacaaggag gaaaaataaa ataccttata aagcactgtt   23820
taatattgta ttaaattgga tcaatttggg ggctagaatg tatgttagag acatgatatg   23880
tccataggtc cttgctatca cagtgaggtc tcagggacag tcgtttggta tcatttggga   23940
tctcataagc agactctctc tgcttgacct gacaaatcag agtctgtgtt ttaacaggtt   24000
cagtgagtga cttacatgca cattggagtt tgggaagctc cactgtaggt gcttagacct   24060
tacctttgtt gttgctaata acaatgcaag catttgggag gaagacctgt gttgctcata   24120
tgtgtccagg tgtagctgag gtggccttgc ttatctgctg tagggccgtt gagcatttct   24180
gtagctgtga tgagtgagct gaggtgagcc tgcggagagc tcccagccat tggtagtggg   24240
actcgcttag atgaactgga aggaccctttt catctgagca gccactatgg agaaaaacaa   24300
ccgaatgagg ggagagacaa tgtgcaattt tatttagggc acaaaggaga gctgtggtta   24360
gaaggtgaca tttgagtgga aagggggcaa gccatgtgta tagcgggaga agagaggtcc   24420
aggcagagtt aacagaaggc agaaatgctt tccatgtttg agaaccagta aggaggccag   24480
tggctgaagt aaggtgaagg gcagaaataa ggatgaggct gcgagagatg agaggttaga   24540
gacgagcgtc ttgtgcacca agataagctt gtgtggtcaa aacaagtagt ttaatttatg   24600
tttttaaaag atcattttgg ctgggcacaa tggttcatgc ctgtaatacc agtagtttga   24660
gacggtgtgg tgggaggatt gcctgaggcc agacgaccag catagccaac atagcagcac   24720
ctataaggtc tctacaaaaa actttaaaaa attagctggg catagtggtg tgtgcctgta   24780
gtcccagcta ctcaggaggc tgaggaggct ggaggattgc ttgagtccag gagttttgagg   24840 ctgcagtgag ctatgattat gccactacac tacaacctgg gcaagagagt gagaccctgt   24900
ctctaaatat acacacacac acacacacac acacacacac acacacacac acacacacac   24960
acacacatat atatgtatat atatgcattt agatgaaaag atcactttga caataccaca   25020
tgctggtgag gatttagaaa aactaggtca cttattgctg gtgggaatat aatatagtac   25080
ggccactctg gaaaacagtt tggcagtttg tcataaaact gaacataccg ttagtataca   25140
gcccagcagc aactacaatc ctgggcatta atcctagaga aatgaaacct taatgttcac   25200
ataaaaacct atactcaagt atgcatagca gctttaccca taatatctaa gaactggaat   25260
cagctcagat gtccttcaac aggtgaatgg ttaaactact cagtaataaa aaggaatgag   25320
ctactgatag catgcaacag tttaggtgaa gttatgctaa tgaaaaaagc caatcccaaa   25380
aggttataca tactgtatga ttctatgttt ttttgcaatg gcacagtttt agggatggag   25440
aatagattag tggttgcctg gggttagaga tggggtagta gagtaggtta gtggtggcag   25500
aggagagaaa agagagggag gtgaatgtgg ttataaaagg acaacacagg ggaatacttg   25560
taatggaaat gctttgtctt tttttttttt tttttttttt tggcgacaga gtcttgctct   25620
gttgcccagg ctggagtgca gtggcatgat cttttctcac tgcaacctct gcctcctggg   25680
ttcaagtgat acttgtgtct cagtctccca tgttcagagt gaaacaaacc agaggtaatg   25740
ttcatccaaa taatccaaca cacatgacat taaaacatca agatcaggtc ggacgtggtg   25800
gctcatgcct gtaatcccag cacttttggg aggccaaggt gggcagatca cttgaggtca   25860
ggagttcgag accagccggg ccaacatgat gaaacccccat cttgactaaa aatcaaaaaa   25920
ttagccgggc atggtggtgt gcacctgtag tcccagctac ttgggaggct gaggcaagag   25980
```

```
aactgcttga acccgagggg cagaggttgc agtgagctga gagtgcgcca ttgcacttca   26040
gcctgtgtga cagagtaaga ctccatctcc aaaaaaaaaa aaccaagatc aattaaaata   26100
cagcattact gggccgggtg tggtggctca cacctgtaat cccagcactt tgggaggccg   26160
agatgggcag atcacgaggt caggagatcc agaccatccc ggctaacacg gtgaaacccc   26220
gtctctacta aaaatacaa aaaattagcc gggtatagtg gtgggtgcct gtagtcccag   26280
ctacttggga ggctgaagca ggagaatggt gtgaacccgg gaggcagagc tggcagtgag   26340
ctgagatcgc gccactgcac tccagcctgg gcgacagagc aagactccgt ctcggggaa    26400 aaaaaaaat aaataaatag aatgctgtag tgtccttgag tttacatgcc cctccttacg    26460
cttgtgtgcc cgtgcagatt gcttgattac acaattagag gaggctggcg gaggattgtt   26520 ttaattttt tttttttgag acagtctggc tctgttcccc aggctagagt gcaatggcgc    26580
aatcttggtg cactgcaacc tctgcctcct gggttcaagc agttcttctg ccgcagcctc   26640
ccgagtagct gggattatag gcgcccgcca ccacgcccaa ctattttttg tattttagt    26700 agagcagcgt ttcaccatgc tggccaggct ggtctcgaac tcctgacctc agatgatctg   26760 ctgcccagc ctcccaaagt gctgggatta caggcgtgag ccacacctgg ccgtttgttt    26820
taattttgaa ggtgaagtga aagtgactac atttaccaaa agtgattgaa aagccaggac   26880
tgttcttacc ctgttttcc agttcttgct cagagcaagg tggtttcttt ttcacttaat    26940
caccatactt acttttcatg tagaacaagt cagtttgagt tatcagttca tcatcttaac   27000
taaattccat gggggaagga attagtttta gtttcttaaa cttccaggtt tgcttattgg   27060
acaaaatgag atagcaaggc agtgttttta agttagattt tttatttctt tggtaataca   27120
attttctcag aaacttagta gtcttttagt ttagttgttt ttagttggtc ctatgttttg   27180
gatcacccct ctctacttta ttttgatagt gccaactgtg aagacatctg aagccatagg   27240 tttgatggg aaggaggcat ctttagcctg atcatcttcg ccaggctgtt tatctccttt    27300
tgcttggctg agaagtctta ataggaggct tattcccagc tatttgggga catagaagca   27360
gttagccatt gcttatattt tactgaggtc tgtgtggtat gttgattgta gtcagttaac   27420
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atcttgggca   27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata ttttgaaaaa   27900
attagccagg cccagtggtg cgtgcctgtg gtccgcgcca ctcaggaggc tgagacggga   27960
ggatcctttc agcctaggag tttaaggcta aagtgagcca tgattgtgct atcgtactcc   28020
agcctgggca gcagagcaag atcctgactc taaaaaaaag taaaataaag taaaatgggg   28080
gaaatgaact gctttagtaa catcatctgt tttttctgtg agcagcgtag cttgacagcc   28140
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
aactaagtgg agtgggtaat tcaacacata ttaatttcct tctttttttt attttagaa    28320
```

```
agaaagaact ttcagctacc aagaaagacc gtgtgaatca ttgtctgaca atatgtgaaa    28380
acatagtggc acagtctgtc aggtaattgc actttgaact gtctagagaa ataagaact     28440 ttgtatattt tcagtcttaa tgggctagaa tattctttgt gtcccagcta tttttaaatgg   28500 attcagaaat ccatttaaga tgaagaagga ccctttttccc atatttctgg ctatatacaa   28560
ggatatccag acactgaaat gaataatgtt ccctttttgt aatcttttat gcaaaaatta    28620
aaaccattat ggtaattgaa caacatgttt atgtttagtt aacacccctta gcaactatag   28680 ttattttaaa accatctatg gtttgatatt tttgcatttg ttgcaatagt aggaacagca    28740
caagacagtt cagtttgtct ctcttatttg cttttttcttg gcagtttgct gtcctattgt   28800
acctctgctc ctagcagtgg ctggagccca ctcctctgtg cttcgggatt agtggggatc    28860
gtggggcatt gactgtaggt cagctttcct tgcttgatct ttctcactgg gatgaactag    28920
cagcaccttc ttttgtagct gctttgcttt tgactatctt tctgaccgtt gttcctagta    28980
gctgtagatg gtaaatatat ttaggcctgt ttccaatggc tcagtaggag acatattcac    29040
ctatgatatc tgaattctgt tacccacatg ggcatgcgtg aaatagttgc cttgccttac    29100
tttcccttgg aataaataat tcatgttatt ctcctggtag aagctagaaa aagcctttat   29160
agtcagtcag aaaaaaattt ttagacaaat aatcttgatt ttagtactga caaaaacgtg    29220
tggtgattct tttttttaatt tttttttgag acggagtttc actcttgttg cccaggctgg   29280
agtgcaatgg cgtgatctcg gctcactgca acctctgcct cctgggttca agtgattctc    29340
ctgcctcagc ctcccaagta gctggagtta caggcatgtg ctactgtgcc cagctaattt    29400 tgtatttta gtagagatgt tggtcaggct gatctcgaac tcccaaccctt aggtgatctg    29460 cccgcctcag cctcccaaag tgctgggatt acaggcgtga gccagggcgc ccggtgattc    29520
atttgttttt tcaaaaaatt tcctcttggc cattgctttt cacttttgtt tttttttttt    29580
ttttgagacg gagtcacgat ctgtcaccca ggctggagtg cagtggcatg atcttggctt    29640
actgcaagct ctgcctccca ggttcacgcc attctcctgc ttcagcctgg cgagtagctg    29700
ggactacagg tgctcgccac cacacccggc taatttttg tattttagt agagatgggg     29760 tttcaccgtg gtcttgatct cctgacctca tgacccgctc aactcagcct cccaaagtgc    29820
tgggattaca ggcgtgagcc accgcgcccg gccctctctt gtcttttat tgtggtaaaa    29880 tgcacataaa attgactgtc ttaaccattt ttagggggtac agttcagtat atatattcgt   29940
aatgttgtac agccatcact gccatctact tcataagttt ttcttctgtc aaaactgaac    30000
atctgtcttc attaaactcc ctatcatcca ttcttttcctg tagtccctttt ctactttctg  30060 tctgtatgag tgtaactgct ctggagacct catgtaagtg gattcctaca ggatttgtgt    30120 ttttttttttg gtgatctgct tattttttaat gcctctgtgc atttgtatta tatactttca  30180
aagtgatttc acaaaaccgt ttcatttttag gttaactcat ttctgttgtt tgtgaaatac   30240
tgtgtatgat tctgttctgt ttctgtctaa tttgtggaaa tgttgtggga agaaaatgaa    30300
ataacaaatg agcatatgtc ctgaaaataa aaatataaaa attctaagtt agcatgctat    30360
tgtagaatac aacgctatga taaaagtagg aaaaaaaaag gtttgaattc tatctctgct    30420
acctgtgtaa gctgggtgac tttagataag ctgtaacgtg tttgagcctt actggctcat    30480
ttttgaaatg taatccctag ttacacagtt cttgtgggat cagatggtac atgtgaaaca    30540
ctgtgaaaaa gcaactgcat agatatgttc attagccacc tgagcgggaa gcgtatccca    30600
ttgcgatgcc catcatccaa agctatatgt tatctttact ttttttttttt tgagacagag   30660 tcttgctctg ttgcccaggc tagagtgcag tggtgcaatc tcagctcact gcaagctcca    30720
```

```
cctcccgggt tcacgctatt ctcctgcccc agcctcccaa gtagctggga ctacaggcac   30780
ccgccaccat gcctggctaa attttttgtat ttttagtaga gatggggttt caccgtgtta   30840
gccaggatgg tcttgatctc ctgacctcgt gatccgcccg cctcggcctc ccaaagtgct   30900
gggattacag gcgtgagcca ctgccccctgg ccatctttac tttttttgtg aaatgactttt  30960 aaatacttgg caaacatttg gtcattgttc atctgatctc caccatccag gtctcagaga   31020
acataatttc tctctgaaag cttattgacc caggaaataa gatctctttc aatctgagtg   31080
cgtcaggctt tattcttgtc attttgtctt ttgataattt tcaaatggaa ttcatggaat   31140
gttggcttat attcatatat tagtaaagta tgttgagaca tcttaagatt gatttgtgg    31200 tctatatgcc atattaaatc aaaataatag ctgttaatgg ttttcacatt agtctgtctc   31260
ttgtttttat ggagtaatgc tgagagttca ttatgcttgt tctacagaag agcatgttaa   31320
aaggagtttt tggagtcaga gaggttattc ttggtttcat aggatacact ctatactttt   31380
tagggatttc agagtatata gctgaaggtg atattttatg taaatatgtt ttatggaaac   31440
ttattgctca tcgctgtttc ctgttaactc tcctaaaata taattaaact tttggaactt   31500
ttttatagct tttgtgctag actaattttt gtctctaatg aggttatata aatggcagct   31560
tctgacgttt tcaatgtagg aagtcattta aaacttcatg tatattgtga aaatgtagtc   31620
tgctttaagc tctctaaagt ggtctaagtt actggttcct aagtatggat gagcatcaaa   31680
atcatctgga aaatttgtta aaaatacagt aatgaaggca cctcactgtc cttttcccca  31740
aacatacttc tgcattctgt ttgagtaggt agggactaca cattttttcac aagtatcctc   31800 ttgggaatac ccaggaatgc ttacttgagc aacctcttac taatatgtac cttgataagg   31860
tggctaggta aacataaata tacaaaaatc catagatctc ccatatatta gcataaatca   31920
gctagaaaat ataacgttta aagatctagt tcacagtagc accaatatat cgaactctaa   31980
ggaatcgata aatatgcaaa aactttataa aaacttctgt taatgttcct gaaagatata   32040
ggtgaccact ttctagatag gaagatttta tattactaag ttgaatttcc tctaaattaa   32100
cacagaaatt taaaataatc ttgatcaaaa ttctagtaga ggtattttg aacttgttca    32160 ctgcaagaat aaatacataa ttgcaaagaa tatctcaaaa tcatcaccag gcctggtgtg   32220
gtggcccatg cctgtaatcc cagcactttg ggaggctgag gcaggcagat cacctgaggt   32280
caagagtttg agaccagctg gaccagtgcg gtgaaacact gcctctacta aaatacaaaa  32340
aattagctgg gtgtggtggt gcatgcctgt agtcccagct acttgggagg ctgaggcagg   32400
agaattgctt gaacccagga ggtacaggtt gcggtgagcc tagatcgcac cactgcattc   32460
cagcctgggc gacaagagca aaattctgtc tcaagaaaaa agagaaaaaa gaaaagaaa   32520 tcaacactaa tatggtgaga cttaatgtat gtgacattaa aatagtgatt ggatgttaaa   32580
acaggtatag aacagaaaga agagtgtatg tgtgtatctg tatgaattta tgatgggtgt   32640
aacatatatg tattagggaa atgagggaaa tgatacattt ctctgacttt gggagaacat   32700
tatatctcta cctcatattg caaacaaaca taaagttcag attaattacc taaatgtgaa   32760
aaaatgaaat aatttcttta aaaaatgtaa tcttagtttg aggaaggtta acattataaa   32820
ggaaaaaact gttttgagtg aatatagtt caatatgtca aaatccacct tcaacaaaat    32880
tgaaagtaaa ttgaacttgg ggaaagtatt gacagcatat agatcaaagg ttactagcct   32940
gtgtaaagag cagttataaa tatcgttaag aaaaacactg tcgacctgtc ggcaccttgt   33000
tctccgactc ccagcctcca gaactgtgac gagtaagtgc ttattgttta aaccacccag   33060
```

```
tctgtatgtg gtattttgtt atagaaactc aagctgatta ggacactagt aatcagtaga   33120
ctgaaactga aacaaaaata agaaccttt ttacctgtca aattggcaaa cattaagaat   33180
attcagattt ttgtcagagg tgatacaacc ttctaagaag gcaatttggg aaaatataaa   33240
gctttagatt attatatgtc tgacctagca gttttacctc tagggtgctt acccctagga   33300
aagtgtgtaa tgatattggt gcagtgccct tcatcccatt agaaaattaa aaataacctt   33360
aatggcctac cactaaaagg ggattgaaaa tttaagatat attattttat gtgtttattg   33420
agatggagtc ttgcactgtc cgcctgggcc agagtgcaat ggtgcgatct cggctcactg   33480
caacctctgc ttcccgggtt catgtgattc tcctgcctca gcctcctgag tagctgggat   33540
tacaggctca caccaccgca cccggctaat tttttgtatt tttagtagag atggggtttc   33600
actgtgttgg ccagactggt ctcgaactcc tgacctcatg atccgcgccc tcggcctcc   33660 cagtgttggg attacaggtg tgagccactg cgcctggcca gatacattta caagagaa   33720 tgttagttaa cattcataga tatttatatt ttgtttactt tttattaaaa aaatttttt   33780 tagagacagg atcttactct gtcacccagg caggatgcag ttgcacaatc atagcccact   33840
gcagcctgaa ctcctgggct taagtgatcc ttctgcctca gccttttgag tacctggggg   33900
actttaggca gtgctactat acctggctaa tttttaaatg ttttatagat gagatcttgc   33960
tgtattgccc aggctggtct agaattcctg ggcccaagtg atcctcccac cttggcctcc   34020
caaagcgctg agattacagg catgagccac cacttctgac caatagatat ttatatttgt   34080
gactggaaaa tatattaaca atgtgttaaa aaattcagtt aaaaaataat gaaagatttt   34140
tgcttctggc taagatagaa taacaaggac agcatttatc ttcttgcctt gaaatagtt   34200 aaaacggaag aaatatatgt aacagtggtt ttcaagttat tgggcatcag gcaaagaaga   34260
atagttatcc caggaaaatg aatgtggaga gccctacaat ttccttacat tactgcctgg   34320
tcatggcaag aggaaaaact gagaggagac tgaggctgag ccagtggttt gctgggttga   34380
ggaggcagag ctgggagtgc agagatgcaa ggtggtgaga gcccatatgg aagaatacca   34440
gggaagagag ctgcagaggg agctccggag acctgcaccc tgccctctca gtaccctgtc   34500
atgtgtgtag ctgagtactg acgagcactt gcttgtgcgg aaatgaccca gggctggagg   34560
tagagccacc tgaaaggatt agaaggaaca gttgctgaaa gtcacacagg gccaggaaga   34620
atttctaatc acaccagttg gagtggaaaa cctcagctct catagagcag gtagggtact   34680
cagaagggtt tgcccaccta gccccagact aagtttcgtt actctgaccc tacctaatat   34740 taaaagaga ttaattaaat tgttcgcaac aaaaataata tatttcagtg tttgtaacac   34800
gtagaagtga attgtatgac aatagcataa aggctggaag agcagaaatt gacatgtatt   34860
tgcgctgggc agaataatgc tcccctcttt ccccaaaaga tatcaagtcc taatccctgg   34920
agcctgtaaa tattacttta tatggaaaat tgttttatga tgtgattaaa ttcaggatct   34980
tgagatgagg gggctatctt ggatgatctg ggtaggcact aaatgcaatc acatatatat   35040 aaaaggagg cagagggaga ttttacacac agagagaagg ccctgtgaag atggaacaga   35100
aagatttgaa ggtgctggcc ttgaaaattg gagtgatgaa gctataagcc aaggaatgca   35160
gcagccacca aagctggaag aggcacggag cagttctcat ttagagccta ctccagaggg   35220
aatgtggtgc tgccaattcc ttttttttt tttttttaa gatatcattt accccttaa   35280 gttggtttt ttttttttt tttttttta gtatttattg atcattcttg ggtgtttctt   35340 ggagagggg atttggcagg gtcataggac aatagtggag ggaaggtcag cagataaaca   35400
tgtaaacaaa ggtctctggt tttcctaggc agagggccct gccacgttct gcagtgtttg   35460
```

```
tgtccctggg tacttgagat tagggagtgg tgatgactct taacgagtat gctgccttca   35520
agcatctgtt taacaaagca catcttgcac cgcccttaat ccatttaacc cttagtggac   35580
acagcacatg tttcagagag cacggggttg ggggtaaggt tatagattaa cagcatccca   35640
aggcagaaga atttttctta gtacagaaca aaatggagtg tcctatgtct acttctttct   35700
acgcagacac agtaacaatc tgatctctct ttcttttccc acatttcctc cttttctatt   35760
cgacaaaact gccaccgtca tcatggactg ttctcaatga gctattgggt cacctccca    35820 gatggggtgg cggccgggca gagggctcc tcacttccca gatgggcgg ccgggcagag     35880 gcgccccca acctcccaga cggggcgcg gctgggcggg ggctgccccc cacctcccgg     35940
acggggcggg tggccgggcg ggggctgccc accacctccc ggacggggcg gctggccggg   36000
cgggggctgc cccccacctc ccggacgggg cgggtggccg ggcggggggct gcccccacc   36060 tcccggacgg ggcggctggc cgggcggggg ctgccccca cctcccggac ggagcggctg    36120
ccgggcggag gggctcctca cttcccggac ggggcggctg ctgggcgag gggctcctca    36180 cttctcagac ggggcggctg gtcagagacg ctcctcacct cccagacggg gtggcagtgg   36240
ggcagagaca ttcttaagtt cccagacgga gtcacggccg gcagaggtg ctcttcacat    36300 ctcagacggg gcggcggggc agaggtgctc cccacttccc agacgatggg cggccgggca   36360
gagatgctcc tcacttccta gatgggatga cagccgggaa gaggcgctcc tcacttccca   36420
gactgggcag ccaggcagag gggctcctca catcccagac gatgggcggc caggcagaaa   36480
cgctcctcac ttcctagacg gggtggcggc tgggcagagg ccgcaatctt ggcactttgg   36540
gaggccaagg caggcggctg ggaggtgaag gttgtagtga cccgagatca cgccactgca   36600
ctccagcctg gcaacactg agcactgagt gagcgagact ccgtctgcaa tcccggcacc    36660
tcgggaggcc gaggctggca gatcacttgc agtcaggagc tggagaccag cccggccaac   36720
acggcgaaac cccgtctcca ccaaaaaaca cgaaaaccag tcagacatgg cggtgcgtgc   36780
ctgcaatccc aggcacttgg caggctgagg caggagaatc aggtagggag gttgcagtga   36840
gtagagatgg tggcagtaca gtccagcctt ggctcggcat cagagggaga ctgtgcgagg   36900
gcgagggcga gggcgaggga attccttaat ttcagtttag tgatactaat tttggactct   36960
ggcctctaaa actgtgaaag aaaaaatttt ttgtttgttt gtttcttta agccacatag    37020 tttgtggtaa tttgttacag cagctgcagg aaactaattt atgctgcatg tgaaatggtg   37080
taataaggta gattgtgatg aagatacata gtataaacaa ttaagcaaca actaaaagca   37140
caacaaggaa ttatagctaa tgaaccaaaa aaggagatta gaataataaa aatggtgaat   37200
cccaaagaag ccagaaatag gggaagaggc aaataaagga agaaagagc ttgatggtag    37260 atttcaacct aactatgtca aaaggacat tacatgtaaa aggcagcgat ttttcagatt    37320
gaatggaaaa gtaagactcg gtatatgctg ctgcctgcaa gaaacacatt ctaaatataa   37380
aggcaaaaat aacctacagg taacagaacg gaaagaagtt cactgtgctt acaagaatta   37440
gatgcaagct agactggttc tgttaatatc agacaaagtg gatttcaaag caaaggctct   37500
tgcccaggat gagatggtca tttcataatg atgaagggga ttcgttcatc agcctggcat   37560
agcaagctga aatgtttatg caccggacta cagagctaaa atacatgaag caaagcctga   37620
cagaactaca agtagaaaca gacaaatcca cagtgataga gatttcagta gccgctctca   37680
atgatttgta gaacacgtag ccataatatc tggatctaga acacttgacc aacactgtcc   37740
cctgtgcaac ctcattggca tttacaggac actccaccca gcaccagcag aagagacact   37800
```

```
ctctcaagtg ctcacagaat gtttgccaag atagagcaga tgctgggcca taaaacaagt   37860
ctctaaatta aaagcattca aattattcag agtatgtttt ctgacctcag tatcattaag   37920
ttggaatata ttataggaag ataacctgga aaagcctcag atatgtggaa aaacccattt   37980
ccacatggcc catgggtcag aagtgaagtc aaaagggaaa tttgaaagtc ttttggattg   38040
actgatataa aaacaataga tttctaaact tgtggggtgc tgttacagca tagtaaatgg   38100
aaatttctag cattaaatgc ctgttttagg aagaaaagat ttcaaatcaa tgacctcagc   38160
ttctaccttt ggaaacttga aaatgacaag caaatggaat ccagagttac cagaagggcc   38220
aggtacggtg gcttatgcct gcagttctgc cactttggga ggccgaggca ggtggattgt   38280
ttgagactgg cagttgaaga ccagcctggg cagcctaggg agaccccata tctacaaaaa   38340
acaaaaaaat tagccaggtg tggtggcatg tgcctgtagt cccagctaac caggagtcta   38400
aggtgggagg attgcttgag tctgggaggt tgaggctgca gtgaactgtg attgtgccac   38460
tgtgttccat cctgggcaac agaatgagac cctgtctcaa aaacaaaaac agttactaga   38520
agaatggaca tcataaagat aggagcagaa gtcagtaaaa tagaaaacaa aaatacatag   38580
gaaatcaata aaaccaaaag ctggttcatc aagaacatca ataaattggt aaagctgata   38640
ggaaaaacag tgaagtcaca aattagcaat atcaggaatg agggagatga cagtagtata   38700
gattatatag atattaaaag gactgtatga ggcaggtgtg gtggttcacg cctgtaatcc   38760
cagcaccttg ggaggccgag gtggacagat cacctgaggt caggagtttg ggaccagcct   38820
ggccaacatg gtgaaactct gtctctacta aaaatacaaa aattagttgg tcgtggtgct   38880
gtgtgcctgt aatcccagct acttgggagg ctgaggcagg agaattgctt gaacctggga   38940
ggcggaggtt gcagtgagct gagattgtgc cgttgcactc cagcctgggt gacagagcaa   39000
gactccatct caaaacaaat aaataaataa aaaggactat atggtaatat tatgaacaac   39060
tttatgccaa taaatttgac aacttataga tgaaatggat gagttccttg aaagacacag   39120
aaactattaa agctctctca agaagatata gataagctga ttagccctat atctatttta   39180
ttgaatttaa atgtaaaaat caatatttag ttactggaaa acttttaagt gtggttggaa   39240
atggtatacg aacttttttca actgaatttt atgaagtcta atcacaggta aaggttttct   39300
gatgaaaatt tagtgtctga attgagatat actgtaaaaa atgttatata tcttaattat   39360
ttcttcacat taattacatg ttgaaataat actttgggtg tattgggtta aattaaatat   39420
tatgaaaatc ttgcctgttt tcttttttact tttgatgcgt cagctaggaa atataaaagt   39480
gtagctcaca ttctgtttct gttgacagta ctgcttggga gcacagtgtt tgaatgatct   39540
atcatttcaa agacctttcc tcagttcgtt attcatggct gtctgtattc cacatagata   39600
aggtctgaaa tactgctaag tggcatgttt tgttttatgc ttttataagt ttgttgatca   39660
ttactgatgt ggacttttgg tgcctcttag gctcattgct atcttccaac cattgtttgc   39720
aatttttacc tagagataaa gagaaagaga catttggttt cagagtagtt agattgggat   39780
catgaaagag caacctcatt ttgatgcttc aaaaatagca catcccccgt attactggga   39840
tttgctattc ttgggattac ttcaagaaca tccttgtgtt actggtttgg atgcttctga   39900
atgctgtgaa gtcagtttca tgtacatggc tcatcagttt agctctctct tggctttgtt   39960
tagacagttg gagcatgatg gcctaaacag cttctttcaa ttaaacattt taaaatagtt   40020
tacaaatagt aaacaaactc cagttttttgt gactctttgt ctcgcacaac aaaaacacaa   40080
tctgaccatg atcatctggc atcttagggt gaaatatggt tatactttgg cccataccga   40140
aagcaagatt aaaaagggc aggagagata gactgctgaa ctgattttca aggttccaag   40200
```

```
aatattgtag gttaagagta aaagtaaact tttggtagaa agcagtgggt tgtctaggat    40260
tgaagtatct gaagttttta aacgaaaatt taaaaagaaa aatgagaatt gccttacaag    40320
tacaatctct tcttttttaa aaataaaact ttattttgaa atagttttag atttatagaa    40380
aaaaattaga tagggtagga agttttcata taccctacat ccagttaccc cagttattat    40440
catcctaatt tagtgtgaga cattttcatg tttaatgaat caatattgat atgctattaa    40500
cttaagtcca gactttattc agattttctt aatttctatg taatgtcctt tttctgttcc    40560
agaattccat gcaggacacc ggatacctca ttacatttca ttgtcatgtc accttaggct    40620
cctcttgaca gtttctcttc tttttttgct tagaaattct ccagaatttc agaaacttct    40680
gggcatcgct atggaacttt ttctgctgtg cagtgatgac gcagagtcag atgtcaggat    40740
ggtggctgac gaatgcctca acaaagttat caaagtaaga accgtgtgga tgatgttctc    40800
ctcagagcta tcattgttgt aggctgagag aagaagcgat cattgagtgt tcttctgttt    40860
tgagtccctg aggatgtctg cacttttttc ctttctgatg tatggtttgg aggtgctctg    40920
ttgtatggtt tggaggtgct ctgttgtatg gtttggaggt gctctattgt atggtttgga    40980
ggtgctctgt tgtatggttt ggaggtgctc ttgtatggtt tggaggtgct cttgtatggt    41040
ttggaggtgc tctgttgtat ggtttggagg tggtcttgta tggtttgcag gtgctctatt    41100
gcatggtttg caggtgctct attgtatggt ttggaagtgc tcttgtatgg tttgaggtg    41160 ctcttgtatg gtttggagat gctctattgt atggtttgca ggtgctctat tgtatggttt    41220
ggaagtgctc ttgtatggtt tggaggtgct cttgtatggt ttggaggtgc tctgttgtat    41280
ggtttggagg tgctctgttg tatggtttgg aggtgctctt gtatggtttg gaggtgctct    41340
attgtatggt ttggagatgc tctggtatct gcctgcattg cttgccacac ctgcccggtc    41400
agaaggcgct atgttgacaa ttgtgcctgc acggtgccta ggtcaatgaa gggaaccgat    41460
ggtagccact ggatgctcct gggaaaatgt cactacaggc accagagaag ccagagctat    41520
gcccaaattt ctatgagtct cagttttctt aaccataaaa tgggatcaat gttttgtgg    41580 catgtgtatg agtgtgtgtc tgtgtatgtg tgaggattaa attgtgtatg tgtgaggact    41640
aattgccact actggatcct caaagtggta agaagtgttc ttattaataa tgacatcctt    41700
acactcttac ccagcaagat tgatgggtgt ggcactgctt ctcttttttcc atcacatggt    41760 ttccatggta tcctttttgcc cagggaatct ttgctttgtg gctagcactt tgttgtttgg    41820
ctaatcacgc tttctgtggt caggacgctg gcttctctgg agccatggga ttctagctcc    41880
ctgtcttgtc cctagagtgg tcactgtctt ctctctccgc ttgcaattcc tgctttgctc    41940
gcatctcact tatgcagtga cgtatatcag tttcaccttg ttctccgtgc ctgctgatca    42000
ttggcaccac ttgcatggtg ccatttaggg cctgcttcca gttaagcttg cttctccaca    42060
ggcctaaata tccttgcttg cttctttat tctcactggc aggaccaggg cggtctgtct    42120
ttgcatgaga cagggtctcg ctcagtcacc caggctggag tgcagtggct gatcacggct    42180
cattgcagcc ttgagctacc gggctcaagc tatcctcctg gcttggcccc ttgagtagct    42240
gggactacag gcgtgcacca ccatgcccag ctaattttta aaattatttg tagagatggg    42300
atctcgccag gttgcccagg ctggtcttga acgcctgggc tcaagtgatc ctccctcctt    42360
ggtttcccaa agtgctggga tcacaggtgt gagccactgt gcctggccct tgatgtttca    42420
gttcttgata tttgatcctc agagtcagaa aatctaaaaa gagggctatc ccaggttgcc    42480
ttggttcatg gcaaatggga cgttaagagg gcagagagaa tatgaacaga aactgttcta    42540
```

```
atattggtca tttaatgtgt aagtattgtt cttttttaaa cctccttcat ttttttttcca    42600 ggaattgctg gacacagtgg cttggtgtgt gtctgaggac tgtaggccat ggccctaggt    42660 tgtggttta ggtctcaggt gctcttcctg gctgtctcct tgcttctttc ccatgtcctc    42720
ttctttgttt ccagccattt ctcccttatg cttaagtttg gtgcagcagg gtttggctgc    42780
tctcagattc ctgcttcctc agatgctgta gttgtcaggc ccagcgggct ggcagcggga    42840
tcaggatctg gctaggtttg ctctcactgt ggcagagtag ggggaggcgt gggagagcac    42900
gtgtgacccc aggccagctg tagggagcat aggcatggtc acgtagcctt caggtcctag    42960
actttgtctt ctcatgagta tggctgtgtg tgtatggtga aaactaggtt ctacttagcc    43020
caagaaaatg ggcacatttt gcatgtggtt tctgtagaga aatgcactgg gtatctgaca    43080
tagcctggca gcatgcctcc ctcaggtagg ttagtctcag gcggtgaagc acgtgtgtcc    43140
agcaagaact tcatatgtgg cataaagtct ccgttctgtg aggtgctggc aaatcaccac    43200
caccgtcaag aggctgaagt gattttttgtc tagggaggca ggaaaggctt cctggagtca    43260
gcagccagta ggtgaaagag tagattggag accttcttaa tcatcaccgc ctcttgtctc    43320
aaggggtgcc aggaagctgt ggaggctgaa cccatcttat gctgccagag agtgggacac    43380
catgagggtc aggtcaaggg gttgtacctt gtttggtaga gaattagggg ctcttgaaga    43440
ctttggatgt ggtcagggga gtgtatcatt taggaagagt gacccggtga ggacgtgggg    43500
tagaggagga caggtgggag ggagtccagg tgggagtgag tagacccagc aggagtgcag    43560
ggcctcgagc caggatggtg gcagggctgt gaggagaggc agccacctgt gtgtctgcgg    43620
aagcaggggc aagagggaag aggccagcag cgtgctgcca tcacccagcg actggcgtag    43680
attgtgagag accattccct gctcttagga ggggctgagt tttagttttc tcttgttata    43740
caataagctt ggtatttgtt tacaaaacat ttgtaaagct aaatcaaggt ttgataaggc    43800
ttctagtttt atttaagaag taatgttgaa ataaatgttt gtccaattcg ctttgctcat    43860
ttaaggactt tcagtacaaa ctgcaacaac aggattagga tttaaacgtt tctgagatgt    43920
ttttactcct cagaatttcc cagaatgtga tctggtttg attttcaagc ttgctgaccc    43980
aataggttaa cccacaagtt ttacgaagac catctcagtc cacttacatc aactgcccat    44040
gccacggtta aagagatcat cgactgatgt ttggcacagc ttcctccctc ttgggtgggc    44100
aagcatttgg aagagaaggc tcctatgggt gagagtgggg caccaaagtc ttccctgtcc    44160
catcccctag cttgagaagc ccttctctaa tgtggacttt gtgccgttag catcgttact    44220
agcttgaagt tgaccatctg gacgtacttt ctggtttagc ctcacaagtg agcaaggagg    44280
gttgagagat gtgctgtgag gaatgtgggg ccccagctgg cagcaggctc tgggtcaggg    44340
gggcagggac cacgggcata cctgacagtg aggaggggcc acacctgcag aaaaggatgc    44400
aggactccgc cttgggaagt gttctaggcc agagcgaggg tctgtggttt ataagtacac    44460
ccacagtgct cgggaccctg cagatgtcca gggtgccgtc tgagcccgta tcatccaaca    44520
gaatgttctg ctagtgaaga ttaaagattt actccagggg ctttaggatt tattatatat    44580
atataaatcc tatatatata atttttttttt ttttttttt tgagatggag tttcgctctt    44640
gttgcccagg ctgagtgca atggcgtgat cttggctcac tgcaacctcc gcctcccggg    44700
ttcaaactat tctcctgcct cagcctctcg agtagctggg attacaggcg cccaccacca    44760
cacccggcta atttttgtat ttttagtag acggagtt tctccatgtt ggtcaggctg    44820
gtcttgaact cctgacctca ggtgatctgc ccgccttggc ctcccaaagt gctgggatta    44880
caggcatgag ccacccccacc tggccaggat ttattgtatt tgaaccatct accatttaa    44940
```

```
ttttgatgtt atgtagtatt tgatgataat gaaagttaaa ttgttttrct ttccatttrt    45000
ctgtttaagt gaatgacctg tatctagttt attcagtaac ttcctgcata tatttgtttc    45060
tttcattctt aatgaatata ttcttaattt agttgctatt atgttttgct ttgccccaaa    45120
attgaaatct tagtttcctt ttagctcgtt ttagaactag tgatgggatg tgtcttccat    45180
aaatctcttg tgatttgttg taggctttga tggattctaa tcttccaagg ttacagctcg    45240
agctctataa ggaaattaaa aaggtgggcc ttgcttttct ttttaaaaa tgttttaaat    45300 tttaaatttt tataggtaca cgtatttrgt aggtacatgt aaatgtatat atttatgggg    45360
tacatgagat atttrgatac aggtatacaa tacataataa tcacaccatg gaaagttgga    45420
tatccatgcc ctcaagcatt tatcctttgt gttacaaaca atccagttac atgctttact    45480
tatttrattt tattttrgag acagagtctt gctttcaccc atgctagagt acagtggcat    45540
gaccttggct cactgcaacc tccgcctccc gggttcaacc gaactttggg ctggtctcaa    45600
actcctgacc tcaggtgatc cgcccgcctc ggcctcccaa agtgttggga ttacaggcgt    45660
gagccactgt gccgggcctg attgtacatt ttaaaataac taaaacagtc agggcacagt    45720
ggctcatgcc tgtaatccca gcattttggg aggctgaggc aggtgatcac ctgagatcag    45780
gagttcgaga ccagcctggc caacatggag aaaccctgtc tctactaaaa atacaaaaat    45840
tagccaagtg tggtggcggg cgcctgtaat cctggctact cgggaggctg aggtagggga    45900
atcgcttgaa cctgggggtg gaggttgcag tgagccgaga tcacgccact gcattccagc    45960
ctgagcgaca gagtgagact ttgtctcaaa aaataaaaat gaaataaaat tgggccgggt    46020
gtggtggctc acaccttagt cccagcactt tgggaacctg aggcaggtgg atgcttgaga    46080
ccaggagttt gagaccagca tgggcaacat ggcaaaacgc tgtctgtaca gaaattagct    46140
gggtgtggtg gtgcacaact atagtctcag ctacttggga gattgaggtg ggaggattaa    46200
ttgagcctgg aaggttgaat ctataggtag ctgagattgt gccactgccc ttcagcctgg    46260
gcgaccaagt gagaccctgt ctcaaaagaa aaacaaaaaa acaaaaaaca aaccactatt    46320
atcgactata tattattgtc tatgatccct ctgctgtgct gtcgaatacc aggtcttggg    46380
cccttatttc catcactgag caaacttcac tctgttaagc agcaggtgtg ggatttcatc    46440
gttattcagt aattcacaat gttagaagga aatgctgttt ggtagacgat tgctttactt    46500
ttcttcaaaa ggttactctt tattagatga gatgagaatt aaaaatggta acttacttta    46560
tatctttata attgaagccc actagacctt aaagtagtta ccagatgttt tatgcattta    46620
aatggccttt tctctaaaat tagaaagtaa caaggaaaga aaatgcttcg tttctatgca    46680
accctcttgg tgactagtat gtgactctta atgcaaccct cattgcaccc cctcagaatg    46740
gtgcccctcg gagtttgcgt gctgcccrgt ggaggtttgc tgagctggct cacctggttc    46800
ggcctcagaa atgcaggtaa gttgtacact ctggatgttg gttttrgtcg ggggccagct    46860
gctactgatc cttatgtct cagctcagat gtcatttcaa aagtctgctc tgccctctcc    46920
aaattgcagt cgaccttgcc ctgtttatgt ttccctcata gcactaatcc atgtcagaaa    46980
ttgtcacgta cagtctatct gtgtgcttgt ttattttcta tcccaccctt ccgcaagaga    47040
cttatgggat gtgtgcccca ggacagcagg ggtcttactg tcttatgctc tgttgcagcc    47100
cagcagcgat aacagtgtct gcacatagta cttgcttaaa agatacttgc caaattgttg    47160
aaggttgagg taccaatttc attattgctg actataggag ttatagcaaa atatccattt    47220
gtctgttaca tgagttaaaa atatggttgt tgcactgtga atagtttggt ttagtcaaaa    47280
```

```
cagttgtatc ttaacggatt gagaaacaaa agcaggacca cttttcatca gctccctcct    47340
tctccttaac cagcaataca tgctgatgct gatatcccat agaccctcag ctccatcctg    47400
agtcactggg aatgtggtct aaaccctcac tattaatatg aactgagttt caataagaat    47460
cttatatggg tcgggcatag tggctcatac ctttgatccc agcacttcag gaggccaagg    47520
caggtggatt gcttgaccca gactaggcaa catggtgaaa cgccgcctct acaaaaaata    47580
caaaacttag ccaggcatgg tggtgcgtgc ctgtggtcac agccactcga gaggctgagg    47640
tgggaggatc acttgagcct gggaggtgga ggtcgtgttg agccaagatc gcaccactgc    47700
actccagcct gggcaacaga gtgagacctg tctcaaaaaa accaaaatcc agaaaagaac    47760
ttatatggct gcagaggtat aatcactaag gaaatttcct tttgtataat cttttttctt    47820
ttactatcat ttaaaaaaat gtgttatatt tctgaagcaa cacatccagg ttctgcacat    47880
agcagccaaa gtgaccttaa agaatataac tgggtcttgt cattcccta tttaaactct    47940 tgtacccatt tcccagtgcc gtttagatag agattccaga ctcgtcaatg gctctgtcac    48000
ctcagacacc ctgcattgac tcattagtct gattagagtc aggttttct tcctcctgat    48060 ggttttttt tcccccttag ttctcagcgg aacagtcact tccttaggga ggtttcccca    48120
gccaccctct gaggccgtgc ttgttgccag actctgccac tagagggcag ggctgcacca    48180
ctcctggcac ctcgcacccg gcctgccctg tcactctgtg tgttgggtga attcctgtga    48240
tctgtgactc actgctctgt gtcctacaca ttcggctttt cttctctccc cacaacccca    48300
ttttataatt ctccttttc aggaaagctt tattcccatt taaaaatttt tgttttaaa    48360 atggtatttt cttacactta ttttctaatt aaaaatgagt gttttaagaa gtattatgat    48420
ttactgcaaa taatttttaa acccagcctt ttagatcctc tgtgatcata agagaaatga    48480
aggatgtctc ccaacacttg agcttcatcc acatttcatc ctcctgttct ttcagctgag    48540
ttttccccat cccattaggg actgttggaa tataaaactg cttttccct aacagggaat    48600 gaattgcttc tgtttctcct gaaggagagc tggaagaatg acttgcgttc ttttgcatac    48660
acaggcctta cctggtgaac cttctgccgt gcctgactcg aacaagcaag agacccgaag    48720
aatcagtcca ggagaccttg gctgcagctg ttcccaaaat tatggcttct tttggcaatt    48780
ttgcaaatga caatgaaatt aaggtatgat tgttgcctca ggtcacaaac atgcgagtga    48840
tgctgtgagt gagtctgtgg agggtgaggg cttctgaaca gggagtcctg tgggagtgct    48900
tcttggggta tgttgtatgt cgtaatttag actaccatca tttgtgttat ttttgaggca    48960
cctaaggact tcttccact tctcatttct tactgtgggg tgaagagttg aattgggaga    49020
tggtttctag atgcaaattg aaaaggcatt tttccagagc agatttgttt tcggcgtact    49080
agagtgactc tttaacctag ctgcgggaag atgactgtgc caagactgca ggtaggagaa    49140
agctcactga cgaggccttg tgggtctgaa cgtcctgcag ctatcagagc ctgttggctt    49200
cctgttgtgc attccaacaa atcatcttca aacccacttt agtgtttgt ttataatgtc    49260 cagaaatagt gaccctgtca catgctctac agattacagg attcttagcc tcttcctttt    49320
tggtaggtca gtcctgggtt tgagcccaag tgaccctcct gggaggtgat gatacacact    49380
gggtagagtg gaatcagatg gacttggatt agaattctgt cctctttact agttattttc    49440
ctctaggcaa actgcccaac agctctaagc tatttccttc gtattctgaa aaataagcct    49500
taatgggacc catataggc aactctgaga gtaaaataaa ggaatatgtg ttagagtgta    49560
gcatagtcac ccacgggaag ggcttagatg ttagctgcta ctgctcttat tagctgaatg    49620
atttggaata aactgttagc ctctctcatg ttttttctct tgagcttcga agttttcttg    49680
```

```
ttaatactaa ggagatattc aaactagtca tggggttttg gaatgacgaa gggagatgat   49740
gaatctaaag aatttagtgt aatatttctt catgctcagt aaatggtagt ttctgctgct   49800
gttattttta ttaccatctc tttggaatgg gagtaggtgc tcctttgtgg tcagaggctg   49860
tgagagctcc acagcgccag tttgcccatc tgtacactgg ggtctgttga aggcagtccc   49920
ctctgtgata tctctggctg tcagagctca gatgatagat ggtattttg tactcttagt    49980 tctcatcatt ttcatgattt cgatcaccat ttgagtatga tgatgctaac actttgttga   50040
acgtagaatc cgttaattac ttccttcctg aacctttggc attaaaaaaa atctattctg   50100
ctacctctct gctcatttat ggttattcaa atttattatc aagagcctgg tacagtggct   50160
tgtgcctata attgtagcta cttgggaggc tgaggtagga ggattgcttg aggccaggag   50220
tttgagacca gcctgggcaa gatagtgaga ccctatctct aaaaaaactg aaaaaaaatt   50280
agctggacat gatggcatgt gcctgtggtc ctagctactc aggaggctga gacaggaggc   50340
tcggttgagc ccaggagttg gagttcgagg ctacactgag ctgtgattgt gccaccacac   50400
tccagcatgg gtggtaaaac aagatgccat ttcttaaaaa aaaaaaatat atatatatat   50460
attatcaatg aaattcagta gtaccaacag gattataaac aaagatagta gttcccttcc   50520
tacttttctt cttaatcctt gtgtctcaca ggcaaacata actcttagta tttcttccaa   50580
tatttacttt catgtttctt tcttttcttt tttttttttc tttgagatgg agttttgctc   50640
ttgttgccaa ggctggagtg caatgacgca atcttggctc accacaacct ctgtctcccg   50700
ggttcaagcg attctcctgc ctcagcctcc tagtagctgg gattacaggc atgcatcacc   50760
acgctcggct aattttgtac ttttagtaga gatgggtttt ctccggttg gtcaggctgg    50820 tctcgaactc ctgacctcag gtgatcctcc cacctcagcc tcccaaagtg ctgggattac   50880
aggcgtgagc cactgcgccc agcaacttcc acatttctaa ataacatgct tctactgcta   50940
tttttttttt caattttaga cattttttta cttcactat agttctatca gaattcagtg    51000
tgtacgttat tatgcctaag taaatagtca tggttgctta cgtattatat ttctttgatt   51060
gtgtttctta tttgatgaga aagctgtgtt ttttgctctg ggttgaaact ggagagagga   51120
cctggggagg aggaggagga cagatgaagt tggtgactgt accttcatgg ccatagctgg   51180
gttctcagca cccggggatc tgctgatcac ctactcatag gccaggcccc tatcgaagtt   51240
ctaggtgacc cagtgctggg gacgggggg ccacctgcaa ggtctaatca tggaggtggg     51300
ggctacagtg ttggcttgtg ctggggccag catccttagg aaggcatctt ggaggtggag   51360
gagacagccg cccacttctt gattggggcc ttcagcagca ccagcttctt gggcaggctg   51420
gtgctggctt tcatcaccat gtcgtgttca atcttcttcc agatcctgac ttctaggttc   51480
agctttcctc agaccctggt tcctttcaga ggccattgct gctgccttgc tctttgctgg   51540
cttgtgcctt gattatatgt ctttgtacaa cttttgttt tcctggagtt aatcttcaca    51600 tctgtttttct tggagttaat cgttacctct atatcgcttg cttattattc tttgcctttt  51660
ttgtcttctc acaccttcca acttctttgt aatatgtgtt tagtacaatt tttcatgaca   51720
ggtagtttac tgaatcagtt ttccccagt gtggtcatcc aacttgagtt atccagctct    51780
ctgccccagt ctgggcaggt tgatcttcag gtctgtagta cacttgtatc ctaggacttc   51840
tctttgccat tagcctggaa tttcctttgc agttctcccg ttggatgccc agttcctaga   51900
tgccatatgt ttttctatcg tctagtagct tcctgagaga agatgaatgg gagggaaatt   51960
gtatgaggtt ttgcattcat aaaaatgcca ttttttttcc tgtacacttg gctgggtatg   52020
```

| | | | | |
|---|---|---|---|---|
| gtgttctggg | gtagaaatca | ttttccctca | gaaatgcaaa | gtctttgccc tgttgtctta | 52080 |
| aaatctccaa | cgtgacccga | ttccttaacc | tatgaatgta | cttttctttg gaagctttcc | 52140 |
| attttttgggg | aggtgaagtg | ctaggtactt | agtaggcctt | ttaatttgga aacttacatc | 52200 |
| ccttcagttc | tgggaaaatt | ttcttaacat | ttctctgaga | agttcttgcc ttttattttc | 52260 |
| tgtgttctct | cctgaaattg | gttagttgga | tgttggtcct | cctagattga ctcacatctt | 52320 |
| acctttttct | tttcttttttc | tggtactttt | tagatatcca | tctcaaactc ttctattcat | 52380 |
| tgttatgttt | ttaacttctt | tcttttcttt | gtctcttgat | ggggtcttgc cctgttgccc | 52440 |
| aggtgtggt | gcagtggtgc | gatcatagct | cactgcagcc | tcaaattcct gggctcaagc | 52500 |
| agctgttctg | cctcacccctc | ccaagtagtt | gggactacag | gtatgcacca ccacgtccag | 52560 |
| ctattttctt | tacttttttt | ttttttttttt | tgagatggag | tcctactctg tcgcccaggc | 52620 |
| tagagtgcgg | tggtgggatt | ttggctcact | taagcctctg | cctcccaggt tcaagcagtt | 52680 |
| ctcctgcctc | agcctctcaa | gtagctggga | ttacaggtgt | gcaccaccat gcccggctaa | 52740 |
| ttttttgtatt | tttagtagag | ccagagtttc | accatgttgg | ccaggctggt ctcgaacgcc | 52800 |
| tgacctcagg | tgatccgcct | gccttggcct | ccgaaagtgc | cgggattaca ggcgtgagcc | 52860 |
| catcattaga | tctttaaata | ccagtatcta | taagtctttt | cctcttgagt cagctagtat | 52920 |
| ccctggaagg | aaattactca | ttttcctgct | tggaggctat | aagcttggct atgtttatcc | 52980 |
| tgcaaccggg | gactggaagg | gaggggactg | acagtgttgc | tggtcagggt gccctcttac | 53040 |
| tttttgtttt | ctgtgtgcat | ctcacgtctg | tcctcagcct | atgtaaacac ctcttgagat | 53100 |
| tatccctctc | aatctttgcc | ggaggtgggg | gagggggctgc | ttcctgggct gccttggatt | 53160 |
| ggagggaaga | cctcaggtga | gtgggtggga | atttgcccaa | ggagccatga gaccagccac | 53220 |
| tatttcaccc | tctccatccc | tccactttca | gatgtatgtg | cgcctccaa agcccgagct | 53280 |
| cttcttggcg | tctgtggctt | caataagctt | gcttttgct | ggtatccctc ctaccctccc | 53340 |
| ctgtccccag | caaagcttgc | atttgaactt | cttcctacgg | gctaacaaat cagtcagtta | 53400 |
| tgtagctctt | gttacttttt | agcttccgaa | gttttgttga | cacccgtagt ctgctaatgt | 53460 |
| ccctgttctg | ttcttttctgt | tcgtgtaaat | atatgcttta | tacaacttct ttacatgatt | 53520 |
| tttgtggggt | ttctgggtag | cagagcttca | caagttcaat | ccagcgtgtt ggattagaaa | 53580 |
| tctcccaccc | tctggtttat | tcttattctc | aaaattacct | gccaaacact gatactccct | 53640 |
| tgtttttcct | tttcctgaca | ggaaatgtac | ataccataca | ggacagaaat cattagtgta | 53700 |
| tcccttggtg | aataaccaca | aagtgaactt | aaccccttgta | accgccaccc aggtcaagac | 53760 |
| agaatattac | caagcactca | gaagcctctc | ccctattccc | ccgtcactgc tcctgccttc | 53820 |
| ctccccaagg | tcatgactgc | tggcttctaa | ttccagagtc | tgttttttaaa ttctgtgtac | 53880 |
| atagaccatg | gattaagtgt | tcttttttgtc | tggtttattt | tggtcgacat taagttcatg | 53940 |
| agagtcttct | atattatcgt | gtgtattagt | attcctgtag | ttttaggagc ttcatagcat | 54000 |
| tccattgtag | ggatatacca | cagtttattc | attgtattat | cactgggttg tttctagttc | 54060 |
| ttggctattg | cgagcagtgc | tactgtgacc | actcttaggt | gtgtcttttg gagtacatgt | 54120 |
| gcaggtttcc | atcttgcaca | gctagaggtg | gagttgttgg | gtgatagggt gtgtgcatct | 54180 |
| cagctgcagt | agaaactgcc | aaatagcttt | ccttgagtgc | ttgtaccagc tcacccttttt | 54240 |
| gccactgtgt | atgggggattc | caggagctct | ggtcctcgct | agcacttgga attgctgatg | 54300 |
| cttttactct | tagccttcct | gatgggtgtt | ttctggaatc | acattatgat tttaatttcc | 54360 |
| attccttaaa | gtaccccttgg | ctctgaagtt | taatgattca | tgcatctctt cccttttgaa | 54420 |

```
gtactcttac aggtatgttg tgcatgtgtt gaaaagtggc actatctatt ctaaaataca    54480
gtatgcctcc tctgtgtttg aacagttgta gcgtggcctt ggggcctcct gttagctggc    54540
ttggagaagg gattcttggg attgtagaga ttagacctga ggaggcccct tggagctctc    54600
tgactaaatt ttattcttta ttattccaaa ctatttaagc tcaccgtgtg ctgactcatc    54660
ataataatga gtagctctca ttgtgcttgt ctatttggac tcatacaatg attttttttt    54720
tttctttgag acagagtctt gctctgttgc ctaggctgga gtgcagtggc acaatctcgg    54780
ctcactgcag cctccacctc ccaggttcaa gtgattcttg tgcctcagct tctcaagtag    54840
ctgagactgc aggtgcgtac caccatgcct ggctaatgtt tgtatttttta gtagagacgg    54900
ggtttcacca tgttggccag gttggtctca aactcctgac ctcaagtgat ctgccttctt    54960
cagcctccca aagtgctggg attacaggtg tgagccactg agcttggcca aagtagtttt    55020
ttaagatgtt agtatctttt cttgcagcta aaaaagtttg tcagagatga ttctactttg    55080
ttctccaggt gttttctcag ggagaaattg gaggcagtaa gccactgggg gagtcctgtg    55140
gctgggggt ggggtagtcc tgtggctcct tgtcagggag tcctgtggct ggcaaggaga    55200
gaagtcctgt ggctgggttg ggagggagtc ctgtggctgg ggtctcatcc tgtgcctaac    55260
agtgtccaga ggtgccgaga ccagctcagt cggggagacc ctaacccagc agcgctagag    55320
gaattaaaga cacacacaca gaaatataga ggtgtgaagt gggaaatcag gggtctcaca    55380
gcctttagag ctgagagccc tgaacagaga tttacccaca tatttattaa tagcaaacca    55440
gtcattagca ttgtttctat agatgttaaa ttaactaaaa gtatcccctta tgggaaacga    55500
ggggatgggc cgaattaaaa gaagaggttg ggctagttaa ccgcagcagg agcatgtcct    55560
taaggcacag atcgctcatg ctattgtttg tggcttaaga atgcctttaa gcggttttcc    55620
accctgggtg ggccaggtgt tccttgccct cattcctgtc aacccacaac cttccagtgt    55680
gggcattagg gccattatga acatgttaca gtgcttcaga attttgtttt atggccagtt    55740
ttggggccag tttatggcca gattttgggg ggcctgctcc caatacagag gtctcgtgta    55800
aattccctgg gaggcgataa gcctctgaga aacagactat gctaaccacg ccatgaaaga    55860
gaaacttatt tataaatcag atgccagtta ctagtttact gcttatttgc ccaggcgtag    55920
ctctgacaga gtccccgact catagtgctt gctcagtgca tgctgaacaa tgattggaat    55980
caagtcatgg ctcagagcat agtttttgaat aatgggaaat ggatgttctt aagtaacata    56040
gtcaccaaga taatgcgact agctgggtca cccctttca attttaggat atttttatca    56100
agatttaaat ggccatcatt agagttatag cactttctcc tttggattgt cctagaggcc    56160
catgagaaag tattccctaa tttcttagga gaacagtttg tgggtagtat gcggtcatgt    56220
ccagttaaat tgcagatatt tccgatcgaa gatgttccag tcctgagaac ttcgtgacat    56280
tagcaggact tctacaagcc atctcttagg gtggggcatt tactgcagtt ggctagtact    56340
cttttctcct taactttgtc atttgttgat tttttttttaa ctgtcccaa atactgtggg    56400
cagagtgtat ctagaattga ggcctccacc attgcggaga ggacatggat gctgagcagt    56460
cccctgagtg aaggttataa agaagcaaat agactacaca tgtctgtaaa ctgctcttga    56520
gtgtcccaaa tttggggtac ttcagttcag ctgtaggaaa agcctcaaac tgtttatact    56580
ttgcaagaat tggaaacttc taattcacgt taagttttat gtaatacatg ataagcttca    56640
taggagcttc atctttttatc tacttggact tttgcttccg taggttttgt taaaggcctt    56700
catagcgaac ctgaagtcaa gctcccccac cattcggcgg acagcggctg gatcagcagt    56760
```

```
gagcatctgc cagcactcaa gaaggacaca atatttctat agttggctac taaatgtgct   56820
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggacctt gctgagctag   57300
ggatgtgggt gtgtagccat tcccagtggg cctcatggcg tactcgttca tgatcatgtt   57360
tgtgccatct tgatctctca ggatctcttc tttttttaaca gattaagccg ggaatctcca   57420
aacagtgagt cagatgttaa gatgtcttgc ttccaccccc acaggcttac tcgttcctgt   57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
cggcagaacc gagagttaga ggtgtggact ctggagctgc gctgctcgtt tccaacccta   57780
ggtgctgacc tctagctgtc ttccctctgt atgtccctgt caccgtgagt caaatgcggg   57840
tgatgcctcc tcaggtgccg tgttacctaa gcctctcaga gaccactgct accctgtttc   57900
taaaaccaga ggtcacgata tgtgttcatc cacccagtaa atactgattg agcacccact   57960
gtgtgctagg ctctgggata ggggctgggt atacaatggt gagtatttca gctgcagctt   58020
ctgccccgtg gaggctgtgg cctagcacac tggtctaggc acggtggtat atgctcactc   58080
aaggagatag ggacgtggtc gtttgggggtg tcggaacaaa atgtcggaac ttctcttttcc   58140
aatgcagaga aaccttgcag taattctaat gtactgtgat tggcagttga cttcagttct   58200
ttgtagcacg cttactcagg ttatttcact aactatgtaa ccatgcagcc tcattttaag   58260
caattggatt ttttgaactt tacttaaaat gttatgtcag ggttttttatt gtgcttaatg   58320
tgtgccattt agctaagttt tgtaggatac gaaattgtaa gtggcttaaa atgattctta   58380
atagaatcat gaattgaaga taatgctaat aatttaagca ctgagttagg tagtgtttgt   58440
aaaatgctta gaatgcttcc tggcacatgt taaggccatg taagtgctgc gtgttgataa   58500
acagctgagc aaaagtggac tcttaagaaa gtattggggc tgagagttct gttccaacca   58560
gctgcccttt ggttattttt cagaataaaa gcagagtctc atgggatatg acatttatat   58620
ttccttcaca aaaacactg ctgagtgttt tgttgagtaa aaagggtgta gccatggtaa   58680
taatacattt aaaatatagt ttatttcatc tttaccttgc cttgtttttt ttttaagcta   58740
gcttttatt gagaattcca cacatacaaa agtatcaact catgaccagt tatatttcat   58800
ttataatcct acttctccct tttttttatta tttgaaagca accccaatt atcctcttat   58860
ttcatctata agtatttcag tatctctata gatgaggact cttctttatt tttaaaactt   58920
tatttttaaa atgatggtca gatgcagtgt tcatgcctgt aatcccagaa ctttgggagg   58980
ccaagctggg cggatcactt gaacctggga gtttgagacc agcccgggaa acatggcgaa   59040
accccatgtc ttaaagaaaa aaatcagcca agtgtggtga tgcatgcctg tagtcccagc   59100
tacttgggag gctgagatgg gagggtcaca tgagcctgga agatcaaggc tgcagtgatc   59160
```

```
catgattgta ccactgcact ccatcctggg tgatggagca agattctgtc tcaaaaaaac   59220
aaaactgcaa aacaacgtca caaaacagtg ccattgttag acctgaaaat attaaacatt   59280
tcctacatca aatacccacc aactcattat caattttttct ctctactctt ttggaatcag   59340
```

```
catctaaata aaattggtcg ataaggattg taaatctctt tgatgaactg gttccctcc    59400 atcccagttt ttttcctta gagttcattt attgagaaac cagattgttt gtcttctaag    59460
ttttcctgtg gtctgatata ctgcttccat ctccactgtg taaattaaca ccttttctc    59520 ttctctgtat ttcctgtaaa tcaataattg gaggaaaagc cttgtcagat ttagtgtata   59580
ttttatatct gagtccagta tttcttatat aatattttaa gataagtgta ctcttttaaa   59640
aagtattgaa actatatgct caatttttttt taactgatgc ttttaagaag gctgcttgat   59700
cataaaagtt tagagatcat tggtctgatg ggaaaagcaa ataattacta aaccgtttag   59760
caaggttgag gtgcacatgg tggggcctgg agaagttcag tcatgagccg tcacttatgg   59820
gcacgtggaa tctgacccgg cacagagttg ggagaagaca ggagctttat agacagaaaa   59880
tgtggtcttt gctaagtccc aggagtgaaa gggtgagaca gtgctcacag cacacgagtg   59940
tgggtgcgta gacagagcaa gggtgggtcc tgaaaaggcc tgcaggcttt ctcatagatt   60000
agcaagagtg ctggttacgg aggtttctaa catttgtgaa cagatcgaaa ctgtgttaaa   60060
ttgggattgc agtaatcctg gaaggacagg gatagaggt gaaggggaaa aagggtatg    60120 gatgtgagac ttaattgctg atttttcttaa gacctttctc caaagtaaat aaatgatgtg   60180
gcacattttt gaactggcaa attctaaact ctagatatga ttatctctat aacatatctt   60240
actccatctt cttttgacta aaaactgttc ttaattaaat taccatgaga cgttcaattc    60300
agcaaatgta gtttggctaa ccatatttaa ttagaattta atataatcct aggcctggcc   60360
aaactattaa gcaagtgtgg gcaaaatatt gataatttta gatatgcagg aacttagttt   60420
gctttccatg tgtgcttttc gaaaaaggaa taaattgaaa aatagaggaa gccctgaaat    60480
ccaagaagca aactctctca cctaggcatg cagtaaaagc aattctagga tgattgctgt   60540
ttggcgcgta gttcgtatta gaaccattc ttcttgaata aatagtatgt ttaagaagct    60600
gggcagaggg aaggcatatg catatattat caacaaggag ggagaaaaag gcaattagta   60660
accatccata ggagggtcag caagatttat aaaggaaatt tgtgatccaa gtatgaagca   60720
aaataaggtg cagaataaat tttaagcaag taatagatta gagtaagaga acccatttga   60780
ccattaacct tgggacattc tctttcaaat gacatggagt agtactgaaa tctttctttc    60840
tttctgagtc taggttattg tgactggact cagaaagaaa tatttcatta ttgcagtgaa   60900
taacatttgt gaacattatt gttcataaat tatgcagtga ataacattta tgaacacgtg   60960
atgtgtaaga tacatactgt ttattttttag ttaagttttt tggctcaact tctaggcaga   61020
gaacattaaa tgtaaatagt gttacctagg agcatgtaaa tggaaatctc catagtatga   61080
aagcagtgct gttgctaaca gaatttagga ggggcagat gaggtgaagg aaatgtgggt   61140
gctgatttcc ttattacatt gagaggagcc aggagattct ttgttcaaaa tggatggctt   61200
aagaagtcaa agtataagct gattacgtag agcaggtacc caaaaatgtt ttgtgtaagg   61260
ggccagatag taaatatttt cagtcttgca ggccatccca agtctgtggc agctactcaa   61320
cactaccttt gtagcatgaa agcagccaca ggcagcccat aaatgtggct ctgttccggt   61380
gaaactttag gtacaaaagc aggtgcaggc cagacctgac ctgtgcactg tggtttgctg   61440
acctgggatt caggggtata gaagttacca tcagaagagc taaaagtgag acttttttact   61500
```

| | |
|---|---|
| ttatactctt ctacactgtc tgattttgaa aaaagaaac atgtatttta taatattaaa | 61560 |
| gataggttg gcaaatagca aataaaaata cagaatacca gtgaaatttg aacttcagat | 61620 |
| acattatgag taattttatg gtgtaagtat attccaaatc atgtgggaca tacttacact | 61680 |
| acaaaattat ttgttgtttg tttacagttt aaatttgagt gccttgtatt ttatctggca | 61740 |
| actgtaatta aagggaaaaa gaataaaattc attatgttca tataatgtga tatagcaggg | 61800 |
| gtccccaacc cccaggctgc agagtggtac tggtccatgg gtccccaacc cccaggctgc | 61860 |
| agagcggtat tggtccatgg cctgttagga accaggctgc ccagcaggaa gtgagcagca | 61920 |
| ggtgagctgg cattcccacc tgagcaccgc ctcctgtcag atcagtggca gcattagatt | 61980 |
| cccataggag tgcaaaccct attgtgaact gcacatgtga ggggtctagg ttgtgcgctc | 62040 |
| cttatgagaa tctaatgcct gatgatctga ggtggaacag tctcgtcttg aaaccatccc | 62100 |
| ctggccctgt ggaaaaattg tctcccatga aaccagtctc tggtgccaga aaggttgggt | 62160 |
| agcactgtga tatagtatta aaagtgctaa taaatatggc atactgcctt taaaatgtct | 62220 |
| ggtagctctt tctcagtggc actcataata gtgtttttg attttaaat gtgtgtcaag | 62280 |
| ctgactctcc cctccgtgta tgctgggctt tattttccct ttcctagtca ccagttttgg | 62340 |
| gaaatagaga tcttcattct catgctgctc ctctagtgca agtgctccat ttattttaa | 62400 |
| ggaattaata taacaaaaaa tcatgggaat ttagaaaaca acatggaagc taatgatcac | 62460 |
| attggtggaa gtgatagga aatatttagg gggagaagtt aaggtataaa ctttgtcaat | 62520 |
| gaagtcctat taaaaacaac aaaaagtga agcttaggat gcattttata aactctgacc | 62580 |
| agaacacctg tgtttctctg tttctaggtt tatgaactga cgttacatca tacacagcac | 62640 |
| caagaccaca atgttgtgac cggagccctg gagctgttgc agcagctctt cagaacgcct | 62700 |
| ccacccgagc ttctgcaaac cctgaccgca gtcggggca ttgggcagct caccgctgct | 62760 |
| aaggaggagt ctggtggccg aagccgtagt gggagtattg tggaacttat aggcaagtta | 62820 |
| ttagcaaggt ctactcttac aattaacttt gcagtaatac tagttacact ctattgatta | 62880 |
| tgggcctgcc ctgtgctaag cagtctgcat tccatcttcc ttgccaaaac ttataataca | 62940 |
| aatttcatct ttattttata aatagggag ttgggctggg tgtggtggct cacgcctgta | 63000 |
| atttcagcac tttggaagga tcgcttcagc ccaggagttt gagacaacct ggccaagtga | 63060 |
| gaccctgtct ctacaaaaaa aaaaaaaaa aaaaattag ctgggcatgg tggcacatgc | 63120 |
| ctgtagtccc agctgctttg gaggctgagg tggtaggatt gcttaagccc aagaggttga | 63180 |
| ggctgcagtg aatcttgatg gcagctgcac tgagcctggt gacagagcaa gatgctgtct | 63240 |
| caaaataaat ttaaaataa aataagagaa ttaaagttta gcaggttggg tggcaaaatg | 63300 |
| aggccacaca tttaaagccc ctcctcctga ttcttttctc tgccttggct gcctcctgtg | 63360 |
| gcattttagg tgctgagaaa tgaaaacagt agggaaaata gttccaggat cctcatgtta | 63420 |
| atttgccaga aatggcatct tcaagtcgtc agagggatct gagagttcct tcctggcctg | 63480 |
| acttgagaaa atccgtctgt ccccagctct gcgtctgcct ccactgccca gtcacctcct | 63540 |
| ctccatgctc ttggggctgg gccctacccc accatgcagt gctgccctgg agcagtgagc | 63600 |
| ttggtgggtc ctgtctggca tgagagctgc ctttgggagc tggatcccag cctctaccac | 63660 |
| tgggtctggt gcctagcagg ctatggataa acttctgctg actccggcct ctcctaagcc | 63720 |
| actgcaacgt ggtcggtgta gtgcacagtg tgtgtgcagc gtggccttac tcacagcctc | 63780 |
| cacattagag agaatctgac tgaagtctta ctgctgcctc gtgtgaacat aaatgtttgc | 63840 |
| cagaaccatg agcaggaaat gttaatctgc cttgtttcct gtcctttaca cggaagaatt | 63900 |

```
tttttctgta tggaatgcgt gccttacaaa taatgagtgg aaatacccat cgctaatgaa   63960
aagttatact tgactgttag tcagctaaat aatctgagat ttctaatact tttaatttgg   64020
cttttacaat gcaatttatc ttagcttttt tgatttctta ggtcatatct ttagaactat   64080
atatttgaat gttaatgtaa ttttcatatt gaaattaaaa tgttgaactg cgatgttaag   64140
tgtttcctgt ggaaaaacgt tcacatttc tctagtttta aagttgaatc aagctgtttg   64200
aagattttca catttcttct agattttatc agcttgttac tttatctgtc actttctgtg   64260
atttgcagct ggaggggtt cctcatgcag ccctgtcctt tcaagaaaac aaaaaggtga   64320
ttatttcaga aatcagagtc ttgtgttgaa tcttactgat tttcttgtat ttctgtaatg   64380
taatgtatct tgtatttctt gtaatactgt attggactct gtgtatatct cttctcagat   64440
gagtgattat atgtgtgaat gttgctggaa tctgataacc aggcctgaat agttttgtag   64500
ggtggctttt aaaaattact ttcatatcag aattgctttg tcataaattt tgaacgcatc   64560
ataaatttct aatgttcggg gtcagcagac ttttttttgta aagggacaga gtgtaaacat   64620 cttagctttta tgggccatat ggtctctttt gcaacattca gctctgccct gtgacaggaa   64680
tgcagttgta aagacatgag ctactggcca gctatgttcc agtagaactt tacttacaga   64740
aacagacagg ctgtagtttg ccaatacctg ccttagggaa tgtgttgtta tattttgtga   64800
gttaccttct cagtaaattt tatttagtat tagtcaggaa tattattaag tagcttcttt   64860
tccagcctgg tcaacatagt gagacccggt ctctaccaaa acaaacaaa acaaaaaaac   64920 agccacgcat gtggcatgtg cctgtagcct cagctgctgc tcagggggct gaggcaagag   64980
gattgtttga gcccaggagt ttgaggtcac agtgagctgt agtcatgcca ctgcactcca   65040
gcctaggcaa cagaatgaga ccttgtgtct taaaaaaaa aagttccctt tgttgggtta   65100
ttttaatttg gacctggtta tcatttttca gccatattta actttgtaca tatcagaatg   65160
ttctgataaa acttaacttt tattaaagtg tttgtgatat aatctgctag ttttggtaca   65220
cattatcttt tgcaatgcca gttatttct tttccagtgt gggtttgcat aggaaaagaa   65280
ttgctgtcac tttctatttt gaaatcttaa aagactgatc ctttttttgtg tcatgatttg   65340 agtatttaat tgagagccta atgcctaata ttatttgcag tattaaatgg gatcttaaca   65400
ggaatagcat tctagccttc attgaattaa gtaaacattt cttaagagaa cttggaatct   65460
ataatatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttttcc   65640 agtggcggtg agaacgaaga tgactgattc acattgctca gatgagttta tcctcttctg   65700
gctgggacat gggatatatc ctgtctcttt taagccttt tggtattttt cccccattga   65760
gagctgtgtc ttcaaactct tctgttatag ctggaaaatc cttttaagt gaaatctgcc   65820 caaattataa gacagatgaa ggtagagttg tgttggatat aggattaggg tgaaagtagt   65880
gggggtgtcc tggagcctct cttctggtgg cagcctagct cttgtgcctt tgaggaaatt   65940
accctgggga cggctctgtg gaacatattt gcaaaccact gatttggaag atagagatgg   66000
cttttgttaa gatctgaatt caccttttg gcattttatt tgatttctca aggtaaagaa   66060
cttattttgt aataaagttt cctattattt agtagatagg ccaagttgct gtgttaattc   66120
catgtagatt ttgggtttcc tttgctcatt ttttcactct taatctcaca tcattgtaag   66180
tttatggaag ttatcatact tctgactttt tctttgaaga gcagaaatta gaaattccca   66240
```

| | |
|---|---|
| ataattattt tgatagtgtc atttaatgac actcacatgt gatgtagcca caaagattta | 66300 |
| atgagttcag ttttaaatca tattaagact gttggtttca tttgttctca ttaatgtaat | 66360 |
| tctgaagatg aacaataaaa tgtattttta gaactttcaa atgaaatatt atttcatcct | 66420 |
| tccagatcat ataatgctta agttctgatt gttaatcata aagtctagaa aattaaaaga | 66480 |
| taataaaatg aaagtgactt ttaggtatta gagttttatt ataaattctg gtgtgtcatt | 66540 |
| ggagctatga catgaatatt tcaaaggcca atagcattgg atctttacag ttataactta | 66600 |
| ccatttttaa gtttaagtag taatatagat tatttaataa tcaaaatcaa taaatattaa | 66660 |
| ttattaaaat gttttgtggt atagtttgag aatcattgct tttaactttt tccatatagg | 66720 |
| tttattgact ttaatagcat tctaaacata acatctctac attctttgtg tttaatactg | 66780 |
| tggaggtata aaaatactta tatatgatga taaactatat tagagtaaat taaatattct | 66840 |
| tatgagtttc attttagagt gcatttactt aattttgaag tccttatttt tagcaaacta | 66900 |
| aaaggaatgt tggtacatta tttactaggc aaagtgctct taggagaaga agaagccttg | 66960 |
| gaggatgact ctgaatcgag atcggatgtc agcagctctg ccttaacagg tagttctcac | 67020 |
| tagttagccg ctggtgtgga ccttcactgt ctgccttcca cccccttgccc ttcctgctcg | 67080 |
| tcccctgca cctggtggac agcacgactg ggggcagcag tggagccagg ttgcttaaat | 67140 |
| ggggcatatt cgggcttctt ttataatact tactctgaag cttgtgtgtc tgtggtgttt | 67200 |
| gcatcatata tttgttgttt tccatggttt aggctgtttt aaaattaggt ttatggcttg | 67260 |
| agcatagggc tttgtgagta ggggatggca ggtcgaaaca tctcatgagt tggatgggtt | 67320 |
| atgctggggg ttgggaaatg ggatgaaaaa ttatgggatg aaaaattgcc tatggatagt | 67380 |
| ttaacttgaa agaatctgcc tttgtttaca gatagttatc ttttttcttt tttgagatag | 67440 |
| agtctcacac tgtcacccag tgcagatacc cagtgtcact ggagtgcagt ggtgtgctct | 67500 |
| tggtgcactg cagcctccgc cttctgggtt ccagcgattc tcctgcctca gcctcccaag | 67560 |
| tagctgggac tacaggtgcc cgccaccacg cttggctaat ttttgtattt ttttgtggag | 67620 |
| acgggttttt gccatgttgg tcaggctggt cttgaactcc tgacctcaag tgatctgcct | 67680 |
| gcctcagcct cccacagtgc cgggattaca ggagtgagcc actgtgcccg gccagttaca | 67740 |
| gatacttatc taatgaaatt ctctgtgtac tttataaaag atgaggatta actgaaggta | 67800 |
| ctaataactg gattatatga gggtggtttt ggttgtataa tcctatctaa aagaatattt | 67860 |
| tagctataac tgaaagtaag acttaaatat ttagagagga aaatctgaat aattctagta | 67920 |
| gtaattattt atttacaaaa taaaaataga ttttttttttg attacacaaa ttaaacaaca | 67980 |
| ataaaacatc acagcaatcc ggatactata aagctcacat gcttaccgac ccaactgccc | 68040 |
| caggagtgac cactgccaac agcttcatgt cgacctttt gccataattt ttatatagcc | 68100 |
| ttttttgttt ttaaatggta atttagaaag tcaactagga aaatgtgtta caggtttatc | 68160 |
| ttccaggaga ataggactgg agtcgagatc ttgaatgtgg cttggaagaa ggcaagccca | 68220 |
| ccccagagag atgagttgac agttgtttct gaccactgct tgcttagagg gcctgcgtgt | 68280 |
| ctgtgaccgc ctagctttgc gcccctgact aggctgcccc ttaattacaa atgtctttat | 68340 |
| atattgctcc agctaaggct tggagtagtc ggttaagaac ttgaacttcg gttttgcag | 68400 |
| tgaaacagca tttgagaata tcaccttctg ataagcctta ttttataagg tgggtactgt | 68460 |
| agtgggaggc agtgtgagag atgcttgaag gatgcactgc tgtcctgcat ttcagcatct | 68520 |
| tcaggatgct gtgcagctga aacatttgat aacggtggaa ctgttcgtta ttttgcaagc | 68580 |
| ctgtgattcc ctattgaatg ttttctctcg ccatttgaca aatgagtgtt tctctgtctt | 68640 |

```
cagcctcagt gaaggatgag atcagtggag agctggctgc ttcttcaggg gtttccactc   68700
cagggtcagc aggtcatgac atcatcacag aacagccacg gtcacagcac acactgcagg   68760
cggactcagt ggatctggcc agctgtgact tgacaagctc tgccactgat ggggatgagg   68820
aggatatctt gagccacagc tccagccagg tcagcgccgt cccatctgac cctgccatgg   68880
acctgaatga tgggacccag gcctcgtcgc ccatcagcga cagctcccag accaccaccg   68940
aagggcctga ttcagctgtt acccctcag acagttctga aattgtaagt gggcagaggg   69000
gcctgacatc ttttttttta tttttattt gagacagagt ctcactccat agtgcagtgg   69060
aggccgggca caggggctca tgcctgtaat cccagcactt tgggagactg aggcaggcgg   69120
atcacttgag gtcaggagtt cgagaccagc ctggccaaca tggtgaaacc ctgtctctac   69180
taaaaataca aaaattagtt gggcgtggtg gcacatgtct gtagtcccag ctgttaggga   69240
ggctgaggca ggagaattgc ttgagcctgg gaggcagagg ttgcaatgag ccgagatcgt   69300
gacactgcac tccagcccgg gcaacagagc aagactccat ttcaaaaaaa ataaaaaaat   69360
aaagtgcagt ggctcgttct cagcccactg caacttctgc ctcccaggct cgagcgattc   69420
tcccgcctca gcctcctgag taggtgggat tacaggtggg caccaccaca ctcagctaat   69480
gtttgtattt tcagtagaga cagggtttca ccatgttggc caggctggtc tcaaactcct   69540
gaccttagat gatccaccca ccttggcctc ctaaagtatt gggattatag ttgtgagcca   69600
ccatgcccgg ccctgccacc tgccatcttt tgagttcttc cctggagacc tagacctgaa   69660
ccctcctgct tgttctcttg ttatctaata cccctattga cagcgcagct tagatcatta   69720
atggagagct tgacctcatc tgataccttc actgaaggaa acaacttagt gtcttttgtg   69780
ttgaacactg aggtaaaaaa ttggaatagt tgattatatg aactctgcta aaattgagtg   69840
cattttacat tttttaaggc cttgttgggc cctggttaaa taattatttt taaaaatcct   69900
taaggagcct attataaaca gatctgtggt cttaatgaaa tgtgattaat actgtgcatt   69960
attttaagaa cttttgactt ttcaaaaaac ttttacaaca tttcccattt gatagcggca   70020
taggtttaag cacttctcat ctctaagtta gtggacaaaa aaccctcatg gatagtctaa   70080
taatgtttgc tacaagtcca tgttgagttt tatactccat tttattttca gttttaaaaa   70140
ctgtggttaa atatgtgtaa cataaaattt atgttcttaa ccattttttg cgtatacagt   70200
tcgctggtat taaatacatt taaataatgt catggaatca ttgctaccac ccatctctgt   70260
aaccttttga tcatgtaaca ctgaagctct gttcccattg aactctattc ctcctttccc   70320
gccaagtccc tggcaaccac gattcttctt tctgtcttct gaatttgact actttgggtt   70380
ctcatatact ttaggagtca cacagtattt gttttactta gcataatgtc cccaaagctc   70440
atgcatgttg tagcctatgt tagaacttcc taatgtttca ggccaaatac tattccattg   70500
tatggatagg ccacattttg cttttccatt cctctgtcca tggacacttg tattgcttca   70560
tgttttagcc attgtgaatc atgctgttat gaacgtgggt gtacagatag ctcctggaga   70620
ctctgctttc cattttttg gctaaatacc cagaaatgga gttgcttta cattccaatt   70680 ttaatttaaa acattcatat cattgagtgt tttacttaat agtatagtag ttaacaaact   70740
taataaaata gtattttggt aataaattgc tggtagtcca ttgttcagtt tttttaggta   70800
aattacacag gacatttcaa gtggacatga acatcttgt gatgtggaat catgccccaa   70860
gctgatggct aaacatatga aataccatac cctaaattta gtagatttag tctttgcaat   70920
ttaggagata acctgttata ttgttaggtt tttgtcgaaa agctttgtcc tcatatttcc   70980
```

```
aacttgctgt aaaatttgtt tgtgaagaca aatattttg  tatgggtttt ttcttttca   71040 tattaaaaag aaatgtccac attggaattt ttttggagtt tttagagcta atagagcttt  71100
tcataatgta gtgggaatga gtgatcagta agctcttagc agtttccatg cgtgcatttc  71160
tgtgccttga aataaatgac agatgagtac atttgtgttc tgtgtgtaaa atgtgctctt  71220
tcctcattgc acttccatgt tggagggctt gtctcttggt gatcacactt caaaattctc  71280 acagccccc  ttgaaccgtt taggtgttag acggtaccga caaccagtat ttgggcctgc  71340
agattggaca gccccaggat gaagatgagg aagccacagg tattcttcct gatgaagcct  71400
cggaggcctt caggaactct tccatgggta tgtggactac aggtgatgcg ctacaaagtg  71460
gtttgtattc agacctggac atcttaatta tatctttgct tccaagaaga agtcctttga  71520
tactgttttc tgagttctga atagctgatg aaaatgacca attgaggaat aatcatactt  71580
tttcttgatc taaatcttat acttttgagt tatcttagca taaatgtata attgtattt   71640 aagtggaaat ttgtcactta atcttgattt ctctgttttt aaagcccttc aacaggcaca  71700
tttattgaaa aacatgagtc actgcaggca gccttctgac agcagtgttg ataaatttgt  71760
gttgagagat gaagctactg aaccgggtga tcaagaaaac aaggtgaggg acataggctt  71820
gagacgactt ggtgtttctg agcttgtgtg aggatttaaa atcgccctgg ctactgtcta  71880
ctttattgct ttcccatccc tgggccttta aatttcccct ttaaatacca gctcttccca  71940
ggcctgttgt tttctgcctt tccaggtact acccacagcc ttgagaattg cctgagttct  72000
gcctcctttg agagtgtgcc ccagacaaat ctattctgta ctgaatgttt ccttgtctga  72060
tttcttggat cattcatttg atggttgcgt atggcctgca acgtttcttg ttttggttct  72120
actgaactgt tctaaaagtc tctcttcata ttatctttt  acatgtaaat gtaactgtct  72180 tcactttaa  ttcctcaagg acaaggaata gcgtttcaca gttcgtccca tcaatcagaa  72240
ttatagcctt tggcatctcc ctatctacca ggcccacttc ctcttagatt tgggcttccc  72300
caggctgttg cctttcccca agtagcttct gcttgtcctg tagaagacct ttcatgcttt  72360
gcttctgcag cagccgttcc tgaatgccta gtgtcaactg ccttcttacc acgcccaccc  72420
tccctgcatg ctgcatttat cccctgccac agccctgtga cctgtgtcc  tgctgcctct  72480 gacttgtctg tttctgcttg gccatggtct ctgtgaggtc aggtgtgcat atgggcacaa  72540
accagggcat ctcttatcc  ccagcacctg gcttaagtgc tgctctggaa ctatctgttg  72600
aatgaactaa tgcatgaatg tattgttgag tatgagacaa acaagtgtca ttgtctcctt  72660
tctagccttg ccgcatcaaa ggtgacattg gacagtccac tgatgatgac tctgcacctc  72720
ttgtccattg tgtccgcctt ttatctgctt cgttttgct  aacagggga  aaaaatggtg  72780 agtacaaaag gggatgtgca cagttgaagg aaataactag gtttcagagg tcagcttggt  72840
ggcctgtttt tgccttgcgt gcagcagagg aagtagaatc tgaggatgag tttggttttc  72900
actagccgag ggggaggagg aaatgatggg agcaggtagg ttattgggtc tggttttgtt  72960
catttgaaaa caatctgttg tttgaggctg aaggtggctt gggtgatttc ttggcagtgc  73020
tggttccgga cagggatgtg agggtcagcg tgaaggccct ggccctcagc tgtgtgggag  73080
cagctgtggc cctccacccg gaatctttct tcagcaaact ctataaagtt cctcttgaca  73140
ccacggaata ccctggtatg ttaaaagttc acatcttatt ttctcagatt taatcattat  73200
tgtaaaaact atttcagtat tgactatttt agtttagag  cagtaagtgt tttgagttca  73260
tttgggatat ttgacctgcg ttgtagctct tcagaaaaca catgaatagt gaagttcttt  73320
gtttcatggg ttcccttag  atgaaaccca tagaggagaa aagtagaaac ctcagcacgt  73380
```

```
aagagccaac atatatacac atcggattta aacctaaagc acaaattgtg cctggtcgca   73440
gtggcgctga gtcgcactca gccaggccag gcattcacac tcagggtgag tgggaaccag   73500
gactggctga ggcagcagtg gacccaagtc tccatcgcgc ccatgcttac tatggagcct   73560
tctcgttctc tcttttcttt tgggtgagag ggtacacttg tgttttgaa tttatatgag    73620 gtaagtgtgt aatagggttt tttctaatct tttttaagtg gaatctggaa ttttaatcag   73680
atttattatc tgacaaccta gaattataat ccagaaagtc tgtggtattg aggacatatt   73740
ggcaatatga tgaatctcta attcttaaat cctgaaactt ttttttttt aatcacttag    73800 ggttattata gtgaagtcat ttctgaattt ggatcttctc ttcacacctc tttttctctt   73860
tcctgagaat taagcttttg tttcgagtta gaaagttgat agtagggaat tgttccatgg   73920
ctgagcaatt tatctccaca gaggaacagt atgtctcaga catcttgaac tacatcgatc   73980
atggagaccc acaggttcga ggagccactg ccattctctg tgggaccctc atctgctcca   74040
tcctcagcag gtcccgcttc cacgtgggag attggatggg caccattaga accctcacag   74100
gtaacggcca gttttttcagc tgtgttttttt ctagttatgc ttactaaggt ttaagtttag  74160
atgatgatgt ttgttgcttg ttcttctggt taggaaatac attttctttg gcggattgca   74220
ttcctttgct gcggaaaaca ctgaaggatg agtcttctgt tacttgcaag ttagcttgta   74280
cagctgtgag ggtgagcata atcttctgtg gaaccatttc ttcacttagt ggacatttta   74340
tcattgctac aattaaaatt ggagcttaat aggaaatatt tccatgcact ctaaagctgt   74400
aaccagtaat acccaccatg tatccatctc tcagctttag aaagaaaacg ttgccagtaa   74460
agttaatgct tcataaactt cagtttaagt tctaattctc agaatatttg tttgaaatag   74520
acctcttcct aaaggatata tttagaaata acctatcatt aagtgtaaag tctgttgaat   74580
atgctgggca cggtgactca cacctgtaat ctgaccactt tgggaggcca aggtggaagg   74640
attgcttgag cccaggagtt caagactatg ggcaacatag ttgaccctgt ccctacagaa   74700
aattaaaaaa aaaaaaaaa aaagtagctg gtatggtgg tgcatacctg tagtctcagc    74760
tactcgggaa gctgaggtgg aggggggatt gcttgagccc cagagatcaa ggctgcagta   74820
aggcgtggtt acaccactgc cctctagcct gggcaacaga gtgagactgt ctcaaaaata   74880
atagtaataa taatcagttg aattaaaaaa aaaaaaaaa aaaccactgt gctaggccca   74940
tagtatggta agagttaaag tgagccttag ggattattta ctcaacctct gtttctgtat   75000
aaagtggaat aggctcaatt ctttaagtga tagcatgttg aaccttttcca taccaactgg   75060 ctcataagtc acaactggcc agtcaacaag agtaaaaatt aactggtaaa aatcaaagca   75120
aaaaacctac aattgtcaaa tttgtgggat aactcccccct tttaaaatgt catgcctgac   75180
agtaatttct ctctagtttc caggtttca gtcagttgtg tcttttttga gcagaaggaa    75240
gcatgctaag agctcaatct tgtggctagc tgggggtctt tgtgtcagcc atgcatgtga   75300
tggtgcccct gggtgcttgg ggctgcaggg gaggggtaca gcagtagggg cctgttctgt   75360
tctctcgtgc tgtggagtac atagtgacat agtgggggtgg tccttggtgt aggtcccttg  75420
ttcctacccc tgggtctgag atttatttag aagtggtgtt ggggctgtgc ggcaggcccc   75480
tctgtaactg atcaatgttt gtgaagttgc tgtttgagag ttgaaccat gacataagca    75540 gaaatggaag gaagaaagaa ccagttatgt gaaagggaca catttacttt taagcttgta   75600
tttactgaga taaagtattc ttaatcaatg ttccttgagag gtgtgggaaa aatgcaacat  75660
cctggttgca gttaaaccca gaacattgtg tgttgaagag tgacggttct caaaccgtca   75720
```

```
agacgcgggt actgagtggg actaacctgc tgtcctcttg ccttggacct tgtgttccag    75780
aactgtgtca tgagtctctg cagcagcagc tacagtgagt taggactgca gctgatcatc    75840
gatgtgctga ctctgaggaa cagttcctat tggctggtga ggacagagct tctggaaacc    75900
cttgcagaga ttgacttcag gtaagtgagt cacatccatt agatttcatg aactaagctc    75960
aattgaaagt tctgggatca cttgatgcaa ggaatgatgt tatcaagtac cctgtccatc    76020
agaaatccga gtggtttagg tagatgacag tgattttctc ctcccagtgg cttttttgctg   76080 aactttgccc tatgcttgga attttatttt attttattat ttatttagag acaagatctt    76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaataaag tagaagagta gattttttt     76440 tttggtagtc ctcgtcattt aagtattctg gatagtggga ataaaagagc ttagaatttt    76500
tcatctttgt cttaaacttt taaaaaaatg tagcttatat taattctgct tgtttaaaaa    76560
gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
caacagagtg agacttggcc tcaaaaaaaa aaaataaca tgagctgtgt tggcactttc     76740
attttctaag agtagttttg gctggagaag ttttctttca gtactttctt ttagaaggga    76800
aattttcctt tataatttag ggtttgtttt tttttttttcc aagccaccttt ttatagagcc   76860 cttgtgggtt atttcattta atccttagaa tgtttataaa tctgggcttg ttctcggctc    76920
cacccacaga tagggacgct gagcgtgcat gagtgggcag caagatagca ggttatggag    76980
ggcccagctc accccttctg tggcttgagc caattttata gggcacttac agagtctttt    77040
gaaatagtat ttattttgaa gaaaaagaaa aacagtttac tgagtactgt cttattgagt    77100
ctggaattgt gagaggaatg ccacctctat ttatttaaag ccattggcct ttttttgttgt   77160 tttgagtaag tgctgcccaa ggtccttcca gggcacctgg atgagcctgc tctggagcaa    77220
gctggcggta agtgtttact gagtaactaa atgatttcat tgttaaatgt gctcttttgt    77280
taggctggtg agcttttttgg aggcaaaagc agaaaactta cacagagggg ctcatcatta   77340
tacaggggta agcggtttat ttttgtgaga tgctgtttta ccttcaagaa ggtgaaagtg    77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
atttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttccttttttt ggttgaagta ctaaaagata    77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
gtaaaaattt tggactatag agaatagtac taagaagaaa aaaaaaatca ccttcaattc    78000
tgctgccacc tggaggtaat cactgttaat attttgctat atactctatg agtttcttgt    78060
tcaaaatcag gtcaaaatta catgcaattt tgtaatctga caatttccac ttaatatttt    78120
```

```
attagcattt tcctgttatg aaacagtaat tttagttatg ggtcgttgtt ttgctatgcg    78180
gttgggataa aattttatat acttttttg gcaattactt attatacata aatgtttgtg    78240
tatagttttc tttttctgag aattcctgga agttgagtta ccaggcccgg ctttgaattt    78300 tttttttat tttttttttg agacagagtc ctgctctatt gtccaggtgc tatctcggct    78360
cactgcaacc tctgtctccc tggttcaagc gattctcctg cctcagcctc ccgagtagct    78420
gggattacag gggcacacca ccacgcccaa ttaattttg tattttagt agagacaggg    78480 tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aatttatca catttctgtc accccaaatg tatccttgtg    78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
caaacaaaga tttgtatttt ctggacattt tatagtactg gggtcatagt atagatggac    79140 ttttgcatttt ggcttctttt acttaattgt gagattggtt cttgttgtag catgtatcag    79200
tagtttgttc atttttattg gcgaaagtat tctattatat gaataatacc atattttatc    79260
tatccatcag atggatatta tagagttcat gttttggcta atttatgaat tatggtactg    79320
tgaacatttg cctgcaagat tttgtgtaga catgtcttca tttctcttga gtagatcacc    79380
tagaagtgga tttttaaata attttggtac ttactgtgaa actgctcttc aaaaacatac    79440
cattgttcct tccttccttc cttccttcct tccttccttc tttccttcct cccttcctcc    79500 ctccccttccc tacttccctc tcccttccc tttcccttcc ccttttccct tcccttccc    79560 gcctgcctgc ctgcctgcct tccttccttc cttccttcgt ttcttctac atatacacat    79620 ttttttaaat ttcaatggtt tttggggtac aagtggtttt tggttacatg gctgaatttt    79680
ggttacatgg tgaagtctga gatttagta cacctgtcac ccgagtagtg taccttgtac    79740
ccaatatgta gttttttgtc cctcaccttc cagccttccg ccttgtgagt ctccaatgtc    79800
cattatacca cactgtatgc ccttgcgtac ccacagctca gctcccactt ctgagaacat    79860
atagcagaaa catgccaaag tatactccca ctaccagaat gtgattgtgc ctgattcttc    79920
tcaccagtac aaatatttca aaaaagtta aatatgtatc agtttttgg gcagaagttg    79980 atacttctct ttatttattt atttttttg agatagggtc tcattctatg atgcccaggc    80040
tggagtgtgg tggtgcgatc tcggctcact gcagtctctg cctcccaggt tcaagtgatt    80100
cccacgtcag cctcccagga agctggaatt acaggcgagg gccaccactg ccagctaatt    80160
tttgtatttt ttggtagaga tggggtttca ccatgttggc cagactggtc tcaagctcct    80220
gacctcaagt gatccacctg ccttggcctt ccaaagtgct gggattacag gcgtgagcta    80280
ccacacccgg ctgatatttc tttttaaaat aacttacctt cttttgaaag taatacatgt    80340
ttaatgaaca gaatttaagg aaaatataaa aaaacgaaat aatctttgta atcaaactac    80400
tgaaaagaaa accaaagtta catttggtg catattcttt ttcatttca tcattgtaat    80460
```

```
ttgcatttct ttgattactt gtgagacact cctttcattt acttaatagg tttatatgac    80520
ttgcctattc agagattttg cagctttacc attttctgca aatgatagca acttcttttt    80580
gtttgtttgt ttgtggagac agagtctcgc tctgtcactc aggcaggaat gcagtggtgg    80640
aatcttggct cattgcaact attgcctcct gggttcaagc gattttcctg cctcagcctc    80700
ccaagtagct gggattacag gagtgtgcca ccatgcccgg ctaattttg tatctttagt     80760
agagatgggg ttttgccatg ttggccgggc tgatcttgaa ctcctggcct caagcggtcc    80820
ccctgtctcg gcctcccaaa gtgctgggat tacaggcgtg agccaccgta cccagccagt    80880
agttacttct tatattctag aaaaaattct actcatgatc aagtctccat gaggaaagag    80940
actttaattg aagatcatgg ggcttgcaga ccaatatgat aaaatagttc attgtttcta    81000
aaagtattac tgagtgttga tggcagatat gaacccttt gttttgtag aaaatgtta      81060
cccgtattct ccatttgaat tcagtttaga tttgttagga atcgcagctt aagctttgcc    81120
atctgggagt gttgggaca gttttgcaga caaaattgca aaagtgccta aggaatgcag     81180
ctggcattca gacctgctct gtgctcagta ctctgtggac agacactgtt cagcacttgt    81240
tgatcagaag gtttagaaag agaactttca aagttggttt ttaattaaag catttaatag    81300
tgtaaataga aagggattaa attttatgac agacaaaaga aagtacagca cccagctggg    81360
cgtgggggct cacgcctgta atccagcact atgggggct gaggtgggtg gatcacgagg      81420
tcaggagttc aagagttcaa gaacagcctg gccaaggtga tgaaaccctg tctctactaa    81480
aactacaaaa attagccggg cgcggtggca ggcgcctgta atcccagcta ctcaggaggc    81540
tgaggcagga gaatcacttg aacctggacg gcagaggttg cagtgagcca agattgcacc    81600
attgtactcc ggcctgggcc acagagtgac attctgtctc aaaaaaaaaa aaaaagaaa     81660
aaagaaagt acagcaccca gttatgtccg agtgggtgca tgagagtgac cctgagattg     81720
gagacaacgc tgtcacgtgc ttgaagaacg ccacctgaga aaggggcga gaagtggtgt     81780
ccgctggtaa ccagaggtgt tggcttagcc atctgcaggg aggagggtgg tctatcacag    81840
gtgagtttca tctactttct taagcaaatt aaccttactt ttgtgttagg cttgtcccaa    81900
agctgtttta taaatgtgac caaggacaag ctgatccagt agtggccgtg gcaagagatc    81960
aaagcagtgt ttacctgaaa cttctcatgc atgagacgca gcctccatct catttctccg    82020
tcagcacaat aaccaggtat gctgacccag tggcatcttc acattgtcgg gaaaatgccc    82080
tttcctgatg cctttcttta ggctttaatt gaaaacattt tattttctag aaaaaagctt    82140
cagctcagga tgtttgagtg taggtcagtc ctttgatagg atattatcat tttgaggatt    82200
gaccacacca cctctgtatt taagctctgc cacaatcact cagctgtgac actgtaaatc    82260
tcttaatagt ttattacatt ccatgtgctg acagttgtat ttttgtttgt gacacttacg    82320
tattatctgt taaaacattt tcactttagt tgtgttacct ttaaagagga ttgtattcta    82380
tcatgcctgt tgattttttg gtgagcgggc tattaaagtc agtgttattt agggttatcc    82440
actagttcag tgatttgcga gattatcatt cacatttatt gtggagcttt tgaatatcgt    82500
gtcaaatggc cacatatatc ccattcttat ctgcttctta ggtgagtggg acacagtgct    82560
ttaatgaagc tataatcttc agaattctag cttgcagaga agattgcaga agtgataaga    82620
cttgtgcttt ttaattttgt cttttaaatg ttattttaaa aattggcttt atatgatact    82680
cttttttct gctgagtaac agtgtttac aaaacttgga ctaaatgact tctaagctta      82740
aatgatcact tgatgctttt tttctgaatt aggaactcag cttatcaaat atcaaagtca    82800
taattcctga ataaataacg tcttttttca tgtaaagact gctttaaaaa acacatggaa    82860
```

```
ggctgggtgc ggtggctcac gcctgtaatc ctaacacttt gggaggccca ggtgggcagg   82920
tcgcttgagc tcaggggttc aagaccaccc agggcaacat ggcaaaaccc acctctactc   82980
aaatacaaaa aattagccag gcgtggtggc gggcccctgt aatcccagct actcgggagg   83040
ctgagggatg agaatcactt gagccccgga ggcagaggtt gcagtgagcc aagattgtgc   83100
cattgcactc ccagcttggg ctacagagtg agactctgtc tcaaaaaaag acacacacac   83160
aaacaaaaaa aacatggaga cattttttg gccaccttaa tatttcccct cagataattt   83220
cctttgttta aactcagaac tggcattttc tctcttggag aagattcagg acaaatactc   83280
ctttaagata agtagaagca gtgaaagagg atttgattat caggaatttg ataagcttag   83340
aataaattgt tgcttcttaa tgtcatttca gaagatgaat atttattaat agatgccaac   83400
tgagatatca ttaaaattga ttactaacta ctacttggaa aagtctccca gttccaaact   83460
tcagcaggcc tcttgacaat tcagctgtgg tcaattgggt cttgcgtgat agatacaatg   83520
accaattgtg cagcagagtg tgctgcttag ctgcctattc tgttagcatt catgtgttaa   83580
cttaaaatca taatctcctt agttttgttg agtgtctccg tggacaagac actgtgaggg   83640
atacaaaatc agattggctt tattcaaacc actggggtat tataattcat ttataattta   83700
ttttatttt tgccttttt ccatgtgttc taaaggaatt agagtttgta tataactata   83760
atggggata gaaattgaca tgtgccatga agggaatgca aaaagtgcc gtgggagatg   83820
agaagtggag aaaggaattt ctttttttctt ggaagcagga ataacttcat gaagcatgta   83880
tttcaactta aacagatagt aggcaacgct gtaaggggag tatggctgca gcaaaagtgt   83940
tcggggcaga ctgggaggaa gggagggaat aaattcagcc attgttatgg aataatgatc   84000
aaaatttatt ttcagcccgt ttcacttaaa agttgagact gcttaacttt ttttaatctt   84060
taatcttaaa cttttaaatg ccatttgatc tttaaaaata tatgttttaa tagtgtattt   84120
taagtctcta tattttgtt attagaatat atagaggcta taacctacta ccaagcataa   84180
cagacgtcac tatggaaaat aaccttcaa gagttattgc agcagtttct catgaactaa   84240
tcacatcaac caccagagca ctcacagtaa gtctctttct tgatcggtct tactgacatt   84300
gtaatagttt ttggtagctt gtatggccag ttagttgtat ggtcatctta cggtgaggtg   84360
cttgtcttac agctcttact tatccatgag gcttgctaag aaattgtgct tctgtgaaaa   84420
gaatctcagc ttactccagg aatgtaaatg actatgtttt ttctgattat taaagtaata   84480
cacgcccaaa ataaaaaaat tcagccaatt taggaagaca caacaattaa aataagccag   84540
gcatggtggc tcatgcctgt aatcccagca ctttgggagg ccaaggttgg gggctcactt   84600
gaggtcagga gtcggatacc agcctggcca acgtggtgaa accccatctc tactaaaaat   84660
acaaaaatta gctgggcgtg gtggcgggcg cctgtaatcc cagctactca ggaggctgag   84720
gcaggagaat cgcttgaacc tgggaggtag aggttgcagt gagctgaggt caagccactg   84780
cactccagcc tgtgcaatag agcgagactc tgtctcaaaa aaaaaaaaa aaaaagaaaa   84840
gaaaaaagta aactactgtc acctgcattg gtaatgtatc agaagtttaa aatgtctaga   84900
ttataattaa ctcagtgacc tggtaatata tactaaggga aaaatattta taatttacat   84960
ttttacattt ttatttttt aattttatta tttttttttt gagacagagt tttgctcttg   85020
ttgcccaggc tggagtgcaa tggcatgatc tcagctcacc acaacctcca cctcccgggt   85080
tcaagcaatt ctcctgcctc agcctcctga gtagctggga ttacaggcat gcaccaccat   85140
gcccggctaa ttttgtattt ttagtagaga cagggtttct ccatgttggt caggctggtc   85200
```

```
tcaaactccc aacctcaggt gatccgccct cctcgacccc ccaaagtgct gggattacag   85260
gtgtgagcca ccatgcctgg ccttacattt ttataataag aatttatgtt gctgacatta   85320
gaaaagaacc ataatatcca agaatccaag aataattaaa ttatgtacat atgctagtat   85380
atagtgtgat gctttggaga attttttaaca atatggagat gtataatctg gattgtaata   85440
ttgagtgaaa aaaggcagaa tacaaacctg gtgggggtat agtcggattt cagttaagaa   85500
aaataatatt tacatatata catttctcac actggcagat aatcaccaag ataaattttg   85560
ggattgtgga tgattttttt cttctttata tttttcagat attctcaaat tttctaaaat   85620
gagcaagtat aacttttgtt atcagaaaaa aataatatac aaaagtaatg ttaatttgct   85680
ggtgaccagg ttaaaccttt ttattttttat tttttgagat ggaatctcac tctgttgccc   85740
aggctagagc acagtggcat gatcttggct cactgcagcc tccgcttcct gggttcaaat   85800
gattctctgg ccccagcctc ctgagtggct ggaattacag gcgtgtggca ccacacctgg   85860 ctaattttttg tatttttagt agaggtaggg tttcaccagg ttggtcaggc tggtctcgaa   85920
ctcctgacct cgtgatccac ccacctcggc ctcccaaagt gctgggatta caggcgtgag   85980
ctactgcgcc cagccagacc ttttttatttt atttgacaaa agaaatactt ccatgttata   86040
gaagactaaa tattgtttgg gctgtctgca gtatggtctt cccttgattt gttcaaaata   86100
tcgtaaactt tgcttattta tttttattgt ggccgactgt gtcgggcact gttgtaggct   86160
tgggatggaa aaacaggatt cctgcccttta gggtttctgc aggctggtca gggagacgat   86220
gtggtaagct ggagctcagc tcctaaggat gtgcaggggc agttgagagg cggaagggtg   86280
ggagatcatt ccagggtgtg ggcagcacag gaacctctct tcattgggat ataattgcca   86340
ttctgataac acgtgtttga ggtgtctaaa gtaggaagtt gtaccatggt gggacagata   86400
tcctgtggtt atcatacaca gatctcagtt ttcttctcat tgtttgtact ttttataaag   86460
ggtaacagga gatataattc aataaaacctt tgtggtgttt gggtgtgatt ttattgtttc   86520
tttcttctca gtttggatgc tgtgaagctt tgtgtcttct ttccactgcc ttcccagttt   86580
gcatttggag tttaggttgg cactgtgggt atgtattttc ctcagtatat attaatagtt   86640
gtctacaaca gtatgacata aacatagtta ttaggatgcc cttttctttt cttttttaagt   86700 cttttatcaa tttggctttt tggaaaaata tctgatggaa tacttgtttc tgctatatta   86760
gctgtgtgag actagtgaca ggagctgtgg gaaatgaatg ccaaatgttc ttaggcattg   86820
atgggaattt cagggtgtgg tcttcaagtt catttaaggg aattttcata tgctggcaaa   86880
aggcttttct cattagcttg actctttcca aaattatttg ctgtgaatta gaagtttagg   86940 aaccttttttt cacttaattg tgacctagca tacgaaatgg tgatgattta ggaactactg   87000
ttcttgtatt aacagctttt atttaaaaat gatttttcctc cagtagatgg ccctactagc   87060
atctgggaaa taatttcaag tcttctccag cattcaggaa taggctttca ttttgtgtat   87120
caattactga gaatgatttt ggtgactcac atcacatttg agaagtaaac ctgcagattt   87180
cttgtgtgtg tcagcaaatg accaactgat atttgcttga agtggattac attatctgct   87240
ctagaatgat tgcttcccca ccttcctcac atacagactg agcagctacg gttttctaatc   87300 ataggtctgg cactagactt cacttctggg caactttggc attggagtaa aatgtattaa   87360
tttaaagaaa gttaaaaatc cgttcaagta aacatacagt tctaatactt tttacaattt   87420
aaaatataga tttaaatgat aaaataaaaa agaaaatatg ggtagacacc ataatcctcg   87480
tttctgcatc tgttcacaag gggttgatat ttatgagttc tattctccat atccattcta   87540
tgttctctta atgctcagtc agcaccctcag gtggttggag ttcaatgctt ggtagtttga   87600
```

```
cttacactgt cttttctagg ggattgagcc ctgggtagtc ctgcttattt gaggttgcaa    87660
tttgtctttc aataacttttt actacaagat atggcgtgtt aaaggatacc attggggaac    87720
caacataata atatcaggaa aactaaccac gtcagacctg ccccattgtg tatcaagtac    87780 actattttc  catagtaata aagagttcac cccagccaat tctctttat  tttgtgcctg    87840 tttactcaat ggcattaaca tgcccaaatg tctgggtagc tgtctcatct ccagttcagc    87900
agaaccattg tcatatgccc tagtaaaagc attccttcat tggacactta gccccaata    87960 ctttcattca gatctactac ctgatttcat ttctcaaatg attttttatgg agctctgatt    88020 tataggaaag atgttagttg attaaaaata aacaatttc  tgagctggta taaaatgtat    88080
tgtgacatgc cttcctcttg gaattgcaag agaaaggaag actgttgttt gcttaaaaat    88140
tgtctataat ttgactttgc aaatgtctgc ttccagagtg cctccactga gtgcctcaga    88200
tgagtctagg aagagctgta ccgttgggat ggccacaatg attctgaccc tgctctcgtc    88260
agcttggttc ccattggatc tctcagccca tcaagatgct ttgattttgg ccggaaactt    88320
gcttgcaggt actggtactg agttgaaaca gggactccag gacttggatt ttgatttcct    88380 taggggggaat ggggggtggtg agcatatgag gggaaaatac tataaggtca ttgccagtga    88440
tggcttgtcc ctttagtcaa atttcagatg ttacctatat gcataaacac atgcagttgg    88500
cagctgttct gtgctgagta ttttaaagta gcctcttccc aatatagccc ctcagttaac    88560
tacaagtaaa ctcattttga atttcatttt aatgggcacc atatgccagt actccctcgg    88620
gcactgggat gttaagaaag tataatgtat ggacttcatt ctcaagttag ttttagatta    88680
gagggggata cacgtaaaca aaagtgcagt ggtcacacag agtggccta  atcactctcc    88740 ttgggcagat ttatgggctg gtaggaaaga gcacaacacg gagagggtgt agcaccttgg    88800
cgatgataat ggaggatgtg gccagcaagg aagacggagt ccattgaaat tgattttggg    88860
agaagttgcc aatctccatg aaagaattgg ggcctgtgct atttgcttca gggggctata    88920
ggagagtttc gtgaaaggga ctaaaagatg agtatttaa  taagatcatt catccaactt    88980 gaacatggc  tggaggagaa ggtagggaga ctcaggagat taatgttgat gctaaggcaa    89040
gataatggct ttgggactgt agggaagaca ctgattgtaa gagaatgaag gaggcagaat    89100
tgccaggcct ggttcaccaa ctgaacttcg gttgtgaaga caaagaaacc tgggatgact    89160
tcacatcctg ggcaggtgtg tggtggtgac agtcatggaa attgggaaca cagatttgtg    89220
cgggaaacat cagtttcagt ttgagtttgg cttatcagtt gaatatcagg cacagatgtc    89280
tggccaactc tcaacatagg gtcttaaatg acttcagttc cccaagcaat ttgtccttcc    89340
catgctattg gggtggagag gtaatgtctg tgcccatatc acagccagtg ctcccaaatc    89400
tctgagaagt tcatgggcct ctgaagaaga agccaaccca gcagccacca agcaagagga    89460
ggtctggcca gccctggggg accgggccct ggtgcccatg gtggagcagc tcttctctca    89520
cctgctgaag gtgattaaca tttgtgccca cgtcctggat gacgtggctc ctggaccccgc    89580 aataaaggta atgtcccact tgggtgctgg attcatacag ccttaatgac tatgggtttc    89640
cagactacct ttgtttagta atctgtccct tctttattct cttttttgctt taaatgaaca    89700 aaattgctca gattgtgaca ctaaatttaa catcaaaatg tgaccatgtg gatgggtgca    89760
gtggctcgtg cctgttattc cagcactttg ggagactgag gcaagtggat cacttgaggc    89820
caagagttcg agaccagcct gggcaacatc acgaaacccc ctctctacta aaaatacaaa    89880
aaattagatg ggttgggccg ggcgtggtgg ctcaagcctg taatcccagc actttgggag    89940
```

```
gccgaggtgg gcggatcacg aggtcaagag atcaagacca tcctggctaa cacagtgaaa    90000 cccgtctct  actaaaaata caaaaaaatt atctgagcat ggtggcgggc gcctgtagtc    90060
ccagctgctc gggaggctga ggcaggagaa tggcgtgaat ccgggaggcg gagcttgcag    90120
tgagccgaga tcgtgccact gcactccagc ctgggtgaca gagcgagact ccgtctcaaa    90180
aaaaaaatta gatgggcatg gtggtgcgtg cctgtaatcc cagctacttg ggaggctgag    90240
gcaagagagt tgcttgaacc tgggaggcgg agtttgcagt aagccttgat tgtgccgctg    90300
cactccagcc tgggtgacag agtcagactc tttccaaaag aagaaaaaaa tgtgaccatg    90360
tgttttatag ctcttttagt atcatcagtc actgttatcc ctaagaggga aatacctagc    90420
tttagtttta ggtttccagc attagccaag aaagctcaga attgatgttc ctggccaagt    90480
acctcattgc tgtctcctta aatcttggtt aatggctact gtcctggcta gcatagttat    90540
ggagcatttc catggttgta gaatgttctg ccaatctcag ggacagtttt gcttttctgt    90600
gaagcaataa aatcaacttc aaaacaaatg ttaactattt gtacaatgga tttaagatag    90660
accagttcac atactttttt ttttttttt ttttgagatg gagtttcatt cttgttgcct    90720
gggctggagt gcaatggtgt gatctcagct cactgcaact tctgcctcct gggttcaaac    90780
gattcttctg cctcagcctc tcgaggcaga ttacagctgg gattacaggc atgcaccacc    90840
acacccagct aatttttttg tagttttagt agagacgggg tttcaccatg ttggtcaggt    90900
tggtctcaaa ctcctgacct gaagtgatct atccgcttcg gcctcccaaa gtgttgggat    90960
tacgggcatg agccaccacg cccagcctaa gatagaccag ttacttact gtttatatct    91020 gattactctc tctttgcctt gtcttctacc tttaaaaatc tccctactaa cttcccattc    91080
tcctttagct gccatcagtc ttctcccttc tctgcaaaca tctctggaga gtcccagcct    91140
cagcccacag agcttcccac tgctctgagg tggaccttgt ttgcaaggct tctttggctc    91200
tcttggcctg gaccctgtct actacttcag ccatccttcc ttaacccctg ctggtggttt    91260
ctgttgccac actccatagc agcgtttccc gcccagatca tgtctttaca tctctgggca    91320
ctgctctggt cctgcctgcc tttccctctt tgtatcctgc aggctgctac ccccatcttg    91380
agtgtcctct tcagttggct ttcagagggc ctcctgggtg ttcccttacc cacttgccac    91440
tccccagtca ctgggttcag tccttcctgc ccaccagcac atgctttcta ggctctgtcc    91500
taggccgtct tctctctttg tagtctctgg gccagtgctg ttctagagag tggcagaatt    91560
ttctataacc atggcagtgc tccatagcta tgccaggcaa gacagtagcc actaaacaca    91620
tatagctgtt gagcccttga aatgcagcta gtgtgactga agaactgaac cccgattcgg    91680
tttaattttc attaaatta aatttaaata accttatgtg ggtagtggct ccagtattgg    91740
gcagggcagc ctgagagtcg gggctgttct cctgtcttca gtgtctagat gagggacctc    91800
agaggacctg tctctggagc tgcagttcaa tgtagccagc tgccccgtga cacttacata    91860
tagctgattt gtggatatgt cagacacggt gtgatgagct cagctttctg tcctcctccc    91920
cacatctgcc cctgccccat ttaccccact tgtgtctta tcaagctaga aacaggtcac    91980
cacaagtctt catttccact caccaagtct tttgtttccc ctactaaata ttttgcgaga    92040
agaaagtgtg taccttttgta ttcacataca tgtacatgca catatacatg cacatatgca    92100
ggggtcccca acctctgtta aaaaccggac tgcaggccgt gcgtggtggc tcacgcctgt    92160
aattccagaa ctttgggagg ccgagaccag tgcatcacaa ggtcaggaga tcgagaccat    92220
tccggctcac acggtgaaac cccgtctcta ctaaaaatac aaaaaaaaat tagccgggtg    92280
tggtggcggg cgcccatagt cccagctacc tgggaggctg atgcaggaga acggcgtgaa    92340
```

```
cctgggaggc ggagcttgca gtgagccgag attgtgccat tgcactccag cctgggcgac   92400
agagcgagac tctgtctcaa aaacaaaaca aaacaaaaaa aaaaaaaacc aggctgcaca   92460
ggaagaagtg agcaagcatt accatctgag ctctatctcc tctcaggcca gtggtggcat   92520
tagattctca taggagcgtg tatgagttcg ttctcacact tctgtaaaga catacctgag   92580
acatataaag aaaagaggtt taattggctc acagttctgc aggctgtaca ggcttctgtt   92640
tctgggaagg cctcaggaaa cttgcagtca tggcagaagg tgaagtgggaa gtaggcacat  92700 cttcacatgg cccacaggaa aaagagagaa ggagagagag agagagacag agagagagag   92760
agaaaaagaa agattgagag ggagagagga gggagaaagg agagtgcctg taggggagt    92820 tgctacacaa aggagcacca gggggatggt gctcaaccat tagaaactac ccccatgatc   92880
caatcacctc ccaccaggcc ccacctccga cactggagat tacaattcag catgagattt   92940
gggtggggac acagagccaa accatatcag agcatgaacc ctattgtgaa ctgcacattt   93000
gagggatcta ggttgcatgc tcctatgag aatctaatgc ctgatgatga tttgaggtgg    93060
aacagtttca tcccgaaacc atcccccgcc aaccctggtt tgtggaaaaa ttgtcttcca   93120
cagaaccggt ccctggtgcc aaaaagtttg gggacctctg cacatatgca tgcacctgta   93180
catggacaca taatacatgt acatatgcat actttatatt ctctgccact tctggtccag   93240
actgatatac tatctcattt ggattactgc actagccttt tgttttggaa acagcattt    93300 ttaaaaaatt taatttaatt ttttttgagat agggtgtcat tctgttgccc agcttggagt   93360
gcagtgtcat gatcatagct cactgcggcc tcgatctccc aggctcaagt gatccttctg   93420
cctcagcctt ctcagtagtt gggactacag gcatacccac catgcccagc taatttttg    93480 atttttttt tttttgaga cagagtctca gcctgtcgcc caggctggag tgggttggcg     93540
cgatctcagc tcactgcaac ttctgcctcc caggttcaag tgattctcct gcctcagcct   93600
cccgagtagt tgggattaca ggcgcctgcc accacaccca gctaactttt tgtattttta  93660
gtagagacgg ggtttcacca tgttggccag gctggtctcg aacttgtgac ctcgtgatta   93720
gcccgcctcg gcctcccaaa gtgctgggat tacaggcgtg agctaccgct cccagccagg   93780
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttaccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct tctaccaagc agggttttca gtgtagcagc ctctctgttt   94080 ttctttttt tttaaattgt gacggaactt ctgcctcccg ggttcaagcg attctcctgc   94140
ctcagcctcc cgagtggctg ggactacagg cccatgtcac catgcctggc taattttttt   94200 ttttttttt tttagtagag atgggtttca acatgttagc cagggtggtc tcgatctcct   94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
tctggaggtt gggaagtcca agatccagga cttttcgcctt gccctcatgt ggtgaggggg   94560
tgaggaagct ctgtggggcc tcttatatat ggatgctaat ctcattcatg aggggtctgc   94620
cctcatgacc cagtcacctc ccaaaggccc cacctcctaa taccatcacc ctggtaatta   94680
```

```
agtttcagtg tataaatttg ggggactata gacattgaaa ccataacaag cacttttcta    94740
agatcaggga gtgagtaagt agcagagcta ggacctcaat tccacatgtc agtcatcttg    94800
ccttcactct gctccatgat ggctgcctcc tagagcattg ggagtctcga tgttctatat    94860
gctctcatgt gttgtgtatt ggagatagtt gaggctttat gaatacatct ggatttgttg    94920
acttctagct ttgctggtaa ccagctgtga ccttgaataa gttacttcat ctctgagcct    94980
gtttcctctt ttagaaacag gagtttaaaa tgctgctttg ggttgggcac ggtggctcat    95040
gcctgtaatt ccagcacttt gggaggctga gatgggagga tcactggagc ttggagttcg    95100
agaccagcct gggcatcata gtgtgagatc ctgtctcctc aagaaattaa aaaattagct    95160
gggtgatgtg gcgtgtgcct gtggtcccat ctactctgga ggctgaggtg gaggattgc     95220
ttgagcccag gaggttgagg ctacaatgaa atatgattgc accccatcct gggtgacgag    95280
tgagaccctg tctcaaaaaa gaaaaaaaaa atgctgcttt gtaccccttt catgtcatgg    95340
cgtcatggcc aacatagaat gccctggttg tttgctgttg gagggcatgg gcctggggc     95400
tccctgaggg ctccttccat cttcaactca ttctctgtgc acctgttagg aagttgtggg    95460
ccagtcccta ccatgtatca ttgtgtgggt aaaagtaaat aaaatgtgta cagtgtctga    95520
actgtacata tcagggtcca agaacaaaat gagtgacatg ggttagctct ttttaataaa    95580
tggtaaaacc aaatattcta attttcagtt ttgttatact tccatcacat gtttttgttt    95640
ttttgttttt tgttttttgtt tttctatttt aggcagcctt gccttctcta caaaccccc    95700
cttctctaag tcccatccga cgaaagggga aggagaaaga accaggagaa caagcatctg    95760
taccgttgag tccaagaaa ggcagtgagg ccagtgcagg taggaaacag cgtggggaag     95820
ggagggacat gagtgcagca tctgtcatgt agaaacatag gatttaagta acttggtgtt    95880
ttagagaaat aaatataata cacatcagta aagtgagaga aagtttctcc aggtgcggtt    95940
caagatatta gaaactaatg actgatgtac acagaccacc ttttggtctg aagcatttct    96000
aagtgccact ggctgacatg cagcccctac agcctccagg cttccagccc tagcatggag    96060
catcactctc ctatgcttcc ctggttgcag gtgatggctg gagaggcctc ctgattttca    96120
gtaagggaag tggtgtagat gcttaggaat agatgtagtg agtgaaaaaa ctgattctga    96180
tatgtcaaaa attctgattg gaaatggaat atttacattt ggaagagcta aaggcgagag    96240
aaagtgggga taaagtcatc tgagttggag gagcttaaac cattcacaag tttggaggac    96300
cttttttac ccatgaaaag gtcagaacag aaggggctag gatttaggtg tgactgcagt     96360
ttattgaatt cccatccata ctgctctcgg tgggcagtgg caggggcagg agaggagcct    96420
ggcaaagcat gaagtgactg ctgctgcctc tgctatctgg gacgcctggc cacctgtctg    96480
tacagtctcc ctccagaccc attctcacgc tgtctcttgg cacccagggg ccagtgatgg    96540
ttctcccatt tgttttgtgt atatagcatt tatatcaagg ctatttattt atttatttat    96600
tttatttatt tatttttttg agacagagtc tcactctgtc acccaggctg gagtgcagtg    96660
gtgcaatctc ggctcagtgc aagctctgcc tcctgggttc aagcaattct cctgcctcag    96720
cctcctgagt agctgggact acaggtgtgc accaccacac ctggctaatt ttttgtattt    96780
tttattagtg gagacggggt ttcaccttgt tggccaggat ggtcttgatc tcctgacctc    96840
gtgatccgtc cacctcagcc tctcaaagtg ctgggattac aggcatgagt cactgtaccc    96900
ggcctatttta tttattttta attgacaaaa ttgtatatat ctgtaatata caacatgatg    96960
tttgaaatat gtgtacattg gccaggcgtg gtggctcaca cctgtaatcc cagcactttg    97020
ggaggctgag gtgggcggat cacgaggtcg ggagttcaag accaaactgg ccagcatggt    97080
```

```
gaaatcctgt ctctactaaa aataccacaa aaaaaaaaaa aaaaaaaaaa agccgggcat    97140
ggtggctcgc gccagtcgtc ccagctactt gggaggctga ggcaggagaa ttgcttgaat    97200
ctggcaggtg gaggttgcag tgagctgagt tcatgccact gcactctagc ctgggcgata    97260
gagcgagact ccgtctcaaa aaaaaaaaaa aagaagaaa tacatatgca ttgtggaatg    97320
gctaattaac ctgtgcatca cctcacgtat cattgttttg tggtgagaac acttaaaatc    97380
tactctttca gtgattttct tgcatatggt acattgctat taactgcagt caccatgcta    97440
tacagtagat ctcttgaact cattcctcct gtctataaat gaaattttgt atccttgacc    97500
aacacattca aggtttttt tgagatggag tcttcttcac ccaggctgga gtaccatggc    97560
acgatctcat ctcactgcaa cctccgcctc ccaggttcaa gcaattctcc tgcctcagcc    97620
tcctgagtag ctgggattac aggcacatgc tactgcacct ggctaatttt tgtattttta    97680
gtagaagtgg agtttcacca tgttggccag gctggtctcg aactcctgac ctcaagtgat    97740
ccgcctgcct tggcctgcca aagtgctggg attacaggtg tgagccactg cacccggcct    97800
caagcgtttt aaaagatgct cttttctaag gattgactgt agtacaggag gaagattgac    97860
ctgttgaaaa gcctcagcct ttacaagtgt aaaattatca gtatattact atcatctttc    97920
tgatgaatta aataaactaa ggactccaag tcaaagtct tcaaactgaa gtagaatagt    97980
tgtatatagt gcttggcact ttaatattta gtatcggttt aatgataatg tttgtgcctt    98040
tgccgtcttt aaaacatttt tacatcatcc ctgtttgatt acttggtgtg ctcatgaagt    98100
tgttggccac taaggaatct taggctcaga gaggttctgg aattggccag tggtccttga    98160
atcagctgct cctatgattc tctaactgat ttctcacaaa gcaaacaagc aatcataaca    98220
aaacaactgt gcacactgct cttcttattt tgttatttaa aaagtactta ggctctactt    98280
atgtttgtta gtcaatttct cattacttct agttaatcaa aaggtcagag gaaatacttg    98340
aatattttca tactagaata ctttaaaaaa tcatgatttc cagtaatctc tttaaaactt    98400
ggcaagttat tttgatctaa aagtttatct tttgtgtgca tatttttaaa gcttctagac    98460
aatctgatac ctcaggtcct gttacaacaa gtaaatcctc atcactgggg agtttctatc    98520
atcttccttc atacctcaaa ctgcatgatg tcctgaaagc tacacacgct aactacaagg    98580
tatgggcctc tgcatctttt aaaaatatat atgcacacat acttacgtct aatggatagt    98640
tgatgttttt cttatgattt gtaggatgta taagcccttt gagatatgag ttacatttag    98700 tttttttcaag tttgtttgtc tttcagctttt gtttatgata gcttctatca tacaggtgtt    98760
ttggattttc atattgtttg tactcacagc taagattgat tacagtgaca gagctaggat    98820
gtgcagccag gttataggg gaagtggccc tggtggagtc tggagggatc cgtgtacagg    98880
cttccttccc tcccgtgagg ctcacacaaa aatacagcaa catgctggtc ctgcaggtac    98940
cctctgccta acatgagcca caattccaga ctcacagaag aaaagcaggt gttcggcata    99000
aaccatgtgt ttcaaatagt ctgggcatgg tgagccactt gttatcagct agggaaagtt    99060
tatgtcagcg taagaaactg ttcaccagat accccccaaga gccagccttt ctgtctaggg    99120
atgttttagt ttttagttc attttttttt ttaactttaa aattttctgt tcatctgcaa    99180
tttgttagat atgaagtatg tgtctaattt aattttgtt tttggttgtc cccaataatg    99240
tttacagaag aattttttctg cactaattgg cttgagttac ttacattctc atagttctct    99300
agtttcagta gtttcattta ttattttgtt atatcaatct atctgtctgc tcatctatta    99360
gaagcatcct tgttttttt tttcttttt tagacagagt cttgctctgt ccccaggttg    99420
```

```
gagtgcagtg gtgcaaccat gcctccctgc agtctcaggg ctcaagtgat cctcccacct  99480
cagctcctga gtacctggga ctaccggcat gtgccaccac acccagctaa ttttacatt   99540 ttttgtagag acagggtctc cctaagttgc ctgggctggt ctcaagctcc tggcttaagt  99600
aatcctccct ccttggcctc ccaaagtgct gggattacag gtgtgagcaa ctgcacccgg  99660
ctacaagtat acttcttaat tattgtagct taatggtatt tatgagggga tcagttcccc  99720
tgttgttctt tagaattttc tggatattct tctttattga ttttgggatg tgaacaatag  99780
aatcaacttc tacttgtaga ttgatttagg gagaacttat acctcagatg ttaagtcacc  99840
ctgtccagaa tgtgggatgc tttcctattt gttcagaact ttttaaatta cctcagaagc  99900
acatgaaatt taaaggattt taaaaaaaac ttaaagatta tttcacatag ctcttgcaca  99960
tttcttgata aatgaatcct caggtattcc tctgttttg ttactaatag ttacttctta  100020 tgggttttt ttcccctgaa aatcatttat caaacgtatg tggcttattt tctgaaggat  100080
gtttgataat tttggaagat atgaaagtct tcatatttta caaggtttga ggtctcttta  100140
agctgcatgg ttctcatgtc agctcccaaa gcagaagacg gcatgttgaa aaatgccgta  100200
gagaagatac ttcttttcca cctgttttca actcatatca tcttgaattt cagggcacct  100260
ttccatgctc ctagtgcttg ctatctgttt attattttcc ttcctgaata ccctgaactc  100320
cagcatgttc tgctgtaatt ctggcctccc tggcatcttg gactcctgtt tcctttgctc  100380
tgtcatcccc gcggtcagct cctgctgcg agcttctcag ctgaagtgcg tttggagtgc  100440
ctggcgtgtc ttgctggatc tttgagtatt gcctctggtt tccttggttc cttctgctga  100500
gttgctcagc gtctccactc cccatttctt gtgtggccct tcctgcactc ctctgattcc  100560
ttttgtcttc cctggtttct tgctttggtt tcgagtctcc acagaacttt tgcagctctt  100620
ctgaagacct ggaagctttt tcatcttaat tctcatctca tgacctcttt tcccttcttt  100680
gagagctaga acttcccatg gtgaacttct cttttccagaa ttccatgcct tcttttccct  100740
cccacttacc tgttgtccag gagaggtcag attgctgtgc atattggagg agaacccttt  100800
cttccctggg ctcttcatct cacatgacat caccacatca cctcgttcct tggaccctca  100860
gtggtgtcac tgctggattt ttcttttcctt tggctggcct tagggcacac ccaggttgac  100920
tagcgtagtc atggtattta gatccactca cattttcagt ttctgtgtct gtctcttgcc  100980
tgcttctgac ttcgcccaga gaaagcttct cttttcacaag ggttcttaga tttatgttca  101040
ctgagcacct tcttttctga ggcagtgttt taccaatatt tattttccta gtcagtctcg  101100
ccttaccttt cttgttatgc atgtctttgg tcctgaccca ttctctgagt ctgtaaaata  101160
gaattgctgt ataatttaat tacatgaaat cctttagaat cttaacacat cttacacctg  101220
atttaatatt ttattgtatc caaattgaac caaccctatg tgaatttgac agtgatttct  101280
cccagggatc ctagtgtata aggaatagga cttagtattt tctatttttt gatataccac  101340
ataccagata ctgattatga tggacattta acccttttt ctcattatga aagaaagtta  101400
ggaattattt cttccagtag cgccagtgta acctgaaagc ctttgaaaga gtagttttg   101460 tatagctatc tgaaaggaat ttctttccaa aatatttttc cagtgctgac aacaaacacg  101520
cagacacacc ctgcaaggtg agtgtacggc gccgcacagt ggaggcatct gctgcagccg  101580
tcgatgtttg tgtctttggt tgtacattat gagatcgtga cagggccagt aaccgtgtgt  101640
tctctccttc accttcccaa ggtcacgctg atcttcaga acagcacgga aaagtttgga  101700
gggtttctcc gctcagcctt ggatgttctt tctcagatac tagagctggc cacactgcag  101760
gacattggga aggtttgtgt cttgtttttt ctccttgggt tgtggctggc acacttgatg  101820
```

```
tgcgtcttct gggctgagtt catctaggat ggagcctggt tctccagggt gcctccggga   101880
gactcctccc tgccccacgt gcttgcgtca caggacccaa gtctgactct gccttagcca   101940
tgaagtttag ggggaagttt ctatttgtat tctattttg tctgttatca tgtattagct    102000
tagacccagt ttagtttgga aaatcagtgg gtttcaaaat gtgtttgtag agtcctttat   102060
ttcttaactt gacctttca agtggaaagg ggcaaaacag acgggtaagg gggcggggcg    102120
ggaggtgtga cttgctcttt tgtgcctgag gaagtaacag agctgggggtt gacagtcata  102180
ttctctgaca cagatagtct ctgacttatc tcacagaaag tcagcggcag agcctgagtt   102240
aaaagtctcg tagattttct ttttcttttt tttggtggct aatttcagtt ttatttatat   102300
ttgtttattt atttattata ctttaagttc tgggttacat gtgcagaatg tgcagttttg   102360
ttacataggt atacacgtgc catgatggtt tgctgcaccc atcaacccat cacctacatt   102420
aggtatttct cctaatgtta tccctccccc agtcccctca ctcccatgg gccccggtgt    102480
gtgatgttct cctccctgtg cccatgtgtt ctcattgttc aatttccact tgtgagtgag   102540
aacatgcggt gtttggtttt ctgatcttgt gatagtttgc tgagaatgat ggtttccagc   102600
atcatccatg tgcctgcaaa ggacatgaac tcatccttt ttatggctgt atagtattcc    102660
atggtgtata tgtgccacat tttcttaatc cagtctatca ttgatggaca ttcgggttgg   102720
ttccaagtct ttgctattgt gactagtgcc acaataaaca tacatgtgca tgtgtcttta   102780
tcgtagaatg atttataatc cttgggtat atgcccagta atgggattgc tgggtcaaat    102840
ggtatttcta gttctagacc tttgaggaat cgccagactg tcttccacaa tagttgaact   102900
aatttacact cccaccaaca gtgtaaaagt gttcctattt ttccacaacc tctccagcat   102960
ctgttgtttc gtgactttt aacgatcgcc atcctaactg gcgtgagatg gtatctcatt    103020
gtgattttga tctgcatttc tctaatgacc agtggtgatg agcattttt cgtatgtctg    103080
ttggctgcat aaatgtcttc ttttgcgaag tgtctgttca tatcctttgt ccatttttg    103140
atggggttgt ttgcttttt ttcgtaaatt tgtttaagtt ctttgtagat tctggatgtt    103200
aatcttttgt cagatgggta gattgcaaaa atttttatccc attctgtagg ttgcctgttc   103260
actctgatga tagtttcttt tgctatgcag aagctcttta gtttaattag atcccgtttg   103320
tcaattttgg cttttgttgc cattgctttt ggtgttttag acatgaagtc tttgcctatg   103380
cctatgtcct gaatgttatg gcccaggttt tcttctagga ttttatggt cctaggtctt    103440
atgtttaagt ctttgatcca tcttgagttg attttttgtgt aaggtataag gaagggtcc   103500
agtttcagtt ttctgcatgt ggctagccag ttttcccaac accatttatt aaataggaa    103560
tcttttcccc attgcttatg tgtgtcaggt ttgtcaaaga tcagatgatt gtagatgtgt   103620
ggtggtattt ctgaggcctc tgttctgttc cattggtcta tatatctgtt ttggtaccag   103680
taccatgcag ttttggttac tgtagtgttg tagtatagtt tgaagtcagg tagtgtgatg   103740
cctccagctt tgttcttcta gcccaggatt gtcttggcta gcaggctct tttttggttc    103800
catatgaagt ttaaaatagt ttttttccaat tctgtgaaga aagtcagtga tagcttgatg   103860
gggggatagc attgaatcta taaattactt tgggcagcaa ggccatttc acgatattga    103920
ttcgtcctat ccatgaacat ggaatgtttt tctatttgtt tgtgtcctct cttatttcct   103980
tgagcagtgg tttgtagttc tccttgaaga ggtccttcac atcccttgta agttgtcttc   104040
ctaggtgttt cattccctta gtagcatttg tgaatgggag ttcactcatg atttggctct   104100
ctgtttgtct gttattggtg tataggaatg cttgtgattt ttgcacattg attttgtatc   104160
```

```
ctgagactttt gctgaagttg ctaatcagct taaggagatt ttgagctgaa ccaataggggt  104220 tttctaaata tacaatcatg tcatctgcaa acagggacag ttttacttcc tctcttccta  104280
tttgaatacc ctttattgct ttctcttgcc tgattgcgct ggccagaact tccaatacta  104340
tgttgaatag gagtggtgag agagggcatc cttgtcttgt gccggttttc gaagggaatg  104400
cttccagttt ttgcccattc agtatgatat tagctgtggg tttgtcataa atagctctta  104460
ctatgttgag atacgttcca tcgataccta gttattgag agtttttagc atgaaaggct  104520
gttgaatttt gtcaaaggcc ttttctgcat ctgttgagat aatcatatgg tttttgttgt  104580
tggttctgtt tatgtgatgg attacgttta ttgatttgcg tatgttgaac cagccttgca  104640
ttccagggat gaagctgact tgattgtggt ggataagctt tttgatgtgc tgctggattc  104700
agtttgccag tattttattg aggattttca catcgatgtt catcagggat attggcctaa  104760
aattctcttt ttttgttgtg tctctgccag gctttggtat caggatgatg ctggcctcat  104820
aaaatgagtt agggaggatt ctctctttt ctattgattg aatagtttc agaaggaatg  104880 gtaccatctc ctctttgtac ctctggtaga attcggctgt gaatccatcc tggactttt  104940 ttggttagta ggctattaac tattgcctca agtttagaac ctgttatcag tctattcaga  105000
gattcagctt ttttctggtt tagtcttggg agggtgtatg tgtccaggaa tttatccatt  105060
tcttctagat tttctagttt atttgggtag agatgtttat agtattctct gatggtagtt  105120
tgtatttctg tgggatcggt ggtgatatcc cctttatcgt ttttattgag tctatttgat  105180
tcttctctct tttcttcttt attagtcttg ctagcggtct acctattta ttgatctttt  105240 caaaaaacca gcacctggat tcattgattt tttttggagg gttttttttc gtgtctctat  105300
ctccttcagt tctgctctga tcttagttat tttttgtctt ctgctagctt ttgaatttgt  105360
ttgctcttgc ttttctagtt cttttaattg tgatgttagg gtgttaattt tagatctttt  105420
ctgctttctc ttgtgggcat ttagtgctat aaatttccct ctacacactg ctttaaatgt  105480
gtcccagaga ttctggtatg ttgtgtcttc gttctcattg gtttccaaga aaattttat  105540 ttctgccttc atttcgttat ttacccagta gtcattcaag agcaggttgt tcagtttcca  105600
tgtagttgtg tggttttgag tgagattctc aatcctgagt tctaatttga ttgcactgtg  105660
gtctgacaga cagtttgttg tgatttctgt tcttttacat ttgctgagga gtgttttact  105720
tccaactatg tggtcagttt tagaataagt gcaatgtggt gctgagaaga atgtatgttc  105780
tgttgatttg gggtgcagag ttctgtagat gtctattagg tccgcttggt ccagtgctga  105840
gttcaagtcc tggatatcct tgttaatttt ctggctcatt gatctgccta atattgcacag  105900 tggggtgtta aagtctccca ctattaccgg gtgggagtct ctttgtaggt ctctaagaac  105960
ttgcttcatg aatctgggtg ctcctgtatt ggggcgtgt atatttagga tagttagctc  106020
ttcttgttga attgatccct ttaccattat gtaatggcct tctttgtctc ctttgaactt  106080
tgttgattta aagtctgttt tatcagagac taggattgca atccctgctt ttttttgct  106140 ttccatttgc ttgttagatc ttcctccatc cctttatttt gagccaatga gtgtctttgc  106200
atgtgagatg ggtctcctga atacagcaca ccaatgggtc ttgactcttt atccaatttg  106260
ccagtctgtg tcttttaatt ggggcattta gcccatttac atttaaggtt aatattgcta  106320
tgtgtgaatt tgatcctgtc attatgatcc tagttggtta ttttgcccgt taactgatgc  106380
agtttcttca tagcgtcagt agtctttaca atttggcatg ttttttgcagt ggctggtact  106440 ggttgttcct ttccatgttt agtgcttcct tcaggagctc ttgtaaggca ggcctggtgg  106500
tgacaaaatc tctgcatttg cttgtctgta aaggatttta tttctcgttc acttatgaag  106560
```

```
cttagtttgg ctggatatga aattctgggt tgaaaatact ttttttaaag aatgttgaat    106620
attggctccc actcttttct ggcttgtagg atttctgcag agagatctgc tgttagtctg    106680
atgggcttcc ctttgtgggt aacccgacct ttctctctgg ctgccctttc cttcatttca    106740
atcttggtgg atctgatgat tatgtgtctt ggggttgctc ttctcgagga gtatcttgt     106800 ggtgttctct gtatttcctg aatttgaatg ttggtctgcc ttgctaggtt ggggaagttc    106860
tcctggataa tatcctgaag agtgtttct aacttggttc tattctcccc atcactttca     106920
ggtacaccaa tcaaacgtag atttggtctt ttcacatagt cccatatttc ttggaggctt    106980
ggttcatttc ttttcactct ttttttctcta atcttgtctt ctcgctttat ttcattaatt   107040
tgatcttcaa tcactgatat cctttcttct gcttgattga atcggctgtc gaagcttgtg    107100
tatacttcac aaaattctcg ttctgtggtt tttagctcca tcaggtcatt taagctcttc    107160
tctacactgg ttattctagc cattagtcta acatttttt caaggttttt agcttccttg     107220
tgatgggtta aacatgctc ctttagctcg gagaagtttg ttattaccga ccttctgaag     107280
cctacttctg tcaattcatc aaactcattc tccatccagt tttgttccct tgctggtgag    107340
gagttgtgat cctttggagg agaagaggtg ttctggtttt tggaattttc agcctttctg    107400
ctatggtttc tccccatcat tgtggtttta tctacctttg gtctttgatg ttggtgacct    107460
acggatgggg ttttggtgtg ggtgtccttt ttgttgatgt tgatgctatt cctttctgtt   107520
tgttagtttt ccttctaaca gacaggcccc tcagctgcag gtctgttgga gtttgctgga   107580
ggtccactcc aggccctgtt tgcctgggca tcaccagcag aggctgcaga acagcaaata   107640
ttgctgcctg atccttcctc tggaaacatc gtcccagagc acgaaggtgt ctgcctgtat   107700
gaggtgtttg ttggccccta ctgggaggtg tctcccagtc aggctacatg ggggtcaggg   107760
acccacttga ggcagtctgt tcattatcgg agcttgaatg ccgtaccggg agaaccactg   107820
ctctcttcag agctgtcagg cacgtatgtt taaatctgga gaagctgtct gctgcctttt   107880
gttcagatgt gcccttcccc cagaggtgga atctagagag gcagtaggcc ttgctgagct   107940
gcagtgggct ctgcccagtt cgagcttccc tgctgctttg tttacactgt gagcatagaa   108000
ccacctactc tagcctcagc agtggtggac accctcccc cagccaagct cctgcatccc    108060
aggtcgattt cagagtgctg cgctagcagt gagcaaggcc ccatgggcgt gggacccgct   108120
gagccaggca caggagagaa tctcctggtc tgctggttgt gaagactgtg ggaaagtgc    108180 agtatttggg caggagtgta ctgctccttc aggtacagtc actcatggct tcctttggct   108240
tggaaaggga agtcccccga cccttgtgc ttcccaggtg aggcaacacc ccgccctgct    108300
tcggcttgcc ctccgtgggc tgcacccact gtccagcaag tcccagtgag atgaactagg   108360
tacctcagtt ggaaatgcag aaatcacctg tcttctgtgt cgatctcact gggagctgta   108420
gactggagct gttcctattc ggccatttg gaagcatccc ttgttttttg aggtggagtc    108480
ttgctctgtc gcccaggctg acgtgcatcg gcacaatctc ggcccactgc aacctttgcc   108540
tcctggtttc aagcgattct cctacctcag cctccggagt agctgggatt acaggcacct   108600
gccaccatgc ctggctaatt ttttgtattt ttagtggaga tggggtttca ccacattggc   108660
caggctagtc tcgaactcct gaccttgtga tccacccacc tcagcctcct agagtgctgg   108720
gatcacaggt gtcagccacc acgcccagcc atatttttcag atctccctct ctttgcccta   108780
aaccactgtg cttaataagt agttttttagt ggccagcagt ctccatgtat aacacatttt   108840
agcaaaatgg aaaatactat atgttttaaa tttgaacgtg agattatact gaaataaaaa   108900
```

```
tcatctaact gggattctttt aaatagtaag attttctttt ttgtatgtgg gttttttttt    108960
aaccttatta ttatgactgt catatataga aatggctgtt tttcagttac agtcagtgaa    109020
tgtatcaaat gctgccttat ccaaataata aaagtaaatt attaataagt cacaatttaa    109080
tgaagattga tgttagttga tctttatatt cttgaaatca gccatatggt tgtgtgtgta    109140
tgtatatatt tttaaaggta cataaagata ataagctcat ctctgaaaat ttttacattt    109200
ggcataagaa taactggata attaagcatc ttattctctg gcctgtgtct ttacagttaa    109260
aggtagattt actcacctct ccttttttgt ttttctaagt tcatctttt tgctgtttca     109320
agacagaggc ccatttagc tttctcgcat atccttttgt ttgtactttg gaagcctcac     109380
ctgcttaatt gttgagtttt tatccgtggt cttttagagg gggatatgta gggtagaagc    109440
tttcacaggt tcttgtttgc acttggcccc tgactgtttt gaggaatctc cctcactgac    109500
tcacagcatg gcaaggtttc agatctcttt ctgccacaca gcagttctga ggcagctgga    109560
aagatatcca gatgcttaga ttgtcaggcc aggcttgaga tatacaaact attgagcctt    109620
atctgtgacc ttgcttaggt gaaggcatca gagcccctgc accaacatgc ataggcctct    109680
gcatgtgtgc ggggctgggt gttgaggtct gagcacaagt gtagctggag aggtgagctt    109740
gatgtggcga cgggtatgag caggttttct tcagacttct gtgagtttac ctagttccag    109800
gatttaaagg cacagagact ttagaattaa aatagaatca ttttcttttt ctaaatagca    109860
acactaggaa taaaaataa taattccaca ttcttgacag gtaatgtttt ttcttgtctt     109920
ctaatcctta tttattccat actcattttt atacataatt gaaatgtatt atgcattgga    109980
ttttctttt gcattatatt atagacgatt tttcatgtaa ctccttactg ttccatttta     110040
tatgttttgt ctggtttaag actttatctg caaaccggga aactgtctct acaaaaagaa    110100
aaacaaaaat agttggccgc agtggcatgc gtctgtggtc ccagctactc ggggctgagg    110160
tgggaggatt gcttgagcct gggaggttg aggctgcaaa gagccatgat catgccattg      110220
cactccagca tgggtgacag actttatact gtctgttttg ggtgatttga taatgatatg    110280
ccctgatgta gtttttttat atcttgtgtt tcttgtgcct gggtttattg aggttgggtc    110340
tgtggcttca tagtattttt aaagtttgga aaatttagg ccattctttc tttcttttctt    110400
tcttttttt tttttgaga cagtgtctcg ctctgtcgcc tgcgttggag tgcagtgaca      110460
ctatcttggc tcactgcaag ctctgcctcc tgggttcacg ccattctcct gcctcagcct    110520
cctgagtagc tgggactaca ggcgcctgcc accacgcctg gctaattttt tgtattttta    110580
gtagagacga ggtttcactg tgttagccag gatggtctca atctcctgac ctcgtgatct    110640
gcccgcctgg gcctcccaaa gtgctgggat tacaggcgtg agccactgca cccagctagg    110700
ccattatttc ttcaaagatt ttttttctgc cctgcctccc tccttttttc cctctcttaa    110760
agggctgtg atttcctgaa tgattgctta gtgttgtccc atagcttact gatgctcttt     110820
tcagtgtttg attgttttat gtgttttctg ttttgtatag tttctattat tgtgttttca    110880
agttctctga tcttttcttc tacagtgtct actctgttgt taatctgtta atctgttgtt    110940
aatcctgtcc agcgtatttt ttttttttgtt tttgaaacag tctcactctg ttgcccaggc   111000
tggagtttag tggtgcgata tcagctcact gcaacctcca cctcccaggc tcaagcaatt    111060
cttctgcctc agcctcccga gtagctggga ctataggcac gtgccaccac acctggctaa    111120
tttgtgtatt tttattagag atggggtttc accatgttgg ccaaactggc cttgaactcc    111180
tgacctcagg tgattcatcc gcctcggtct cccaaagtgt tgggattata ggcatgagcc    111240
accgtgtctg gcccctgttc agtgtatatc actaatttg ttttatctc tagaagtttg      111300
```

```
atttaggtct tttaaaaatg tctccctgtg tttctgttta gctttgtgaa cacaattgta   111360
ataactgttt taatatcctt ctctgctagt tctaagatct tctaataact tcccagttct   111420
tggtgtttct cattggttga ttgatactcc tcgttttggg ttgtattttc ctgcctcttt   111480
gtatggctgc caatttttta ttggatgccc aaccttgtga attttacttt gttggatgct   111540 atatatttt gtgttcccat agatcttctt gagctttgtt ctgaggttag ttgagttaca    111600
tatagatggt ttactctttt gggtcttgct ttataatttg tcagatgggt tggagcagtg   111660
cttagtttag gactaatttt tttttggac taattattcc tctttaggaa taattaggta    111720
ccatgcttag gaggcaagac catcctgagt actctaccta atgaaccaga aagtttgggt   111780
tttccagtcc gcctgctgag aacagtgact ttctagccct gtgtgagcgc tgagctctgc   111840
tccttctaat cctttccaat gcttctttcc ctggcctcag ggagttttct cacacacata   111900
tctctgctga gtactcgaga gggaccttcc ccagatctcc agagctctct ctgtcttgtt   111960
ttctcttctc tggtgctctg tcttatgaac tgtggctgtc ttggtctcct tagattctca   112020
gcacctcttc aattcagagg gttgcctgtc cctcctcctt gtgccacagc ctaggaactc   112080
tctcaaagca gcgagttggg gcagccatag ggctgactta gtctctcgtc tcccagggat   112140
cactgtcctt cattgctcat gtccagtgtc ttgaggactc tgggttttgt ctgttttgtt   112200
ttttggtttg ctttggttgt ctcaggcagg agggtaaacc cagtccctca ccctcattgt   112260
gctcagtagt ggaagtctca ctctattaca ttagatatta gtatttgtag cagagccctg   112320
gttccctggt acttggggag ctcttgaaag gccagaaaca gcatgctttc tcaccttttc   112380
cagggcttca gtttctggtg cacatcaagc attccataca catttgttaa agtcctttgt   112440
tagacaagta gtgattcaca ggttctattt gtaatttttt cagttaacat gtattgggta   112500
tctgctggga gctagtaaaa acaaaaagtg gtgtgtgaca aattcaattc tgacaagaac   112560
aaccttaaac acttagaata tactttgagc atatcagaat tttaaaaatg tgtggccctt   112620
gagtatttga aaccaacaag aatctattgc ttattagtag aggatatttt gttaaacaag   112680
tggagagaga ggcattttca gtctaattgg tgttggcttt tagcagctga tggaaaccag   112740
ttcgtgatta gccaggcagt ggtgaaacag gctgtgcatt ctgaatgcct aggtatctag   112800
gcattcagaa tggtggcgct cttttgagtta gcatcttctt cttcttgat tctttttttt   112860 tttttttga gatggacttt cgctcttgtt gcccaggtaa caactccagt gcaatggcgc   112920
catctcggct cactgtaacc tctgcctccc tggttcaagc gattctcctg cctcagcctc   112980
tcaagtagct gggattacag gtgtgcgcca ccacgcctgg ctaattttgt attttttgta   113040
gagatggggt ttcactatat tggtcaggct ggtcttgaac tcctgacctc aagtgatgca   113100
cctgcctcga tctcccaaaa tgctgggatt acaggcgtga ccaccactc ccagcccctt    113160 cttgattctt gaaaaggaca ttgggtgctg tacatctcgt tatagatgtt gataaaaatg   113220
cttgtgagaa gagtaacatt aaggtagtta tttggtcatt tttgcagatt attttaagac   113280
aattctagga ctgatttgtg gtaaatcaca cattgctgta tcatagttgt gttcactgaa   113340
catattcagg ggctctacag atgcagggct cttagctgct ttgcacactt ctgaattcct   113400
gccctgcgaa caggactgga tacctaatag acaacaggta cttgataaca gtttattgaa   113460
ttaatgagtg aatgaacaga tacataaatg catgaaagaa tggttgtaat gtatataact   113520
tggatttcaa gacttttttac tgactgttca aaataagaaa ttgaaaactt tcctctgatt   113580
ttcctctact atttacacaa tttaaatgga agttatcttg taccttcaat ttctgtctag   113640
```

```
gattcgtaca ataacgggtc atctctgagt cgcttaatgt ctcacttgtc tttctacagt   113700
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcactttttg gctcagtcca tgattgagcc aagaggccat   113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct catttttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtggaagca cgaaagagca agcaggaaat actttgtaaa agaataaaaa cgaaaatgt    114600 tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgtttttttt tttttgaga cggagtcttg   115080 ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact aaatttatg tttgtgtttt    115380 taatgcctag tatacaggac ttcttaaatt gccttaagta tgaacaggta tttgagttgc   115440
taatctgtat agtagcaata atagaatccc ttgttttcc tttataaat ttagcgatta     115500 aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
gtagccttct gcgagtgagg agacttgatg gctgtcaggc agctgtaaac tctaaataga   115920
gtgtcattat ctgaagaggg cgatgctgcc acactgagtg gcctttcaag ttgtttctca   115980
atctgacacg ttctgatcgt gtgaatgtga aattggtttg agcaggagta tatctgagtg   116040
```

```
cagaggagat tatttaaaga tattctcatt ctctgcttcc cttttattcc catttggcag   116100
atggtttgat gtcctccaga aagtgtctac ccagttgaag acaaacctca cgagtgtcac   116160
aaagaaccgt gcagataagg taaatggtgc cgtttgtggc atgtgaactc aggcgtgtca   116220
gtgctagaga ggaaactgga gctgagactt tccaggtatt ttgcttgaag cttttagttg   116280
aaggcttact tatggattct ttctttcttt ttttcttttt tatagaatgc tattcataat   116340
cacattcgtt tgtttgaacc tcttgttata aaagctttaa aacagtacac gactacaaca   116400
tgtgtgcagt tacagaagca ggttttagat ttgctggcgc agctggttca gttacgggtt   116460
aattactgtc ttctggattc agatcaggtt tgtcacttt atctttcatc catcatacct   116520
gttcctaatt tagtacaaat taccctaaaa gacactgaaa tctactttaa agaaatgtgg   116580
tctgcatgtt tccctcatca gttgctgctg cttatctttt tcatgcacct agctggtgca   116640
gaaggcctgg ggcatagcca gcctcagcaa gtcagcatcc ttgccccagc tccctggact   116700
caaggctaac ctggggttgg ctgttaggga tttccaaagg tttgtcccat ccacttgcct   116760
cccctccaaa ataagtttga atttaaattg tgagatacaa ttaagattta ttgtttgggg   116820 aacattttg caaaatctag agttagttta aacagattat caattattac cataattgat   116880
catctgcagt ttcaagctat ctaacaggtt cacttacctc tttaaaaagg aatggaattt   116940
agcaggacag taactgagac ccgtgctcct ggagtccatg tgggagctgt gtggctctgc   117000
acaagcattt gcacgcttcc cctcttgact gcattacctt cctcctatag ttgctgtggg   117060
caccagattc tggctagtcc tgtcccttca tgatgcacat tttcctcaag attcgtccca   117120
gttaaatcac tgcagatgaa actgcctttt catcgtcaaa atttaactgt cattttgag    117180 ccgtgatctt gggctacttt cttatgtggg gtaggaatat ttgtgagtta gaaatattac   117240
acttctctat ttccttctag acgtaaatct gttaatcctg tcagcactgt tactcacctg   117300
aaagggtctg tttccctagg agaactgagg gcactcggtc aacactgatt ttccacagtg   117360
ggtattgggg tggtatctgc ttgttttttt tgttgttgtt gtttgttttt ttttgttttt   117420
tttttgagat ggagtctcgc tctgtcaccc aggctggagt gcaggggtgc gatctcggct   117480
cactgccagc tccgcctcag aggttcacgc cattctcctg cctcagcctc ccgagtagct   117540
gggactacag gcacccacca ctacgccagg ctaattttt gtatttttag tagagacgag    117600
gtttcactgt gttagccagg atggtctcca tctcctgacc tcgtgatctg cccgcctcgg   117660
cctcccaaag tgctgggatg acaggcgtga gccaccgcgc ccggcctggg gtctgctttt   117720
aatgaaggag gcatcaaggg gtgggctttg cgttggcctg atgctttcat ctttctttca   117780 caaacctgt ccgaagaaaa tccgtctaaa tgggccattg ctctcctcag gaaatagtca    117840
ttgggaactt ctttctcttt cctttgacac taggaggctg actggggaga gccctggtc    117900 tatggctgtg ggcagcaggg gctgagagga gcaggctctc aggggggcac gggtacccca   117960
agggaagcca gagccctgat tgttccatt ctagtaagaa caaagactgc tctggttca    118020 tgtttgttct gattgccttt catcaaccgg tccccttct cccagttctt aagattcagt    118080
acagtgacag ttttatgaac aagaatagaa cactagaaca gacaaaccat tgaactctat   118140
gctgataaag atttattgag ctcctgctgt atgtttgcat tctgcccaga ggctctgaga   118200
aaaccaggcc atatgctcca tgctttatcc atggaagctc cccgtcaggt tgggaaagct   118260
gacagctgca gggaatacag tgtgacacaa aactggctcc catgcagccc ttacgtgtcg   118320
cctctcagat ggttggggga cgaaggtcga ctcctttggg tatcttatta ctaaaccagt   118380
```

```
ttcagggaat ctgtgccacc ctatctgcca ttaacgtgaa cagatgagtc cccaaggtgt   118440
aattttgggt attgtctgat gtctcttgga atttattatt tgttttttcca atgagatttc   118500 acctcagggt atagtaaagt tgttgagggg attcctggat gtgttctgca attatctagg   118560
ctgatttcag aatagagtta tgcttatagt caaatttatc agctgtcaag aattttattt   118620
aaaatttatg cagataagca ggaggaaaag aagcctggtt tttacatttt aatcctatta   118680
ttgatgtgaa attttatttt ccttcctgta ggtgtttatt ggctttgtat tgaaacagtt   118740
tgaatacatt gaagtgggcc agttcaggta atagcatttt attattttag atttttttct   118800
tcttcttgtg tacttacatg taatttaggt tattaagtga atgtttaaac tactgttagg   118860 cattttttgct gttttctta aatggaaatc tgactaacat actgtgcatt tttgcttctc   118920
ttaaaaatta atgtatatct caagacttgt ttggaagtag ttatgtatct gaaaattcca   118980
tatgttgtca gtattcattg cacatttcaa agcatttaat tgtgttgaca gatggtggaa   119040
tgaaatcttg tggtggagca ctagttttta aatcttctta gagaaagcag ttttatataa   119100
tgttgtcttt agtaattatt atgcatttgt attctctgca gctttttctt gctagatgtt   119160
gaggttttaa tacttcttgc tagtccatta caggtttata attattaaaa gttaaaattc   119220
ttttagtacc taaaatgctt aataaacatt gtaattagga aaatttagtg cagaaggaaa   119280
gtgttcccag attccctggg gtctggaaac atagtgttta ttctaattac atgacacctc   119340
cactgtgttt tggggcaagt tactgtttct cttttgagtt tcaatttctt caagagcaaa   119400
gaggcagagg agagctagga agatcgtagc tgctgtgccc ctgtgccgtc gggtgccttc   119460
tacctgctgc ctccgaacct ttacacatgt ccctgctctg cgcgagggca cagatgggat   119520
gcactgtggc aggggtgggg ttagagtaga tcacggacac ctgttagctt gatgtgtgct   119580
tgctgtcaag gttaatcat gaattatttt atgttgctta tattgatatg tatcttaatt   119640
ttaaaagaaa ggtctaaatg gatgttttttg tttttaggga atcagaggca atcattccaa   119700 acatctttttt cttcttggta ttactatctt atgaacgcta tcattcaaaa cagatcattg   119760
gaattcctaa aatcattcag ctctgtgatg gcatcatggc cagtggaagg aaggctgtga   119820
cacatggtaa cgggacacac cttttcactgt cgtcttcggt gtcgtgatgt gcttggcagt   119880
gttcgttttc atatacccac tttgaacgtt gtcagtggca gccatgtgct tctcaggctc   119940
tgcatgtgtg tctgtgtatg tgaaggtact ggttagagac gtttcaaaag agaagagagc   120000
atattcttta ctctcagcaa tttgtaatct tctcagggaa aaaaattcaa gaaacagtaa   120060
gataacctaa ggtacagata gattctgaat ataaagttcc tgttcattca catgaaacgc   120120
taaaagttct tcacttgatc ttagccaaaa ggccaagaag cgatgcaaca ctaaaaattc   120180
ttaaatcgaa cttgccgtga attaaatttt gatctctcat ccagtggtat tggagatata   120240
gtttgacttg ggttcagggc tttctgtttt gcctgatgat tttgctggag cttaaataag   120300
gaacccagga gatggccagc tgtgcaagcc cccagcctgt ggaaggagct agtgtggttt   120360
tatgaatgag ttgcaaatct ttctttgagc tttttgaact gatcttccag cattgcccta   120420 ttgaccccctc cctgactcct ttgctggaat ctgtaggctt tgaactttg acaggacac   120480 atcctaagac ccttgcaaac tcccagatgt gagaatggca ctactactta gagtctttc   120540 gactcagcgt gtgtgcagaa gagcatcaac cgggctgtgt tgcgaggcag ggccttggct   120600
gacctctcag tgtttacata gctaagccag ttagtgtttg ccacggcctc acaagggctt   120660
cagattcaca cagccaaagt atagattatt aaaggcatag gtgtttggtt tcctggactt   120720
ggagggtctt tggacagaaa atcagtaggc aaccacaccc agtactttgt gctgggaagc   120780
```

```
ttggtcatct gtgagagggt cagagagtat acccatgcgt gcatgccacc gaagggtcag   120840
tgagtattcc tgtgtgtgca tgtctcaggg ccggagagag tatgtgtcac tgagaggtca   120900
gagtgtttgt gtgtgtgtca aagagggttg cattgtgccc ttcactgagg ggtcagaggg   120960
tgcctcgcgt gtgtgtgtgt gtacgtgtgt gtgtgtcact gaggggtcag agtgtgcctg   121020
tgtgtgtgct tgtgtgtgcg tacatgtcac tgaggggtca gagtgtgcct ctgtgtgtgt   121080
gctcatgtgt gtgcatacgt gtcactgagg ggtcagagtg tgcctctgtg tgtgctcatt   121140
tgtgagcgta tgtgtcactg agggggtcag agtgtgcctc tgtgtgtgtg ctcatgtgtg   121200
agcgtatgtg tcactgaggg ggtcagagtg tgcctctgtg tgtgctcatg tgtgagcg    121260 tatgtgtcac tgagggtca gtgttcctat gtgctcatga cattgagggt cagagtgtgc   121320
ctgtgtgcca atgaaaggca tttcttatat ttttttatat gtggtcatag tagaccagtt   121380
aatttatttt gactcctgtg ttagaccaaa ataagacttg ggggaaagtc ccttatctat   121440
ctaatgacag agtgagttta cttaaaaaag cataataatc cagtggcttt gactaaatgt   121500
attatgtgga agtctttatt gtcttttcag atgaatcaag tagattattc ttgagaccag   121560
gaatgttgct gttttggtta tttggaaagt tttatcattt tcaaattgac ttttgaattt   121620
gagtcacctt ttttcagaag tggtgttaaa ttataggagc cctaggtttt ttttcttttt   121680
ttagaagtca tcacaaaatg atcagtgttc agaggaagag ctttgacctt ccacatggta   121740
taatgattga taaccttaat tcatctctta ccataaacca agtatgtgta agggttttct   121800
ttatttcttg aaagcatttt gtagatgttg agagcagttt tccaaatgta atttccatga   121860
aatgcctgat aagggtaccc ttttgtcccc acagccatac cggctctgca gcccatagtc   121920
cacgacctct ttgtattaag aggaacaaat aaagctgatg caggaaaaga gcttgaaacc   121980 caaaagagg tggtggtgtc aatgttactg agactcatcc agtaccatca ggtaaagga   122040 atgtatgttg gaactgtcgt ggatacttta ttgacccgtg cagatggaag gaagtgccat   122100
gtggtaacgc tcactgttaa ctgtgttact ttgaaccagg tttgggcttt ctggggcctg   122160
ggtagatgcc ggtgcagggg gatggggagg gaggcggggg gtgggggggt gtggtggagt   122220
tggggaggtg cagtggcagg aggtgttgtt ggtgtgtatc cttttttttt ttttgagatg   122280
gagtctctct ccgtcgccca ggctggagtg tggtggcacg atcttggctc attgcaagct   122340
ccacctcccg ggtttaagca attctcctgc ctccacctcc cgagtagctg ggattacagg   122400
catgcaccac catgcccagc aaatttttt ttttgtattt ttagtagaga tggggtttca   122460
ccatgatggc caagctgttt cgaactcctg acctcaagtg atcctcctgc cttggcctcc   122520
caaagtgcta ggattacagg cgtgagccac catgcccagc ctggtgttta tctttaaagt   122580
gggcacagcc acaggagttc acctgactcc tggtctgaga gtcacgagat cgttcaagat   122640
agtgaggccc tcttttccaa aacgaggacc aaaaatcaat tgacagtgtt ggtcaagatg   122700
gtagaaacct taaaatgata gaaatctcaa ctctgaaata aaaactttat ttgtatattt   122760
atttaccact attttgacat agggctaagg tctttttctt tgagctgatt tctggtttttg  122820 ttttcttaaa gtggcataag aattcaaaga catttgaggg aaggctgagt gcagaaatct   122880 ctcttttaa atgacttctc ctttcttta acttgcactg ttgtctagcc ctcacttatt   122940
ttgtcaattc tttttagctg tttgtctttg aatcttcata aagccatagc ttttctcata   123000
agaagcagca cttctttgt tcattcatat tttaatgaac ccctgtagta tttaattaaa   123060
tacttaatgc ctaattaaat cacataattg caatgcaaaa gtacatgtat cataaagagg   123120
```

```
tctgaaaatg agcaactggc aagcaggtgg tggcaggcag agctgcttgg gtgggtgggt    123180
gtcatggaga ggagttcatc agccacatgt tcagtgagct ctggatatgt ctgtttagaa    123240
atgatcacta ataaacttgt gctcaaccat gtataccyct gggaagcagg tgctcttcag    123300
tagattgcct ctgcagagaa cacagaattg aagtgaatgt ccacaaaggc aatgagccac    123360
ctgcagaata gtttagtcaa ggctgtgttt gaagtttgcc aaagattaat atacatttga    123420
ttttcatgtt gtgccttttc tctgattgtg aaatattaca aattctatac aaataacaat    123480
gatggcaaat cctcctgagc aaagtgtgca ccttgtatgt gccctagagg aacttgtgtt    123540
tcgttctgat tcccctacat ttctcatgtc atagagtggg ggttgcatta gtgtcccccct   123600 gtcctcgctg ggatcacatc tgtttggatc ctagagtctt ccagctgaac tgggacaagt    123660
ataacagacg gacacgtagg ggtggaaagg cgtctcttgg cagcagactt tctaattgtg    123720
cacgctctta taggtgttgg agatgttcat tcttgtcctg cagcagtgcc acaaggagaa    123780
tgaagacaag tggaagcgac tgtctcgaca gatagctgac atcatcctcc caatgttagc    123840
caaacagcag gtttgtcccc gcagccttgg cttgttgttg catagtgatg gtagcttaag    123900
gtccttgtga aggtgggtg gctggaatca gctcttcctt cagtcctaat ctgtgccttg     123960
atagcagttc tccgtgctag tcatgggaca gctgacttca tttcttctca caatgccatc    124020
tcaggttggt attgcccacc tactttacag gggggatccc acagctccga gaggttatgg    124080
aggtgatcag gcagcacaca gctttagagt gctggggtga gggcgggcca aggctaactc    124140
taaagcccga acccttacct cctacactgc ctcctgcatt ctggtcaacc cagtgtttta    124200
tttggtggtt agattttgt ttttgttacc ttactgcttg taatttagca gttttccttt     124260
cctttccctt cctttccttt ccgacagggt ctcactctgt cacccaggct agagtgcagt    124320
cgtgtaatct cactgcaaca acctctgcct cccaggttca accaattctc ccacctcagc    124380
ctcctgagta gcaaggacca caggtgtgca ccactacgcc tggctagttt tttgtatttt    124440
tagtagagat gaggtctcgc tgtgttgccc aggctggttt taaactcctg ggcgcaagtg    124500
atccaccaac cttggcctgc caaagtgctg gcattacagg tgtgagccac ctcgcctggc    124560
ctattcatca ctaatcagaa tttctatgat caaatgacat gaatcattgt ttccacaact    124620
gcagtggaag gaaatggcct ggcagtgcca gtttcagaag cagcctgccc ccagtcaggc    124680
acaggccact gtgcccccag tgtagcagca cctctgtagc tcacagagaa gggtggtggg    124740
gacctccttg aggcagctct gccagaaaat ctcatgagct gcctggcaca gcttgaggtt    124800
gccttttaag tggactcagc aaatacatgt ttgttcatct tgattataca caataaacaa    124860
ctactctgta tagtacgagt agtccgtggt ttttggcatt tgatttaaac ttagaggcat    124920
gtgatattga tgttactgcc ttcatgactg caccccccatt ctgatttcat aatgaatgt    124980 tatcttgaga ccagttagac aacaggacag ggatcttggc ttctggtgag attgacagca    125040
gttttagtgt ggtcagggtc tccctgccta cagatggttt tagaatggtg ccctggaagc    125100
tttatcccat tcttttctgt gcgtaatctg agtagagtgg agatcgaagg cctgaataca    125160
tagtaaatac ctgacttaat atctgccgca atggaaattg tgtgatacaa catttatgaa    125220
acgcttagtg cagcacctgc caggtagctc accacaggtg catgttgcat tcagaagtag    125280
tgctagatac tatcctgtta ctggcagtgc atacatcagt gatcaaagca gattaaagaa    125340 agacccctg ccttcttgga gtgaagattt tgttgggatg cgggtaaggg gacagacaat     125400
agaaaagcaa gtgagtgaag tctataccat ggcggctgat caggaacacc gtacagaaga    125460
atccaggagg gaagagagtt aggtggtgtc tgcggtggga gtggcattgt tcagctggtg    125520
```

```
atgagaagaa gctttggtga tctggtgaca tttgagtgaa tttgcagaaa ggaaagatac    125580
aagcctagga gatacctggg gaaggaacat tccaggcaga gcaaatagca gtgcaaaggc    125640
cctggcgggg ggcggacatg ctgttagggt acaagcaatg agggtggagg agtggggcag    125700
ccatggggag ggaagggagt gaggcctggt ggggtgaggc cagtgtggag gagccttgag    125760
agggtttgcg ctgatgtggt gtaggtttta gcaggatcat tcttattcct gagttgagaa    125820
tagccttgag gggaggtga  gggcagagca gggccaccca tgtgagaccc ggcactggag    125880
tggaatggcc caagtcagca tcccttggca gcatgaaagc aaaaccagca aggtttgctg    125940
gtggcttaga tgtggcatgt gagagagagc agggctttgg gggtgatttc agggtgagga    126000
cagggtggct gtggacaagg tagggcagac attgggggca gcaggaggtc agagcctgtc    126060
tggatgtagc agttgagacc ccataggtgc ctaatgaggt gaggccagca tcaggtgtat    126120
gagcctggag ttgtcgagag actgtggggc aggggtcag  catctgagat gtccactcac    126180
agtggaccca gactggctgg agaggaggag gagcttgaat accgagcctg ctgagtccca    126240
gctccaaggt caggtaggtg aggggagcca gtgctgggc  aggggagta ggcaggtgtg    126300 gggttcctaa agccaagatt ttttttaagg cattttgtgc aggagggcga catctgctgt    126360
cagcaccttg ggaacttggc ccaggtttgg cagcaccgag ggcactgatg agtgcttttg    126420
gaggagcaaa gggagccaaa ccctaatggg aatgtgttcc tgaaaggaca ggagagagac    126480
ttgggaaaag gttttacttg aagagggaac ggagaaatag ggcagtagcc agaggaggag    126540
aggagtcggc aatgggttaa gttggcagaa atgaaggcct gtttacgcac tgagggcaga    126600
agcaacaggg aggatcagtt catgacacag gagacacaaa tcgccgttgt ggtgttcaca    126660
gacatgggtt aggattggct gcatggatga cagagcactg tgggttctcc cagagttgct    126720
ggggaggagg cagagttggt gagcacaggc gagggtccag gatgcaggaa tcctggagct    126780
caagtcagtt gttcccttgt tgtaagatgt ggccagtgtt gtgagcttca catctgtgcc    126840
ttgaaaaaca ccacatctgt ttgcagagtt gtttactatg tatacacact cagtagaaac    126900
aaaaattgga aacagtcagt gcccaccatc aataagtaat ggttgaacac actgtggtat    126960
aagcttagac tatttttagct tgggctattt tgcatgatta aaaatgttct ggccaggtgt    127020
ggtggctcat gcctgtaatc ccagcacttt gggaggccaa ggcaggcaga ttgcttgagc    127080
tcaggagttt gagaccagcc tggcaacat  ggtgaaaccc tgtctctact agaaatacaa    127140
aaagtagctg ggtgtggtgg tgtgcgcctg tagtcctggc taactcagga ggctgaggtg    127200
ggaggatcac ttgagcccat tcgtgcgcca ctgcactcct ggggcacaga gtgagactct    127260
gttagaaaga gagagagaga aagaagagag agggagggag gaaggaagga aggaaataaa    127320
tggaagaaat ggaagggagg aagggaggg  aggaaggaag aaaggaagtt cagccagttg    127380
ccttgggagt tctccattgc actgggttaa gtgagaagag cagagacgtt tatgattttt    127440
caaaacaact aaaacaaaac ctctgtgggt gagggggcaa ggatatggct ataggaacat    127500
ggggcagatt aagaaaggga tatacacaca ccacttagca tttgttacaa ctgttgtggg    127560
agggatggag tgcagaaaaa gaaaaaaaaa agtgcacacc atcccatgta tgtgtataca    127620
aagggacgct tggaagactg gtccccaaaa tgttggtaat gattgtgtca gggtgctgca    127680
gtgctagttg attttttttc acactttgt  atatttgagt cttttacaga aagcatttat    127740
tatttatgta ataaaatct  aaatgacaag atttctgtta tgggaaaaat gtagctatac    127800
agtgttgttg taaaaatgtt tgcttggttc accactgaac ttaaaatgct tttaaatgag    127860
```

```
ggaaggtgac gatgagatga ttatgatgat ttgcccttga gttacatagc tggtgtacag    127920
gaagctgtcg tttcttttgg cttacgtaga aatgtttgtg gtgtctaatt ccacagatgc    127980
acattgactc tcatgaagcc cttggagtgt aaatacatt  atttgagatt ttggcccctt    128040
cctccctccg tccggtagac atgcttttac ggagtatgtt cgtcactcca aacacaatgg    128100
tgagtctctc gcctggctca gcagatgaat ctggacggct tgttcaggct ctgattactg    128160
ggaccacccc cagaatgtct gagtcagtca gtttgggtag ggcttcttga gagttttgctt   128220 tttttttttt tttttttttt ggtgtggggg tggtgcggaa cagagtctca ctctgtcgcc    128280
caggctggag tacagtgtca tgatctcggc tcactgcaag ctctgccttc agcttcaca     128340 ccattctcct gcctcagcct cccgagttgc tgggactaca gcgcccacc  accacgcccg    128400 gctaattttt ttgtattttt agtagagatg gggtttcacc gtgttagcca ggatggtctt    128460
gatctcctga cctcgtgacc cgcccatctc agcctcccaa agtgctggga ttacaggcgt    128520
gagccaccgc acccggcctt tttattttt  ttggagatgg agccttgctc tgtcacccag    128580
gctggagtac agtggcgcta cctcgactca ctgcaacctc cgcctcccgg gttcaagcaa    128640
ttttcctgcc tcagcctccc gagtagctgg gactacaggt gcgtgccact gtgcccggct    128700
aattttttgt attttttagta gagacggggt ttcactgtgt tagccaggat ggtcgcgatc    128760
tcctgacctt gtgatccgcc cgcctcggcc tcccaaagtg ttgggattac aggtggctct    128820
cgcaccaagc caagagtttg catttttagc aaattcccag gtgaaactaa tgcctgcttt    128880
tctgggagca cactttggga ctcagtgata gagaggttta ttggtaggat agtaaaatag    128940
gagttatttt ctttcacaaa attggcaatt gggggaaatt taatcttcct ttttcttca    129000 gctgtgactt atgtattatg tttattttag gcgtccgtga gcactgttca actgtggata    129060
tcgggaattc tggccatttt gagggttctg atttcccagt caactgaaga tattgttctt    129120
tctcgtattc aggagctctc cttctctccg tatttaatct cctgtacagt aattaatagg    129180
ttaagagatg gggacagtac ttcaacgcta gaagaacaca gtgaagggaa acaaataaag    129240
aatttgccag aagaaacatt ttcaaggtat gctttctatc tgagcctata actaacccat    129300 gcctttrtggg aagtcacgtg atgttttcaca gtcagtaagt ctggaataat acctggtctt   129360
gcttcacttc tgagttgggt aaagaagtct gtatcagtgt aattttctaa tccgtcctgc    129420
attatctatg gctcttggtt catacctgtc ttgaagttct gtcatgttct gtctcttgtc    129480
ctcagtagag atgctacagc agtggctcgc ctcaggcagg gcagggcagt ggggtggctg    129540
tcctgggggc aggcagtagg ggcacgctga cgtcagggaa gttgaaaccc aagagaagcc    129600
agtaaaagtg agtctcagat tgtcaccatg tgctggcagt tttacacgct gtcagtaata    129660
aaagtcttct ccctgcaggg cagcctgcct ccaataaata cgtgtagtat caaatcctgt    129720
cttccctcat aaaattgtttg gaagctcccc aaggacagtg atgaggcact cgtaagtgct    129780
tgctgcctag atgggtccct ctccaccttt gctagattct gagcattcac tgagttagag    129840
ctgcttctgc aaatgtgctg cttctgctaa gtggctgtga cttcatgcag ccttcacttg    129900
gtttgtcatc agtggagatg ccctgtgttg tcgaaggaga taagcccagt aagcctgctg    129960
ggcacctttt ggtttgcagg ttcagcaggc agcccatggc tttccctgtg tcgcattgaa    130020
gcagctggct aaaattgatg atacattaaa ttcctgtgac agatgatcag cttgtatttg    130080
tgtaatggtg tacagttcac aaagcttaaa aaaatgctac ctgccatttc atcctcagtg    130140
aggaaggtga tacacagaga gaccaagtga ctgtgtccac ggcgacggcg ctctgcattt    130200
cactttagcg gttaatgtac tctacctata tttttacttt atatttacca tatatctttt    130260
```

```
catgtatact tggcgtaagt gctttatagt agtcacctaa ttcactgtca tcttttttgt   130320
ttcttggaag gtttctatta caactggttg gtattctttt agaagacatt gttacaaaac   130380
agctgaaggt ggaaatgagt gagcagcaac atactttcta ttgccaggaa ctaggcacac   130440
tgctaatgtg tctgatccac atcttcaagt ctggtaggtg aatcacatta gtcttcctgg   130500
agtgtctcgt tccccattct gcactataca ctctcagagt gtaggagctg tgctgcccgg   130560
tagaaactct gccttgccca gtgtgccagt tgaaaatatt tgttgctgta agagtacacc   130620
tgataccatg tgacccagca gttccactct tgggtatata cccaaaagaa tggaaagcag   130680
ggtggtgaaa agatatttgc atgccagcat tcatagcagc attattcacg atagctaaaa   130740
tgtggaacca actgaagtgt ccctcgatgg atgaatggat aagcaaaatc tggtgtatat   130800
ttacagtgga atattattca gccttaaaaa aaggacattc tgacacatgc tacaacatgg   130860 gtgacccttaaggacattat gctaaatgaa ataagccagt cacaaaagga caaatactat   130920
gtgattccac ttacatgagg gacctggagt agttaattca tagatataga aagtagaatg   130980
gtggttgcca ggggctgcag gggaggggag ttatttttac aagatgaaga gagttattct   131040
agaaatgaat ggtggtgatg gttgtataac attatgaatg tacttaatgc tactgaactg   131100
tacagttaaa aatagttaag aggaccaggt gtcatggctc atgcctgaaa tccaagcact   131160
ttgagaggcc aaggcaggag gattgcttga gccaaggagt tgagaccag cctcagcaac   131220 atggtaggac cccatctgta caaacaaact agccggggat agtggtgtgc atgtggtccc   131280
agctactcag gagactgagg ctggaggatc gcttgagccc aggaggttaa gtctctagtg   131340
agatgtgttc atgccactgc actccagcct cggctataga gtaagaccct gcctcaaaaa   131400
aacaaaacaa aacaagacaa gagccaaaaa tggttaagat gggccaatca cagtggctta   131460
tgcctgtaat cccaacactt tgggaggtca aggtaaaagg atcacttgaa gccaggagct   131520
tgggaccagc ctgagcaaca tatcgagacc cctatctcta caagaaaat caaaaactag   131580 ctagatatgg tgggcacatg cctgtagtcc cagctacttg ggaggctgag gtgggaggat   131640
ctcttgagct caggagttcg aggctgcagg gagctattat tgcactccag cctgggctac   131700
agaatgatac cctgcctctt attaaaaaaa aatccaaaaa aaaaaaaaag taaacctgag   131760
agcttcctcc tcctgtgtta aatttggagg ccaagatgtt tttgttactt ttacaaatga   131820
tcaaggacgt gaaggttgg gcatggtagc tcacacctga atcccagca ctttgggagg   131880 ctgaggcggg gtgatcgctt gagcttgaga ccagcctgga caacatagca agagacccca   131940
tctccacaaa aataaaaaaa taaaaaaaaa tagccaggag tagtggcatg agcctgagcc   132000
caggaggtca agctgtagtg agccatgatc atgccactgc actccagcct gggcgagatc   132060
gagaccatgt ctctagagaa agaaaatgac aaggacagtg aacccaagaa agtcataaga   132120
tgccagctgt gcagcaagca tggaaagcag ccagtccaaa ttaggacagt gtgtttcca   132180 agaagaacga tcgtttgtaa tgagaatgct ttgctttaaa taaatgacta aatagctaga   132240
agcctagttc taggggatag gcacgtcttt cttctctcaa gaaaatagaa aggcaattct   132300
aatttctagt aacagcaaac agcattaagt catggtccaa atatgaggca aaccaaaatg   132360
tggcttgatt gttcagcagt tgatctgttg gaagcccttg atattaaaaa ggttctcctt   132420
taagcggctt aggagtcacg atcaaagacc tatagaaaga gatgccatcc ttctaggatc   132480
cttggctctc ttgggaacta gattcagata gtcataatgt aaatactgct tgagcttcct   132540
ttctttcttt ctttctttct tttttttttt gagacagagt ttcactcttg ttgcccatcc   132600
```

```
tggagtgcaa tggtgccatc tcggctcacc gcaacctctg cctcccaggt tcaagcaatt    132660
ctcctgcctc agcctcccga gtagctggga ttacgggcat gcaccaccac gcctggctaa    132720
ttttttgtat ttttagtaga gacagggttt ctccatgttg aggctggtct cgaactcctg    132780
acctcaggtg atccacccgc ctcggcctcc caaagtgctg ggattacagg tgtgagccac    132840
cgcacccggc ccgagctttc attttttgaaa tcaatgtatg actgaaacac tgaagactta    132900
ctgacttaat tatggtttca gaacagaatg aaaatgtctt cggttctgat gaatataaaa    132960
ggaaaactaa ccaagttaat ttggcaagta gatggtagag atagaggtgg ggagtggaag    133020
gggaactaaa atcttcacct agcattgttg ggattatatg gttacatcat ctgaagttga    133080
cagaccaaaa tatagaggct tcagaggtct ccaaatagaa ctaaacatgt aattcagatt    133140
gttaggaggt agtataaatg agctaaatct catctttatt acggtagagt taatgggtga    133200
tgtctaaagt tgtctgaagt ctataaatca tgacaaatta tgatgtggtg attgtattca    133260
acagtctttc agttgcaggg ataaaacccc agtttaaact agagtaagag aaagaatgtg    133320
ttggtttaag ctcctggaaa gtgcaggcaa gggtagttgg taggactgca tctagtgttg    133380
taattctgtg gtctgcattg tatatttatg catctcagct ctgctttctt cttttcattt    133440
atataatttt taaattttat tttaaagata gggtctcact ttgtcgccta ggctgaagtg    133500
cagtggcatg aagtgcagtg cgaggctcac tctagcctcg aactcctggg ctctagagtt    133560
cttcctgcct cagccttcta agtagctgag acaataggca tgtaccaaca tgcctggata    133620
ggttttaaaa ttttttgta gaaatggaag tcttgctgtg ttgcccaggc gggtctttaa    133680
ctcttagctt caggcgatcc tcctgcctct gcctcccaaa atgctgaggt tataggtgtc    133740
acccaccacg cccagtctca tctctgcttc ctgtgttagt tttgttctct ggtgggctgt    133800
tttcacatga ccgaagatga cctctagcag gctgtgttct cagcccctca agtaggccta    133860
tgtgattggc cttgcatgag taatatgggt gaccataaac ccctgaatgc tctggtccac    133920
atgggccaaa tgggagactg gacagcattc cattgatgag gaggtggggc tggtctccgg    133980
gagtaaggga gaggagcaca tgcagtaact gatggtctgc tgcaagggat agcagcacag    134040
cagttagaat tttggaggta actaccagaa ctgaaaacag aaatgataac aagtagttgc    134100
cttaaaaagg gatgggagca gggtgctttt gtgatcaaag ctcctttctc ttactggatt    134160
tttgtacaca ttttgcatac atatcttaga gtaaaagata gcattttcag ccttggtcca    134220
tttgaggata ctcttggcgt ggcccgcctc catgctagca ggctctggtt gtgccaagtt    134280
cagttgagca tcctggctct tgcctgcacg gaacttccag tcagtgcgtc agtatcacaa    134340
gtcttgatat ttcctatgaa gaagaacagt agtgcagtga cagacgaaat gggtgggcag    134400
gcagaggcag gatttctgag ggagagaagt agctagcttt ttgcagagaa gagttccggc    134460
acccaagaga gcagctgaga gtacaggcag gcaggcagga tgccggtagg gcccggccgc    134520
acggcgccac agaatcctgg agaaaggggc ctcttcatgg cctctgcatt cagctgctgt    134580
caccctccgc acaggccatg gccaaaattt aattttcata gtggactcta gttttttgagc    134640 cttacttgct attattgaaa taattttctt gtttcttttt aaagatcttc ggattatgct    134700
tcactgacca ctgtaataag tttaaagttg agaaaatatg gcttgttaat gaatgatagg    134760
tcaattttag tatgttggtc attttaatat tttgccacca gttggtttgg atttgatgcc    134820
aggaggagac agcctcattt ctaaggacta gtcttgcctt tgtgggataa gggtggtgtg    134880
ttctgtgtcc ttctacatgt ccgagcgatc tctgtgcagc tcaaatgtgg tcactgtctt    134940
attgcgctga tttcctctcc ttccatctca caattgaggc aaaatattgt tactgttgaa    135000
```

```
gtgttgtcca ataggacttc cagcagagac aggatgtctg cactgtctaa tttagttgcc   135060
tttagccaca tgtggtgttc tgtacctgaa atgtggctgg tctgattgga tagcttaatt   135120
tataatttta tttaattta attaacttaa atttaaacag ctctgtgtgg atagtggctc   135180
ctgtatgaga cagtgcaggt ctgttgagaa gcagctttac tggtgggagt ggagggcttg   135240
gagagggcac gtgggtttcc tgctggtatc ttttgacctt atttaatctg cccaacattt   135300
gcaagtaagt tgtgtgtgtg tgtatatata aatgtgtgtt tctgtcttct tgtttccttt   135360
gactgcattt atttgaaaga cactaggtgg cagaattact gtatttgatt ggtttcaaga   135420
taagagttga aataattcat ctcgtgtttt tatataagta aggtgtgttt agcatgtaaa   135480
attggtaata tgtattcacg tactgcttaa acaaaggcta tgaattccac ccataaaccg   135540
aaaatgaaga cctttaaatt tgtccatttc aggcgtgggt acttcttaaa taatacctgg   135600
ttcaggaact agtcagaatg gcacccttga ctttttgttt cctgcttttc ctcttgttgg   135660
gagaggaggg tattcatccc aaagtggttt gcctatttca cattccatct aggataagca   135720
gaatagccaa gaaagatagc tgtcctcctg tttacaacat ttggggtaac cagcatccct   135780
ctcttttggt ccaagataga ctggtttaga aacagatgat ggcaccagag gcccaggagg   135840
tggaaacatc agctttgttt gttgtccatg tggctgaatt agagctgtct ggccttgtag   135900
cctcaacacg gccttccagc tttgctcacc gtgattttca aggacacatc ttgtgctctt   135960
ccctgcctgc catccagact atacccagtc agggtggcag gagctgctgc cccttcctcc   136020
ctgagtcctg gtcgtgggtg gtggagatgt gccatgacgc tcacggaggc atgctcaccc   136080
cttcctctgt ggcagagggg atggctgcac gacagctctt ccctgtcctt tccaaagcgt   136140
ctgtggttcc acttttgggg gcaaagcagg aatactggaa gagagagaaa gtggtccttt   136200
ctatagtaat aaagttgaca ttgattcaag ttcatgcttg gggaaaggac agggctacta   136260
acaattataa tgctgggagc aatggaattt tctcatgggt atgtggtagg tttaatttta   136320
attatcccag ttaattctta gaactgctct gtgaagtatt tcccgctttg tgcttaagtt   136380
ctaaaagatc ctgtgccaaa accaagaatg aaaacccaag cattctttct tgcccatcga   136440
tctttctctc atcaggccac ttcttgggtt gatagtggtg agtgtagccg ctgccacttt   136500
cagaataccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800 cctccttttcc tgcactgcca tcgtggtctc cgggcacttg gtccctttct cttccctga   136860 gtccctttgg ctcccctgtg ccaccttgt gatccacagg ctctgccttc tttctgtctc   136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgtttct tggttttatg   137100
acaatgtatt gagggtgttc ttggttcacg gatggttttc ctccatgtgg gaattcgggg   137160
acccaggctc cttttccttct tttggttctg ttctccaggc cttcacatcc tctgtgtctg   137220 gttgggaca aggagaggga aggtaaagaa ggctttgtgg ccttggataa gtgacaggca   137280
tgcctttgct ggtgttctct cgtggtgaca ggtcacagcc ccaccctgta aaagggact   137340
```

```
gagagacgtc gtcctgctgc ttcccagcag cagcactgtg gtctctgatg tgttttctgt   137400
gaggataaaa acaggtgatt ccaggatgag gaaagtcagg gaaacccttg aaggaggggg   137460
accaggcggg tgtcaccatg ggattagtgg tggcttcaga atgagctgca gcgagtgcca   137520
tgccttctaa agcttttgct attctgatat gcccacacca tgcccagcag gtgtctgcct   137580
tgctctccgc agagagagtg atgaatcctt ctcatgagcc tctgtccagt tgttcctccc   137640
tccacctgga agggaccctg ggttcctcat aacatcccag cggaacaggg gaccttctat   137700
cctgtcccca agttcatcct catcctcctg ccggcttcct ggcccctctt atgtctgctt   137760
cctgacgcca catccttctg gattctctgg aattgaattt tgcctttgat gcttatttaa   137820
aaatatccat tgcaggccag gtgtggtggc tcacacctgt aatcctgtgc actttgggaa   137880
gccaaggtgg gcagattgct tgagcccagg agtttgagat tagcctgagc aacatgttga   137940
aatcctgttt ctatagaaaa tacaaaaatt agctgggcat ggtggcgcac acctatactc   138000
ccagctactc aggaacctga gacaggagga tcaattgagc cccggaggcc aaagctacag   138060
tgggctgtga tcgtgccact gtactccagt ctggtcaaac agagtgagac cctgtctgaa   138120
aaaaaaaaaa aaatccattg catacttcac cgtagcgaaa catgtatgtc ttacctttcc   138180
tttcctgcct gtagctgctc ttttacactt aacagccaca ctaagccagc cttaaatgaa   138240
aaacaaacca gcacttcctg tgcccctcct cttccttcat gaggggtccc tccctctgtg   138300
tacactccat tctcattgcc catggtggtt tgtttccctc ttgtttctca gccatggca   138360 gcctgcctct tgccctcttt actaaaaagg cctttgcaga ggctgcctgt gttctttctt   138420
tctaggtctc tctcatccta ggccctccag cttgattctg tggagctgcc ctcttgtcac   138480
tcagtagctt gtggggtctt ctctgtctag ccacttaatt gattgtgttc ctcgagttgc   138540
tgtccatggt ctctcgttac tgtttctct gtgtttctgc ctctctcctt ggccttggta   138600
ggtccatccc ctttgtgacc ttggctgttg ctctcatgga caactttctc ttgctggtcc   138660
ttgtagtcct ggcatccagc ttctcgacac gggacttgtc ctgccagtac ctcagacttg   138720
cacttaaaat tgaactagca ccactgtcac tctccagggc ctcttcttgt taattagatc   138780
attagggatg ttcagaatcc cagcatcata gtatgttcct cctcccgcta ccccaggaac   138840
cctaacctta cctcctcctc tctatctact aggaggtggc cctcagagtc cgtctcatct   138900
tccacctgaa cttccctaat aggctccagc agctgccacc ccgggggctg agtacttcct   138960
ccatgccttg tgcagtgctg agcccttac ctgggttctc ctgtttgctc cttattacag   139020
ccctgcgaac agatactgct cttaattcca tcttacacct aaggaagctg aggcccagg   139080 taaggtgcat ccaaggtcac ccaggtagta gacagtagag ccacgatctg aaccaggcag   139140
tctgattcag agcctgtgtt gacactcagc cacctagaac acagcttgga ttgtgggttt   139200
ctattacctg ttcaaaaccc ctacatcccg ggtctgtccc tgcacgtgct ctgtggcctg   139260
gctgcatctt ccttgaaggc agtgcatgcc tcttcactca gggggcccat gcaggaacag   139320
agggccccac agaaggatga ggccagtgca gaatgggctg gaggggacaa tgctgaccag   139380
gaagcaagtg tagagaaatc ccaggaaacc tggaggagcc agagacaagg cattagaact   139440
cctcgtcgtg acctggtctg cattctctga gtgtgctgct tctgttagct cgcttccttg   139500
gtctcaggtt atagtttaag gcattgtgga gccctaaaaa gcctgtactc tgtttttacc   139560
tgttttagga ccctttcact ttggggatgt gttgattttt ttttttttt ttttttttt   139620 tttgagatag agtctcgctc cattgcccag gctagagtgc agtggcacga tcttggccac   139680
tgctgcccct gcctcctggg ttcaagcaat tcttgtgctc ccgcctccca aatacctggg   139740
```

```
attacaggca cccgccacca cactcggcca attttttgtat ttttagtgga gacagggttt    139800
taccatgttg gtcaggctgg tctcgaactc ctgacctcaa gtgatctgcc cacccttggcc   139860
tcccaaagtg ctgtgattat aggcgtgagc caccacaccc ggcctgaaat ttaaatcaga    139920
aataaaattt tgatcccaac agtgatgcca ggcagcccag atctggggga gagggtggcc    139980
ttggccagct gggcctttct ctgtttccca agtcttgctg cctctccctg ctgggctttg    140040
cagcctgtgc atgtctctgt gcctttgacc ttgtttatcc aaaggagagg atagaatgaa    140100
gtcatgattc ctggagccct gagaaggatg ctgtggagaa atttgccggt agaatctagc    140160
tgagtgtgtt gctgaggtgc cagcattgtg tgtgggagg ctgaccgctt ggcctgccta     140220
ggcccaggat gctccatggc cgggcacaga ggccacttgg ctgtcaggtg tcaggagcct    140280
gcagagggca cacagagcct ggaccgcagg ggggtcctgc tttctcacct ggcctccttc    140340
agcatttctg tccctcagtc cttagcaagc ccaggagctg ttgagtttgg caggtgccga    140400
gtgctgttcc tgcctgtgta gctgtggctc agtcctgtgg gggccccgct gtggcccgag    140460
tgcagtgatt cgaggcgctg agtgttccct gactccttct ccaggagctg tgttcagact    140520
ttcgcagctc ttggcttgga gctcctggag ggcttggcat tgccgaccaa tgtgaggtc    140580
gacagtgaga gaggaggaat gctagctttc ttgaccagtc cattaaataa gtgggatatt    140640
ggccaggcac ggcggctcac gccttaatcc cagcactttg ggaggctgag gcgggtggat    140700
cacgagctca ggagttcaag accagcctgg ccaacatggt gaaaccccct ctatactaaa    140760
aatacaaata ttagctgggc gtggtggcag gcgcctgtaa tcctagctac ttgggaggct    140820
gaggcaggag aacagcttga aaccggaagg tggagtttgc agtgagccaa gattgcgcca    140880
ctgcactcca acctgggcaa caagagcaaa actctatctc aaaaaaaaaa aaaaagtag    140940
gatatctgtt tctgcttaga aaaatcagaa ttttctaaat gccaggtgtt ctgaatacgt    141000
aagtatggga gacgactcag cctgtttcat ttttatgtaa aatcttcgcg tagccatgtg    141060
gcactggacc gagatgaaag caaagacatt tctccttaac tttgtttcta ggaatgttcc    141120
ggagaatcac agcagctgcc actaggctgt tccgcagtga tggctgtggc ggcagttttct   141180
acaccctgga cagcttgaac ttgcgggctc gttccatgat caccacccac ccggccctgg    141240
tgctgctctg gtgtcagata ctgctgcttg tcaaccacac cgactaccgc tggtgggcag    141300
aagtgcagca gaccccgaag taggttcata atgccccaca gccagggcg ccagcccagc     141360
accctgtcct gagactccca gtaacctgag cttttggccac cgttaaagca ttttcatttt    141420
ccattttttg tgagggcttg tgaaatttct gctgcatatt aatattcctt tcatggacag    141480
catattattg ggacaaacat gcggtccagc taaaggcatt caaaatagca gttgctttct    141540
aaaatgcgatt ttctttggca ggttctttga caccattgca tcttgtggga tatgcttgtc   141600
atgctctgtg gctcctacta agttctagtc cttaaattgg ttccatagcc agacatgttg    141660
caatgtctta acctcattat aaagtaaatg tggttctggt tatccttaga taatgaagta    141720
acagtgtagc aaatttcaaa acctcttgga aatgttattt taccattcaa aaaggcttac    141780
taaggttctc gttatgggtg gccctctttt tgcaaaaggt tttcaggctt aagctccatt    141840
tctaggtgct ccaacactcc attatttgta tatgtatgga aataaaagct gtgaccaccc    141900
ccaaccctgg cccccgccca gctgaatcct cagcacagta tttctggaag gctcaagatc    141960
ccacgctggg gaaaagaagt tctggagaca aaagagggca ggtgctgccg tgcctctctg    142020
ctcagtatgg atactggacc ttgtgctgcc agggctccca gtagggccag ttcatggcac    142080
```

```
tcagctggaa agtccactgt tgggaggcat tcttaaccat ccactctgtg ccgtatgtag   142140
tggggtctgg tcattctgtt ggaggagaca gaccagtgac gacatttgaa atgcttggtg   142200
gatgtcttag gcctgttacg atgactgagc actgtggggg caggagacag aaagtcagtg   142260
tctcctagtt ctgtgctgct ttaacgtgca tagaaatcag ctgcggattc agcagatcac   142320
tccttttctg acagatgggc ctgcttactc tgatgttata tcagaaagct ctgaatctgg   142380
gaattgtgtc ccctgaattg gagtaacaga aatgcttaga tgatgagtgt ttaaaagaaa   142440
taaaccaaag gtaaatttag tttggaattc agcaagcgtc ttcattcagc cctctgaggg   142500
caaactacag cttttttgtaa atgtaggtaa attctgtgac tgtttcgtga ccccctctga   142560
tccagttttc ctttataacc ttctgtattg ttccttctat tatcctgaaa taacattaat   142620
agattaggct gggcgtggtg gctcatgcct ataatcccag caccttggga agccaaggcg   142680
ggcagatcac ctgaggccag gacttcgaga ccagcctggc caacatgatg aaatgctgtc   142740
tctactgaaa ataacaaaaa ttagccgagc atggtgacag gtgcctgtag tccctgctac   142800
tcagaaggct gaggcgggag aatcgcttga acctaggagg aaaaggttgc agtgagctga   142860
gatcgcgcca ctgcactcta gcctgggtga cagagtgaga ctccatctca aaaaaaaaaa   142920
aaaaaaaaa aaattaatgg atcaatggat ttttaaccta ataattaaat ttcaaaaaat   142980
atcgttcttt aatggtaatg taaaggtaaa attaagataa tatgtaacaa gcatgtgagt   143040
gtctaaggtg tccccgtggt ggaaggaaaa aataaatccc cataagtgtc caagatgccc   143100
atagagagca gagctgttct ggtttaaacc cctgctctta gcactgtgtt tttccagctg   143160
tgggtggtgg gggatgagta tcttttttatt tccatgagat gagaaaaatg aattactaga   143220
agtgtgaaat acaaaacaca gctgctcttt ttttagccat agactcagca gccataaaat   143280
tgctgtatcc agttgcagaa attcctgctg cttactcttg accctctctc ggtttgtgtg   143340
catctcctct caggctggct cccagatggg agctggctcc aggcgacact gggtgctctg   143400
ctccaggagg tccttatgtg ggtcctgccc tagcctagcc cctctcttat ggactctgtc   143460
actgtgggtt tatgattcac tctcaatctg tcttacctct tggtgaactg ttagagtcct   143520
gcctatactt tggcgcttgt gggtgtgttg tggtacacat gatgtgttgg tcacttccca   143580
gctcatcttg ttctgagtca ccctagattt gggacattca ttcgccacca gtaccgggcg   143640
gtgtatggcc tgagatttgg gggggcttgt gctgctacaa attggggctg aatttgagtt   143700
gacagtggac cttctttatg tctactgctc atatttgaat tgcaaatact gcctcttctc   143760
tttcagaggc tcattaccct atagctgtat tattgcaaag tgcacaatta cagcttgagt   143820
gtaagtcaca ctgcgctggc aggacggccc actgagaaag ggcacgtttc ctgttcgtta   143880
gttttcacat tgcacataa tttacaatac agtaaaatgt acttttctat caactgtagt    143940
cagtaacagc cccctcccc caaccacatc aagatataga ggagtgctgt cacttcaaac   144000
agttccctct tcctctgcca catcctgccc ctccccaggt ctaaccacca atccgtgctc   144060
tgtccctctg ttcagcccat tgcagaaggc catagaaata gaatctatag gctaggtgtg   144120
gtggctcatg cctgtaatcc cagtattttg agaggctgaa gtgggaggat gacttgaggc   144180
tgggagttca agactagcct gggctgccta gcaagacccc atctccagaa aaaaaaaatt   144240
taaaaattac aatcacgtcc ctgtagttca gctgcttggg aggctgaggc aggaggatca   144300
cttgagctca ggagttagag gttacagtga gctatgatcg tgccactgtg ctccagccta   144360
ggtgacacag caagacgttg tctctgggga aaaagaaag aaacggaacc acgcggtgtg   144420
cagccttctg agtctggccc ctttcggtga gcagtgtcta aagttctgtc gcgtgttgcc   144480
```

```
cacgcgtcgg tggctcgctc cttgcaactg ctgagcattg tatggctagg ctgtagtttg 144540
ttttcacttc accagttggg aaacagagaa aaggcacttt ttaaaaagtt taaatctgta 144600
gaattttggt ttttaccagt tctcttctaa atcctgaggg attacaggaa aagttgttgt 144660
atttcagaat attcttagct tgatgtgacc tctgtccccg ttaaggccct ttgccgcaat 144720
gggaaggacg tcgctcggtc agaccctgaa ggtcagaggg gcagtttggg agtgtgtcaa 144780
cattttaact gtatggacta gagccaagag tctcaaggtt tataattccc acgtattcaa 144840
aaagaaaaaa acaataaagt gagaagtcag tgtagagtga ataacctgt gttagtgggg 144900 aagaagtgtt tttaaacagg atttccataa cgtataacat caacatgttt agagtggtga 144960
tgtttcattg ggaaacgaac agtaaaacat gaaagcaggg aggttttcat tctggcagtt 145020
ggcaactttc acggcagatg gagaatttca aaagcaattg ctcaattatc aaacatagcc 145080
agtgtgagtt ctgaaataaa ggtgctgatt gaatgtgcag ctttatggtg gattttgcta 145140
ttcaggcaag catttttaatt ttctgcctgt taaattctgt tttcttttagt ttttcatatg 145200 tggtttattg tagcttagga atagataact gagagtatat attacacata caacattctg 145260
atatggcaat atttaaaaca acttgtctgt tttagaacta gaattaaaca taatcatctt 145320
cagtattttg caaataagct cactgccatc cagaaacatt gtcaatgcat ctgttgctcc 145380
ttctagaaga cacagtctgt ccagcacaaa gttacttagt ccccagatgt ctggagaaga 145440
ggaggattct gacttggcag ccaaacttgg aatgtgcaat agagaaatag tacgaagagg 145500
ggctctcatt ctcttctgtg attatgtcgt aagtttgaaa tgcctgtaaa cggggttgag 145560
ggaggtgggg accaggagaa catcctgtgt agatgacact tgcatggacc ctctggaacc 145620
cagaccgccc ggtgtcctgc caagctccat cgaaactaaa tctagaatga atgtttactt 145680
ctgctgtgac atataattgg agaccaggcc tggccttcca gtcactggat tctaagttgg 145740
actgtgagag ttttttgcagc tgactcattt atcaaatgcc cggctattgg ctcacgccta 145800
catgatgctg ggtatgtttg ttaatttgag ggaagcaatg gaataataat aactaatgat 145860
ttaaaaaaca aagtaagtgc attgactgta gtggggttct gattttaaat ttttttaaaa 145920
attaatacca ggagcagtgg cttatgccta aattccagca actcgagagg ctgaggtagg 145980
aagatcactt gagcccagga gtttgagaca agcctgggct atggtgtgag acacccatct 146040
ctaaaaaaat aaaaaataaa aaattatcca agtgtggtgg ctcgtgcctg taatcacagc 146100
tctttgagaa gctgagggcg gaggatggct tgagcctggg agttcgagac cagcctggca 146160
acacagagaa accctgcctc taccaaaaaa agaaagagag gaagaaagaa aaattagcct 146220
ggcgtggtgg tgcatgcctg tggtcccagc cacctgagag actgagaagg gaggattgct 146280
tgagcccaga agtttgaggc tgcagtgagc tgtgactgtg tcactgcact ccggcctggg 146340
tgacaaggcg agacccctgc tctaaaataa ttttttttaag ttaatttgta gaaaaggtgt 146400
tagatgttct ttgtcacatt ttatgatgga ttcctgttta aatgccgttc tctttaaaga 146460
aaaaaaaata acttgtggga gtttttaacc ataaaactag catcacatat ttaccatgga 146520
gaatttacaa aaaaacaaat aaacggagga aaataaaacc tcctgtaatc atactactca 146580
gagataactt gctgttagat tttggtctag atttaatact ttttctatat ttatattaaa 146640
aatatttaaa acatatgcat ttcttttgtca caaacatggt atcttataga tactactgtc 146700
acatagcaaa acagtgttaa atattctgaa tcagaaaagg aagccgactc tccaactgaa 146760
agaggtgtta tcctagagac ttttttctggt gatgacaatt tattaatagt cacttttttgc 146820
```

```
tttactttct ctattgaagt agttttctta ttttgttcta cttttaagga taatataatt   146880
tataatgctg tttttcacag aaatataaga aaaagataca taattttata agttaataaa   146940
gtttgatcat cccaaatcca aaaatctgaa atccaaaatg ctccaaattc tgaagctttt   147000
tgagtgctga cattatgttc aaaggaaatg ttcattggaa ggtttcagat tttcggattt   147060
agggagctca acaaataagt ataatgcaca tatttcaaaa cctgaaaaaa atcctaaatt   147120
cagaatactt ctgatcccaa acatttcaga taagggttat tcaacctgta ctgtcagatg   147180
atcccaaatg aaaaatatta atcgttaacc aaatatcaag gaattgatca cattttacag   147240
tttctgccta ggattatgaa tcaagatgaa aaggctctgc atgtttaaaa atatatattt   147300
ttatttcttt ataaatctta aatatctaca cttaagattt atttgatatg tgggatccat   147360
tcatattttg gattcaacag ttctgtcaaa actgtggcag tgataggga ttcttttttt    147420
cccactgaac tatcacaaaa ttggaaaaag agtaattgga gaaccccact ggcttagccg   147480
gcccgaagcc cggagagggg caggcagtgc tgtggatggg gtcatcccag cgcaacgctg   147540
cccctgctac ctgcggatct cgctgaggcc tgcctttgtc ctttgaccct tggccatttg   147600
ttagtgtctc tgagagctgg actgctgtac cctacttccc cagggggcct aacttcacac   147660
agcctctgcc gcagtgcgtg gttggaggtg acggccttgg taaatcgagt ttcctacctc   147720
ctcaattatt tgtgctcata cactgtatat ttttagtgag gtttatattt gggatgtgtt   147780
ttctccttct tacccttcct ggcctttcta tggcattaat acctggtctc ttcttgtgta   147840
cttgaaaatg aatctctcat catattttc cttagtgtca gaacctccat gactccgagc    147900
acttaacgtg gctcattgta aatcacattc aagatctgat cagcctttcc cacgagcctc   147960
cagtacagga cttcatcagt gccgttcatc ggaactctgc tgccagcggc ctgttcatcc   148020
aggcaattca gtctcgttgt gaaaaccttt caactgtacg tcttcatcct gccgactatt   148080
gccagttgca gttttccctg ccttaaaaat ggagtattga aattttttaac tttaatttct   148140
gatttgcaaa atagtcatct tttgttcttt tccttcttgc tgttagccaa ccatgctgaa   148200
gaaaactctt cagtgcttgg aggggatcca tctcagccag tcgggagctg tgctcacgct   148260
gtatgtggac aggcttctgt gcacccctt ccgtgtgctg gctcgcatgg tcgacatcct    148320
tgcttgtcgc cgggtagaaa tgcttctggc tgcaaattta caggtattgg aagagaaac    148380
cctgatattg atttatattg aaaatttagc aggccaagca aaacaggtgg ctggcttttt   148440
cctccgtaag tatggtcttg acatggtcac cgatagaaac atggaaacat ctgcaaactt   148500
gccgttactc gtgtgtccga tctgactgtt tcttgtattt ttttctagtc tgcccttact   148560
aggatgaact gtacacatca gttcatcctt tttaaatgag catgaggtta ttttgggttg   148620
ttaggtgtta caaacacact aatgtgtttt tgtctattag agcagcatgg cccagttgcc   148680
aatggaagaa ctcaacagaa tccaggaata ccttcagagc agcgggctcg ctcagaggta   148740
atgctgaaaa cacaggtcgt ccttgtgtta ggacaaccca ggatataaag gatatagatt   148800
tgtacgggaa taaattcaca ggacaagaaa tcgatgtgcc ttataggtgg gtttactgca   148860
gaagtgccat aatagaacct tcctactttt aaaacaacca gatctcactt tctaaagagt   148920
aaaggatgac cggcaggatc acgtctgtga cgtgagtgga ggcagtttgc actcctggtg   148980
gctgtttgag aggtagcatt tagaatgcct gtattcactg tcctgtgatg agtgggaaaa   149040
taggttatca ggtttatctt agcaaaatca aagcatgtca tctaattgct aaacaagagt   149100
tggcaaatct gagagacatt actcaatcct tggcatgcag gacttacatc tgcatcctgt   149160
tgccatttta tgtcttcaaa gcatttaatc atttagttgt gtttgcaaag tctttgagaa   149220
```

```
gcctttgtca gaaatcccta catctcctat gtgagtgtat ttccatgact gcagaataag    149280
ttaaactttt acctttttcc ttcccttgcg gggcggggtg gggggcaggg attgtgtgtg    149340
tgagagggag agagagacag cagagaagga gaatataatt atcatgctgt gtactttgag    149400
ctgaaactgc aaaaaggaa aaacacacaa aaattattat gcttttcagt ctttagagta    149460
ccttgtctat tatgcttttc agtctttaga gtaccttgtt gatggtgttt taaatggga    149520 ttgggcacaa ttaggtggac agtttgggat gattttcag tctgtagggc caagctcttt     149580
tgtaatttgc attatgaagt tgtcactctc atagcagatg gcgggagata aactattatt    149640 acttttgac cctagactta gtcttcagtc cagatgaggg agattaaaag attataaata     149700
tcttgtgcca gatgaggtga ttttattttg aaatgaccat gaattcctat cagttgtctt    149760
actgggatat tgatagtgg aatttgtgca tttgagtctt agatgatctg ttttacattt     149820
attaagaaag cctttattag cttttatact gtgtattgcc tgttgcagtg tttgagtata    149880
aatgaaattt ctgaaaaata ttaatggagt acaaactgtg atacttaaaa gtaaactagg    149940
gcctgcattt gtatcatgac ctgtttgagt attgatgaga agatagctgt gaagaaaaag    150000
gtttaaacaa gtgtattttc ctttaagaag ccactaatag tgcatctcct tagagtgtat    150060
atttctagaa tcctagtgtg cagagtttag actaagacta aaaaaaaaa aaaacaaatt     150120 atactgtaat ttcattttta tttgtatttt agacaccaaa ggctctattc cctgctggac    150180
aggtttcgtc tctccaccat gcaagactca cttagtccct ctcctccagt ctcttcccac    150240
ccgctggacg gggatgggca cgtgtcactg gaaacagtga gtccggacaa agtaagtgtc    150300
cagcgtgtct gcatgggagg cacagggcgc tgagtgcctc tgtcacctgt ggcagataca    150360
gagagtgcag aggaggtgcc gtggacccaa ggagttctgg cgctcggctc ggctcagtga    150420
agctgtggtt agagacgtgg ggggccatca aggtctgagg gagccaagca gtgctgatgt    150480
gggacccttt tggtaggagt gtggggtgag tagttagtgg gtgaatcaag gaatagtcgg    150540
ccgtggcctg caggcccctg actgcacagg ccttcaagca catgtcaatg ccgttagcct    150600
ccctccatct cctcatacct tctggccacc tgtgagttgc actgccactg ccagccattc    150660
tggtatgttg tcagcacctc cactgctcat acctcatggt tagggaccac ctggagcctt    150720
ggtagagcct tggtagagcc ttggtactct actttcctgg acaaagttca gcttatgaat    150780
atgaatttag atttcaaaaa ccagcagccc aagtataaga aagcgaaggt tcagtcctgc    150840
cttcttaggc tctattcgct aagcacctgc cctgccctgg ttgctgggga gagatgagta    150900
aagcagacaa cccaggagag gatggcaaag gggccgctaa cccttagtgg tttagctata    150960
tttggaaggc ctattggaag ttcaccaggt gaaggggag gctgtgaggg tgcccaggca     151020
ggtaacagaa gtccaaaggg gaaaacctgt ggtgtggtga ccgtatagc cacagcctgc     151080 cggccggcag ccctctcagc ctagtgcggt gttcccaagc actggcctag gcctgtagct    151140
ccagggatgt gaagtcccct tgaacgccgc ccatcatgtt cccttatcc attttttct      151200 tcccaggact ggtacgttca tcttgtcaaa tcccagtgtt ggaccaggtc agattctgca    151260
ctgctggaag gtgcagagct ggtgaatcgg attcctgctg aagatatgaa tgccttcatg    151320
atgaactcgg tacgggggga gcagtggagg caaggaatcc tcagcttttc ttgtgacttc    151380
caagtgggat ttgtctcatc atcatgtgac ccacttgttg acaacacatg ttggggactc    151440
cagtctgggc agggacggga tgtcggagag actccactct gaatgggcc gggaagtggg     151500 gaggactcca tttcagatgg ggtcgggaca tggggggttat gctgatcgag acagaaaagc    151560
```

```
acattgtttc agccacatta gaatccacgg aggtgttgtt ttgaaatcca gctggcccca   151620
aggctgggtg tatggtttgg gatgagaact atctggcctc cactggagga acaaacacag   151680
gatgttatca tctaagctcc atggccaaga cagaatggaa gtcaaggttg cgtatttgcc   151740
gtagacttca acacagtgtc gtaatgcgtg acgtcaataa cttgttttcta gtgtcttgga   151800
agttgatctt tagtcgtaaa agagacccctt ggatgcagcg agatttcctc tactcacacc   151860
tctgttagat gtagtgaggt tcttcacccc ccaaccccag atgtcagagg gcaccctgcg   151920
cagagctagg aggccatgca aagccttggt gtccctgtcc ctcacccgtg ggcaggtcct   151980
gtgagcagtg gggggggccac ctcttgggta tggtgcagcc atggcccaag cagggcttct   152040
tctcagacct actaggacgg gagaaacctc ctggtgcttt agccctgcgt tgatatgcag   152100
caaatgggag ggaagtgggc acctgggagg acaaatgcct gtagaggccg ggagtgacgg   152160
caggtgttca tgaaaagaga ccttgtgggg agggcaacac aacagtgtgt tctgatgtac   152220
tgaagagctc aactgaaaac aacaggagaa ttagcccaaa atccatttac taaaattgtt   152280
tatcttttt ttttttttg agacaaagtc tcgctgttgt cccccaggct ggagtgcaat   152340
ggcgctatct tggctcactg caacctccgc ctcctgggtt catacgattc tcctgcctca   152400
gcctcccaaa tagctggtat taacaggcat gcaccaccac gcccggctaa ttttttgtatt   152460
tttagtagag acgggatttc accatgttgg ccaggctggt ctcaaactcc tgacctcagg   152520
tgatccgccc acctcggcct cccaaagtgc tgggattata ggcctgagcc accacgcccg   152580
gcctaaaatt gtttatctta agattcatgc agtgaaagct aacttactga gtgataaatt   152640
tgcttagtga tctgtttatt aggttttcca aatttgctaa ttgggctttg aacagctgta   152700
aaagttctga ctgtaaaaga aagcttcaac ttttggcatt catgatgctt ttctgagtat   152760
taaactaaga tagatgtttt acctgaagga tcggccacca atctttaaat ggctaaacaa   152820
aagggttgct aaaacataat ccaaattgac ataagaaata ccattttcc aaccaaaatt   152880
ttggcattca tatggctact tttacgtatt tcagctgcat ttgaacatct ttttcaaact   152940
ttagggtggt tggtgtatca ctgaggtctt ggatgacact ttagctttga ttttgttttt   153000
atgaattaaa attgtcatac caaaattttt atttcaagca aatccaagag cataaaaaat   153060
taaaatatta cttaaaatac taagagagaa cagatatata ttttactaag catatgttga   153120
atgaaattgt tcaaatattt ataacaggca tagagtagaa ttttcttaaa aatatttttg   153180
atggtatacc aatttgtatt ttctcagaaa catttgcctt attcttttt ctgttgtgtt   153240
tttcttacct gattgaaagc tcataatctg ttgttattgt ttgttaacct ttaatgctct   153300
gatttcagga gttcaaccta agcctgctag ctccatgctt aagcctaggg atgagtgaaa   153360
tttctggtgg ccagaagagt gccctttttg aagcagcccg tgaggtgact ctggcccgtg   153420
tgagcggcac cgtgcagcag ctccctgctg tccatcatgt cttccagccc gagctgcctg   153480
cagagccggc ggcctactgg agcaagttga atgatctgtt tggtaattaa aattaaaatt   153540
tatcttattt ttaaaaagca ttccagggcc agtatagtac tttgcaccaa gtaaatgtac   153600
aataaaggca gtggatctaa tacattgaaa gcgtttacag aggtagctaa agagcagcac   153660
gggtgtcctc ggctcagaat ttcttcctgt gtgtttgcca cttttgccatt cattgacatg   153720
gtcatggaca tagggctcta agcccttgag gaaggctggg ccagacctca ggggagatgc   153780
agccccaaac cacgtgcagt cctgtggacg gatgtgtaga gtgccactg aggaacaatg   153840
tcttgagctt tcatcagatt ctcagagaat tgcttgactg cctttcgaag ttgatgcatc   153900
tgtgctcacg tttgcaccca cccacgaggt ccttctgttt caggggatgc tgcactgtat   153960
```

```
cagtccctgc ccactctggc ccgggccctg gcacagtacc tggtggtggt ctccaaactg   154020
cccagtcatt tgcaccttcc tcctgagaaa gagaaggaca ttgtgaaatt cgtggtggca   154080
acccttgagg taagaggcag ctcgggagct cagtgttgct gtggggaggg ggcatggggc   154140
tgacactgaa gagggtaaag cagttttatt tgaaaagcaa gatctctgac cagtccagtc   154200
acttttccat ctcagcctgg cagtaagtct tgtcaccgtc aagttattgt agccatcctt   154260
caccctcacc tcgccactcc tcatggtggc ctgtgaggtc agccaggtcc ccttctcatc   154320
tgcacctacc atgttaggtg gatcctaatt ttagagacat gaaaaataat catctggaag   154380
tactttatgt cttaagttgg cctggacatg tcagccaagg aatacttact tggttttgtgt   154440 tagtgcttgt aattcgcccc cagaatgtgt acacgttctg gatgcattaa agtctggcct   154500
gtatccttaa agggccatcg ctgtgctgcc tgccctcagc aaggacacac tttgcagacc   154560
cacagaggct ccgcctccac ctcacaccaa agaaagggag gagtccaaag ggcatcagtg   154620
ccattactca caaaatgata aatacaccct tattctgaac cacgtggagt catatggttt   154680
gtgatccctg tccttcaggt ttcagcttag tggggaagtg ggaaagtcag cgtgtgatca   154740
cagcacaggg tgattgctgc tgattatatt atgtgcctgc tgtatgcagg atgaaatact   154800
ttatatgcgt catcttattt gactctcaca accccctgtg agataggctc tgttactccc   154860
atttgacagt gaggaaagc aaggcttaga gaatttcagt gacttgccca ggtcctctga   154920
gctaggaagt agccattctg gcatttgaac ccaaggcctg ctatccctag aacccacgct   154980
ctcaaattca acctatgaca gaggcaagcc ctggtgctgt gggagcccca aggaagagcc   155040
tctggcctgg tggccacgta gcccaggaga gatttctaca ggagcccaca gcgctgaagg   155100
agagagaggc agcagagtaa gggggctttg tggcagagag gggactggca ctttggggaa   155160
taggtgggtc aggactgaat gtaatggagc catgtcagag ctgtccttct ggaagggcaa   155220
gggcacctgg acgcgctgcc cctcagtgct ttggacggtt ccacaactgt gattcacacg   155280
gcttccccaa acgaaggtac acgagtgggc attctgtgac tcggtacttc cctttaggcc   155340
ctgtcctggc atttgatcca tgagcagatc ccgctgagtc tggatctcca ggcagggctg   155400
gactgctgct gcctggccct gcagctgcct ggcctctgga gcgtggtctc ctccacagag   155460
tttgtgaccc acgcctgctc cctcatctac tgtgtgcact tcatcctgga ggccggtgag   155520
tccccgtcca tgaacggtgg gttcctatca tagttcctgt ctgcttcacc atgtttttat   155580
tttgtgctgc ctgtttgcca ggtactaagc taggaattgg ggatggagag gtagataaaa   155640
tatgcatcag gaagggctgg gccccatctc ttactctcca atatattgga gtctacactg   155700
gaatttaact ggaatttgct ttttagtca ttttatttag attttgaagt ttcagctttc   155760
atcaaaaata cctctaaact ttatgtctct gtgatctttg gtcttagctg ttttatgtat   155820
ttagtcttat atgatcataa gattaataac attacattca gaagattatt tgttttctgt   155880
cagagttaaa atgtttgttt ttatactgca ttgtaatatt aacgtactgt aaaataaaag   155940
tggcttgttc tttttcaagga acagtatcct caacaagggt cattagccac aatttttaaa   156000
aaattggacg tcatagtttta catgttagag ggcgttttga agctttgtat ttttaaatta   156060 aatgtttatag agtgatgttt tcatgtttca taattgtttt catctgtgca tttgtagcca   156120
acttgaaaac aaagatccag ggattactac ttaaaagcca gacttcttgg aggttatagt   156180
gatgattttg atagtatctt gagccgtctc ataataacct cagggtgaga gatggccaac   156240
aggagacagt cgagggactt agaaatctga atgaaatctg aagttcaaat cttcagacat   156300
```

```
ataccactaa ccaagagatt ggtacctcag tctagtattg tctgtttgtc taaaattggt  156360
tctaaggaat ctaggctagt ctgtctatcc ctttcaactt ttgtgaggct gcacaaatgt  156420
aaaatgttga ataaaaagca ctgatggaag tgtgtagaaa ttcttctctt tgttctgttg  156480
taattttagt tgcagtgcag cctggagagc agcttcttag tccagaaaga aggacaaata  156540
ccccaaaagc catcagcgag gaggaggagg aagtagatcc aaacacacag agtaagtctc  156600
aggacccatt tttttcttac atgttgttcc tccaggactt aaaaatcatt cacagagacg  156660
tgcaccgcgg tgagtgtgga ctcctggaag cgcaccgtag ctccgctgtg tcctgctgct  156720
cctccctagc tgtcagggag gctgtagtcc attgctttgc cagctctttt gtttccgagt  156780
gaacacctta tccgtacaca tgcggctgtc tctgacccta cagaccagct gggatgccac  156840
tgggggagcg ctcccttccc cccgcacttc ccacactctg cagttattct gagatccttg  156900
agggcaggga acaggtttgt cttctttgtg ttctcagaaa ttaatgctcg gcctctggtc  156960
agcaagcaac aacctttgt tgagtgataa tgaataaata aatgtttccc acatgagtat  157020
tcagtaacct cagtgtcagg ttcagccatc tgttttggtg atatttaaa agaaaattcc  157080 gcttttccta cagaaaaaaa aaaaaatcca aatcccagtg atttaagcca gttatagact  157140
tagacatata ctacggcttt tcatgcactt tcctcccaat tctagagtag gtattttact  157200
aggaaaatgg tggcagtgcc tgttgggagg aagattcttt ggccaagtgt cttttgttct  157260
tgccagggcc cctaggctgc tggggtgctt cagcttcttt agcccagtgt ctggtgggga  157320
atggcccctg ttgcctgtcc cacagaggtg ggggtgcctc acctggagcc tgtccacaca  157380
ttttacacag cacgcttacc tggagcatca ggcatctttt ccatgctctg tggctcagga  157440
aacacgcctt ttcaatcatg agtgcaccag tgcttttggg cttttctcc ccgcttttgt  157500 gcaatcctgg ttgtggatgg agttttcctg tctttagtct tctgcatagt acttttctct  157560
tctggttccc ggttcaaggt tttgtaatta gagaatgacc cagaagcaat ggcattttaa  157620
tgcacagcca aggacttctc tgaatttgta tctcaaacct ctgtgggtcc ttcaggcttc  157680
agtttgtgat ttcatgattt cttgttgcta cctaaggaat atgaaaacac ccacctccct  157740
actctgcatc ttccagccga gtggcacctc aggctgtgga tcctgtgctt ctgtggtgag  157800
gataagaata gtgccaaccg tgtggattga aatcaatcag ttaatccctc catgtaaagc  157860
acctggaacg gatgacagtc ttgttatgaa tactcaacaa atgctatcat gatttttagt  157920
tagatttcca ttgctttaaa acagttgaga catcttggcg gtttgagtta gagcaacggg  157980
ccctgaagtg ggttctgttt gggtgaagat gattatgctt attccccatg gccctcttta  158040
ggcaagagtg ggaagctttc tttgtttttt taatcacctc gataggacgt tacttcttaa  158100
aggtcatcca ataaatatta ataggccggg cgcggtggct cacgcctgta atcccagcac  158160
tttgggaggc cgaggcgggc ggatcacgag gtcaggagat cgagaccatc ccagctaaaa  158220
cggtgaaacc ccgtctctac taaaaataca aaaaattagc cgggcgtagt ggcgggcgcc  158280
tgtagtccca gctacttggg aggctgaggc aggagaatgg cgtgaacccg ggaggcggag  158340
cttgcagtga gccgagatcc cgccactgca ctccagcctg ggcgacagag caagactccg  158400
tctcaaaaaa aaaaaaaaat attaataaag ccaactcgtt agcgtgggc ttaattgctt  158460 aagtccaatg agaagtcctt ctctatccta ggaagttgcc caaactgtag aatctcgtgg  158520
cctgtgggta atagccacgt aatacacact cactgcctca acaaatcata ttttagtagg  158580
tatgatattc tagactcaag acaccattct gtggatcttc ccaagggtgt gaagtgtcca  158640
cagcgtctgc cttgggagtt tccatgccca ccagaaccat gccccaagcc cctcaagcac  158700
```

```
tctgacctag gaaagccagt gaagcaagga tgacaacatg gcccttgat actagctgag    158760 ggacagacac aggtcctggg agaccagaga aagacgaggg gcagaggagg tgtcctaaag    158820
gaagtctgag gctgaggagc cacaggatgg cttccagctg tcacaggctg ctgctggcct    158880
tatcacagag agtgggccag agggctggga accaaggcca gagctcaggt tcaggaccat    158940
tccagcaatc ccagcagaaa atggggagaa ttgtatggta taggcggata tgaaggtaga    159000
atctgcaggc cttcagtggc caactcagag tctaagtgga ttccacagtt acagcttgag    159060
cagctggttg taggtcatgc tttctacact gggcatatag gatgtgtttt ttaaaaagtc    159120
ctctcttaac cgttgcttgt ttagatccta agtatatcac tgcagcctgt gagatggtgg    159180
cagaaatggt ggagtctctg cagtcggtgt tggccttggg tcataaaagg aatagcggcg    159240
tgccggcgtt tctcacgcca ttgctaagga acatcatcat cagcctggcc cgcctgcccc    159300
ttgtcaacag ctacacacgt gtgccccac tggtgagtct gctcgttcct tgcagaagac    159360
caagtacggt gaaaggcacc ggtaggccct gggctgggca cacgtgagag ggcgggacag    159420
aatccccgca gcccagaggc tgcctgctgt ggttctggtg cccactgtgg ttctggtgcc    159480
aggctgcttt cctcaggcac cacgtgtgga ggtcgctagt agaaatactg gttttctaa    159540 aatgaactga ggccctacat ccctaagaga ttagtgttag acctgattct agagcaacta    159600
gaccactttg cttaatagca gaccagaaac cacaccccct cgagtgagtg agattttcct    159660
ttggagataa ttcatgtttt tctacacagt tttgcagttg tcttcagaat tggtttaaag    159720
taggtgttat tgccaggcgc agtagctcat gcctgtaatc ccagcacttt gggaagccaa    159780
ggtgggcgga tcacttgagg tcaggatttc gagaccagcc tggccaacat ggtgaaaccc    159840
catctctact aaaaatataa aaattagcca ggtgtggtgg tgtacgcctg taatcccagc    159900
tactcaggag actgagacag gagaatcgct tgaacccagg aggcgaaggt tgcagtaagc    159960
cgagatcgcg ccactgcact ctagcctggg caacagagca agactccgtc tcaaaaaaaa    160020
aaaaggtagg tgttattgat cagaacccctt gtttcagata acatgaggag cttagcttga    160080
ggagagtgag ggttgatgga gggggactga cttctgccca gtgaaatggc atcatctccc    160140
accagcccgc tgaaataaga tgatgggcc tgttccttag ggcctgcagc atcctcaggc    160200
aggaaagaaa ggccgacctg gcagggtgtg agccagcagg tgtaggtcag ggagaatgga    160260
gccaggtccc agggaagagg cttgtggctg cctgagaagg gtgcgtgcct gcctgtgtgt    160320
gtgtgtgcac gtgtgtgtat gtatgctgga gagtctaggg aggcttgctc caaggacgca    160380
gtattgtttg atcctgagag ataaggattc tgccgcaggg aatgaaggta ttccagatgg    160440
cgggcttatt ccgaagaaga ggccagtgcc tggcggtgct ggaagcagtt gcagaacagg    160500
gagttgtagg ctttcctggg aagagagcag caggggtgct ggagaagcag gccacacttg    160560
ctgcatgggg ttgctctcgg ccccactctt ggtgcacagc gagtcactgt gggttcatta    160620
gcatctggtt atgagacagt aactgctcct ttggagggc tcgtggagac catgcaggag    160680
ggcacggtct tgaggtcatg ccgtccagag cacacctgag gataggccag gacgggctgc    160740
acgctgtagg taaaattcct ccagcaagct cttcactggc attgaggagt tccctgagtg    160800
cggtcatctg gaaggcagct gtaacaggca ctgcagtctc tccctgggtg ggtaccagag    160860
aggagcatag gggagcataa ccgatttaaa gagagggctt tcctgtggtg aggtaagaga    160920
ttagctggtc attatcatag agccccctct gcctttgtgc agatgggctg tgggaatcct    160980
ggggttccgt tgggtccttt gtcacctcac tgaaggcatg taagctgagc tggccagacc    161040
```

```
gtgagctgat cctgccactt gaacagcatc aagcctgcct ctggattctt ctgtgcatgg 161100
cacttgtctg agcacctcac gcacagagaa ctggacttca gagtttacag aaataagctg 161160
tatggttcat tttcatgcct gcttgccaat aaacatatct gagctgaacc tcattgaacg 161220
cctgccttta ttctagcaca gcacctgctg tttgtgggcg aggggtgctg tctctaactc 161280
ctgcctgctt ctcccagcac tccctgagtg gggtgtgcca gcagcctcag gatgaggaca 161340
ggaagtggga gggcagagca gatttgggag ggccacttga tggggaagga agtcccagga 161400
agcagttgga gctgttttct gggggagaag gtgccagctc tgggacagtg ttggggtagt 161460
gaggagggag cccagtggag agaagtcggg cttcctgctt cctcacagta tgtctgtcct 161520
gactcaactc ggatgatgtc acttcctttt catcttctca ggtgtggaag cttggatggt 161580
cacccaaacc gggagggat tttggcacag cattccctga atccccgtg gagttcctcc 161640 aggaaaagga agtctttaag gagttcatct accgcatcaa cacactaggt actcttgggg 161700
cctctccttc aggtcaccat tgtcggacat ctaccgggag gaaatccaga gcccccagta 161760
ctgggatctt ctcatttgac tccagaaaag atttaagcat gataataata caaacctatg 161820
tgaatacatt ttgcagtgtt ggcaaaactc cttttatact gagaaaatag atcccagttc 161880
ctgtgttttg tggcttgaat cccagctttg tgtattccgg gcttgtttga agtcaggaaa 161940
ggttcatgtg tagtggacaa cgtgagacca aattctgcct tagattttgc atttaggcta 162000
aacagtggca gcacttgtct cagaatgttt tcttgtgttc accagtctga tcctgttgtg 162060
tctcagtggt ccattttctc atatgggaac aagcagacgg gagcagatgg agtcaggttt 162120
cttggcactc gccttcccca gagcctagag gcagcatggg gagaaagcag gcttgggggct 162180 cagacagtcc tggtctgctt ccagccctcc tacctgagca gcgcagggca agtccgtcta 162240
acctctagag acccctcagtt ttgtcatatg taaaatgggg gtcgtgtcta tttcatagaa 162300
ttgttgcaga tttagaaatt acatttctaa acaaatgtta cccttatttt ctaaataagt 162360
gtctaaatga ataagtcacc acttttgccc ctatttgatg gcaagaggtg tgatcttgtg 162420
gtgggactgt aatcagtcag ttctcagtga ctgtgccctg ctgtggtgtt tcctggaatg 162480
ttcctgtctt gtcctagaaa gtctggcagg ggcaccctga ctccactgtc cagtcctctc 162540
cccagtccct cgggcttctg cagatttgag gcttgtttgg atcccagaag gttgtggcag 162600
gagacacctt gcctctactt tccccttttat aattcaatgt ccaaagagag ccctgagcag 162660
gtacctcacg ccagctgcct cacggagctc ctcctcttcc tggctgtgag gatcggtatc 162720
agtggcctcc tgctctctcc cccttgccta acacgagcac cttttgcttac ttgggtgccc 162780 ttgctcttga actgccatc ggacgtgcgt gacccaagac tgtgccgcag tccttgcctt 162840
gtctgtgctc atttttctttg ttcattttttt tccctgtaac gtaaattgtt atatttgtct 162900
gtatctgtgt ctgaatcagt cctgcacgct ctccttctct ctgtctcttg ttctttcttt 162960 accccgtttta tcacggggac cccgatgtcc attgctctag ttctcctgtc ctaagcaccc 163020
catcccgtct ctctggcctt accacaagtg gcgtggctgc ctcagacatc atgatgggga 163080
catgaagcac agctgtcaga aacaactgtt cgttagatac actcgaatgc agctcatcaa 163140
tagggatgga gggtctgtcg gatgtatttt cactgaatcc ccgttcctac cttgatacac 163200 tcttttaat ctattcttct agacaggtca gaggaaccat tactttgact tttaaatttt 163260
tagcagcttt attgaggtag aattcacata ctacagattt cacccactct aagcggacag 163320
cttggtggcc attagttta tccacagagt tgtgcagcca gctgcacagt ctcagggctg 163380
gactccaggg aagattttag cccatttagt gagtggggca gaagtggccc tggccctgca 163440
```

```
cgaggttgcc tgcatgggcg tccctgccct gtccctgtgt ctgctccact gggggttgac 163500
caggctgcca gggccgactt gggcctgtgc cacctgcctc tcatgtgtct cggacagtgc 163560
agccgatgtc tatacttcgg tttcctcaat gatgaaatgg aggggatagt gttccccgca 163620
tcatagaact gtgtgaggtt taagggactc actgccttg gcgtggagcc ttctccaggg 163680
gccgtgctgt gtcggcgtag ctgtcagctc tccgttacag gcttgagaag ggttgacact 163740
ctctcatgta acatttatat ttctaggctg accagtcgt actcagtttg aagaaacttg 163800
ggccaccctc cttggtgtcc tggtgacgca gcccctcgtg atggagcagg aggagagccc 163860
accagaagta aggccacacc ctgtgctggt tggcacatgg gcagttatgg ccgcttgcag 163920
gcctttggtg gggaataaaa taaggcagca agctggtgtt cttttttct cttaccttat 163980 ttttgaaaga gtagctgaat ggtgtcttga ctgatattcc agagcaggga caaagcctgc 164040
tgaggtctgg gggctgcgat taccaatggc tggaatgcat tttattacgg tgcattccat 164100
gttaaggatc aatacgattg tgccctttct ggaaaatatc ttttagttta tcaatattca 164160
gaggagtgta ggttgaatta aaatgaaaag gcactttata aaggccatga gtagtacctg 164220
gtttcatttt tctaatgtct tgcagagatt ttatcaggct tcttgaagtg ttcacgtaca 164280
ttacgctaac acgatattaa taataactgt gctctggtac agcggagcca gcagaatggg 164340
aagttgtgga atgcaggccc ttgattctga tagaaggtgt ggtttgaact cacagaaatg 164400
acagtttgga gggtagacat atgtcacaag tcatcaagat tgtctttaaa ttcatgcata 164460
gaagctaaca gggtgtcata agcaaggcct gtaaaatgta tgagggaatt caaagataat 164520
ttattaaaaa gtaattcatg tttggagttt tgtgcccaaa ggagtccttg atttgaaaaa 164580
tgggcttttg cccatcagat tgtttcaggg cccgtgtgtg cggaggccct gccttgtgcc 164640
ccgtgagctc agcctgacag aaatccttg gtagcactta aggctcctct tcctcccatt 164700
gaggcaggga agactctggg ttctgcaggc agaggtggtt gtgggtgtct tgctgctctt 164760
gttgacatgt gggctctcct tccaggaaga cacagagagg acccagatca acgtcctggc 164820
cgtgcaggcc atcacctcac tggtgctcag tgcaatgact gtgcctgtgg ccggcaaccc 164880
agctgtaagc tgcttggagc agcagccccg gaacaagcct ctgaaagctc tcgacaccag 164940
gtttgcttga gttcccacgt gtctctggga catagcaggt gctggggaca gtgggttccc 165000
cgctgaagcg tccagcagct tcaaccaggc cgttttcctt cattgctaga attgaaaaca 165060
ccgtccgtgt ggcctgtgca ggagatgcag acccaaaggt ggcctcctgg tcagtgagaa 165120
gctgaaaacg tgacaggaac tgacgtgggg ttattgagca tttaggggaa gacgttagca 165180
gagcaggaat gagcaggcaa ctagtagaac acccacttaa gggctcacgg acaggtgctc 165240
acttaggaag tgagtttcat ttggtattac accaggttcc tttaggcaaa gcggagggaa 165300
agttctggtg ttttttcactt gtaagatttt gaaggaaaca aaacactctt taccttttt 165360 ctaaaatgta ggtttgggag gaagctgagc attatcagag ggattgtgga gcaagagatt 165420
caagcaatgg tttcaaagag agagaatatt gccacccatc atttatatca ggcatgggat 165480
cctgtccctt ctctgtctcc ggctactaca ggtacctgag ggaaagggtg cgggggagcg 165540
gttgtacttg ggctagaatg agagaagact ggcatgctca ccacaccagt gatgcggaa 165600 gacctgagtg tggtctgagt tggaggctgt ggtgctaaat acgctgcccc tttcataagc 165660
aggagtctta gtcaggccca gggaggaagt aaaatctgga aatgaatgag aagcattctc 165720
tcctgccagt caagaaatga gaagcgaaag aattctcacg ggctgtaaga ccagcaggat 165780
```

```
ttaaaagttg aattagttgc ttatgttaag aactcaacca agttcatcta cacaagctga   165840
atctccagct tttcctaaga aaccatgtgt ggcagtggct gcagggcagg gcacagctgg   165900
gcctgagcac cccgctccct gcacctctcc cctccctggg ccctgcctgt cactgcccac   165960
tctcccacca agccttccgg ttgtgtgcct gccctatcac aggcatcgga gcttgtcacc   166020
tggtttaaaa gaagagagtt gtgtggggat ttgggatgca cgttttttcac tcaaaagtat  166080 tttagcgtag agctctgtga ttccgtagct atttaggagt ttaagcacct tgaaggcttt   166140
aattgcagaa agttctatgt ggacgtgcaa tgtgttatac gcagtgtcta tgagactcaa   166200
atgtttatta gggcgttgaa gtaaactgag cacttggagg gccatggatc cagccttcaa   166260
ggagctcata agtcaggagg acccaggagc aatgacctgt catagaaggc agaaaagagg   166320
ggcacagagg tgggtgggag gcatacacag gcagctcctg gagctccaag gggagcaagt   166380
gcttccaggg aagggggcgt ggaggcccct ttggaggagg caagttgatc tggggtctgg   166440
cagagggtta gctggggaca tttagcggga ggctggtgcc cgggaattgg ggggatgccc   166500
agcagaaaga catgaggagg ctggcctggg gcgtggggggg gtgtgaaagg ttaagtgggg   166560
gcattatcct gctcccgctc ctgccggctg tatctggtca gcctgggcac cgaggtgggg   166620
ttctggaagg cactgttcac caaaatgctt atctgggtcc cccagagagc ttgcctgcct   166680
ggactgtcgg ctcgcctgca actgctgact cctaagcttt tgcagctcag cccacaacca   166740
gttcctattc acagaggtgg gagctgaggg gtgacaagtg actgctgcag tcttatttgt   166800
catagagaaa aagtgacaga gtccagcttg cccactggcc ctgccagctt aactggttat   166860
aaagtgacaa atccccaaga cccacagggc tctgcacaac ctgggccctc ctgccagtgg   166920
cggcgagggc aggtggctca cggctgggtg cctgtctggg caggagctgg gctggtatgg   166980
ggtgggcctg cggccctgcc cccctgtgca gatcaagact cagggtgctg gtgttcacag   167040
gtgccctcat cagccacgag aagctgctgc tacagatcaa ccccgagcgg gagctgggga   167100
gcatgagcta caaactcggc caggtcagtc tcgcgccccc gccgcctggc ctctgtccgt   167160
ttctgtcctc agactttggc gcttgacaca cccaggagaa aagctcagtg cacttttttaa   167220 atgaaaggaa gttttccttt tttttaaaaa aaaattttaat gttcattgtt tttatctgtt   167280
ttattcctag gtcccgcaag cagaggaagc attagttttg ttttttattta tgttctgtat   167340 tccagaaagt agttaagaga cctcacatgt agcgatagaa atgtgtgtaa gagacagtga   167400
gagggcgtga cttggactta agcaaggacc gtgagacaca aaaaggggggg tgaggacaga   167460 gtggagtcag ctgaaatgct caggaggaag tagacgccat gaagggccat ggtatggggg   167520
gccgcaggcg tggccgtgag tgtccctggg gccagctctt gggggggctcc ctgagtgtcc   167580 ctgtccctgt ggccagttct gggtgggagc cccgtgtgca ggcagacagc tcggccactt   167640
cctagcaggt cacattggtc tgtgcttctg tttcctcctc agataagtga agggattcaa   167700
gggtctgggt gtggtggcta acacctgtaa tctataacat tttaggaggc tgaggcagga   167760
ggcttacctg agctcaggag gttgaggctg cagtgagcca tgattgcacc actgcactcc   167820
agcctgggca acagaccagt actctgtccc ttaaaaaaaa atgtaaacag aaacgtaggg   167880
ccatttgcat atgatggcac atggcgtgga gccctacagg tgtatgctgg gcggggcccg   167940
gctgtgctgg ccgacttgca cctttccctc caccccggtg ctgtgtcttt cgctcaccgg   168000
gttcctgatt tagtgaaagc agttgtgcag gacagttctc tttgtagctt tgtttctgt    168060 ggaaatgggt cagaatatgg tgtttagaaa cacttatgag ctctgagagt ttcctcttct   168120
gagttcctgg cctgcagcct tcacagcaga aaccctgtga tgtcacaagc ctgttctgt    168180
```

```
tccctgctct ctgcctgtac tgtcctgttt tgtgcctgcc ggtttcagtg acaggaagca 168240
gggagctact ggaccagcct gtatttttct agacatagtt ggaaaaagaa gtcccactct 168300
tctgtccttt cacctttgac agatgtttcc accccaagat aagtgaaaat gaccaatagg 168360
atgcactgta tttttcatga aagtgtttct gaagggcagg ctgagagtga gaggcctggg 168420
gctcactggg tgcctctggc cttgtcctgg gcccagggac actggtctgt gcccgaggta 168480
ttccctatcc ccccaacccc gctgcatttg gccacatcct tcaatgtttg cgttgtgtcc 168540
agcgtccgca aaccaactgt catgggatca tactggggct gaagtacggt cccacccctg 168600
ccctgtctgg ggctgaagta cagtgccacc cctgccctgt ctggggctga aggacagtgc 168660
cacccctgcc ctgtctgggg ctgaagtaca gtgccacccc tgccctgtct ggggctgaag 168720
gacagtgcca cccttccct gtctggggct gaaggacagt gccacccctg ccctgtctgg 168780
ggctgaagga cagtgccacc cctgccctgt ctggggctga aggacagtgc caccctgcc 168840 ctgtctgggg ctgaaggaca gtgccacccc tgccctgtct ggggctgaag gacagtgcca 168900
cccctgccct gtctggggct gaaggacagt gccacccctg ccctgtctgg ggctgaagga 168960
cagtgccacc cctgccctgt ctggggctga aggacagtgc caccctgcc ctgtctgggg 169020 ctgaaggaca gtgccacccc tgccctgtct ggggctgaag gacagtgcca ccctgccct 169080 gtctggggct gaaggacagt gccacccctg ccctgtctgg ggctgaagga cagtgccacc 169140
cctgccctgt ctggggctga aggacagtgc caccctgcc ctgtctgggg ctgaaggaca 169200
gtgccacccc tgccctgtct gggatgttta gccctagat gccactggac tgagccgcta 169260
cttgcttttg ggaaagaggg gtgggggtta ggggtctggg cgaggggagt gcaggggctc 169320
ctccttggcc tgagagctgt tcatacagac tcctcgccca ctccctgcag ggtgctgggt 169380
cccagggggg aaatggccct tggtgccaag aacgtgagtt ggggctagtg ccagtgatga 169440
tggagaacag ctttttatgg gcacacagcc cacagcactg tgccaagtgc tcgaggcttc 169500
ccgagaacca ggcagaaagg aggacagtcg aggtgtgctg actgcgtggt ggctgcgtga 169560
tctagagcgc gggtcacaaa ggcgcgaggg agctctggcc ttgggtttac cgcaatgact 169620
gccagtgcgg gagactggaa aaggaatctc acgtattggt tccgtgtttt ggggactcca 169680
ttcagatgtc acttaggagt gaaagcatcc cttcgtagag cctctttctg tgtcaccctc 169740
ctcagctgct cctggggttg actggcccct gattcatgcc tttagcatgt gctggagctt 169800
cccagcagct gtccagcccc tgccccaccc tctctgtggg ctcccttgcc cgtaacctgg 169860
ggtgtctgaa cgaccttgc taaggggcag actgttagac ggtaggcatg tgctgagtcc 169920
cagtggccac acccacccac caggagcctg gcactgtggc cgcagcactg agcagtgccc 169980
cgtttctgtg gcaggtgtcc atacactccg tgtggctggg aacagcatc acaccctga 170040 gggaggagga atgggacgag gaagaggagg aggaggccga cgcccctgca ccttcgtcac 170100
cacccacgtc tccagtcaac tccaggtttt ccaatggcct ttttctttt aacagaaatt 170160 tgaaatttct tatcagtcat ttgatttgtt tgaggtgctt cttgaaatga gcctctcatc 170220
tcatgtactt ggaaaatacc catctcgcat attccacagg aaacaccggg ctggagttga 170280
catccactcc tgttcgcagt ttttgcttga gttgtacagc cgctggatcc tgccgtccag 170340
ctcagccagg aggaccccgg ccatcctgat cagtgaggtg gtcagatccg taagtgagcc 170400
ttcccattcc cctcacacct gcacgtgcca cacgcaccac acacgccaca caccccacac 170460
acacacaccg cccacacaca tgccacttgc acacacaccc ctcatgcatg caacacacac 170520
```

```
acaggccaca cgcaccatag acaccacaca cacatgccac atgcacacac atacacggca  170580
tgcaccatac acacaacaca cacagcacac atgccacaca cacacgccac accacatgca  170640
ccacacacat gccacatgca cacacactcc acatgcatgc accacacaca cacacacaca  170700
ccacacacac cacatgcacc acaccacaca ggttacatgc acaacacaca catgccac    170760 gtgcacacac cccacacacc acatgtatgt gccacacaca gcacacaacc acacacatgc  170820
accacacaca tgccacatgt gcatgcacca gacacatggc acacactaca cacacgccac  170880
gtgcacacac cccacacaca tgtacgcacc acacacatgc cacacacaca tgcaccacac  170940
acatgccaca tgtacacaca tgtatataca caccccacac cacacacaca ccacttgcac  171000
accacgcaca cacaccacat gcgcacacac acaccacata cgccacatgt acacaccata  171060
cacacaccat acatgcacca cgtgtaccac gcacccacac agacacagca cacgcataca  171120
ccacacacac acgcacacat gcgtcccgca cagtaatgtc tcttgggtgt aagaacacga  171180
cttgccagta gtagcgttct ggatgcgttg cctggattct aacagcgcga ttctcccctt  171240
gccctcctgg ttttccacat ctccagcttc tagtggtctc agacttgttc accgagcgca  171300
accagtttga gctgatgtat gtgacgctga cagaactgcg aaggtgcac ccttcagaag  171360 acgagatcct cgctcagtac ctggtgcctg ccacctgcaa ggcagctgcc gtccttggga  171420
tggtaagtga caggtggcac agaggtttct gtgctgaagc cacggggggcc catctgcctt  171480 gggacctggt gttggccaga ggtgccgggt gcggctgcct ccttccaaga gttgacccga  171540
accggactcc acggcccacg tgagctgcag tgcttctcag atggagggggg ttcagcgacg  171600 gtcagtgcca ttcacaggtc actgtgatgt gggttgtggc ggccaagcca tggtttgggg  171660
tcccgtatcc ctgggcttat gacatcattg tagtagccca tccccacaga accacggtgt  171720
gtggtggcgc tgaggcatcg tagatggtgg aaatgctact ggcttcccca tgctctgccc  171780
tgaggcctga ctgcctcact ccccttctca gttatgttcc aggccccccg agcttcctgg  171840
ctggacagct tctctcctgg gggccgtttt gtcacagtga ccctgtgttt ctagtcccaa  171900
atctgggtgc tatagtctct ttttagcgtg gtggttgtct tagtcttttt tggctgctac  171960
cacaagttac cttagactgg gtaatttata aacagtggaa atttacttct caccgttctg  172020
ggggctggaa gttttcatgg tcaaggtgcc agcagatttg gtgtgtgatg agggctgctc  172080
tctgcttcat agatggcatc ttctggctgg gtcctcacgg tggaaggagt gaacaagctc  172140
cctcaggcct tttagaaggg ccccaatcca caagggctct cccatcatga cctcatcacc  172200
tcccaaggcc ccaccttctt gtactgtggc actgcaaatt aggtgtcagt gtaggagttt  172260
caggagggat agaaacattc agaccatccc agcggtcaag tgttcatcct cttgagttcc  172320
tccttattct gcttctggtt tatcaggatt cagccagtgc agcatggtac ctgtattctg  172380
tggcacatca ccacatggta tttgccaagt atccatcacc tgcacacgtg aaatcattgc  172440
ccgtgggtcc cgacatctgg cgaagcatat tcaaggatgg cagaactgtc agagctggca  172500
cctctggttc cttgtcatgt ggcattacct agtaatccat tttatgatag caatggaaac  172560
tcatttcttc aacaaacacc tgagtggctg ccgtgtgcca gccgtctggg gcccttggtg  172620
agaatggcat ggtggtgccc atcagggcct gcctagcccg tgctctggac gggctcctgt  172680
gtgtcaggaa cgacaatgct gtcatgacgg tgaatgattt tttttttttgc catcactcca  172740 gccgctaaca tttgcggagc tcttcctccc gcacccccac ctgacaaggc caagggtgac  172800
cttggcccca ccctaggcgg ccaaggtcag aggttagctg gcttgtctgg gtcacacaaa  172860
atgcagcaga ggttgaggtg agcacatgtc cgtgacctgg agcctgactc cctctctgcg  172920
```

```
agtcttgact gctcttgcct agactctgtc ctccccgagc ccaaacgcca gtcatcttcc   172980
cttgtgggtg tccttcagcc tggtgccatg ctggtgactc agcagccgtc cagggagtgg   173040
aaacaattga gtgtgtgggt tccctgtgtg ggcatctctc ttcacggcga acaccctctg   173100
ggtgttgccc acacgatgtc aaagcggctc ttggaagggg tccttctcct ttgtgggaag   173160
tttcagctgc tgggctaact tgaattgtaa ctgtggtttt gtgctcaggc ccagatcccc   173220
ctaggcaagt gttgtgccat cagtaatcaa atgagaaata atcattttga aaagcagatc   173280
ctaaggcagg atggtcatgg acactcactc ccagctcttt gtgcactcat gctttctgga   173340
agatggccat cctctgtgaa ggttttcagc gcgtcatgct tggtacccac gtatccagag   173400
catgtcgttt tgaggtattt gcccaccgtt gtgaaatccg tgccacccga gagcaggtcc   173460
tgatgtgggg ctttcagaag tgggacctgg ggccgtacgc agtccttagg gaggggccgt   173520
gtggcgttgt gcgtgtgagg ggatagcaca gggtgaggtg ggggcccaag aaggaagtga   173580
cccacaaaga acagcctcct cttttggtcc ttgttcctgg gatggctggg agtggcttct   173640
gtgtcgtccg gccatttccc ctgcggagag gctcctacca ctgccgagaa cctcatcatt   173700
ccacaaaaac aagaggccgc ctggccatcc agcgctccat gggaattctg tgtccccata   173760
gtcttgggct gaaggagggt gacattcctt gctgacttct gcaggggtct cctcactgtt   173820
aaagagcaga ttgaaagtga agaacgtggg ctaagtgttt aggtcgatat ttaaccctgc   173880
taggttttgg atactaagtg aaattgaggc cattttggtt gaagttgaca gaaaccacta   173940
tcagggatcc ccaagactac cccaggcttt tctagaaaga ctctcagcta agatgtgtta   174000
tggtaaaagc acacaaaaca aaatcagcaa agaaaattag caagggcaga ggcccatggg   174060
gcgatgtccc gaggacacca ggcttgagct tccagaatcc tctcccagcg gggtcgtgca   174120
ggacgcactt aactccccgc acagtgagcc gtgacagcgc gtgtgcagtg tcgtcgccag   174180
gaaagcacac tagagactcg gtgccagggt ttttactggg ggctgggcac atgggcaccc   174240
tctgcctgcc tcgtgcccag actctggact cccggaggga aggcaagttc tcagcaccaa   174300
ccctggtgcc cacacaagca gctgagcaca gggagcccct cctcagtgag gatggtgggc   174360
accgtcccaa caccagccag gggccagcct tgcacacagg cctctcagga tggtctccgg   174420
cctgctgtgt agtctcttct gcacacaagc gtgagggcag cgcccccgcc tcggctgtgg   174480
ggaggagcca ctgggacgtg agctctggtg gcatgcagca gcttttgtct gtgtgtgcct   174540
aggacaaggc cgtggcggag cctgtcagcc gcctgctgga gagcacgctc aggagcagcc   174600
acctgcccag cagggttgga gccctgcacg gcgtcctcta tgtgctggag tgcgacctgc   174660
tggacgacac tgccaagcag ctcatcccgg tcatcagcga ctatctcctc tccaacctga   174720
aagggatcgc ccagtgagtg ggagcctggc tgggctgggg gcggggtct  cagaatgagc   174780 tgtgaaggaa gcagcatcac cctctccaag tgcccaggct cctggccaga tggcaggcca   174840
ggtatcagtg ggaacccagg tgggtgccat ggctgaggtc agtgagacgc aagagacag   174900 gtgcgtccta gaggcttcct cgggcacctc cagcgagctg gagctctcgc ctctgctgct   174960
gtctcatgtg gcgcttagca cactctccca cgtgcccatt cctgactctg ctctcgaggc   175020
catcggctct cattctctgc tcccagaacc ctgttattac ccaggctagc ctcctctctg   175080
caccttcccc gccctggccc agtacctccc tcttgtttcc actgtgattc cgacctcacc   175140
ttatcttaaa gctgctggac ggcaggttct gtacacacgt gtccttgaca aagcacggct   175200
ggtgccgcaa cccctcagcg agcaagtcaa gctcttcaca gcgatgtctt acaagcgcag   175260
```

```
agggctctgt gacaccctgg tctcaccgcc actcttccaa agtcgcagag gctttagcag   175320
agatgggccc agcctctctg agtcataggc ttctgcacac gggagctgtc tttagaggga   175380
gggtggaatt tcatcagcca cccacatggg ggagttgagg gcaagaatta ggagcaaaga   175440
tgggaagggg tctgggagga atggccagtg atccccttig acaagtgggc aggaaacggg   175500
ggctaggtca aagttgagtg aagacctggg agggagacgg gaaggtctct gtaggcacag   175560
ttcagacagg agggaggtgt gagccagggc acatgccggt ggccgtctgg caggatttgg   175620
gacatgctgg agcagggaca gcggctcatc agggccatt gccctcatcc aggccagagt   175680
gtcacaagcc cgtggggagg cccttctcgc ctgtcatcct tgctgggcag tgggtgctgt   175740
gctagcagga caggcggacg gctggcaact gtctctgcat ccctggagcc tggcataggg   175800
ccaagtcaca cggggcacag gcctgcaaat caggcacata tgttggtgca gtgacgtgat   175860
tttgggggc agccccagaa caggcccag acacaggcca aagccctgcc tgtgctggtg   175920
tgttgggctg ttctatggct cttgctgtgg gcatggagga ctcagggaag gagagttgag   175980
gtggtccagg agttgcgttt gggatgcaga gagcttgtgg catccaggta gaaatggtgc   176040
gtggggctga cctcagcacc atgggcagag gggccgtgtc acgtgcctcc gaggtggagg   176100
tgggaccacg tggtgacaga tatacgcatc actgggcacg tttttgtggg tgttgggggg   176160
catcgtattg gctcctctgt tcacagtggc cactcattca gtccctggct accaggtcct   176220
cactgtgcca tgggaaggc cggcgctgtc ggggatcac agaaggcagc acgtcatgat   176280
ggcatgtgcc atgaaggaaa agcacagggc actcaggaag tagaggggac tggcctgggg   176340
tgtgggaatc tagggcctcg ttagggaca gagagaggaa gtgtgtggtg ccagcatgg   176400
aggtggccac agggagggct gagttaggcc gagagggcag ggcgttgggg aggtagacgg   176460
gctcagccca tcagggagtg gtcaagcaga ggctgaaggg tcaggccagg ttgcaggggc   176520
ctggggagc cactcagggt aggcgctccc gggagcccgc ctgcccata gctctacact   176580
cccgcgtggg gccggacatg ctgtgaagcc ctctccacgt tggatgggg tggctgagcc   176640
tggatgctgt ctcccgtttt cagctgcgtg aacattcaca gccagcagca cgtactggtc   176700
atgtgtgcca ctgcgttta cctcattgag aactatcctc tggacgtagg gccggaattt   176760
tcagcatcaa taatacaggt gagtgggccc tggctgtctt cctctgcaca cggggagtgg   176820
gcttccccttc tcttttcctt gcaggatcat accagtgggc cagttttgac ttggtcggga   176880
ggaggcatga acacctgaga ctgtgcagcg attctttgac acagaggcct ttctccctgt   176940
gcagatgtgt ggggtgatgc tgtctggaag tgaggagtcc accccctcca tcatttacca   177000
ctgtgccctc agaggcctgg agcgcctcct gctctctgag cagctctccc gctggatgc   177060
agaatcgctg gtcaagctga gtgtggacag agtgaacgtg cacagcccgc accgggccat   177120
ggcggctctg ggcctgatgc tcacctgcat gtacacaggt gagcatgtac acggtgccca   177180
taaggccagc ccaagtcctg ttcaagggag gcaggagcat gctcactcaa gggacctcga   177240
ctaggtgccc tctgatttca cacttctggt gttgccccaa gccggcccca tcaccttgca   177300
agaaaggctc tggagccccc agggctggag tacctggtca gggttgaccg tccctgtggt   177360
cactcatccc atgtggctga gctggctgg gtcctgggca agcaagggc tgatatcacc   177420
tgctttcaga tctccaggga ctcactggac ccctgtgtac aaagcactgt ctacagagcc   177480
tattggttg tatagaggta accttcgtac tgaacacttt tgttacagga aaggagaaag   177540
tcagtccggg tagaacttca gaccctaatc ctgcagcccc cgacagcgag tcagtgattg   177600
ttgctatgga gcgggtatct gttctttttg ataggtaaga agcgaagccc catccctcag   177660
```

```
ccgttagctt ccctagaact ttggcctgaa gctgtgcttt tgtgtgtgtc tgctgatccc    177720
ctggcgctgt tgctggagtc ctgccagtga ttccccacca cagcctgacc atgggctgcc    177780
ttggctcagg gttccactgg cgagctggtg gtccttggac cccagcactc aggtgtagcg    177840
ttgaccagtt ccaaggttgt cccagtgcct gcccatctct cctgagggct caggacagt     177900 acctggcagt tgggggtgtg gcaggggca ggaatgacca gcctctggga gggtggggca     177960
gaagcctgta cagtgaggag gagctggctc agcctggctg cctatcgtga gaggggagcc    178020
cacggggctg tgggaggggg gccgtggtgc ctgtgagcag ggtgaggagc agcggcagga    178080
ggatgaaggt ggaacccaca catgcatctt tgagacccgt gtggtcagtg gcttctgccc    178140
cccaccaccc cccactgctg tgcgtgcata gaattggctt ccctcacctg ctctggaagt    178200
gggttaggag cttggtaggg cttttctca aggacaaggg cccctgattt gctctcaggc      178260
ctcagtcctg gcgacatggt ggatctggag ccttgttgca ctgccttgcc tgtgctctcc    178320
aatcagggtg gccagtgggg agccatttgg cttttctcaa gagcatactc aggtggacct    178380
tgctccactg tttgaccaga tgaggcattc tgaacagcca agcctgtgct ggtctgtttt    178440
catgttgatt tttttttttc ttttcttttt gagatggagt ttttcccttg tcacccaggc    178500
tggagtgcaa tggtgtgatc tcggctcact gcaacctccg cctcccgggt tcaagtgatt    178560
ctcctgcctc agcctcccta gtagctggga ttacaggcac acaccaccat gcccagctaa    178620
tttttgtgtt tttagtagag acggggtttc accgtgttgg ctgggctggt ctcgaactcc    178680
tgaactcaag tgatccaccc tccttggcct cccaaagtgc tgggattgca ggcgtgagcc    178740
actgcgcccg ccccccatgt cgatttttaa atgcacctct gcatcgttct tcagtcccca    178800
tatgctcact gagcaccact gcgactggca gacgggcaca gggaggcgcc acgaccagtc    178860
ctggccttca aggggcttgt ggtctagtgg gcccaatgct aggtggcgag tgctccaaag    178920
agtgtggtgc acgccttccg cttgaccgct ctccagacgc cacagggagg cacctcgcag    178980
ctgaccacag atttctctct gtggagcagt gtcttcagag cggctgccat gccactgctg    179040
ggcgagggtc tgcgggcggg tagagccagg agcacctgtg aggaagtgca ctgccatttt    179100
cgtagctgct tcccgtgtgt ctcagttaca cacggctggc atgtgtgcac tgatgagacg    179160
ggaacgtgat ggttgctttt cagcactgaa agggatactg ctcaggggc gtgtttcagg     179220 atctggttag ggaagaagca gcgagagcac agatggggcc ctgtgtggta acaagaaaaa    179280
agtcctggtt gacaacagtg ccacgaagcg ttagaacaca tagggatgtt tgtggagcat    179340
ttgcatgtgg aaagcagcaa aaacataatg ggaacgggtt cttttgttat gattttaaa     179400 aatctctttt gtaacatcct tcccgctgcg ccgtttctgc atattccttt atgtagcttt    179460
caaactcctc ttaggagttc tggtccctac agggcgtggg agcccaggct ttacgtagct    179520
ttcaaactcc tcttaggagt tctggtccct acagggtgtg ggagcccagg gcctgtgccg    179580
agcagcctgc ctccacgagc tagacagagg aagggctggg gttttgcctt tttagtctca    179640
aaattcgtac tccagttgct taggctctga ctttccccac ttggaaagtc cctcacggcc    179700
gagggtccct cccagccctg atttcacatc ggcatttcc ccagtattag agccaaggcc     179760
ctccgcgggc aggtggggca gctgtgggag ctggtgccag tctctgacct gcgtccctcc    179820
tcccaggatc aggaaaggct ttccttgtga agccagagtg gtggccagga tcctgcccca    179880
gtttctagac gacttcttcc caccccagga catcatgaac aaagtcatcg gagagtttct    179940
gtccaaccag cagccatacc cccagttcat ggccaccgtg gtgtataagg tgaggttgca    180000
```

```
tgtgggatgg ggatggagtg ggaaagcctg gaggtggagt tgcctccgac ttcccagcag    180060
attcgccagc agagcccagc tcctccgctt taaagcagca atgcctctgg cccccacccc    180120
acccccgcca cccaggcgca gcaggtgctt cccgtccccc cagccctgac actcaggcac    180180
ctgcttgctc cttgcaggtg tttcagactc tgcacagcac cgggcagtcg tccatggtcc    180240
gggactgggt catgctgtcc ctctccaact tcacgcagag ggccccggtc gccatggcca    180300
cgtggagcct ctcctgcttc tttgtcagcg cgtccaccag cccgtgggtc gcggcgatgt    180360
atcctctctg ggtccctggt gctggccccg tttcccttgt caacaccgag gctcatgttt    180420
catgataagg ttttgaaacc taacctttgc aaaaacccca cagatgccag ggtgacaggc    180480
cctcagcccc agggaagtaa aatgctgaca ggggtacaga aaggagcacg tccagacatt    180540
tgctgaccag ggcctctcag aggggccggt gtatggcagg agggtcgcag ctgaggggcc    180600
tttctgtgga gggcctgggt gaggggagcg agggtgggcg gtggtctctg cagacgtccc    180660
gcccactcgc gggctctgtg tggctgggct tctcctgaca ctgcttctca ttagctttgg    180720
tcattgtgcc tcgatcgccc tctcgggaa aggcttaagt aaagatccag ttcccacccc    180780
cagatgctgg ctgccaggag tttcccttc cacagcccctt ccccaagaca gaccacaaga    180840
gcctccaagc agcacagttg tcctggtgct gacagcacag ccttgcccgg cgtgcctggc    180900
acggctctgc cctcactgca ttggagcagg gctagtggag gccagcggaa gcaccggcca    180960
ccagcgctgc acaggagcca ggccaggtga gtgctgccga gtgggtgccc tgcctgcagg    181020
gcatccagcc agccaagggt tgcaggaatg gaggtggagg cgctgatgca gctggaggca    181080
tccaggtggc ccttccgggg ctctgctcgc tctccaggct ccctggaccc ctttgtagac    181140
tgtttcagga gaggaactcc caggtgagga cagggaggca gcattcccct catttgccgg    181200
cctttttcct taactcctgc accagcctcc cacatgtcat cagcaggatg ggcaagctgg    181260
agcaggtgga cgtgaacctt ttctgcctgg tcgccacaga cttctacaga caccagatag    181320
aggaggagct cgaccgcagg gccttccagt ctgtgcttga ggtggttgca gccccaggaa    181380
gcccatatca ccggctgctg acttgtttac gaaatgtcca caaggtcacc acctgctgag    181440
cgccatggtg ggagagactg tgaggcggca gctggggccg gagcctttgg aagtctcgcg    181500
ccttgtgccc tgcctccacc gagccagctt ggtccctatg ggcttccgca catgccgcgg    181560
gcggccaggc aacgtgcgtg tctctgccat gtggcagaag tgctctttgt ggcagtggcc    181620
aggcagggag tgtctgcagt cctggtgggg ctgagcctga ggccttccag aaagcaggag    181680
cagctgtgct gcaccccatg tgggtgacca ggtcctttct cctgatagtc acctgctggt    181740
tgttgccagg ttgcagctgc tcttgcatct gggccagaag tcctccctcc tgcaggctgg    181800
ctgttggccc ctctgctgtc ctgcagtaga aggtgccgtg agcaggcttt gggaacactg    181860
gcctgggtct ccctggtggg gtgtgcatgc cacgccccgt gtctggatgc acagatgcca    181920
tggcctgtgc tgggccagtg gctggggtg ctagacaccc ggcaccattc tcccttctct    181980
cttttcttct caggatttaa aatttaatta tatcagtaaa gagattaatt ttaacgtaac    182040
tctttctatg cccgtgtaaa gtatgtgaat cgcaaggcct gtgctgcatg cgacagcgtc    182100
cggggtggtg gacagggccc ccggccacgc tccctctcct gtagccactg gcatagccct    182160
cctgagcacc cgctgacatt tccgttgtac atgttcctgt ttatgcattc acaaggtgac    182220
tgggatgtag agaggcgtta gtgggcaggt ggccacagca ggactgagga caggccccca    182280
ttatcctagg ggtgcgctca cctgcagccc ctcctcctcg ggcacagacg actgtcgttc    182340
tccacccacc agtcagggac agcagcctcc ctgtcactca gctgagaagg ccagccctcc    182400
```

```
ctggctgtga gcagcctcca ctgtgtccag agacatgggc ctcccactcc tgttccttgc   182460
tagccctggg gtggcgtctg cctaggagct ggctggcagg tgttgggacc tgctgctcca   182520
tggatgcatg ccctaagagt gtcactgagc tgtgttttgt ctgagcctct ctcggtcaac   182580
agcaaagctt ggtgtcttgg cactgttagt gacagagccc agcatccctt ctgccccgt    182640
tccagctgac atcttgcacg gtgacccctt ttagtcagga gagtgcagat ctgtgctcat   182700
cggagactgc cccacggccc tgtcagagcc gccactccta tccccaggcc aggtccctgg   182760
accagcctcc tgtttgcagg cccagaggag ccaagtcatt aaaatggaag tggattctgg   182820
atggccgggc tgctgctgat gtaggagctg gatttgggag ctctgcttgc cgactggctg   182880
tgagacgagg caggggctct gcttcctcag ccctagaggc gagccaggca aggttggcga   182940
ctgtcatgtg gcttggtttg gtcatgcccg tcgatgtttt gggtattgaa tgtggtaagt   183000
ggaggaaatg ttggaactct gtgcaggtgc tgccttgaga cccccaagct tccacctgtc   183060
cctctcctat gtggcagctg gggagcagct gagatgtgga cttgtatgct gcccacatac   183120
gtgaggggga gctgaaaggg agcccctcct ctgagcagcc tctgccaggc ctgtatgagg   183180
cttttcccac cagctcccaa cagaggcctc ccccagccag gaccacctcg tcctcgtggc   183240
ggggcagcag gagcggtaga aaggggtccg atgtttgagg aggcccttaa gggaagctac   183300
tgaattataa cacgtaagaa aatcaccatt ccgtattggt tgggggctcc tgtttctcat   183360
cctagctttt tcctggaaag cccgctagaa ggtttgggaa cgaggggaaa gttctcagaa   183420
ctgttggctg ctccccaccc gcctcccgcc tcccccgcag gttatgtcag cagctctgag   183480
acagcagtat cacaggccag atgttgttcc tggctagatg tttacatttg taagaaataa   183540
cactgtgaat gtaaaacaga gccattccct tggaatgcat atcgctgggc tcaacataga   183600
gtttgtcttc ctcttgttta cgacgtgatc taaaccagtc cttagcaagg ggctcagaac   183660
accccgctct ggcagtaggt gtcccccacc cccaaagacc tgcctgtgtg ctccggagat   183720
gaatatgagc tcattagtaa aaatgacttc acccacgcat atacataaag tatccatgca   183780
tgtgcatata gacacatcta taattttaca cacacacctc tcaagacgga gatgcatggc   183840
ctctaagagt gcccgtgtcg gttcttcctg gaagttgact ttccttagac ccgccaggtc   183900
aagttagccg cgtgacggac atccaggcgt gggacgtggt cagggcaggg ctcattcatt   183960
gcccactagg atcccactgg cgaagatggt ctccatatca gctctctgca gaagggagga   184020
agactttatc atgttcctaa aaatctgtgg caagcaccca tcgtattatc caaattttgt   184080
tgcaaatgtg attaatttgg ttgtcaagtt ttgggggtgg gctgtgggga gattgctttt   184140
gttttcctgc tggtaatatc gggaaagatt ttaatgaaac cagggtagaa ttgtttggca   184200
atgcactgaa gcgtgtttct ttcccaaaat gtgcctccct tccgctgcgg gcccagctga   184260
gtctatgtag gtgatgtttc cagctgccaa gtgctctttg ttactgtcca ccctcatttc   184320
tgccagcgca tgtgtccttt caaggggaaa atgtgaagct gaaccccctc cagacaccca   184380
gaatgtagca tctgagaagg ccctgtgccc taaaggacac ccctcgcccc catcttcatg   184440
gaggggggtca tttcagagcc ctcggagcca atgaacagct cctcctcttg gagctgagat   184500
gagccccacg tggagctcgg gacggatagt agacagcaat aactcggtgt gtggccgcct   184560
ggcaggtgga acttcctccc gttgcgggt ggagtgaggt tagttctgtg tgtctggtgg   184620
gtggagtcag gcttctcttg ctacctgtga gcatccttcc cagcagacat cctcatcggg   184680
ctttgtccct ccccgcttc ctccctctgc ggggaggacc cgggaccaca gctgctggcc   184740
```

```
agggtagact tggagctgtc ctccagaggg gtcacgtgta ggagtgagaa gaaggaagat   184800
cttgagagct gctgagggac cttggagagc tcaggatggc tcagacgagg acactcgctt   184860
gccgggcctg ggcctcctgg aaggaggga gctgctcaga atgccgcatg acaactgaag    184920
gcaacctgga aggttcaggg gccgctcttc ccccatgtgc ctgtcacgct ctggtgcagt   184980
caaaggaacg ccttcccctc agttgtttct aagagcagag tctcccgctg caatctgggt   185040
ggtaactgcc agccttggag gatcgtggcc aacgtggacc tgcctacgga gggtgggctc   185100
tgacccaagt ggggcctcct tgtccaggtc tcactgcttt gcaccgtggt cagagggact   185160
gtcagctgag cttgagctcc cctggagcca gcagggctgt gatgggcgag tcccggagcc   185220
ccacccagac ctgaatgctt ctgagagcaa agggaaggac tgacgagaga tgtatattta   185280 atttttaac tgctgcaaac attgtacatc caaattaaag gaaaaaaatg gaaaccatca    185340
gttgttgctg tgtgaggctt gctttgcttc atgagaacct agaccttgct gagctggagt   185400
cttaggaagc agtctcctaa gtgcttctcc agcagggca gaaactgtcc caccagctaa    185460
catctggcat tatggagggt cccccaggca gctgccagca gggacaggcc ccgtgttttc   185520
tgtagccagg gatgaggaag tggccccagg gcatgggcct ggctgggtgc ttctgcaagg   185580
gccttcccaa accacagtac aggtggtctt cctgccctgc agatgggagc tgtgggagct   185640
gctggagctg ctggagcctt catggtcaag tgacatcata agcttatatg acatacacaa   185700
gcctcaggac ttggcccatg gcactgaagc aggtcatcag gcccagcaca gagactagag   185760
ctgtgttctc acagggccca ccaccttcc acctccttgg ccattgacac ctgcgtccct    185820
ggcccagctg ctcccaggta accccaaag cagctggcac atcccacctc tggtgtggcc    185880
ggggctgctg tgtgtccgca gggcctgccc cgtctattct agcttgtttg tcctgtctga   185940
accagcgcct actccaagaa gcctctgctc agcccagcgg ggatgcttct aagctccgga   186000
cgagcctctc ggaagccttg gtgattggtg gtgtagtcat cttgggatgc agatgtctta   186060
ccaacctgca agaacaaaaa ccctgtggct tcctctggtg cagggtattt agtcaatgtt   186120
tgctgaggtc ccgtctggtt ctggctaatt ggcagggtc gtccacccat tctttccctg    186180
ctctgctgtc tgtgccagga gagacggggg ccagtcggcc aagggggccag ctcctgctgc   186240 ctgctcctct tgggcacgtg cgggggcccc ctttctctga gcaggatag ggatcagtct    186300 gccggaggga tgtggtggac aggcctaaag catttgggc ggggcatgcc acttgagctc    186360
cctaaatctg tctcctcata ggtgacaccg ctccagggcc cccagtggc ctctcctttc    186420 agagctacct aaaattctggt cacttcagag aaatggagca ccccctttctc cctggtccag   186480 gtgtggacag cctggcacac tgagcacacc tggcatggct ggtaattca gaaagaagag    186540 gggccggggt ccagtgggaa gcagcggtga accctcgtg agtgggcttt gcagtccctc    186600
cccatgccac ggcagagctg ccctcaacac agccttcctc ttcctcatcg gagagcacac   186660 cctgtccct tgccgagctg tgccctgtgc cttcggtggt atttgatttt ggctgctact    186720
ggctttgttg ggatctggaa gtcgcttccc ctgcgtggtg cgtggagcac tgtaagtcag   186780
atgagggaag tagccagggt gaggtgagta ccgggtggag ccgccactga agggactggg   186840 tagggggcc ttgcctctac atgatgtgac acagccaacc gaggacagag gaagcccgt     186900 tcctggggt gtggggtgca cccctcaggg aagcctgcag tggggcctga ggaaaggcat    186960
cctccgcgag cccacgagtc tggtccatga gcaccgtgac agtgtctgtg ggtagaggt    187020 gacccggcct tgtgtcatca ccaggacctc ttttgggaaa ccatgtggac atcgcttgcg   187080
ggtcccccag gctctgcagc cccagcagcc tggctgcctt ttgggcaagt ggcttgagcc   187140
```

```
acagaggacc cagtcctgtt gcagccacat cctctggggg ggcccgccag tgtggccggc 187200
tttctccacc ctacaccagg cctccaggtg tcctggtcgg gggtgtctgg gccctgggtg 187260
ggccctgtgg acctgtgagg tcagggtcag ggcatcactg gaggcagagg gctgaagttg 187320
tgggtctggg ttccccttgt gtgcacaggc ccctgccctc catgcttggt caggcagcta 187380
cccccaaaac tgctaggaca ggctggtcct gaggtggatc ctggcccctg taccctctgg 187440
acagcccacc cgcccaacct tctaccctgc cccagcggcg gcagtgttgg ccacatcctt 187500
cccctcctgg ccccaattgc tctggggaag tccaggctcc ggagcctgcc caggggcccc 187560
ccgtgatttg ggcccaggac tccacgtggt tctctgcctt cacccaagcc ctgaactcct 187620
cagctgccaa atccccaccc atctgcacag gctgtgctca ccactgctgc tcctggaagg 187680
tgcccctcag tgggacgccc acctcctctc tgggcttctg tgtttgggag ccctgctgcc 187740
cccacccttg gtcagtcccc atgtcctgct ggcctgtcag gcagggcaga aaatccaccc 187800
agaaatgctg agcaggatga gagtctagtt gggcccagcc tcattattta gaagggatgg 187860
aggcctaggg agcatgcttc tagcctgagc ccagcagggc cccgcccatg tcccaggtct 187920
gcaccaggga cagctcctgc cgaggcctga cctgcccctt ctccctcagg tgctgctggt 187980
tgaccagcct ctggccctag gagaccccgt agcgactgag ggtcccagca ggccatgcag 188040
ctttgccaag gtacgagccc ctccccagca ggggacagat gtgggacccc tccaggcag 188100
gagcagctgg gtgcctggtg ctgccatctg ctgcctgcct ggttcttgtc ctcacattgg 188160
aggtcagtgt gagggctctg cctcgggaaa ggccatggag cttgccctgt ccagggcctc 188220
ccatgtgcac tgagcctggg aagagagggt tggagttgag ccttttaccc tgggaatgct 188280
gcctggagga tggtgcgggt gtggggtggc accctgccag gcagggccct gcctccctgc 188340
gcccactgga actcgggcag gcaggggtgt aggtgcctcc tctagagccg tccggtgggg 188400
gccccggca gtggtggtgg tgtccactgg ccagcagctg ccccttcagc caggacagta 188460
ggcctgacgc tgtccccagc agctccaagg tggatttgtg gaaggggta gagggcacgt 188520
agaggcccca tgacctcccc agggttctgg gagggctgtg cccccttagc cagcaccatg 188580
ctgggtgata tagtcagatc ctgttacccc tgttgtggag gtgaggaaac aggttagtgg 188640
ggaggacatg actaaggtcc atgctgagtc gctagagctg cacccagaac cactgctggg 188700
accccatgcc tttctgctta ccccttgtgc cgggagatgc caagagatgc tgggagccag 188760
ccccacctct gcccttggag tcatggctac ggaaagggca ttcggaccgg tccctgacct 188820
caccggggag ggccgaaccc tgttcctgag gagccagggc ttcctagagg aggtaggcct 188880
tctagtcact ccttcatctg caggcactcc acagagctct ctgtgccagc ccccagcacg 188940
gagggctgac cttagtcgag tggagatgcc ccagtgccag gcagtaggga tgatgtctcc 189000
tgaggcccag atggaaggga ctggactagt ctcatggggc tgatggtggg gccaggcctt 189060
gaccagggac ccagtgtagg gggtgcagag acccctctga gttcctcaca catccctggg 189120
gccctcccca tacacttcct atcctgactg cgggcaagag ggagccccag ttcgccttcc 189180
ctatgctggg cacccacagt ggggctgggc acccccgcca tgcccctgcc ctgtccttcc 189240
cctgagagcc tcggtcccac ctccaaggtg cctcagagga cagcaggggc agcgggcaga 189300
ggccgagatg cctcctcatt ccaggctcag ctgcccttct tggggcagcc cacacctgag 189360
agtctcctgc agttggtcag gcctgaggag ggcagggggg tgcctgctgt ccctctgctg 189420
accacagtgg catttagcct gggcaccgcg cccagcacag tccatgctgc acaggtgccg 189480
```

-continued

```
tgggctccac agagccctgc ctgacatgca tgtgttacgt ttcgggtgcc gatgcccttg    189540
ggcggcactt ctccgggcag aaccccagg ccaccgctcc ggttccggtt ccgctgcatc    189600
tggggctctc ggcaggctgt ggtcctccgg ccagcctggg ggcatctcag tccctcagcc    189660
ccacaggggc ctgccccgca gcctgggcct cgagccccgt ctccgcacgc tgtgccgaat    189720
ctggctgccc atcagctccc tgcgtaccca gactgtgccc tgccatgccc gtggctcttc    189780
ccaggagtgc cctgtggcct cccctggct tgctgggctg attccctcct gtgtctcaaa    189840
cagagctcac ctttgccatc actgctgtcc tcaccggccg gtgccagagg cccgtgtctg    189900
tgtaccctgt gtctgcacct ctgggcaggg cctggctctg accaacccgg gcttccagtg    189960
tccacagacc taaggcccag ggcgcctggg ggctggagca agagaagcaa aaggagccaa    190020
gggtgggggt ttgggttct tgtgaggggcc cagcccagg accccaggac caggacccc    190080 aggagcccca gggcccagcc ccagttcaga aggcaggggc cttctgaggg agcttaaggg    190140
tcccacagcc caggaccccc accagggcca gtgccagcg ttgggggact cagcctcctc    190200
gtcgctcgtc ctctctgttt ctcccacctt ttgccccctt tctccttgcc tgttcccacc    190260
cgaggccccc tcttggcctg cgtgagccgg ggcggcactg aactgggggc cgatccgcct    190320 gggcggcgg gagaggcagg gccggagcc gggccgctgg gtttgggcct ggcccgctcg    190380
ccgcaatatt gatggcccgt cagtgcagcc ctgattcctg tgctttcagt taaaaggttt    190440
ctgttgttgt agcttatgca gttgctctgt tgctatggaa acgtgacatc aaaatgacgt    190500
ttcccgttta aaagcttta actaaattcc tgcctgtcag atgtaggccc cattttgagc    190560
gtggagctgc cttcgagcga gcgtgagcgg cgcctcccgc ccatggtgcg tggggccggg    190620
ccggggccct cgctgagcgc gctctctcac cccacaggcg cctccggcat ggcggcggcc    190680
gaggggcccg gctacctcgt gtctccccag gcggagaagc accggcgggc ccgcaactgg    190740
acggacgccg agatgcgcgg cctcatgctg gtctgggagg agttcttcga cgagctcaag    190800
cagaccaagc gcaacgccaa ggtgtacgag aagatggcca gcaagctctt cgagatgacc    190860
ggcgagcgca ggctgggcga ggagatcaag atcaagatca ccaacatgac cttccagtac    190920
aggtgggcga gcgggcagtg tgggcccac caggacgggg gggcccgggc gtggcggggcc    190980 gctcctgact ttcttggagc tctgagtcgg gacgatgtgt gggtcgtggc ctgcctgtcg    191040
gtctcctctg gccgggtatg ggcagaaccc cacggggtga gacggggccc acggaaaccg    191100
tgtgtgcagc cttccattgg ggaagtgggg aaactgaggc ccagcaaggg caggaaacca    191160
gtctaagagc tgaggggtag caggggtggg gctggtgctg ggcagaggcc aggatggctc    191220
ccaggacgta tgggcggtct gggcactgtc cctcggaggc agcaacactc atggtggtgc    191280
ccactgacct cacaccctgc tcccccatag ggaggcggcg gctgccagtg ccctcccccac    191340 caccaagctc ccaagctcag caggggtttc aggggcctac tgcgtcattg ggaaattga    191400 gactgcaagt gagaaggagg ctcagtgctc tgcgacttgg agcatccact gagcctctgc    191460
catgagccgg tgagccccac tggggctggc cctagggtca cggtggggta tttccagaaa    191520
tcaccaggtg aggtgcagga ccagccagcg catgggtggg gcttacggtg cgaagaagaa    191580
agaggtggag gcctgccctg gcccaggact cccagcgtgg gggctcccgg cctgccccca    191640
cctctgctcc tgctacatgg caggtgggcc cttcctgccc tggcaacctg cagggaaggc    191700 cggagggac cacccagcca gggagatgtt ggcgtctagg aggggacagg tgtggtccca    191760
cacacccagc atcttaaagt gcgtgggtcc ccagcccatt aggacagggt cccggggtggg    191820 caggggtcat ggtggggtga aggtctcagg cacaggcaag gtcacaggtg cggtgagggt    191880
```

```
cttgcagggt gtgaaggtca taggtgtgcg gtgaaggtca caggtgtggg gtgatggttt  191940
tgggtgtggg gagggtcttg cacggagcga gggtggcagc aagagctgga agctgcaggg  192000
ggagaatggc agcagagagc acccggccct gtgggcggcc tggacagggc tgggcctggg  192060
gctgccggag agcctgtcag cttccaggat gggagtggcc tcactcagct gctccacctc  192120
cgggtcaggc aggtgagcct ggggcagaga ggctgagagc acctgagcca cttgtgggag  192180
aggccacccc cactgccccc ctcaggcgag gagccggcct ccagcacagc agaagggaac  192240
ccccagtccc cagccctagt gggagtgggg aagaggccca gcaaggcccc ggacagaccg  192300
ccagcctgtg aggtctccgc tttcagttgc gttgatttga ttttttctga gccttgaagg  192360
aggggtccgg ggcctggccc tgcccaaagg cccctaggca ggcccaaag ccgggaccta  192420 gggtgctgag catgacggat gttgggtttg agcggctggc ttgcgacgtg agggctgagg  192480
tgtgagcctg ggtatcttca gaggttcggt ggacacaggc agctgcccgc ggccccactg  192540
ttcccgtggc ctcctagtcc tgctcaggca cctggtgagg aagggacgca gagggcagtg  192600
ggaggtggcc acgactgttc cagcaggctc ccctctgact caggaattca cgggcaccac  192660
ctccctggct ggctctggtt ggtgtctggc caggttattc attatttatg ctgaaagcct  192720
cttcagagtc ccaggggagg gttctgtct ccattcctgg aggctgagag atgagggtgc  192780
agcagagtgg gggcctccac tccagaccct gcagtctggg ctggccaagg gctgcaccgg  192840
tgcactgcac gtcatggctg atgaagcact tccacaccgc agcccctcag agctgccaca  192900
gtcagcctta gttcaccgag ggggaagctg aggcccagag catgagaggg acttgcccag  192960
ggccacatag tccttagcag aggaagctgt ggctgggtga ctcgatcttt gtccttttc  193020 tttatacccg cagtctcccc atagcagagg ctttttcttt tttttctttt tctttttt  193080 ttttttaca agaactcttt atatattaag gctgttgggc tgaagaagcc tgagagggtg  193140
gctggttctg tggagcatgg tttgttgaag tacagtttgg gggcctccta cactgagaat  193200
aggccttttc tcgtttctcc aaagagtggg ctggctcaag tagggcagag agagaagcct  193260
ggggcagagg ttagggatgg gcacccagcg cctgccctca cacgctctgt gctggtgtct  193320
tcacagccac gtgccaccct gggcagcatc ccctgctcac catctggctg tgcctgtttg  193380
ctgggggcac tcattcaga atccagctta ttgtttccaa cggccaatgg ccacaccctg  193440
gcaggtagca agagtaggag agaggagaca cccactccga gcacaggttg ggtttggagc  193500
ccggccttgg ggcactctgt cactcaaagg cagagtgggg agtgggcact gggccttagg  193560
aggtactggg tccagtgagg cagagatgcc cctgccccac ccccaccttg tggcttcttc  193620
cctggcctgg ccagagctgt ctggccgcca tggggccctg tgtctcctgc cttgacctcc  193680
cagagggcag ccgaggccca ggggaggcct ggggacttag cctctcaggg caggacctgt  193740
ctgcaggagt aggtgggtgc tggggggtccc agtggtaatg aggcatcagg cagtgtggga  193800
agggggccat ccgcccacc ccagggcctc tgggcaggtt gcaggttgta gcgctggatc  193860
taggctcctg cccagactgt aggttcaacc aagaatggca tgggagccca gcctgctgtt  193920
tgctttatta aatctgccct gtagctgggg gaggggctta ctttgatcat cactatgtca  193980
ttgatataaa aatagaggct cagagaggtg aatgaacctg cccaaagtca cacagcaaag  194040
tgtggagatg agatactgac tcagggctgt ggacactgaa gcctgtgctc taacgccagt  194100
ggctgtcgct ccctgaggca ttctctcccg aacaacacag ttattatatt acaaaatatt  194160
atcactatat ttatatatct tataatacct tattattaca ataaaacctt attactctac  194220
```

```
ctttcaaaat gaattattta aaaagcagta tttgctcatt gcagagagtc tagaaactat  194280
agaaaagcaa gggaaaagca ataggaccag ccccaaggtc ccagcatgca cagataacct  194340
tagtaatact gggacgtgtg cttccttttt aacatctgag cccgtgtagg tcctgaagcc  194400
cagcttcttt ctaagtccat tgtcatcttg accctggagc ctggccgatt ttgctgggga  194460
ggcccttgcc agccgagagc ggctcctgcc tgtgccggcg tggcgcgccc ctctgctgag  194520
gctgggcagg acaggggctg ggccagctct gtttctcacc cttggctctt gtgtctctcg  194580
tttcaggaaa ttaaaatgca tgacagatag cgagtccgcc ccgcccgact ggccctatta  194640
cctagccatt gatgggattc tggccaaggt ccccgagtcc tgtgatggca aactgccgga  194700
cagccagccg ccgggccct ccacgtccca gaccgaggcg tccctgtcgc cgcccgctaa  194760 gtccaccct ctgtacttcc cgtataacca gtgctcctac gaaggccgct tcgaggatga  194820
tcgctccgac agctcctcca gcttactgtc ccttaagttc aggtagtgtg tctgcttgtc  194880 cttccctgc cctggggtat ctcagccccc accatttaga gaaagggact gggagtggca  194940
aggccggcgg cggcggccac agtggttgca gaggccgtgg ctgcgggcag cgcctccagg  195000
gacaggcggc ctcagaccag ggagggcttt agtgtccaca ggcagaccga gtttgtctcc  195060
cagctccatc acttttgagc tgcacggaaa gttccttgac ttctctggcc tcagtctccc  195120
tcctataaaa tgggggtaaa tcagtacctt tctcagaggg tggctgggag catcacagga  195180
gagaagacgc agcatgggc ccggcacacg gagggagacc aagccccaga ccccagaatg  195240 cgcccctgg cctcccttag cccacacaga ccccacctc acaggctagc tgccctctca  195300
gcactgggga gggtgtcggg ctgcacctca tcacgtgttg ccgtgggcat gacccgtccc  195360
ctctgccatc catcccacac ctcagacccg tcccgtgctg ccacgtgac tgtgcctgca  195420 agatgctcac agggcagccg ggagccaggc agcatgcagg acagacacct gcggggtggg  195480
cctggggagc ccagagaagg tgcttttgag gaggggacat ttggggtggg ctttcaaggt  195540
aaaatagaag ttggccattt ggaggcaaga acaggaagat tgtggatttg agtcacagct  195600 tctccctgc cctggtcttc aagtctttct gacaggaggt gtcagaaaag tatctttagt  195660
agagaaggcg tctccgagga gggtccctct catgccgggg gccgctgctt gactcaggat  195720
ttctcattga agacctgaga caaaaacgct tttgctggca gctagaagga accagcagga  195780
ggcctgagat ttgtggctgt tgttcccgtg gactgagccc agttctcaga ctcagctgcc  195840
tggggccttg cacaggactg gggcgtgggg gctgccctcc ctgatcaggc caaagcgcg  195900 gatctcacgc ccctgaggtt ggctgtaccc tctcagctca gagcagagtg tgggccaggg  195960
atgagcaggc actggagcag ggccctgggg tctgtgggtt ttggcagctc cctgcccttc  196020
agggaggtct gctgagacca cgggtggccc ctaccccagc agcagagctc tcaggaggcg  196080
cccacagggc tggactgcct ttactcacca cctctaccag agctctgagg tcctggggag  196140
agagcccagg cctcttgtgg gccccacacc ctctaggtgc ctgtccttct gcctctctac  196200
caaggtgtgc cggcccatt tctaggccgc cgggagataa gggggctcac atctcaggcc  196260
cttccttctg ggacctcagt ttccccatct gcctaaggcc gggtggggct ggtggtcttg  196320
gcttccctac aggggtcctg agtactctgc actacccagc accccccacc cctgccttca  196380
tctctccctg ggggtggtct ctccacccct ggcccccaac tggggctgag ccccacctg  196440 cccagtttgg tgggtgaagg gtgctccctg gcaggatatg cccctctgca gcccagaaca  196500 tcccacccctt tccagaccga aggggtgtgg attgtcctgg gacccctggtc attgggtca  196560 tccgctagtc gcaaaggacg gcaatgcctg tggcctctct ttctttcttt tctttttt  196620
```

```
tttttttttga gacggagtct cgctcttgtg cagagagcag tggcgcgatc ttggctcact 196680
gcaacctccg cctcgtgggt tcaagcgatt ctcctgcctc agcctcccga gtagctggga 196740
ttacaggcac ccgccacaac gcctggctaa ttttttgtatt tttagtagag atggggtttc 196800
accatgttgg ccaggctggt cttgaactcc tgacctcagg tgatccacct gcctctgcct 196860
cccaaagtgc tgggattaca ggcataagcc tccacacccg ccacccctg ttactttctg 196920
tcaaaggcgg tgggttctgg cccctccttt gcacatggaa tatgagaccc tgagtaagtg 196980
acctgactcc ctgggccctc agtttcccca tttgcccagt aggattgtcg ggagggtccg 197040
gtgaggcccc tggtgtgccc aggctctgtg ccagcacgt ccacagccgg cactgtcctt 197100
ccaggtcgga ggagcggccg gtgaagaagc gcaaggtgca gagctgccac ctgcagaaga 197160
agcagctgcg gctgctggag gccatggtgg aggagcagcg ccggctgagc cgcgccgtgc 197220
aggagacctg ccgcgaggtg cgccgcgtgc tggaccagca gcacatcctg caggtgcaga 197280
gcctgcagct gcaggagcgc atgatgagtc tgctggagag gatcatcacc aagtccagcg 197340
tctaggccag caggcggcgg cggcggcggg gccgggcggc tggtggtact gctcaggcca 197400
cccagggcag gccactcagg ccaggcgggc aaggggggccg ccccgcgagc ggagaccgcc 197460
ttccacctgg cctctggcag gatgtcccctt ctgagggta ttttgaggaa ccccaggcc 197520
ctggggaccg tgaggctcca gtctccagca tgaatgccct tcctcggaca caggccaggg 197580
cctctggggt tcactccgag taagaacgtc ctagagccac tctccagtgt cgttactatc 197640
aatgatactt gacgtggctt tgatattaaa cgtatacttt ttcattcttg cctggaacgc 197700
acagtttgct gttgctggct tggtgaggat gccctgattg atggatcccg aaaatgaaag 197760
cagatggaaa cgggttgggg caggctggag ctgggggagc tctctcctga agggaaccct 197820
gtgtcctccc tcaccaggac ctctgcgtct ctccttaaat ggcctctgac gcctgatgaa 197880
aaccccagcg accttccagg aggcttttat tcagctctgt ttggagcatc aggtgtttcc 197940
actgcctcct tagcaatgac actaataaaa gtcgtaacac ctgttcacat gcacagccct 198000
gttgagtgtt ctgggtgctg gagatatcat ggtggatgac acaaaggccc tggcctcttg 198060
gagcttatgc tcccatgcgg ggaagacaca tgggtcagta gagaaatggt tgcaggttgt 198120
gataagtgct ggaagggagg ggttggcctg aggacacgga ggcagacata cgtggagctg 198180
ggaacagtgg ccacacaggg aacggccagt gcgaaggccc agaggcagag gacactggag 198240
caagcccagg agcagctagg aggctggtgg ccagcagcca ggccacggaa gcccgtgcag 198300
cccgtgggga ggagtgttca tgcttttcaa gcttagtggg agtcttttgg ccagtgcagc 198360
tctgggtctg acatcggtgg gggacagagg ggtggtggag cggccacagc tgcaagctca 198420
cctcactgcc ggcccttcca ccagtttcaa actctttcta gaagctccag ctttcccaaa 198480
gctgaattct ctatgagcct ccttggccgg gactcgggcg tctggttgcc ctggctgcaa 198540
aggaggctgg ggccaggtgt gtttgagtca cctcctggaa ttaggcaagt tgctgcccaa 198600
atagaaggtt gttggcaggt gggtcagcag gtgaacagca tggtttgact cagggttcag 198660
aaaaatctcc ctctggctgc caagcgagca ggccgtggag acaggtgcag aggcaggtgt 198720
ggcagcaggc atcctgccag gcagtgctgc agtcatcctg cgacaagcag cagcagctca 198780
tcctacccctc taggggggtct tgaggtcagc caggcaagag agcagcttgg actccactgg 198840
gtgtgggacc agcctgtgga ccatggtggt gtggagggtg ccctcggcct gcctgtgtga 198900
aggagaggcc ggcgtgttct gtggagccca aaggggagct gggcaagcag gattcacttc 198960
```

```
actctgaggg tcctggagct cccaccctcc tcagccatct ccccagagcc tgtgtgccga   199020
ggactcggcc catgttgctg tgggatgaga ggcagagtgt cgtgagggtg taaggagcgg   199080
cggcagtggt gggaggaggg agcagcagcc agcgctacgg tgccagtttc cagctgccag   199140
atgacgccgc tgaccctgtg gttgagaaga gatgcacaga gccagctctt gcaagccagt   199200
gtggctgcca tagcacctgc cgagaagcag aaggaagggt ggccccagga ggacagagga   199260
tgcgggcaca tctgatgcgg gcctgagttt tgggagcttt tgctctagcc agtttccagc   199320
tccgggaccc acccgcctcg taggcaagac accacccaag aaatcatttg cttaacaaac   199380
acactgggct ccaactggac acctgtgcca ccctagatgc tgggaaccca gccatgacac   199440
aggcacctgc ccccagctgc tgaccactga ggctggctag cagctcccat ggggccagtg   199500
tggggttccc cagcctccta acagggagcc agtcacaagc cctcgagagg gaagggtgcc   199560
cgcggccctg gcaggaaggt taggctggac gctcccacaa gacataacag atggaggttc   199620
taaatgatgt agcaacttct tcaccctgaa actgctgtag agtcagccat gacgcaccgg   199680
tacttcagta actgccaggc atccgggaca gcacaccgcg agtcgctgct gtgcttgggt   199740
tagaagtggt ttggtctgtt ttcttctcgc cctctctaat cagagtcagt gattcatgcc   199800
cttccatcac cttagagaag gggcaggcgc tgcccgacct tctccaggct ggagcagcat   199860
cgcctcatgt cagcagaact cagctgtaga atatcgtggg gttggtgcct ttcatcagca   199920
gcatgtcctt aacaactttc tgatttcttc cttagttgtt ggtccattaa ggagaaaaaa   199980
aatgatctca gccattgcta aaatatttga taagattcag caaagcagca tgttaacatt   200040
gaaaactaga atcaggagcc aggcagatgt gcttgctttt cacctgtagt atttcatgtt   200100
gttttgacgt ttttagctaa tgcattaaga taaataaaca aaagccgggc acggtggttc   200160
acgcctgtaa tcccagcact tgggaggct gaggcgggag gatcctctga ggtcaggagt   200220
tcaagaccag cctgaccaac atggagaaac ctcgtcatta ctaaaaatac aaaattagct   200280
gggcgtggtg gtgcatgcct gtaatcccag ctacttggga ggctgaggca ggagaatcgc   200340
ttgaacccgg gaggcggagg ttgcagtgag ctgagattgc accactgcac tccagcctgg   200400
gtgacagtga aactcggtct caaaaaaaaa aaaaattaa aaaagataa ataaataag    200460
caggataaga aatgaagaaa gtagagttac ctttgttttc agatttcatt tttgtatacc   200520
cagaaagcca aatgtacaaa agactgggag ctctttaaac cagcttaaac ttgttgaaaa   200580
tgaggatgaa gaaatatccc attcagagtt ggaatgaatt taacccagaa ggaacaggac   200640
ctctactgaa gagaactatg cagtcttact gaaaaatcta aataataccct gagcgctgga   200700
gaaacttcgc acactcctga aagctccaaa gtcaatgtca tcattttatt aatgtcattc   200760
caaacatagt ctcaataata tcacttcttg gttttgacat ggacgcgatg atgtttaaat   200820
tcatatgaaa aagaacggg gccaaaagtc caaggccagt cagcgtgaga agaccgctcg    200880
gcctccctcg gagtcgggga gttggaaccg cagactgaga tcatgtggct gctgaggcc    200940
aggacgaacg tcgggaaatg gagactcctg cgttgctggt gggatgtggt gcagccgctt   201000
ccaggagcaa tttggtgtcc cgtcctaaag ctgaagaaac gcatttcctc tggtcagtgc   201060
cactcctaga caggccaccc tgcggcagcc gtcctcaaac tggtctgagg acccctcaac   201120
gctcttaaaa atcattaaaa gtgggccagg tgcggtggct cacacctgta atcccagcac   201180
tttgggaggc caagacaggc ggatcacgag gtcaggacat tgagatcatc ctggctaaca   201240
cggtgaaacc ccgtctctac taaaaataca aaaaattagc cgggcgtggt ggcgggcgcc   201300
tgtagtccca gctacttggg aggctgagcc aggagaatgg cgtgaaccca ggaggtggag   201360
```

```
cttgcagtga gctgagatca ctccactgca ctccagcctg ggcagcagag cgagactctg    201420
tctcaaaaaa aaataataaa taaataaata aaaataaaat aaaataaaat tcattaaaag    201480
tgccaaagaa cttttgctta tgtgagttct aatgaccaat attaatacac attagaatat    201540
cttattagaa attaaacctg agacctttag aaaacatgta ttcatttcaa aatagcaata    201600
aacccatgac atattaacat aaataacaat tgtatgaaaa atatattttc caaaacaaaa    201660
agttttcggg agaagtgtgg catagtttta catggtcgta aatctctggc ttaagagaag    201720
cccactggcc tctcagcagg ctctgggtcc gtccactttg ggggtgtttt ggttgtgaag    201780
tataggagtg aatggagaag ctcattctta cccagatgtg tatttgaaaa gaaaaggaac    201840
attttaataa cctttgcaaa taatcggtat attcttccgt gatcctattc caacactgga    201900
caggtggtgg tttgttttt tttttggag acggagtccc gctctgtcac tcaggctgga    201960
gtgcagtggc gcgatttcag ctcactgcaa gctccgcctc c                        202001

<210> SEQ ID NO 2
<211> LENGTH: 13481
<212> TYPE: DNA
<213> ORGANISM: Homo sapiens

<400> SEQUENCE: 2
gctgccggga cgggtccaag atggacggcc gctcaggttc tgcttttacc tgcggcccag      60
agccccattc attgccccgg tgctgagcgg cgccgcgagt cggcccgagg cctccgggga     120
ctgccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgcccccgcc     360
gccgccccg ccgccacccg cccggctgt ggctgaggag ccgctgcacc gaccaaagaa     420
agaactttca gctaccaaga aagaccgtgt gaatcattgt ctgacaatat gtgaaaacat     480
agtggcacag tctgtcagaa attctccaga atttcagaaa cttctgggca tcgctatgga     540
acttttctg ctgtgcagtg atgacgcaga gtcagatgtc aggatggtgg ctgacgaatg     600
cctcaacaaa gttatcaaag cttttgatgga ttctaatctt ccaaggttac agctcgagct     660
ctataaggaa attaaaaaga atggtgcccc tcggagtttg cgtgctgccc tgtggaggtt     720
tgctgagctg gctcacctgg ttcggcctca gaaatgcagg ccttacctgg tgaaccttct     780
gccgtgcct actcgaacaa gcaagagacc cgaagaatca gtccaggaga ccttggctgc     840
agctgttccc aaaattatgg cttcttttgg caattttgca aatgacaatg aaattaaggt     900
tttgttaaag gccttcatag cgaacctgaa gtcaagctcc ccaccattc ggcggacagc     960
ggctggatca gcagtgagca tctgccagca ctcaagaagg acacaatatt tctatagttg    1020
gctactaaat gtgctcttag gcttactcgt tcctgtcgag gatgaacact ccactctgct    1080
gattcttggc gtgctgctca ccctgaggta tttggtgccc ttgctgcagc agcaggtcaa    1140
ggacacaagc ctgaaaggca gcttcggagt gacaaggaaa gaaatggaag tctctccttc    1200
tgcagagcag cttgtccagg tttatgaact gacgttacat catacacagc accaagacca    1260
caatgttgtg accggagccc tggagctgtt gcagcagctc ttcagaacgc ctccacccga    1320
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
```

-continued

```
atgcagccct gtcctttcaa gaaaacaaaa aggcaaagtg ctcttaggag aagaagaagc    1500
cttggaggat gactctgaat cgagatcgga tgtcagcagc tctgccttaa cagcctcagt    1560
gaaggatgag atcagtggag agctggctgc ttcttcaggg gtttccactc cagggtcagc    1620
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt accccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttaacagg cacatttatt    2040 gaaaaacatg agtcactgca ggcagccttc tgacagcagt gttgataaat ttgtgttgag    2100
agatgaagct actgaaccgg gtgatcaaga aaacaagcct tgccgcatca aggtgacat    2160 tggacagtcc actgatgatg actctgcacc tcttgtccat tgtgtccgcc ttttatctgc    2220
ttcgtttttg ctaacagggg gaaaaaatgt gctggttccg gacagggatg tgagggtcag    2280
cgtgaaggcc ctggccctca gctgtgtggg agcagctgtg gccctccacc cggaatcttt    2340
cttcagcaaa ctctataaag ttcctcttga caccacggaa taccctgagg aacagtatgt    2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760 aaccctttgca gagattgact tcaggctggt gagcttttg gaggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgttttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taaccttttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggct ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aaccccccctt ctctaagtcc catccgacga aggggaagg agaaagaacc    3720 aggagaacaa gcatccgtac cgttgagtcc caagaaaggc agtgaggcca gtgcagcttc    3780
tagacaatct gatacctcag gtcctgttac aacaagtaaa tcctcatcac tgggagtttt    3840
```

```
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt ctttctcaga tactagagct ggccacactg caggacattg ggaagtgtgt    4020
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga aacagtttga atacattgaa gtgggccagt tcagggaatc    4620
agaggcaatc attccaaaca tcttttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct tcctccctcc gtccggtaga    5100 catgcttttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta aagaacacag tgaagggaa     5340 acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccaggcaa ttcagtctcg ttgtgaaaac cttttcaactc caaccatgct    6060 gaagaaaact cttcagtgct tggagggggat ccatctcagc cagtcgggag ctgtgctcac    6120
gctgtatgtg gacaggcttc tgtgcacccc tttccgtgtg ctggctcgca tggtcgacat    6180
```

```
ccttgcttgt cgccgggtag aaatgcttct ggctgcaaat ttacagagca gcatggccca    6240
gttgccaatg aagaactca acagaatcca ggaataccct cagagcagcg ggctcgctca    6300
gagacaccaa aggctctatt ccctgctgga caggtttcgt ctctccacca tgcaagactc    6360
acttagtccc tctcctccag tctcttccca cccgctggac ggggatgggc acgtgtcact    6420
ggaaacagtg agtccggaca aagactggta cgttcatctt gtcaaatccc agtgttggac    6480
caggtcagat tctgcactgc tggaaggtgc agagctggtg aatcggattc ctgctgaaga    6540
tatgaatgcc ttcatgatga actcggagtt caacctaagc ctgctagctc catgcttaag    6600
cctagggatg agtgaaattt ctggtggcca aagagtgcc cttttgaag cagcccgtga     6660
ggtgactctg gcccgtgtga gcggcaccgt gcagcagctc cctgctgtcc atcatgtctt    6720
ccagcccgag ctgcctgcag agccggcggc ctactggagc aagttgaatg atctgtttgg    6780
ggatgctgca ctgtatcagt ccctgcccac tctggcccgg gccctggcac agtacctggt    6840
ggtggtctcc aaactgccca gtcatttgca ccttcctcct gagaaagaga aggacattgt    6900
gaaattcgtg gtggcaaccc ttgaggccct gtcctggcat ttgatccatg agcagatccc    6960
gctgagtctg gatctccagg cagggctgga ctgctgctgc ctggccctgc agctgcctgg    7020
cctctggagc gtggtctcct ccacagagtt tgtgacccac gcctgctccc tcatctactg    7080
tgtgcacttc atcctggagg ccgttgcagt gcagcctgga gagcagcttc ttagtccaga    7140
aagaaggaca aataccccaa aagccatcag cgaggaggag gaggaagtag atccaaacac    7200
acagaatcct aagtatatca ctgcagcctg tgagatggtg gcagaaatgg tggagtctct    7260
gcagtcggtg ttggccttgg gtcataaaag gaatagcggc gtgccggcgt ttctcacgcc    7320
attgctaagg aacatcatca tcagcctggc ccgcctgccc cttgtcaaca gctacacacg    7380
tgtgcccca ctggtgtgga gcttggatg gtcacccaaa ccgggagggg attttggcac     7440
agcattccct gagatccccg tggagttcct ccaggaaaag gaagtcttta aggagttcat    7500
ctaccgcatc aacacactag gctggaccag tcgtactcag tttgaagaaa cttgggccac    7560
cctccttggt gtcctggtga cgcagcccct cgtgatggag caggaggaga gcccaccaga    7620
agaagacaca gagaggaccc agatcaacgt cctggccgtg caggccatca cctcactggt    7680
gctcagtgca atgactgtgc ctgtggccgg caacccagct gtaagctgct ggagcagca    7740
gccccggaac aagcctctga aagctctcga caccaggttt ggggaggaagc tgagcattat    7800
cagagggatt gtggagcaag agattcaagc aatggtttca aagagagaga atattgccac    7860
ccatcattta tatcaggcat gggatcctgt cccttctctg tctccggcta ctacaggtgc    7920
cctcatcagc cacgagaagc tgctgctaca gatcaacccc gagcgggagc tggggagcat    7980
gagctacaaa ctcggccagg tgtccataca ctccgtgtgg ctggggaaca gcatcacacc    8040
cctgagggag aggaatgggg acgaggaaga ggaggaggag gccgacgccc ctgcaccttc    8100
gtcaccaccc acgtctccag tcaactccag gaaacaccgg gctggagttg acatccactc    8160
ctgttcgcag ttttttgcttg agttgtacag ccgctggatc ctgccgtcca gctcagccag    8220
gaggaccccg gccatcctga tcagtgaggt ggtcagatcc cttctagtgg tctcagactt    8280
gttcaccgag cgcaaccagt ttgagctgat gtatgtgacg ctgacagaac tgcgaagggt    8340
gcacccttca aagacgaga tcctcgctca gtacctggtg cctgccacct gcaaggcagc     8400
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
ggagtgcgac ctgctggacg acactgccaa gcagctcatc ccggtcatca gcgactatct    8580
```

```
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc     9000
agtgattgtt gctatggagc gggtatctgt tcttttgat aggatcagga aaggcttttcc     9060
ttgtgaagcc agagtggtgg ccaggatcct gccccagttt ctagacgact tcttcccacc    9120
ccaggacatc atgaacaaag tcatcggaga gtttctgtcc aaccagcagc catacccca    9180
gttcatggcc accgtggtgt ataaggtgtt tcagactctg cacagcaccg ggcagtcgtc    9240
catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agcccagga agcccatatc accggctgct     9540
gacttgttta cgaaatgtcc acaaggtcac cacctgctga gcgccatggt gggagagact    9600
gtgaggcggc agctgggcc ggagcctttg gaagtctgcg cccttgtgcc ctgcctccac      9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga gcagctgtgc tgcacccccat   9840
gtgggtgacc aggtcctttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgccccg tgtctggatg cacagatgcc atggcctgtg ctgggccagt    10080
ggctggggt gctagacacc cggcaccatt ctcccttctc tcttttcttc tcaggattta     10140
aaatttaatt atatcagtaa agagattaat tttaacgtaa ctctttctat gcccgtgtaa    10200
agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
ttccgttgta catgttcctg tttatgcatt cacaaggtga ctgggatgta gagaggcgtt    10380
agtgggcagg tggccacagc aggactgagg acaggccccc attatcctag gggtgcgctc    10440
acctgcagcc cctcctcctc gggcacagac gactgtcgtt ctccacccac cagtcaggga    10500
cagcagcctc cctgtcactc agctgagaag gccagccctc cctggctgtg agcagcctcc    10560
actgtgtcca gagacatggg cctcccactc ctgttccttg ctagccctgg ggtggcgtct    10620
gcctaggagc tggctggcag gtgttgggac ctgctgctcc atggatgcat gccctaagag    10680
tgtcactgag ctgtgttttg tctgagcctc tctcggtcaa cagcaaagct tggtgtcttg    10740
gcactgttag tgacagagcc cagcatccct tctgccccg ttccagctga catcttgcac     10800
ggtgacccct tttagtcagg agagtgcaga tctgtgctca tcggagactg ccccacggcc    10860
ctgtcagagc cgccactcct atccccaggc caggtccctg gaccagcctc ctgtttgcag    10920
```

```
gcccagagga gccaagtcat taaaatggaa gtggattctg gatggccggg ctgctgctga   10980
tgtaggagct ggatttggga gctctgcttg ccgactggct gtgagacgag gcagggctc    11040
tgcttcctca gccctagagg cgagccaggc aaggttggcg actgtcatgt ggcttggttt   11100
ggtcatgccc gtcgatgttt tgggtattga atgtggtaag tggaggaaat gttggaactc   11160
tgtgcaggtg ctgccttgag accccccaagc ttccacctgt ccctctccta tgtggcagct  11220
ggggagcagc tgagatgtgg acttgtatgc tgcccacata cgtgaggggg agctgaaagg   11280
gagcccctcc tctgagcagc ctctgccagg cctgtatgag gcttttccca ccagctccca   11340
acagaggcct cccccagcca ggaccacctc gtcctcgtgg cggggcagca ggagcggtag   11400
aaaggggtcc gatgtttgag gaggcccttta agggaagcta ctgaattata acacgtaaga   11460
aaatcaccat tccgtattgg ttgggggctc ctgtttctca tcctagcttt ttcctggaaa   11520
gcccgctaga aggtttggga acgaggggaa agttctcaga actgttggct gctccccacc   11580
cgcctcccgc ctcccccgca ggttatgtca gcagctctga cacagcagta tcacaggcca   11640
gatgttgttc ctggctagat gtttacattt gtaagaaata acactgtgaa tgtaaaacag   11700
agccattccc ttggaatgca tatcgctggg ctcaacatag agtttgtctt cctcttgttt   11760
acgacgtgat ctaaaccagt ccttagcaag gggctcagaa caccccgctc tggcagtagg   11820
tgtcccccac ccccaaagac ctgcctgtgt gctccggaga tgaatatgag ctcattagta   11880
aaaatgactt cacccacgca tatacataaa gtatccatgc atgtgcatat agacacatct   11940
ataattttac acacacacct ctcaagacgg agatgcatgg cctctaagag tgcccgtgtc   12000
ggttcttcct ggaagttgac tttccttaga cccgccaggt caagttagcc gcgtgacgga   12060
catccaggcg tgggacgtgg tcagggcagg gctcattcat tgcccactag gatcccactg   12120
gcgaagatgg tctccatatc agctctctgc agaaggagg aagactttat catgttccta   12180
aaaatctgtg gcaagcaccc atcgtattat ccaaattttg ttgcaaatgt gattaatttg   12240
gttgtcaagt tttgggggtg ggctgtgggg agattgcttt tgttttcctg ctggtaatat   12300
cgggaaagat tttaatgaaa ccagggtaga attgtttggc aatgcactga agcgtgtttc   12360
tttcccaaaa tgtgcctccc ttccgctgcg ggcccagctg agtctatgta ggtgatgttt   12420
ccagctgcca agtgctcttt gttactgtcc accctcattt ctgccagcgc atgtgtcctt   12480
tcaaggggaa aatgtgaagc tgaaccccct ccagacaccc agaatgtagc atctgagaag   12540
gccctgtgcc ctaaaggaca cccctcgccc ccatcttcat ggagggggtc atttcagagc   12600
cctcggagcc aatgaacagc tcctcctctt ggagctgaga tgagcccccac gtggagctcg   12660
ggacggatag tagacagcaa taactcggtg tgtggccgcc tggcaggtgg aacttcctcc   12720
cgttgcgggg tggagtgagg ttagttctgt gtgtctggtg ggtggagtca ggcttctctt   12780
gctacctgtg agcatccttc ccagcagaca tcctcatcgg gctttgtccc tccccgcctt   12840
cctccctctg cggggaggac ccgggaccac agctgctggc cagggtagac ttggagctgt   12900
cctccagagg ggtcacgtgt aggagtgaga agaaggaaga tcttgagagc tgctgaggga   12960
ccttggagag ctcaggatgg ctcagacgag gacactcgct tgccgggcct gggcctcctg   13020
ggaaggaggg agctgctcag aatgccgcat gacaactgaa ggcaacctgg aaggttcagg   13080
ggccgctctt ccccccatgtg cctgtcacgc tctggtgcag tcaaaggaac gccttcccct   13140
cagttgtttc taagagcaga gtctcccgct gcaatctggg tggtaactgc cagccttgga   13200
ggatcgtggc caacgtggac ctgcctacgg agggtgggct ctgacccaag tggggcctcc   13260
ttgtccaggt ctcactgctt tgcaccgtgg tcagagggac tgtcagctga gcttgagctc   13320
```

| | |
|---|---|
| ccctggagcc agcagggctg tgatgggcga gtcccggagc cccacccaga cctgaatgct | 13380 |
| tctgagagca aagggaagga ctgacgagag atgtatattt aatttttttaa ctgctgcaaa | 13440 |
| cattgtacat ccaaattaaa ggaaaaaaat ggaaaccatc a | 13481 |

<210> SEQ ID NO 3
<211> LENGTH: 3160
<212> TYPE: DNA
<213> ORGANISM: Homo sapiens

<400> SEQUENCE: 3

| | |
|---|---|
| cctccctcg cccggcgcgg tcccgtccgc ctctcgctcg cctcccgcct ccctcggtc | 60 |
| ttccgaggcg cccgggctcc cggcgcggcg gcggaggggg cgggcaggcc ggcgggcggt | 120 |
| gatgtggcag gactctttat gcgctgcggc aggatacgcg ctcggcgctg ggacgcgact | 180 |
| gcgctcagtt ctctcctctc ggaagctgca gccatgatgg aagtttgaga gttgagccgc | 240 |
| tgtgaggcga ggccgggctc aggcgaggga gatgagagac ggcggcggcc gcggcccgga | 300 |
| gccctctca gcgcctgtga cagccgcgg gggcagcgcc ctcggggagc cggccggcct | 360 |
| gcggcggcgg cagcggcggc gtttctcgcc tcctcttcgt cttttctaac cgtgcagcct | 420 |
| cttcctcggc ttctcctgaa agggaaggtg gaagccgtgg gctcgggcgg gagccggctg | 480 |
| aggcgcggcg gcgcggcgg cggcacctcc cgctcctgga gcgggggga gaagcggcgg | 540 |
| cggcggcggc cgcggcggct gcagctccag ggaggggtc tgagtcgcct gtcaccattt | 600 |
| ccagggctgg gaacgccgga gagttggtct ctcccttct actgcctcca acacggcggc | 660 |
| ggcggcggcg gcacatccag ggacccgggc cggttttaaa cctcccgtcc gccgccgccg | 720 |
| caccccccgt ggcccgggct ccggaggccg ccggcggagg cagccgttcg gaggattatt | 780 |
| cgtcttctcc ccattccgct gccgccgctg ccaggcctct ggctgctgag gagaagcagg | 840 |
| cccagtcgct gcaaccatcc agcagccgcc gcagcagcca ttaccggct gcggtccaga | 900 |
| gccaagcggc ggcagagcga ggggcatcag ctaccgccaa gtccagagcc atttccatcc | 960 |
| tgcagaagaa gccccgccac cagcagcttc tgccatctct ctcctccttt ttcttcagcc | 1020 |
| acaggctccc agacatgaca gccatcatca agagatcgt tagcagaaac aaaaggagat | 1080 |
| atcaagagga tggattcgac ttagacttga cctatattta tccaaacatt attgctatgg | 1140 |
| gatttcctgc agaaagactt gaaggcgtat acaggaacaa tattgatgat gtagtaaggt | 1200 |
| ttttggattc aaagcataaa aaccattaca agatatacaa tctttgtgct gaaagacatt | 1260 |
| atgacaccgc caaatttaat tgcagagttg cacaatatcc ttttgaagac cataacccac | 1320 |
| cacagctaga acttatcaaa ccctttttgtg aagatcttga ccaatggcta agtgaagatg | 1380 |
| acaatcatgt tgcagcaatt cactgtaaag ctggaaaggg acgaactggt gtaatgatat | 1440 |
| gtgcatattt attacatcgg ggcaaatttt taaaggcaca agaggcccta gatttctatg | 1500 |
| gggaagtaag gaccagagac aaaaagggag taactattcc cagtcagagg cgctatgtgt | 1560 |
| attattatag ctacctgtta aagaatcatc tggattatag accagtggca ctgttgtttc | 1620 |
| acaagatgat gtttgaaact attccaatgt tcagtggcgg aacttgcaat cctcagtttg | 1680 |
| tggtctgcca gctaaaggtg aagatatatt cctccaattc aggacccaca cgacgggaag | 1740 |
| acaagttcat gtactttgag ttccctcagc cgttacctgt gtgtggtgat atcaaagtag | 1800 |
| agttcttcca caaacagaac aagatgctaa aaaaggacaa aatgtttcac ttttgggtaa | 1860 |
| atacattctt cataccagga ccagaggaaa cctcagaaaa agtagaaaat ggaagtctat | 1920 |

```
gtgatcaaga aatcgatagc atttgcagta tagagcgtgc agataatgac aaggaatatc     1980
tagtacttac tttaacaaaa aatgatcttg acaaagcaaa taaagacaaa gccaaccgat     2040
acttttctcc aaattttaag gtgaagctgt acttcacaaa aacagtagag gagccgtcaa     2100
atccagaggc tagcagttca acttctgtaa caccagatgt tagtgacaat gaacctgatc     2160
attatagata ttctgacacc actgactctg atccagagaa tgaaccttt gatgaagatc      2220 agcatacaca aattacaaaa gtctgaattt ttttttatca agagggataa aacaccatga     2280
aaataaactt gaataaactg aaaatggacc ttttttttt taatggcaat aggacattgt      2340
gtcagattac cagttatagg aacaattctc ttttcctgac caatcttgtt ttaccctata     2400
catccacagg gttttgacac ttgttgtcca gttgaaaaaa ggttgtgtag ctgtgtcatg     2460 tatataccctt tttgtgtcaa aaggacattt aaaattcaat taggattaat aaagatggca   2520
ctttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc taccccttg cacttgtggc aacagataag tttgcagttg gctaagagag     2700 gttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160

<210> SEQ ID NO 4
<211> LENGTH: 26
<212> TYPE: DNA
<213> ORGANISM: Artificial sequence
<220> FEATURE:
<223> OTHER INFORMATION: Primer

<400> SEQUENCE: 4
aatggctaag tgaagatgac aatcat                                          26

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
tgcacatatc attacaccag ttcgt                                           25

<210> SEQ ID NO 6
<211> LENGTH: 30
<212> TYPE: DNA
<213> ORGANISM: Artificial sequence
<220> FEATURE:
<223> OTHER INFORMATION: Probe

<400> SEQUENCE: 6
ttgcagcaat tcactgtaaa gctggaaagg                                      30
```

-continued

```
<210> SEQ ID NO 7
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 7
ucgagaacau cc                                                            12

<210> SEQ ID NO 8
<211> LENGTH: 12
<212> TYPE: DNA
<213> ORGANISM: Artificial sequence
<220> FEATURE:
<223> OTHER INFORMATION: Synthetic oligonucleotide

<400> SEQUENCE: 8
ggatgttctc ga                                                            12

<210> SEQ ID NO 9
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 9
taaattgtca tcacc                                                         15

<210> SEQ ID NO 10
<211> LENGTH: 30
<212> TYPE: RNA
<213> ORGANISM: Artificial sequence
<220> FEATURE:
<223> OTHER INFORMATION: Synthetic oligonucleotide

<400> SEQUENCE: 10 agacuuuuc uggugaugac aauuuauuaa                                          30

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
gtctgtgcat ctctcc                                                        16

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
ttcagtcatg acttcc                                                        16

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 13
gccaggctgg ttatgactca                                              20

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
aagttgtagt agtcgc                                                  16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
gcatgttctc acatta                                                  16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
acatcttcag atcatt                                                  16

<210> SEQ ID NO 17
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 17
aaggaaguca ugacugaagc                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctgctagcct ctggatttga                                              20
```